United States Patent
Seen et al.

(10) Patent No.: US 10,709,763 B2
(45) Date of Patent: Jul. 14, 2020

(54) GPCR HETEROMER INHIBITORS AND USES THEREOF

(71) Applicant: GPCR THERAPEUTICS, INC., Seoul (KR)

(72) Inventors: DongSeung Seen, Seoul (KR); Eunhee Kim, Seoul (KR); Jae-Yeon Jeong, Seoul (KR); Chang Soo Yang, Seoul (KR); Milim Lee, Seoul (KR); SoHui Kim, Seoul (KR); Won-Ki Huh, Seoul (KR); Yong Bhum Song, Daejeon (KR); Chul O Park, Seoul (KR); Hyeryung Park, Seoul (KR); Jiyeong Lee, Seoul (KR)

(73) Assignee: GPCR THERAPEUTICS, INC., Seoul (KR)

( * ) Notice: Subject to any disclaimer, the term of this patent is extended or adjusted under 35 U.S.C. 154(b) by 0 days.

(21) Appl. No.: 16/224,450

(22) Filed: Dec. 18, 2018

(65) Prior Publication Data
US 2019/0183976 A1    Jun. 20, 2019

Related U.S. Application Data

(60) Provisional application No. 62/732,946, filed on Sep. 18, 2018, provisional application No. 62/679,598, filed on Jun. 1, 2018, provisional application No. 62/607,876, filed on Dec. 19, 2017.

(51) Int. Cl.

| | | |
|---|---|---|
| *A61K 38/19* | (2006.01) | |
| *A61K 31/403* | (2006.01) | |
| *A61K 31/138* | (2006.01) | |
| *A61K 31/395* | (2006.01) | |
| *A61P 35/00* | (2006.01) | |
| *A61K 31/451* | (2006.01) | |
| *A61K 31/495* | (2006.01) | |
| *A61K 31/5415* | (2006.01) | |
| *A61K 31/4545* | (2006.01) | |
| *A61K 31/47* | (2006.01) | |
| *A61K 38/12* | (2006.01) | |
| *C07K 16/28* | (2006.01) | |
| *A61K 39/00* | (2006.01) | |
| *A61K 39/395* | (2006.01) | |

(52) U.S. Cl.
CPC .......... *A61K 38/195* (2013.01); *A61K 31/138* (2013.01); *A61K 31/395* (2013.01); *A61K 31/403* (2013.01); *A61K 31/451* (2013.01); *A61K 31/4545* (2013.01); *A61K 31/47* (2013.01); *A61K 31/495* (2013.01); *A61K 31/5415* (2013.01); *A61K 38/12* (2013.01); *A61K 39/3955* (2013.01); *A61P 35/00* (2018.01); *C07K 16/286* (2013.01); *C07K 16/2866* (2013.01); *A61K 2039/505* (2013.01); *A61K 2039/507* (2013.01); *C07K 2317/21* (2013.01); *C07K 2317/76* (2013.01)

(58) Field of Classification Search
CPC ...... A61K 38/195; A61K 38/12; A61K 31/47; A61K 31/4545; A61K 31/5415; A61K 31/495; A61K 31/451; A61K 31/395; A61K 31/138; A61K 31/403; A61K 2039/505; A61K 2039/507; C07K 16/286; C07K 16/2866; C07K 2317/21; C07K 2317/76; A61P 35/00
See application file for complete search history.

(56) References Cited

U.S. PATENT DOCUMENTS

| | | |
|---|---|---|
| 6,855,807 B1 | 2/2005 | Devi et al. |
| 7,405,053 B2 | 7/2008 | Milligan et al. |
| 7,741,064 B2 | 6/2010 | Milligan et al. |
| 9,216,189 B2 | 12/2015 | Devi et al. |
| 2001/0053848 A1 | 12/2001 | Patel et al. |
| 2011/0160081 A1 | 6/2011 | Javitch et al. |
| 2016/0200822 A1 | 7/2016 | Devi et al. |
| 2017/0038367 A1 | 2/2017 | Cotnoir-White et al. |

FOREIGN PATENT DOCUMENTS

| | | |
|---|---|---|
| EP | 1625159 B1 | 3/2011 |
| EP | 2464973 B1 | 10/2016 |
| KR | 10-2011-0020825 | 3/2011 |
| KR | 101029972 B1 | 4/2011 |

(Continued)

OTHER PUBLICATIONS

Abd Alla et al., 2009, "Calreticulin enhances B2 bradykinin receptor maturation and heterodimerization," Biochem Biophys Res Commun., 387(1):186-190.

(Continued)

*Primary Examiner* — Ruixiang Li
(74) *Attorney, Agent, or Firm* — Jones Day

(57) ABSTRACT

This invention relates to inhibitors of CXC receptor 4 (CXCR4)-G protein-coupled receptor (GPCR) heteromers (CXCR4-GPCR heteromers) associated with cancers, where CXCR4 forms a functional heteromer with other G protein-coupled receptors (GPCRx). More specifically, this invention relates to GPCRx that form heteromers with CXCR4, which upon co-stimulation with CXCR4 agonists and GPCRx agonists leads to enhanced signaling downstream of CXCR4. This invention also provides for the use of inhibitors of the interacting GPCR partner of the CXCR4-GPCRx heteromer or CXCR4-GPCRx heteromer-specific inhibitors including inhibitors of the formation of the CXCR4-GPCRx heteromer and CXCR4-GPCRx heteromer-specific antibodies, and in the diagnosis and/or therapy for cancer.

18 Claims, 51 Drawing Sheets

Specification includes a Sequence Listing.

(56) References Cited

FOREIGN PATENT DOCUMENTS

| WO | WO 1998000538 A2 | 1/1998 |
|---|---|---|
| WO | WO 1998000715 A2 | 1/1998 |
| WO | WO 2005103721 A1 | 11/2005 |
| WO | WO 2009138519 A1 | 11/2009 |

OTHER PUBLICATIONS

Adalta Ltd., 2017, "BRIEF-Adalta receives orphan designation for AD-114," Reuters, retreived from internet: www.reuters.com/article/idUSFWN1F70Y0 on Jan. 16, 2019 (1 page).
Agrawal et al., 2004, "Role for CCR5Delta32 protein in resistance to R5, R5X4, and X4 human immunodeficiency virus type 1 in primary CD4+ cells," J Virol, 78(5):2277-2287.
Albrandt et al., 1995, "Molecular cloning and functional expression of a third isoform of the human calcitonin receptor and partial characterization of the calcitonin receptor gene," Endocrinology, 136(12):5377-5384.
Allen et al., 2004, "Germinal center dark and light zone organization is mediated by CXCR4 and CXCR5," Nat Immunol, 5(9):943-952.
Ara et al., 2003, "A role of CXC chemokine ligand 12/stromal cell-derived factor-1/pre-B cell growth stimulating factor and its receptor CXCR4 in fetal and adult T cell development in vivo," J Immunol, 170(9):4649-4655.
Armando et al., 2014, "The chemokine CXC4 and CC2 receptors form homo- and heterooligomers that can engage their signaling G-protein effectors and betaarrestin," FASEB J 28(10):4509-4523.
Ayoub et al., 2015, "Functional interaction between angiotensin II receptor type 1 and chemokine (C-C motif) receptor 2 with implications for chronic kidney disease," PLoS One, 10(3):e0119803.
Barmania et al., 2013, "C-C chemokine receptor type five (CCR5): An emerging target for the control of HIV infectionm," Appl Transl Genom, 2:3-16.
Bartolome et al., 2009, "The chemokine receptor CXCR4 and the metalloproteinase MT1-MMP are mutually required during melanoma metastasis to lungs," Am J Pathol 174(2):602-612.
Batlle et al., 2017, "Cancer stem cells revisited," Nat Med, 23(10):1124-1134.
Bazin et al., 2002, "Time resolved amplification of cryptate emission: a versatile technology to trace biomolecular interactions," J Biotechnol, 82(3):233-250.
Beck et al., 2017, "Strategies and challenges for the next generation of antibody—drug conjugates", Nature Reviews Drug Discovery, 16(5):315-337.
Bjarnadottir et al., 2006, "Comprehensive repertoire and phylogenetic analysis of the G protein-coupled receptors in human and mouse," Genomics, 88(3):263-273.
Bodart et al., 2009, "Pharmacology of AMD3465: a small molecule antagonist of the chemokine receptor CXCR4," Biochem Pharmacol 78(8):993-1000.
Braadland et al., 2014, "beta-Adrenergic Receptor Signaling in Prostate Cancer," Front Oncol 4:375.
Broxmeyer et al., 2005, "Rapid mobilization of murine and human hematopoietic stem and progenitor cells with AMD3100, a CXCR4 antagonist," J Exp Med, 201(8):1307-1318.
Brueggemann et al., 2014, "Differential protein kinase C-dependent modulation of Kv7.4 and Kv7.5 subunits of vascular Kv7 channels," J Biol Chem, 289(4):2099-2111.
Buckley et al., 2000, "Persistent induction of the chemokine receptor CXCR4 by TGF-beta 1 on synovial T cells contributes to their accumulation within the rheumatoid synovium," J Immunol. 165(6):3423-3429.
Burbas Si et al., 2010, Alterations of CXCR4 function in mu-opioid receptor-deficient glia. Eur J Neurosci, 32(8):1278-1288.
Burger et al., 1999, "Chronic lymphocytic leukemia B cells express functional CXCR4 chemokine receptors that mediate spontaneous migration beneath bone marrow stromal cells," Blood 94(11):3658-3667.
Burger et al., 2006, "CXCR4: a key receptor in the crosstalk between tumor cells and their microenvironment," Blood, 107(5):1761-1767.
Burger et al., 2009, "CXCR4 antagonists: targeting the microenvironment in leukemia and other cancers," Leukemia, 23(1):43-52.
Burger et al., 2011, "Potential of CXCR4 antagonists for the treatment of metastatic lung cancer," Expert Rev Anticancer Ther, 11(4):621-630.
Bushlin et al., 2012, "Dimerization with cannabinoid receptors allosterically modulates delta opiold receptor activity during neuropathic pain," PLoS One, 7(12):e49789.
Callen et al., 2012, "Cannabinoid receptors CB1 and CB2 form functional heteromers in brain," J Biol Chem, 287(25):20851-20865.
Campeau et al., 2009, "A versatile viral system for expression and depletion of proteins in mammalian cells," PLoS One, 4(8):e6529.
Campos et al., 2018, "Molecular Profiling of Liquid Biopsy Samples for Precision Medicine," Cancer J., 24(2):93-103.
Canonica et al., 2011, "Antihistaminic, anti-inflammatory, and antiallergic properties of the nonsedating second-generation antihistamine desloratadine: a review of the evidence," World Allergy Organ J, 4(2):47-53.
Cao et al., 2017, "Cordycepin induces apoptosis in human bladder cancer cells via activation of A3 adenosine receptors," Tumour Biol., 39(7):1010428317706915.
Cashen et al., 2007, "AMD3100: CXCR4 antagonist and rapid stem cell-mobilizing agent," Future Oncol, 3(1):19-27.
Chatterjee et al., 2014, "The intricate role of CXCR4 in cancer," Adv Cancer Res, 124:31-82.
Chen et al., 2013, "Adenosine receptors as drug targets—what are the challenges?" Nat Rev Drug Discov, 12(4):265-286.
Chen et al., 2015, "CXCR4 inhibition in tumor microenvironment facilitates anti-programmed death receptor-1 immunotherapy in sorafenib-treated hepatocellular carcinoma in mice," Hepatology, 61(5):1591-1602.
Cheng et al., 2017, "The Role of SDF-1/CXCR4/CXCR7 in Neuronal Regeneration after Cerebral Ischemia," Front Neurosci, 11:590.
Cho et al., 2013, "Inhibition of tumor growth and histopathological changes following treatment with a chemokine receptor CXCR4 antagonist in a prostate cancer xenograft model," Oncol Lett, 6(4):933-938.
Choi et al., 2012, "AdHTS: a high-throughput system for generating recombinant adenoviruses," J Biotechnol, 162(2-3):246-252.
Chong et al., 2009, "Targeting the CXCR4/CXCL12 axis in systemic lupus erythematosus," Expert Opin Ther Targets 13(10):1147-1153.
Choy et al., 2016, "Inhibition of beta2-adrenergic receptor reduces triple-negative breast cancer brain metastases: The potential benefit of perioperative beta-blockade," Oncol Rep, 35(6):3135-3142.
Chu et al., 2017, "CXCL12/CXCR4/CXCR7 Chemokine Axis in the Central Nervous System: Therapeutic Targets for Remyelination in Demyelinating Diseases," Neuroscientist, 23(6):627-648.
Chung et al., 2010. "CXC Chemokine receptor 4 expressed in T cells plays an important role in the development of collagen-induced arthritis," Arthritis Res Ther, 12(5):R188.
ClinicalTrials.gov, ClinicalTrials Identifier: NCT00001756, "Study of Mast Cell Precursors," Last Update Posted Jan. 31, 2019, retreived from internet: clinicaltrials.gov/ct2/show/NCT00001756 on Feb. 5, 2019 (7 pages).
ClinicalTrials.gov, ClinicalTrials Identifier: NCT00089466, "Safety and Activity of the Oral HIV Entry Inhibitor AMD11070 in HIV Infected Patients," Last Update Posted Oct. 31, 2012, retreived from internet: clinicaltrials.gov/ct2/show/NCT00089466 on Feb. 5, 2019 (7 pages).
ClinicalTrials.gov, ClinicalTrials Identifier: NCT00512252, "AMD3100 Plus Mitoxantrone, Etoposide and Cytarabine in Acute Myeloid Leukemia (AMD3100+MEC)," Last Update Posted Dec. 12, 2016, retreived from internet: clinicaltrials.gov/ct2/show/NCT00512252 on Feb. 5, 2019 (8 pages).
ClinicalTrials.gov, ClinicalTrials Identifier: NCT00591682, "MSX-122 Administered Orally in Patients With Refractory Metastatic or Locally Advanced Solid Tumors," Last Update Posted Mar. 26,

(56) References Cited

OTHER PUBLICATIONS 2008, retreived from internet: clinicaltrials.gov/ct2/show/ NCT00591682 on Feb. 5, 2019 (6 pages).
ClinicalTrials.gov, ClinicalTrials Identifier: NCT00694590, "Study of AMD3100 (Plerixafor) and Rituximab in Patients With Chronic Lymphocytic Leukemia or Small Lymphocytic Lymphoma," Last Update Posted Mar. 20, 2015, retreived from internet: clinicaltrials. gov/ct2/show/NCT00694590 on Feb. 5, 2019 (7 pages).
ClinicalTrials.gov, ClinicalTrials Identifier: NCT00903968, "Combination Plerixafor (AMD3100)and Bortezomib in Relapsed or Relapsed/Refractory Multiple Myeloma," Last Update Posted Nov. 14, 2017, retreived from internet: clinicaltrials.gov/ct2/show/ NCT00903968 on Feb. 5, 2019 (9 pages).
ClinicalTrials.gov, ClinicalTrials Identifier: NCT00906945, "Chemosensitization With Plerixafor Plus G-CSF in Acute Myeloid Leukemia," Last Update Posted Apr. 4, 2017, retreived from internet: clinicaltrials.gov/ct2/show/NCT00906945 on Feb. 5, 2019 (12 pages).
ClinicalTrials.gov, ClinicalTrials Identifier: NCT00943943, "Granulocyte-colony Stimulating Factor (G-CSF) and Plerixafor Plus Sorafenib for Acute Myelogenous Leukemia (AML) With FLT3 Mutations," Last Update Posted Mar. 29, 2017, retreived from internet: clinicaltrials. gov/ct2/show/NCT00943943 on Feb. 5, 2019 (8 pages).
ClinicalTrials.gov, ClinicalTrials Identifier: NCT00967785, "A Phase I Study of Mozobil in the Treatment of Patients With WHIMS," Last Update Posted Jan. 15, 2019, retreived from internet: clinicaltrials. gov/ct2/show/NCT00967785 on Feb. 5, 2019 (8 pages).
ClinicalTrials.gov, ClinicalTrials Identifier: NCT00990054, "Study of Plerixafor Combined With Cytarabine and Daunorubicin in Patients With Newly Diagnosed Acute Myeloid Leukemia," Last Update Posted Mar. 24, 2015, retreived from internet: clinicaltrials. gov/ct2/show/NCT00990054 on Feb. 5, 2019 (8 pages).
ClinicalTrials.gov, ClinicalTrials Identifier: NCT01027923, "IV Plerixafor With Mitoxantrone Etoposide and Cytarabine for Acute Myeloid Leukemia (AML) (AML)," Last Update Posted Jan. 26, 2015, retreived from internet: clinicaltrials.gov/ct2/show/ NCT01027923 on Feb. 5, 2019 ( pages).
ClinicalTrials.gov, ClinicalTrials Identifier: NCT01058993, "AMD 3100 for Treatment of Myelokathexis," Last Update Posted Jun. 15, 2012, retreived from internet: clinicaltrials.gov/ct2/show/ NCT01058993 on Feb. 5, 2019 (6 pages).
ClinicalTrials.gov, ClinicalTrials Identifier: NCT01065129, "Plerixafor and Granulocyte Colony-stimulating Factor (G-CSF) in Combination With Azacitidine for the Treatment of Myelodysplastic Syndrome (MDS) (MDS)," Last Update Posted Mar. 20, 2017, retreived from internet: clinicaltrials.gov/ct2/show/NCT01065129 on Feb. 5, 2019 (8 pages).
ClinicalTrials.gov, ClinicalTrials Identifier: NCT01160354, "Plerixafor and Clofarabine in Frontline Treatment of Elderly Patients With Acute Myelogenous Leukemia (AML)," Last Update Posted Mar. 24, 2016, retreived from internet: clinicaltrials.gov/ct2/show/ NCT01160354 on Feb. 5, 2019 (7 pages).
ClinicalTrials.gov, ClinicalTrials Identifier: NCT01206075, "Evaluating the Safety and Effectiveness of Mozobil Mobilization in Adults With Beta-Thalassemia Major," Last Update Posted Dec. 30, 2014, retreived from internet: clinicaltrials.gov/ct2/show/ NCT01206075 on Feb. 5, 2019 (8 pages).
ClinicalTrials.gov, ClinicalTrials Identifier: NCT01236144, "A Trial to Establish the Feasibility of Combining Either the Tyrosine Kinase Inhibitor AC220,CXCR4 Inhibitor Plerixafor or HSP90 Inhibitor Ganetespib With Chemotherapy in Older Patients With Acute Myeloid Leukaemia and High Risk Myelodysplastic Syndrome. (AML18 Pilot)," Last Update Posted Jun. 11, 2014, retreived from internet: clinicaltrials.gov/ct2/show/NCT01236144 on Feb. 5, 2019 (8 pages).
ClinicalTrials.gov, ClinicalTrials Identifier: NCT01288573, "A Combined Study in Pediatric Cancer Patients for Dose Ranging and Efficacy/Safety of Plerixafor Plus Standard Regimens for Mobilization Versus Standard Regimens Alone," Last Update Posted May 16, 2017, retreived from internet: clinicaltrials.gov/ct2/show/ NCT01288573 on Feb. 5, 2019 (8 pages).
ClinicalTrials.gov, ClinicalTrials Identifier: NCT01301963, "Filgrastim With or Without Plerixafor in Treating Patients With Multiple Myeloma Previously Treated With Lenalidomide," Last Update Posted Aug. 6, 2014, retreived from internet: clinicaltrials.gov/ct2/ show/NCT01301963 on Feb. 5, 2019 (7 pages).
ClinicalTrials.gov, ClinicalTrials Identifier: NCT01319864, "POETIC Plerixafor as a Chemosensitizing Agent for Relapsed Acute Leukemia and MDS in Pediatric Patients," Last Update Posted Sep. 7, 2018, retreived from internet: clinicaltrials.gov/ct2/show/ NCT01319864 on Feb. 5, 2019 (8 pages).
ClinicalTrials.gov, ClinicalTrials Identifier: NCT01339039, "Plerixafor (AMD3100) and Bevacizumab for Recurrent High-Grade Glioma," Last Update Posted Nov. 17, 2017, retreived from internet: clinicaltrials. gov/ct2/show/NCT01339039 on Feb. 5, 2019 (12 pages).
ClinicalTrials.gov, ClinicalTrials Identifier: NCT01352650, "Decitabine and Plerixafor in Elderly Acute Myeloid Leukemia (AML)," Last Update Posted Jul. 2, 2018, retreived from internet: clinicaltrials. gov/ct2/show/NCT01352650 on Feb. 5, 2019 (8 pages).
ClinicalTrials.gov, ClinicalTrials Identifier: NCT01373229, "Lenalidomide + Plerixafor in Previously Treated Chronic Lymphocytic Leukemia (CLL)," Last Update Posted Feb. 5, 2018, retreived from internet: clinicaltrials.gov/ct2/show/NCT01373229 on Feb. 5, 2019 (8 pages).
ClinicalTrials.gov, ClinicalTrials Identifier: NCT01374503, "First in Man Study of ALX-0651, a Nanobody Inhibiting CXCR4," Last Update Posted Apr. 17, 2012, retreived from internet: clinicaltrials. gov/ct2/show/NCT01374503 on Feb. 5, 2019 (5 pages).
ClinicalTrials.gov, ClinicalTrials Identifier: NCT01391130, "A Study of LY2510924 and Sunitinib in Patients With Metastatic Renal Cell Carcinoma," Last Update Posted Apr. 24, 2017, retreived from internet: clinicaltrials.gov/ct2/show/NCT01391130 on Feb. 5, 2019 ( pages).
ClinicalTrials.gov, ClinicalTrials Identifier: NCT01413568, "Safety and Efficacy of POL6326 for Mobilization/Transplant of Sibling Donor in Patients With Hematologic Malignancies," Last Update Posted Feb. 26, 2016, retreived from internet: clinicaltrials.gov/ct2/ show/NCT01413568 on Feb. 5, 2019 (8 pages).
ClinicalTrials.gov, ClinicalTrials Identifier: NCT01435343, "Treatment of Relapsed or Refractory Acute Myeloblastic Leukemia," Last Update Posted Apr. 25, 2017, retreived from internet: clinicaltrials. gov/ct2/show/NCT01435343 on Feb. 5, 2019 (7 pages).
ClinicalTrials.gov, ClinicalTrials Identifier: NCT01439568, "A Study of LY2510924 in Patients With Extensive-Stage Small Cell Lung Carcinoma," Last Update Posted Jan. 5, 2017, retreived from internet: clinicaltrials.gov/ct2/show/NCT01439568 on Feb. 5, 2019 (8 pages).
ClinicalTrials.gov, ClinicalTrials Identifier: NCT01610999, "Pilot Study of Lymphoid Tumor Microenvironmental Dysruption Prior to Autologous Stem Cell Transplantation," Last Update Posted May 9, 2017, retreived from internet: clinicaltrials.gov/ct2/show/ NCT01610999 on Feb. 5, 2019 (6 pages).
ClinicalTrials.gov, ClinicalTrials Identifier: NCT01837095, "Dose Escalation of POL6326 in Combination With Eribulin in Patients With Metastatic Breast Cancer," Last Update Posted Sep. 14, 2018, retreived from internet: clinicaltrials.gov/ct2/show/NCT01837095 on Feb. 5, 2019 (6 pages).
ClinicalTrials.gov, ClinicalTrials Identifier: NCT01905475, "CXCR4 Antagonism for Cell Mobilisation and Healing in Acute Myocardial Infarction (CATCH-AMI) (CATCH-AMI)," Last Update Posted Jun. 10, 2016, retreived from internet: clinicaltrials.gov/ct2/show/ NCT01905475 on Feb. 5, 2019 (7 pages).
ClinicalTrials.gov, ClinicalTrials Identifier: NCT01916577, "Autologous CD117+ Progenitor Cell Mobilization for Lung Transplantation," Last Update Posted Feb. 8, 2018, retreived from internet: clinicaltrials. gov/ct2/show/NCT01916577 on Feb. 5, 2019 (7 pages).
ClinicalTrials.gov, ClinicalTrials Identifier: NCT01977677, "Plerixafor After Radiation Therapy and Temozolomide in Treating Patients With Newly Diagnosed High Grade Glioma," Last Update Posted Oct. 23, 2018, retreived from internet: clinicaltrials.gov/ct2/show/ NCT01977677 on Feb. 5, 2019 (8 pages).

(56) References Cited

OTHER PUBLICATIONS

ClinicalTrials.gov, ClinicalTrials Identifier: NCT02056210, "Stem Cell Mobilization With Plerixafor in Diabetic vs Control Subjects," Last Update Posted Oct. 24, 2014, retreived from internet: clinicaltrials.gov/ct2/show/NCT02056210 on Feb. 5, 2019 (6 pages).
ClinicalTrials.gov, ClinicalTrials Identifier: NCT02179970, "To Assess the Safety of Continuous IV Administration of Plerixafor in Patients With Advanced Pancreatic, Ovarian and Colorectal Cancers (CAMPLEX)," Last Update Posted Dec. 24, 2018, retreived from internet: clinicaltrials.gov/ct2/show/NCT02179970 on Feb. 5, 2019 (7 pages).
ClinicalTrials.gov, ClinicalTrials Identifier: NCT02462252, "Phase IIA Open Label Study to Evaluate Efficacy and Safety of BL-8040 Followed by (hATG), Cyclosporine and Methyprednisolone in Adult Subjects With Aplastic Anemia or Hypoplastic Myelodysplastic Syndrome," Last Update Posted Aug. 18, 2017, retreived from internet: clinicaltrials.gov/ct2/show/NCT02462252 on Feb. 5, 2019 (9 pages).
ClinicalTrials.gov, ClinicalTrials Identifier: NCT02502968, "BL-8040 Addition to Consolidation Therapy in AML Patients (BLAST)," Last Update Posted Sep. 21, 2015, retreived from internet: clinicaltrials.gov/ct2/show/NCT02502968 on Feb. 5, 2019 (7 pages).
ClinicalTrials.gov, ClinicalTrials Identifier: NCT02639559, "Safety and Efficacy of BL-8040 for the Mobilization of Donor Hematopoietic Stem Cells and Allogeneic Transplantation in Patients With Advanced Hematological Malignancies," Last Update Posted Nov. 5, 2018, retreived from internet: clinicaltrials.gov/ct2/show/NCT02639559 on Feb. 5, 2019 (10 pages).
ClinicalTrials.gov, ClinicalTrials Identifier: NCT02667886, "Trial of X4P-001 in Patients With Advanced Renal Cell Carcinoma," Last Update Posted Oct. 19, 2018, retreived from internet: clinicaltrials.gov/ct2/show/NCT02667886 on Feb. 5, 2019 (8 pages).
ClinicalTrials.gov, ClinicalTrials Identifier: NCT02678533, "Mobilization and Collection of Peripheral Blood Stem Cells in Patients With Fanconi Anemia Using G-CSF and Plerixafor (FancoMob)," Last Update Posted Dec. 21, 2017, retreived from internet: clinicaltrials.gov/ct2/show/NCT02678533 on Feb. 5, 2019 (7 pages).
ClinicalTrials.gov, ClinicalTrials Identifier: NCT02737072, "A Study of LY2510924 and Durvalumab in Participants With Solid Tumors," Last Update Posted Nov. 17, 2017, retreived from internet: clinicaltrials.gov/ct2/show/NCT02737072 on Feb. 5, 2019 (6 pages).
ClinicalTrials.gov, ClinicalTrials Identifier: NCT02763384, "BL-8040 and Nelarabine for Relapsed or Refractory T-Acute Lymphoblastic Leukemia/ Lymphoblastic Lymphoma," Last Update Posted Oct. 31, 2018, retreived from internet: clinicaltrials.gov/ct2/show/NCT02763384 on Feb. 5, 2019 (11 pages).
ClinicalTrials.gov, ClinicalTrials Identifier: NCT02765165, "Phase 1/2 Study of USL311 Alone and in Combination With Lomustine in Subjects With Advanced Solid Tumors and Relapsed/Recurrent Glioblastoma Multiforme (GBM)," Last Update Posted Jan. 17, 2019, retreived from internet: clinicaltrials.gov/ct2/show/NCT02765165 on Feb. 5, 2019 (9 pages).
ClinicalTrials.gov, ClinicalTrials Identifier: NCT02790957, "Plerixafor in Diabetic Wound Healing (MOZOBL07740)," Last Update Posted Jun. 9, 2016, retreived from internet: clinicaltrials.gov/ct2/show/NCT02790957 on Feb. 5, 2019 (7 pages).
ClinicalTrials.gov, ClinicalTrials Identifier: NCT02823405, "X4P-001 and Pembrolizumab in Patients With Advanced Melanoma (X4P-001-MELA)," Last Update Posted Jan. 4, 2019, retreived from internet: clinicaltrials.gov/ct2/show/NCT02823405 on Feb. 5, 2019 (7 pages).
ClinicalTrials.gov, ClinicalTrials Identifier: NCT02826486, "Study Assessing Safety and Efficacy of Combination of BL-8040 and Pembrolizumab in Metastatic Pancreatic Cancer Patients (COMBAT/KEYNOTE-202) (COMBAT)," Last Update Posted Jan. 9, 2018, retreived from internet: clinicaltrials.gov/ct2/show/NCT02826486 on Feb. 5, 2019 (10 pages).
ClinicalTrials.gov, ClinicalTrials Identifier: NCT02907099, "Pembrolizumab and BL-8040 in Metastatic Pancreatic Cancer," Last Update Posted Jan. 30, 2019, retreived from internet: clinicaltrials.gov/ct2/show/NCT02907099 on Feb. 5, 2019 (8 pages).
ClinicalTrials.gov, ClinicalTrials Identifier: NCT02923531, "Addition of X4P-001 to Nivolumab Treatment in Patients With Renal Cell Carcinoma," Last Update Posted , retreived from internet: clinicaltrials.gov/ct2/show/NCT02923531 on Feb. 5, 2019 (6 pages).
ClinicalTrials.gov, ClinicalTrials Identifier: NCT02931214, "Placebo-Controlled Single Dose Study to Evaluate Safety and Pharmacokinetics of GMI-1359 in Healthy Volunteers," Last Update Posted Jun. 1, 2018, retreived from internet: clinicaltrials.gov/ct2/show/NCT02931214 on Feb. 5, 2019 (5 pages).
ClinicalTrials.gov, ClinicalTrials Identifier: NCT02954653, "A Study of PF-06747143, As Single Agent or in Combination With Standard Chemotherapy in Adult Patients With Acute Myeloid Leukemia," Last Update Posted Nov. 30, 2017, retreived from internet: clinicaltrials.gov/ct2/show/NCT02954653 on Feb. 5, 2019 (8 pages).
ClinicalTrials.gov, ClinicalTrials Identifier: NCT03005327, "A Trial of X4P-001 in Patients With WHIM Syndrome (X4P-001-MKKA)," Last Update Posted Jan. 14, 2019, retreived from internet: clinicaltrials.gov/ct2/show/NCT03005327 on Feb. 5, 2019 (7 pages).
ClinicalTrials.gov, ClinicalTrials Identifier: NCT03019809, "A Trial of Plerixafor/G-CSF as Additional Agents for Conditioning Before TCR Alpha/Beta Depleted HSCT in WAS Patients," Last Update Posted Dec. 12, 2018, retreived from internet: clinicaltrials.gov/ct2/show/NCT03019809 on Feb. 5, 2019 (7 pages).
ClinicalTrials.gov, ClinicalTrials Identifier: NCT03154827, "A Phase Ib/II, Multicenter, Single Arm, Open-Label Study, to Evaluate the Safety, Tolerability and Efficacy of the BL-8040 and Atezolizumab Combination for Maintenance Treatment in Subjects With Acute Myeloid Leukemia Who Are 60 Years or Older—The BATTLE Study," Last Update Posted Jul. 10, 2018, retreived from internet: clinicaltrials.gov/ct2/show/NCT03154827 on Feb. 5, 2019 (7 pages).
ClinicalTrials.gov, ClinicalTrials Identifier: NCT03182426, "Stem Cell Mobilization (Plerixafor) and Immunologic Reset in Type 1 Diabetes (T1DM)," Last Update Posted Jul. 24, 2018, retreived from internet: clinicaltrials.gov/ct2/show/NCT03182426 on Feb. 5, 2019 (10 pages).
ClinicalTrials.gov, ClinicalTrials Identifier: NCT03193190, "A Study of Multiple Immunotherapy-Based Treatment Combinations in Participants With Metastatic Pancreatic Ductal Adenocarcinoma (Morpheus-Pancreatic Cancer)," Last Update Posted Dec. 25, 2018, retreived from internet: clinicaltrials.gov/ct2/show/NCT03193190 on Feb. 5, 2019 (16 pages).
ClinicalTrials.gov, ClinicalTrials Identifier: NCT03226691, "Peripheral Blood Stem Cell Collection for Sickle Cell Disease (SCD) Patients," Last Update Posted Jan. 17, 2019, retreived from internet: clinicaltrials.gov/ct2/show/NCT03226691 on Feb. 5, 2019 (6 pages).
ClinicalTrials.gov, ClinicalTrials Identifier: NCT03277209, "To Assess the Safety of Continuous IV Administration of Plerixafor and Assess Impact on the Immune Microenvironment in Patients With Pancreatic, Ovarian and Colorectal Adenocarcinomas," Last Update Posted Aug. 29, 2018, retreived from internet: clinicaltrials.gov/ct2/show/NCT03277209 on Feb. 5, 2019 (7 pages).
ClinicalTrials.gov, ClinicalTrials Identifier: NCT03281369, "A Study of Multiple Immunotherapy-Based Treatment Combinations in Patients With Locally Advanced Unresectable or Metastatic Gastric or Gastroesophageal Junction Cancer (G/GEJ) (Morpheus-Gastric Cancer)," Last Update Posted Dec. 12, 2018, retreived from internet: clinicaltrials.gov/ct2/show/NCT03281369 on Feb. 5, 2019 (12 pages).
ClinicalTrials.gov, ClinicalTrials Identifier: NCT03337698, "A Study of Multiple Immunotherapy-Based Treatment Combinations in Participants With Metastatic Non-Small Cell Lung Cancer (Morpheus-Non-Small Cell Lung Cancer) (Morpheus Lung)," Last Update Posted Nov. 5, 2018, retreived from internet: clinicaltrials.gov/ct2/show/NCT03337698 on Feb. 5, 2019 (11 pages).
Coke et al., 2016, "Simultaneous Activation of Induced Heterodimerization between CXCR4 Chemokine Receptor and Cannabinoid Receptor 2 (CB2) Reveals a Mechanism for Regulation of Tumor Progression," J Biol Chem., 291(19):9991-10005.
Comps-Agrar et al., 2011, "Cell-surface protein-protein interaction analysis with time-resolved FRET and snap-tag technologies: application to G protein-coupled receptor oligomerization," Methods Mol Biol, 756:201-214.

(56) References Cited

OTHER PUBLICATIONS

Contento et al., 2008, "CXCR4-CCR5: a couple modulating T cell functions," Proc Natl Acad Sci USA, 105(29):10101-10106.
Cooper et al., 2013, "Genetic polymorphisms in the PACAP and PAC1 receptor genes and treatment response to venlafaxine XR in generalized anxiety disorder," Psychiatry Res, 210(3):1299-1300.
Covic et al., 2002, "Activation and inhibition of G protein-coupled receptors by cell-penetrating membrane-tethered peptides," Proc Natl Acad Sci USA, 99(2):643-648.
Crawford et al., 2008, "AMD070, a CXCR4 Chemokine Receptor Antagonist: Practical Large-Scale Laboratory Synthesis," Organic Process Research & Development, 12(5):823-830.
Dacquin et al., 2004, "Amylin inhibits bone resorption while the calcitonin receptor controls bone formation in vivo," J Cell Biol, 164(4):509-514.
D'Alterio et al., 2012, "Inhibition of stromal CXCR4 impairs development of lung metastases," Cancer Immunol Immunother, 61(10):1713-1720.
Daniels et al., 2005, "A bivalent ligand (KDAN-18) containing delta-antagonist and kappa-agonist pharmacophores bridges delta2 and kappa1 opioid receptor phenotypes," J Med Chem, 48(6):1713-1716.
Davey et al., 2008, "Calcitonin receptor plays a physiological role to protect against hypercalcemia in mice," J Bone Miner Res, 23(8):1182-1193.
De Clercq, 2003, "The bicyclam AMD3100 story," Nat Rev Drug Discov, 2(7):581-587.
De Falco et al., 2007, "Biological role and potential therapeutic targeting of the chemokine receptor CXCR4 in undifferentiated thyroid cancer," Cancer Res, 67(24):11821-11829.
De Graaf et al., 2011, "Crystal structure-based virtual screening for fragment-like ligands of the human histamine H(1) receptor," J Med Chem, 54(23):8195-8206.
De Klerck et al., 2005, "Pro-inflammatory properties of stromal cell-derived factor-1 (CXCL12) in collagen-induced arthritis," Arthritis Res Ther, 7(6):R1208-1220.
De Nigris et al., 2012, "CXCR4 inhibitors: tumor vasculature and therapeutic challenges," Recent Pat Anticancer Drug Discov, 7(3):251-264.
De Poorter et al., 2013, "Consequences of ChemR23 heteromerization with the chemokine receptors CXCR4 and CCR7," PLoS One, 8(2):e58075.
Debnath et al., 2013, "Small molecule inhibitors of CXCR4," Theranostics, 3(1):47-75.
Decaillot et al., 2008, "Cell surface targeting of mu-delta opioid receptor heterodimers by RTP4," Proc Natl Acad Sci USA, 105(41):16045-16050.
Decaillot et al., 2011, "CXCR7/CXCR4 heterodimer constitutively recruits beta-arrestin to enhance cell migration," J Biol Chem 286(37):32188-32197.
Demmer et al., 2011, "PET imaging of CXCR4 receptors in cancer by a new optimized ligand," ChemMedChem, 6(10):1789-1791.
Depoortere, 2001, "Motilin and motilin receptors: characterization and functional significance," Verh K Acad Geneeskd Belg, 63(6):511-529.
Desmet et al., 2013, "Identification of a pharmacologically tractable Fra-1/ADORA2B axis promoting breast cancer metastasis," Proc Natl Acad Sci USA, 110(13):5139-5144.
Dipersio et al., 2009, "Phase III prospective randomized double-blind placebo-controlled trial of plerixafor plus granulocyte colony-stimulating factor compared with placebo plus granulocyte colony-stimulating factor for autologous stem-cell mobilization and transplantation for patients with non-Hodgkin's lymphoma," J Clin Oncol, 27(28):4767-4773.
Dipersio et al., 2009, "Plerixafor and G-CSF versus placebo and G-CSF to mobilize hematopoietic stem cells for autologous stem cell transplantation in patients with multiple myeloma," Blood, 113(23):5720-5726.
Domanska et al., 2013, "A review on CXCR4/CXCL12 axis in oncology: no place to hide," Eur J Cancer, 49(1):219-230.
Donzella et al., 1998, "AMD3100, a small molecule inhibitor of HIV-1 entry via the CXCR4 co-receptor," Nat Med, 4(1):72-77.
Doranz et al., 2001, "Safe use of the CXCR4 inhibitor ALX40-4C in humans," AIDS Res Hum Retroviruses, 17(6):475-486.
Doring et al., 2014, "The CXCL12/CXCR4 chemokine ligand/receptor axis in cardiovascular disease," Front Physiol, 5:212.
Doucette et al., 2017, "Prostaglandins in the eye: Function, expression, and roles in glaucoma," Ophthalmic Genet, 38(2):108-116.
Du et al., 2015, "Prognostic Value of High CXCR4 Expression in Renal Cell Carcinoma: A System Review and Meta-Analysis," Dis Markers, 2015:568980.
Eidne et al., 2002, "Applications of novel resonance energy transfer techniques to study dynamic hormone receptor interactions in living cells," Trends Endocrinol Metab, 13(10):415-421.
Endres et al., 1996, "CD4-independent infection by HIV-2 is mediated by fusin/CXCR4," Cell, 87(4):745-756.
Fagerberg et al., 2014, "Analysis of the human tissue-specific expression by genome-wide integration of transcriptomics and antibody-based proteomics," Mol Cell Proteomics, 13(2):397-406.
Fahham et al. (2012). In vitro and in vivo therapeutic efficacy of CXCR4 antagonist BKT140 against human non-small cell lung cancer, J Thorac Cardiovasc Surg, 144(5):1167-1175.
Farran, 2017, "An update on the physiological and therapeutic relevance of GPCR oligomers," Pharmacol Res, 117:303-327.
Feig et al., 2013, "Targeting CXCL12 from FAP-expressing carcinoma-associated fibroblasts synergizes with anti-PD-L1 immunotherapy in pancreatic cancer," Proc Natl Acad Sci USA, 110(50):20212-20217.
Fernandez-Duenas et al., 2015, "Untangling dopamine-adenosine receptor-receptor assembly in experimental parkinsonism in rats," Dis Model Mech, 8(1):57-63.
Ferre et al., 2009, "Building a new conceptual framework for receptor heteromers," Nat Chem Biol, 5(3):131-134.
Ferre et al., 2010, "G protein-coupled receptor heteromers as new targets for drug development," Prog Mol Biol Transl Sci, 91:41-52.
Filmore, 2004, "It's a GPCR world," Modern Drug Discovery American Chemical Society Nov. 24-28, 2004.
Fitzpatrick et al., 2004 "Table 20:2" (Mass: Sunderland).
Fotiadis et al., 2006, "Structure of the rhodopsin dimer: a working model for G-protein-coupled receptors," Curr Opin Struct Biol, 16(2):252-259.
Frederick et al., 2015, "Evidence against dopamine D1/D2 receptor heteromers," Mol Psychiatry, 20(11):1373-1385.
Furusato et al., 2010, "CXCR4 and cancer," Pathol Int, 60(7):497-505.
Gao et al., 2008, "Flexible modulation of agonist efficacy at the human A3 adenosine receptor by the imidazoquinoline allosteric enhancer LUF6000," BMC Pharmacol, 8:20.
George et al., 2000, "Oligomerization of mu- and delta-opioid receptors. Generation of novel functional properties," J Biol Chem, 275(34):26128-26135.
Gerard et al., 1994, "C5A anaphylatoxin and its seven transmembrane-segment receptor," Annu Rev Immunol, 12:775-808.
Gianetti et al., 2008, "Kisspeptin and KISS1R: a critical pathway in the reproductive system," Reproduction, 136(3):295-301.
Gomes et al., 2004, "A role for heterodimerization of mu and delta opiate receptors in enhancing morphine analgesia," Proc Natl Acad Sci USA, 101(14):5135-5139.
Gomes et al., 2013, "Identification of a μ-δ opioid receptor heteromer-biased agonist with antinociceptive activity," Proc Natl Acad Sci USA, 110(29):12072-12077 and corrections, 110(42):17160-17161.
Gomes et al., 2016, "G Protein-Coupled Receptor Heteromers," Annu Rev Pharmacol Toxicol, 56:403-425.
Goodman et al., 2007, "Kisspeptin neurons in the arcuate nucleus of the ewe express both dynorphin A and neurokinin B," Endocrinolog, 148(12):5752-5760.
Gourni et al., 2011, "PET of CXCR4 expression by a (68)Ga-labeled highly specific targeted contrast agent," J Nucl Med, 52(11):1803-1810.
Gregorio et al., 2017, "Single-molecule analysis of ligand efficacy in beta2AR-G-protein activation," Nature, 547(7661):68-73.

(56) References Cited

OTHER PUBLICATIONS

Griffith et al., 2014, "Chemokines and chemokine receptors: positioning cells for host defense and immunity," Annu Rev Immunol, 32:659-702.
Griffiths et al., 2016, "i-bodies, Human Single Domain Antibodies That Antagonize Chemokine Receptor CXCR4," J Biol Chem, 291(24):12641-12657.
Griffiths et al., 2018, "Anti-fibrotic Effects of CXCR4-Targeting i-body AD-114 in Preclinical Models of Pulmonary Fibrosis," Sci Rep, 8(1):3212.
Guidolin et al., 2015, "G-protein-coupled receptor type A heteromers as an emerging therapeutic target," Expert Opin Ther Targets, 19(2):265-283.
Guidotti et al., 2017, "Cell-Penetrating Peptides: From Basic Research to Clinics," Trends Pharmacol Sci, 38(4):406-424.
Gullberg et al., 2004, "Cytokine detection by antibody-based proximity ligation," Proc Natl Acad Sci USA, 101(22):8420-8424.
Guo et al., 2016, "CXCL12/CXCR4: a symbiotic bridge linking cancer cells and their stromal neighbors in oncogenic communication networks," Oncogene, 35(7):816-826.
Gustafsdottir et al., 2005, "Proximity ligation assays for sensitive and specific protein analyses," Anal Biochem, 345(1):2-9.
Habert-Ortoli et al., 1994, "Molecular cloning of a functional human galanin receptor," Proc Natl Acad Sci USA, 91(21):9780-9783.
Hansen et al., 2009, "Lack of evidence for AT1R/B2R heterodimerization in COS-7, HEK293, and NIH3T3 cells: how common is the AT1R/B2R heterodimer?" J Biol Chem, 284(3):1831-1839.
Hartimath et al., 2013, "[(9)(9)mTc]O(2)-AMD3100 as a SPECT tracer for CXCR4 receptor imaging," Nucl Med Biol, 40(4):507-517.
Hassan et al., 2011, "CXCR4 peptide antagonist inhibits primary breast tumor growth, metastasis and enhances the efficacy of anti-VEGF treatment or docetaxel in a transgenic mouse model," Int J Cancer, 129(1):225-232.
Hatse et al., 2002, "Chemokine receptor inhibition by AMD3100 is strictly confined to CXCR4," FEBS Lett, 527(1-3):255-262.
He et al., 2011, "Facilitation of mu-opioid receptor activity by preventing delta-opioid receptor-mediated codegradation," Neuron, 69(1):120-131.
Heakal et al., 2011, "Neurotensin receptor-1 inducible palmitoylation is required for efficient receptor-mediated mitogenic-signaling within structured membrane microdomains," Cancer Biol Ther, 12(5):427-435.
Hendrix et al., 2000, "Pharmacokinetics and safety of AMD-3100, a novel antagonist of the CXCR-4 chemokine receptor, in human volunteers," Antimicrob Agents Chemother, 44(6):1667-1673.
Hendrix et al., 2004, "Safety, pharmacokinetics, and antiviral activity of AMD3100, a selective CXCR4 receptor inhibitor, in HIV-1 infection," J Acquir Immune Defic Syndr, 37(2):1253-1262.
Henson et al., 2005, "Galanin receptor 1 has anti-proliferative effects in oral squamous cell carcinoma," J Biol Chem, 280(24):22564-22571.
Hernandez et al., 2003, "Mutations in the chemokine receptor gene CXCR4 are associated with WHIM syndrome, a combined immunodeficiency disease," Nat Genet, 34(1):70-74.
Herrmann et al., 2016, "First-in-Human Experience of CXCR4-Directed Endoradiotherapy with 177Lu- and 90Y-Labeled Pentixather in Advanced-Stage Multiple Myeloma with Extensive Intra-and Extramedullary Disease," J Nucl Med, 57(2):248-251.
Hillion et al., 2002, "Coaggregation, cointernalization, and codesensitization of adenosine A2A receptors and dopamine D2 receptors," J Biol Chem, 277(20):18091-18097.
Hsu et al., 2015, "CXCR4 Antagonist TG-0054 Mobilizes Mesenchymal Stem Cells, Attenuates Inflammation, and Preserves Cardiac Systolic Function in a Porcine Model of Myocardial Infarction," Cell Transplant, 24(7):1313-1328.
Hu et al. 2002, "Visualization of interactions among bZIP and Rel family proteins in living cells using bimolecular fluorescence complementation," Mol Cell, 9(4):789-798.
Hu et al., 2015, "A meta-analysis for C-X-C chemokine receptor type 4 as a prognostic marker and potential drug target in hepatocellular carcinoma," Drug Des Devel Ther, 9:3625-3633.
Huang et al., 2009, "A CXCR4 antagonist CTCE-9908 inhibits primary tumor growth and metastasis of breast cancer," J Surg Res, 155(2):231-236.
Hubner et al., 2016, "Structure-guided development of heterodimer-selective GPCR ligands," Nat Commun., 7:12298.
Hutter et al., 2009, "Long-term control of HIV by CCR5 Delta32/Delta32 stem-cell transplantation," N Engl J Med, 360(7):692-698.
Ichiyama et al., 2003, "A duodenally absorbable CXC chemokine receptor 4 antagonist, KRH-1636, exhibits a potent and selective anti-HIV-1 activity," Proc Natl Acad Sci USA, 100(7):4185-4190.
Inokuchi et al., 2011, "Potent CXCR4 antagonists containing amidine type Peptide bond isosteres," ACS Med Chem Lett, 2(6):477-480.
Jafari et al., 2017, "A3 Adenosine Receptor Agonist Inhibited Survival of Breast Cancer Stem Cells via GLI-1 and ERK1/2 Pathway," J Cell Biochem, 118(9):2909-2920.
Jahnichen et al., 2010, "CXCR4 nanobodies (VHH-based single variable domains) potently inhibit chemotaxis and HIV-1 replication and mobilize stem cells," Proc Natl Acad Sci USA, 107(47):20565-20570.
Jenkinson et al., 2010, "Blockade of X4-tropic HIV-1 cellular entry by GSK812397, a potent noncompetitive CXCR4 receptor antagonist," Antimicrob Agents Chemother, 54(2):817-824.
Jiang et al. 2011, "Advances in the assessment and control of the effector functions of therapeutic antibodies," Nat Rev Drug Discov, 10(2):101-111.
Kaczor et al., 2011, "Oligomerization of G protein-coupled receptors: biochemical and biophysical methods," Curr Med Chem, 18(30):4606-4634.
Kalatskaya et al., 2009, "AMD3100 is a CXCR7 ligand with allosteric agonist properties," Mol Pharmacol, 75(5):1240-1247.
Kasama et al., 2015, "Adenosine A2b receptor promotes progression of human oral cancer," BMC Cancer, 15:563.
Kawai et al., 2009, "WHIM syndrome: congenital immune deficiency disease," Curr Opin Hematol, 16(1):20-26.
Kawano et al., 2007, "Receptor binding properties and antinociceptive effects of chimeric peptides consisting of a micro-opioid receptor agonist and an ORL1 receptor antagonist," Biol Pharm Bull., 30(7):1260-1264.
Keating, 2011, "Plerixafor: a review of its use in stem-cell mobilization in patients with lymphoma or multiple myeloma," Drugs, 71(12):1623-1647.
Kerppola, 2006, "Design and implementation of bimolecular fluorescence complementation (BiFC) assays for the visualization of protein interactions in living cells," Nat Protoc, 1(3):1278-1286.
Kim et al., 2008, "Inhibition of the CXCR4/CXCL12 chemokine pathway reduces the development of murine pulmonary metastases," Clin Exp Metastasis, 25(3):201-211.
Kim et al., 2010, "The CXCR4 Antagonist AMD3100 Has Dual Effects on Survival and Proliferation of Myeloma Cells In vitro," Cancer Res Treat, 42(4):225-234.
Kitazawa et al., 1995, "Excitatory action of [Leu13]motilin on the gastrointestinal smooth muscle isolated from the chicken," Peptides, 16(7):1243-1252.
Kitazawa et al., 1997, "Functional characterization of neural and smooth muscle motilin receptors in the chicken proventriculus and ileum," Regul Pept, 71(2):87-95.
Klein et al., 2004, "Immune and nervous system CXCL12 and CXCR4: parallel roles in patterning and plasticity," Trends Immunol, 25(6):306-314.
Klos et al., 2013, "International Union of Basic and Clinical Pharmacology. [corrected]. LXXXVII. Complement peptide C5a, C4a, and C3a receptors," Pharmacol Rev, 65(1):500-543.
Knutsson et al., 2002, "Distribution of mRNA for VIP and PACAP receptors in human cerebral arteries and cranial ganglia," Neuroreport, 13(4):507-509.
Kristensen et al., 2016, "Applications and Challenges for Use of Cell-Penetrating Peptides as Delivery Vectors for Peptide and Protein Cargos" Int J Mol Sci, 17(2):185.

(56) References Cited

OTHER PUBLICATIONS

Kroeze et al., 2015, "PRESTO-Tango as an open-source resource for interrogation of the druggable human GPCRome," Nat Struct Mol Biol, 22(5):362-369.
Kuhne et al., 2013, "BMS-936564/MDX-1338: a fully human anti-CXCR4 antibody induces apoptosis in vitro and shows antitumor activity in vivo in hematologic malignancies," Clin Cancer Res, 19(2):357-366.
Lagane et al., 2008, "CXCR4 dimerization and beta-arrestin-mediated signaling account for the enhanced chemotaxis to CXCL12 in WHIM syndrome," Blood, 112(1):34-44.
Lambert et al., 2018, "Antibody—Drug Conjugates for Cancer Treatment," Annual Review of Medicine, 69:191-207.
Larocca et al., 2010, "β2-Adrenergic receptor signaling in the cardiac myocyte is modulated by interactions with CXCR4," J Cardiovasc Pharmacol., 56(5):548-559.
Law et al., 2005, "Heterodimerization of mu- and delta-opioid receptors occurs at the cell surface only and requires receptor-G protein interactions," J Biol Chem, 280(12):11152-11164.
Le Naour et al., 2014, "Putative kappa opioid heteromers as targets for developing analgesics free of adverse effects," J Med Chem., 57(15):6383-6392.
Lee et al., 2006, "Sensitization of B16 tumor cells with a CXCR4 antagonist increases the efficacy of immunotherapy for established lung metastases," Mol Cancer Ther, 5(10):2592-2599.
Lee et al., 2008, "Receptors for complement C5a. The importance of C5aR and the enigmatic role of C5L2," Immunol Cell Biol, 86(2):153-160.
Levoye et al., 2009, "CXCR7 heterodimerizes with CXCR4 and regulates CXCL12-mediated G protein signaling," Blood, 113(24):6085-6093.
Li et al., 2007, "Prostaglandin E(2) receptors in bone formation," Int Orthop, 31(6):767-772.
Li et al., 2017, "Role of CXCR4 and SDF1 as prognostic factors for survival and the association with clinicopathology in colorectal cancer: A systematic meta-analysis," Tumour Biol, 39(6):1010428317706206.
Liang et al., 2012, "Development of a unique small molecule modulator of CXCR4," PLoS One, 7(4):e34038.
Liang et al., 2015, "Chemokine receptor CXCR4 expression and lung cancer prognosis: a meta-analysis," Int J Clin Exp Med, 8(4):5163-5174.
Liao et al., 2015, "AMD3100 reduces CXCR4-mediated survival and metastasis of osteosarcoma by inhibiting JNK and Akt, but not p38 or Erk1/2, pathways in in vitro and mouse experiments," Oncol Rep, 34(1):33-42.
Liles et al., 2003, "Mobilization of hematopoietic progenitor cells in healthy volunteers by AMD3100, a CXCR4 antagonist," Blood, 102(8):2728-2730.
Ling et al., 2013, "The CXCR4 antagonist AMD3465 regulates oncogenic signaling and invasiveness in vitro and prevents breast cancer growth and metastasis in vivo," PLoS One, 8(3):e58426.
Liu et al., 2009, "Design of multivalent ligand targeting G-protein-coupled receptors," Curr Pharm Des., 15(6):682-718.
Liu et al., 2011, "Unidirectional cross-activation of GRPR by MOR1D uncouples itch and analgesia induced by opioids," Cell, 147(2):447-458.
Liu et al., 2017, "A novel CXCR4 antagonist IgG1 antibody (PF-06747143) for the treatment of hematologic malignancies," Blood Adv, 1(15):1088-1100.
Lohse et al., 2012, "Fluorescence/bioluminescence resonance energy transfer techniques to study G-protein-coupled receptor activation and signaling," Pharmacol Rev, 64(2):299-336.
Lowe et al., 2015, "Gene-by-social-environment interaction (GxSE) between ADCYAP1R1 genotype and neighborhood crime predicts major depression symptoms in trauma-exposed women," J Affect Disord, 187:147-150.
Luker et al., 2009, "Imaging chemokine receptor dimerization with firefly luciferase complementation," FASEB J., 23(3):823-834.

Machado-Carvalho et al., 2014, "Prostaglandin E2 receptors in asthma and in chronic rhinosinusitis/nasal polyps with and without aspirin hypersensitivity," Respir Res, 15:100.
Markovic et al., 2017, "Structural features of subtype-selective EP receptor modulators," Drug Discov Today, 22(1):57-71.
Marlo et al., 2009, "Discovery and characterization of novel allosteric potentiators of M1 muscarinic receptors reveals multiple modes of activity," Mol Pharmacol, 75(3):577-588.
Martinez-Munoz et al., 2014, "CCR5/CD4/CXCR4 oligomerization prevents HIV-1 gp120IIIB binding to the cell surface," Proc Natl Acad Sci USA, 111(19):E1960-1969.
Masuda et al, 1992, "A novel anti-HIV synthetic peptide, T-22 ([Tyr5,12,Lys7]-polyphemusin II)," Biochem Biophys Res Commun, 189(2):845-850.
Medhurst et al., 2003, "Pharmacological and immunohistochemical characterization of the APJ receptor and its endogenous ligand apelin," J Neurochem, 84(5):1162-1172.
Mellado et al., 1999, "Chemokine control of HIV-1 infection," Nature, 400(6746):723-724.
Metcalf et al., 2012, "The δ opioid receptor agonist SNC80 selectively activates heteromeric μ-67 opioid receptors," ACS Chem Neurosci., 3(7):505-509.
Miller et al., 1995, "Somatostatin receptor subtype gene expression in pituitary adenomas," J Clin Endocrinol Metab, 80(4):1386-1392.
Milligan 2008, "A day in the life of a G protein-coupled receptor: the contribution to function of G protein-coupled receptor dimerization," Br J Pharmacol, 153(Suppl 1):S216-229.
Milligan et al., 2007, "Allosteric modulation of heterodimeric G-protein-coupled receptors," Trends Pharmacol Sci., 28(12):615-620.
Miwatashi et al., 2008, "Synthesis and biological activities of 4-phenyl-5-pyridy1-1,3-thiazole derivatives as selective adenosine A3 antagonists," Chem Pharm Bull (Tokyo), 56(8):1126-1137.
Moreno 2017, "Eicosanoid receptors: Targets for the treatment of disrupted intestinal epithelial homeostasis," Eur J Pharmacol, 796:7-19.
Morimoto et al., 2016, "Enhancement of the CXCL12/CXCR4 axis due to acquisition of gemcitabine resistance in pancreatic cancer: effect of CXCR4 antagonists," BMC Cancer, 16s:305.
Muller et al, 2001, "Involvement of chemokine receptors in breast cancer metastasis," Nature. 410(6824):50-56.
Mumal, 2017, "AdAlta Presenting Data on Therapy Candidate AD-114 at Inaugural IPF Summit," Lung Disease News, retreived from internet: lungdiseasenews.com/2017/08/23/adalta-present-research-on-investigative-therapy-ad-114-at-ipf-summit/ on Jan. 16, 2019 (4 pages).
Murakami et al., 2009, "The novel CXCR4 antagonist KRH-3955 is an orally bioavailable and extremely potent inhibitor of human immunodeficiency virus type 1 infection: comparative studies with AMD3100," Antimicrob Agents Chemother, 53(7):2940-2948.
Mustafa et al., 2010, "Uncovering GPCR heteromer-biased ligands," Drug Discov Today Technol, 7(1):e1-e94.
Mustafa et al., 2011, "G protein-coupled receptor heteromer identification technology: identification and profiling of GPCR heteromers," J Lab Autom, 16(4):285-291.
Mustafa et al., 2012, "Identification and profiling of novel alpha1A-adrenoceptor-CXC chemokine receptor 2 heteromer," J Biol Chem, 287(16):12952-12965.
Nakai et al., 2014, "Control of lymphocyte egress from lymph nodes through beta2-adrenergic receptors," J Exp Med, 211(13):2583-2598.
Nakasone et al., 2013, "Single oral administration of the novel CXCR4 antagonist, KRH-3955, induces an efficient and long-lasting increase of white blood cell count in normal macaques, and prevents CD4 depletion in SHIV-infected macaques: a preliminary study," Med Microbiol Immunol, 202(2):175-182.
Norel et al., 2016, "Prostanoid receptors: EP3 receptor," IUPHAR/BPS Guide to Pharmacology.
O'Boyle et al., 2013, "Inhibition of CXCR4-CXCL12 chemotaxis in melanoma by AMD11070," Br J Cancer, 108(8):1634-1640.
O'Callaghan et al., 2012, "Turning receptors on and off with intracellular pepducins: new insights into G-protein-coupled receptor drug development," J Biol Chem, 287(16):12787-12796.

(56) References Cited

OTHER PUBLICATIONS

O'Callaghan et al., 2015, "Prostaglandin E2 and the EP receptors in malignancy: possible therapeutic targets?" Br J Pharmacol, 172(22):5239-5250.
Ogi et al., 1993, "Molecular cloning and functional expression of a cDNA encoding a human pituitary adenylate cyclase activating polypeptide receptor," Biochem Biophys Res Commun, 196(3):1511-1521.
Okada et al., 2001, "Activation of rhodopsin: new insights from structural and biochemical studies," Trends Biochem Sci, 26(5):318-324.
Otani et al., 2012, "Suppression of metastases of small cell lung cancer cells in mice by a peptidic CXCR4 inhibitor TF14016," FEBS Lett, 586(20):3639-3644.
Overington et al., 2006, "How many drug targets are there?" Nat Rev Drug Discov, 5(12):993-996.
Owen et al., 2013, "Macrophages and chemokines as mediators of angiogenesis," Front Physiol, 4:159.
Page et al. 2003, "Characterization of the endokinins: human tachykinins with cardiovascular activity," Proc Natl Acad Sci USA, 100(10):6245-6250.
Pal et al., 2018, "Loss-of-Function Mutations in Calcitonin Receptor (CALCR) Identify Highly Aggressive Glioblastoma with Poor Outcome," Clin Cancer Res, 24(6):1448-1458.
Parameswaran et al., 2011, "Combination of drug therapy in acute lymphoblastic leukemia with a CXCR4 antagonist," Leukemia, 25(8):1314-1323.
Park et al., 2005, "Diversifying the repertoire of G protein-coupled receptors through oligomerization," Proc Natl Acad Sci USA, 102(25):8793-8794.
Patel et al., 2002, "Ligand binding to somatostatin receptors induces receptor-specific oligomer formation in live cells," Proc Natl Acad Sci USA, 99(5):3294-3299.
Patel et al., 2012, "Identification of ghrelin receptor blocker, D-[Lys3] GHRP-6 as a CXCR4 receptor antagonist," Int J Biol Sci, 8(1):108-117.
Peled et al., 2012, "Development of novel CXCR4-based therapeutics," Expert Opin Investig Drugs, 21(3):341-353.
Pello et al., 2008, "Ligand stabilization of CXCR4/delta-opioid receptor heterodimers reveals a mechanism for immune response regulation," Eur J Immunol., 38(2):537-549.
Peng et al., 2015, "Identification of LY2510924, a novel cyclic peptide CXCR4 antagonist that exhibits antitumor activities in solid tumor and breast cancer metastatic models," Mol Cancer Ther, 14(2):480-490.
Percherancier et al., 2005, "Bioluminescence resonance energy transfer reveals ligand-induced conformational changes in CXCR4 homo- and heterodimers," J Biol Chem., 280(11):9895-9903.
Pfeiffer et al., 2002, "Heterodimerization of somatostatin and opioid receptors cross-modulates phosphorylation, internalization, and desensitization," J Biol Chem, 277(22):19762-19772.
Pfleger et al., 2006, "Illuminating insights into protein-protein interactions using bioluminescence resonance energy transfer (BRET)," Nat Methods, 3(3):165-174.
Pin et al., 2007, "International Union of Basic and Clinical Pharmacology. LXVII. Recommendations for the recognition and nomenclature of G protein-coupled receptor heteromultimers," Pharmacol Rev, 59(1):5-13.
Planesas et al., 2015, "Studying the binding interactions of allosteric agonists and antagonists of the CXCR4 receptor," J Mol Graph Model, 60:1-14.
Plieth, 2017, "Bristol failure makes small dent in CXCR4-blocking approach," Vantage Kickstarting Ideas, retreived from internet: www.evaluate.com/vantage/articles/analysis/bristol-failure-makes-small-dent-cxcr4-blocking-approach on Jan. 25, 2019 (2 pages).
Pondel, 2000, "Calcitonin and calcitonin receptors: bone and beyond," Int J Exp Pathol, 81(6):405-422.
Qin et al., 2011, "Inactive-state preassembly of G(q)-coupled receptors and G(q) heterotrimers," Nat Chem Biol, 7(10):740-747.
Rashid et al., 2007, "D1-D2 dopamine receptor heterooligomers with unique pharmacology are coupled to rapid activation of Gq/11 in the striatum," Proc Natl Acad Sci USA, 104(2):654-659.
Redondo-Munoz et al., 2006, "MMP-9 in B-cell chronic lymphocytic leukemia is up-regulated by alpha4beta1 integrin or CXCR4 engagement via distinct signaling pathways, localizes to podosomes, and is involved in cell invasion and migration," Blood, 108(9):3143-3151.
Reubi et al., 2000, "Vasoactive intestinal peptide/pituitary adenylate cyclase-activating peptide receptor subtypes in human tumors and their tissues of origin," Cancer Res, 60(11):3105-3112.
Reubi, 2000, In vitro evaluation of VIP/PACAP receptors in healthy and diseased human tissues. Clinical implications, Ann NY Acad Sci, 921:1-25.
Reya et al., 2001, "Stem cells, cancer, and cancer stem cells," Nature, 414(6859):105-111.
Rios et al., 2006, "mu opioid and CB1 cannabinoid receptor interactions: reciprocal inhibition of receptor signaling and neuritogenesis," Br J Pharmacol, 148(4):387-395.
Roccaro et al., 2014, "SDF-1 inhibition targets the bone marrow niche for cancer therapy," Cell Rep 9(1):118-128.
Rodriguez-Frade et al., 2004, "Blocking HIV-1 infection via CCR5 and CXCR4 receptors by acting in trans on the CCR2 chemokine receptor," EMBO J, 23(1):66-76.
Roess et al., 2000, "Luteinizing hormone receptors are self-associated in the plasma membrane," Endocrinology, 141(12):4518-4523.
Rozenfeld et al., 2010, "Receptor heteromerization and drug discovery," Trends Pharmacol Sci, 31(3):124-130.
Rozenfeld et al., 2012, "Receptor heteromerization expands the repertoire of cannabinoid signaling in rodent neurons," PLoS One, 7(1):e29239.
Rubin et al., 2003, "A small-molecule antagonist of CXCR4 inhibits intracranial growth of primary brain tumors," Proc Natl Acad Sci USA, 100(23):13513-13518.
Saka et al, 2007, "Nuclear accumulation of Smad complexes occurs only after the midblastula transition in Xenopus," Development, 134(23):4209-4218.
Salanga et al., 2009, "Modulation of chemokine receptor activity through dimerization and crosstalk," Cell Mol Life Sci., 66(8):1370-1386.
Sanjana et al., 2014, "Improved vectors and genome-wide libraries for CRISPR screening," Nat Methods, 11(8):783-784.
Sato-Jin et al., 2008, "Epistatic connections between microphthalmia-associated transcription factor and endothelin signaling in Waardenburg syndrome and other pigmentary disorders," FASEB J, 22(4):1155-1168.
Scala, 2015, "Molecular Pathways: Targeting the CXCR4-CXCL12 Axis-Untapped Potential in the Tumor Microenvironment," Clin Cancer Res, 21(19):4278-4285.
Scarlett et al., 2018, "Agonist-induced CXCR4 and CB2 Heterodimerization Inhibits Gα13/RhoA-mediated Migration," Mol Cancer Res., 16(4):728-739.
Schimanski et al., 2006, "Dissemination of hepatocellular carcinoma is mediated via chemokine receptor CXCR4," Br J Cancer, 95(2):210-217.
Sedor et al. 1984, "Actions and metabolism of histamine in glomeruli and tubules of the human kidney," Kidney Int, 26(2):144-152.
Shen et al., 2016, "SSTR2 promoter hypermethylation is associated with the risk and progression of laryngeal squamous cell carcinoma in males," Diagn Pathol, 11:10.
Sicoli et al., 2014, "CCR5 receptor antagonists block metastasis to bone of v-Src oncogene-transformed metastatic prostate cancer cell lines," Cancer Res, 74(23):7103-7114.
Sierro et al., 2007, "Disrupted cardiac development but normal hematopoiesis in mice deficient in the second CXCL12/SDF-1 receptor, CXCR7," Proc Natl Acad Sci USA, 104(37):14759-14764.
Smith et al., 2004, "CXCR4 regulates growth of both primary and metastatic breast cancer," Cancer Res, 64(23):8604-8612.
Sohy et al., 2007, "Allosteric transinhibition by specific antagonists in CCR2/CXCR4 heterodimers," J Biol Chem, 282(41):30062-30069.

(56) References Cited

OTHER PUBLICATIONS

Sohy et al., 2009, "Hetero-oligomerization of CCR2, CCR5, and CXCR4 and the protean effects of "selective" antagonists," J Biol Chem, 284(45):31270-31279.
Song et al., 2010, "Inhibitory effect of CXC chemokine receptor 4 antagonist AMD3100 on bleomycin induced murine pulmonary fibrosis," Exp Mol Med, 42(6):465-472.
Song et al., 2014, "Monitoring G protein-coupled receptor activation using an adenovirus-based beta-arrestin bimolecular fluorescence complementation assay," Anal Biochem, 449:32-41 with supplemental data.
Song, 2012, "Global analysis of GPCR dimerization using AdBiFC assay," A Thesis Submitted in Partial Fulfillment of the Requirements for the Degree of Doctor of Philosophy, School of Biological Sciences, Seoul National University, 126 pages.
Stefan et al., 2007, "Quantification of dynamic protein complexes using Renilla luciferase fragment complementation applied to protein kinase A activities in vivo," Proc Natl Acad Sci USA, 104(43):16916-16921.
Stevenson et al., 2012, "Identification of galanin and its receptor GalR1 as novel determinants of resistance to chemotherapy and potential biomarkers in colorectal cancer," Clin Cancer Res, 18(19):5412-5426.
Stone et al., 2007, "Multiple-dose escalation study of the safety, pharmacokinetics, and biologic activity of oral AMD070, a selective CXCR4 receptor inhibitor, in human subjects," Antimicrob Agents Chemother, 51(7):2351-2358.
Struyf et al., 2001, "Diverging binding capacities of natural LD78beta isoforms of macrophage inflammatory protein-1alpha to the CC chemokine receptors 1, 3 and 5 affect their anti-HIV-1 activity and chemotactic potencies for neutrophils and eosinophils," Eur J Immunol, 31(7):2170-2178.
Sugimoto et al., 2015, "Roles of prostaglandin receptors in female reproduction," J Biochem, 157(2):73-80.
Swift et al., 2010, "Altered expression of neurotensin receptors is associated with the differentiation state of prostate cancer," Cancer Res, 70(1):347-356.
Taichman et al., 2002, "Use of the stromal cell-derived factor-1/CXCR4 pathway in prostate cancer metastasis to bone," Cancer Res, 62(6):1832-1837.
Tamamura et al., 1998, "A low-molecular-weight inhibitor against the chemokine receptor CXCR4: a strong anti-HIV peptide T140," Biochem Biophys Res Commun, 253(3):877-882.
Tanaka et al., 1998, "Novel mutations of the endothelin B receptor gene in patients with Hirschsprung's disease and their characterization," J Biol Chem, 273(18):11378-11383.
Tanaka et al., 2008, "Structure-activity relationship study of CXCR4 antagonists bearing the cyclic pentapeptide scaffold: identification of the new pharmacophore," Org Biomol Chem, 6(23):4374-4377.
Tanaka et al.. 2009, "Structure-activity relationship study on artificial CXCR4 ligands possessing the cyclic pentapeptide scaffold: the exploration of amino acid residues of pentapeptides by substitutions of several aromatic amino acids," Org Biomol Chem, 7(18):3805-3809.
Tang et al., 2010, "A κ Opioid Pharmacophore Becomes a Spinally Selective κ-δ Agonist When Modified with a Basic Extender Arm," ACS Med Chem Lett., 2(1):7-10.
Taylor, 2017, "Lilly puts two-thirds of midphase cancer pipeline up for sale in major shake-up of R&D priorities," FierceBiotech, retreived from internet: www.fiercebiotech.com/biotech/lilly-puts-two-thirds-mid-phase-cancer-pipeline-up-for-sale-major-shake-up-r-d-priorities on Jan. 16, 2019 (4 pages).
Terrillon et al., 2004, "Roles of G-protein-coupled receptor dimerization," EMBO Rep, 5(1):30-34.
Topaloglu et al., 2009, "TAC3 and TACR3 mutations in familial hypogonadotropic hypogonadism reveal a key role for Neurokinin B in the central control of reproduction," Nat Genet, 41(3):354-358.
Torvinen et al., 2005, "Trafficking of adenosine A2A and dopamine D2 receptors," J Mol Neurosci, 25(2):191-200.
Tripathi et al., 2014, "CXC chemokine receptor 4 signaling upon co-activation with stromal cell-derived factor-1alpha and ubiquitin," Cytokine, 65(2):121-125.
Tripathi et al., 2015, "Heteromerization of chemokine (C-X-C motif) receptor 4 with α1A/B-adrenergic receptors controls α1-adrenergic receptor function," Proc Natl Acad Sci USA, 112(13):E1659-1668.
Van Rijn et al., 2010, "Novel pharmaco-types and trafficking-types induced by opioid receptor heteromerization," Curr Opin Pharmacol., 10(1):73-79.
Vaudry et al., 2000, "Pituitary adenylate cyclase-activating polypeptide and its receptors: from structure to functions," Pharmacol Rev, 52(2):269-324.
Velasco-Velazquez et al., 2012, "CCR5 antagonist blocks metastasis of basal breast cancer cells," Cancer Res, 72(15):3839-3850.
Vincent, 1995, "Neurotensin receptors: binding properties, transduction pathways, and structure," Cell Mol Neurobiol, 15(5):501-512.
Waldhoer et al., 2005, "A heterodimer-selective agonist shows in vivo relevance of G protein-coupled receptor dimers," Proc Natl Acad Sci USA, 102(25):9050-9055.
Walenkamp et al., 2017, "CXCR4 Ligands. The Next Big Hit?" J Nucl Med, 58(Suppl 2):77S-82S.
Wang et al., 2008, "Blockade of SDF-1/CXCR4 signalling inhibits pancreatic cancer progression in vitro via inactivation of canonical Wnt pathway," Br J Cancer, 99(10):1695-1703.
Wang et al., 2009, "CXCR4/CXCL12 hyperexpression plays a pivotal role in the pathogenesis of lupus," J Immunol, 182(7):4448-4458.
Wang et al., 2010, "Dysregulated expression of CXCR4/CXCL12 in subsets of patients with systemic lupus erythematosus," Arthritis Rheum, 62(11):3436-3446.
Wang et al., 2015, "Elabela-apelin receptor signaling pathway is functional in mammalian systems," Sci Rep, 5:8170.
Wang et al., 2015, "NK Cell-Mediated Antibody-Dependent Cellular Cytotoxicity in Cancer Immunotherapy," Front Immunol, 6:368.
Wang et al., 2015, "Norepinephrine attenuates CXCR4 expression and the corresponding invasion of MDA-MB-231 breast cancer cells via beta2-adrenergic receptors," Eur Rev Med Pharmacol Sci, 19(7):1170-1181.
Wang et al., 2016, "Predictive role of the overexpression for CXCR4, C-Met, and VEGF-C among breast cancer patients: A meta-analysis," Breast, 28:45-53.
Watts 2010, "Endothelin receptors: what's new and what do we need to know?" Am J Physiol Regul Integr Comp Physiol, 298(2):R254-260.
Watts et al., 2013, "Identification and profiling of CXCR3-CXCR4 chemokine receptor heteromer complexes," Br J Pharmacol, 168(7):1662-1674.
White et al., 1998, "Heterodimerization is required for the formation of a functional GABA(B) receptor," Nature, 396(6712):679-682.
Wong et al., 2014, "Targeting CXCR4 with CTCE-9908 inhibits prostate tumor metastasis," BMC Urol, 14:12.
Woodward et al., 2011, "International Union of Basic and Clinical Pharmacology. LXXXIII: classification of prostanoid receptors, updating 15 years of progress," Pharmacol Rev, 63(3):471-538.
Wreggett et al., 1995, "Cooperativity manifest in the binding properties of purified cardiac muscarinic receptors," J Biol Chem, 270(38):22488-22499.
Wu et al., 2010, "Structures of the CXCR4 chemokine GPCR with small-molecule and cyclic peptide antagonists," Science, 330(6007):1066-1071.
Wu et al., 2017, "Apelin/APJ system: A novel promising therapy target for pathological angiogenesis," Clin Chim Acta, 466:78-84.
Wurth et al., 2016, "Subventricular zone microenvironment protects glioblastoma cells from radiotherapy cytotoxicity: role of the chemokine CXCL12," Translational Cancer Research, 5(Suppl 6):S1098-S1101.
Xie et al., 2005, "Interaction of bivalent ligand KDN21 with heterodimeric delta-kappa opioid receptors in human embryonic kidney 293 cells," Mol Pharmacol, 68(4):1079-1086.

(56) References Cited

OTHER PUBLICATIONS

Xie et al., 2005, "Roles of histamine and its receptors in allergic and inflammatory bowel diseases," World J Gastroenterol, 11(19):2851-2857.

Xu et al., 2009, "Direct evidence that bevacizumab, an anti-VEGF antibody, up-regulates SDF1alpha, CXCR4, CXCL6, and neuropilin 1 in tumors from patients with rectal cancer," Cancer Res, 69(20):7905-7910.

Xu et al., 2017, "The function of oxytocin: a potential biomarker for prostate cancer diagnosis and promoter of prostate cancer," Oncotarget, 8(19):31215-31226.

Yagami et al., 2016, "Pathophysiological Roles of Cyclooxygenases and Prostaglandins in the Central Nervous System," Mol Neurobiol, 53(7):4754-4771.

Yang et al., 2008, "The A2b adenosine receptor protects against vascular injury," Proc Natl Acad Sci USA, 105(2):792-796.

Yang et al., 2012, Distinct roles of central and peripheral prostaglandin E2 and EP subtypes in blood pressure regulation, Am J Hypertens, 25(10):1042-1049.

Yang et al., 2014, "Antitumour activity of the recombination polypeptide GST-NT21MP is mediated by inhibition of CXCR4 pathway in breast cancer," Br J Cancer, 110(5):1288-1297.

Zabel et al., 2011, "The novel chemokine receptor CXCR7 regulates trans-endothelial migration of cancer cells," Mol Cancer, 10:73.

Zatelli et al., 2007, "Control of pituitary adenoma cell proliferation by somatostatin analogs, dopamine agonists and novel chimeric compounds," Eur J Endocrinol, 156(Suppl 1):S29-35.

Zeelenberg et al., 2003, "The chemokine receptor CXCR4 is required for outgrowth of colon carcinoma micrometastases," Cancer Res, 63(13):3833-3839.

Zhan et al., 2007, "Discovery of small molecule CXCR4 antagonists," J Med Chem, 50(23):5655-5664.

Zhang et al., 2002, "A point mutation that confers constitutive activity to CXCR4 reveals that T140 is an inverse agonist and that AMD3100 and ALX40-4C are weak partial agonists," J Biol Chem, 277(27):24515-24521.

Zhao et al., 2015, "CXCR4 over-expression and survival in cancer: a system review and meta-analysis," Oncotarget, 6(7):5022-5040.

Zhou et al., 2003, "Cell-cell fusion and internalization of the CNS-based, HIV-1 co-receptor, APJ," Virology, 307(1):22-36.

Zhu et al., 2010, "Dipyrimidine amines: a novel class of chemokine receptor type 4 antagonists with high specificity," J Med Chem, 53(24):8556-8568.

Zitzer et al., 1999, "Somatostatin receptor interacting protein defines a novel family of multidomain proteins present in human and rodent brain," J Biol Chem, 274(46):32997-33001.

Jordan et al., 1999, "G-protein-coupled receptor heterodimerization modulates receptor function," Nature, 399(6737):697-700.

Borroto-Escuela et al., 2014, "The G protein-coupled receptor heterodimer network (GPCR-HetNet) and its hub components," Int J Mol Sci., 15(5):8570-8590.

Goupil et al., 2013, "GPCR heterodimers: asymmetries in ligand binding and signalling output offer new targets for drug discovery," Br J Pharmacol., 168(5):1101-1103.

Haack et al., 2011, "Functional Consequences of GPCR Heterodimerization: GPCRs as Allosteric Modulators," Pharmaceuticals (Basel), 4(3):509-523.

Park et al., 2016, "Press Releases: Chungbuk Creation Economic Innovation Center, following the role model of win-win cooperation, accelerates the leading role of creative job creation", Ministry of Science, ICT and Future Planning, Chungbuk Center for Creative Economy & Innovation, Apr. 8, 2016, pp. 1-25, retreived from internet: eiec.kdi.re.kr/policy/material/view.jsp?num=153050. Full article in Korean and English translation of p. 18 provided.

International Search Report and Written Opinion of International Patent Application PCT/KR2018/016166 dated Apr. 18, 2019 (12 pages).

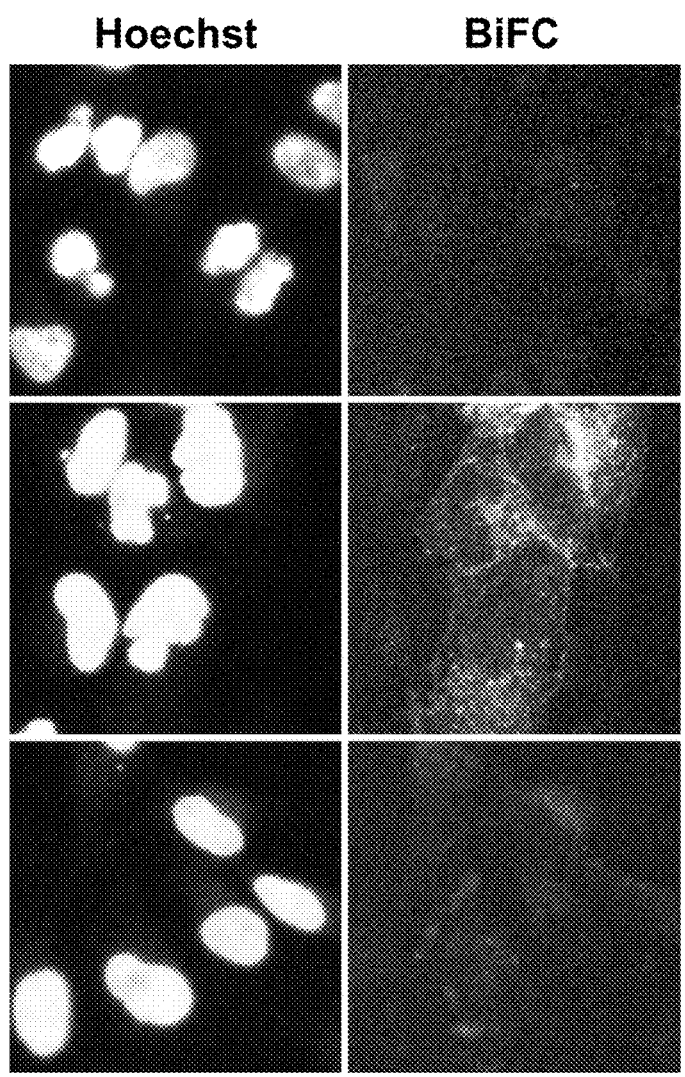

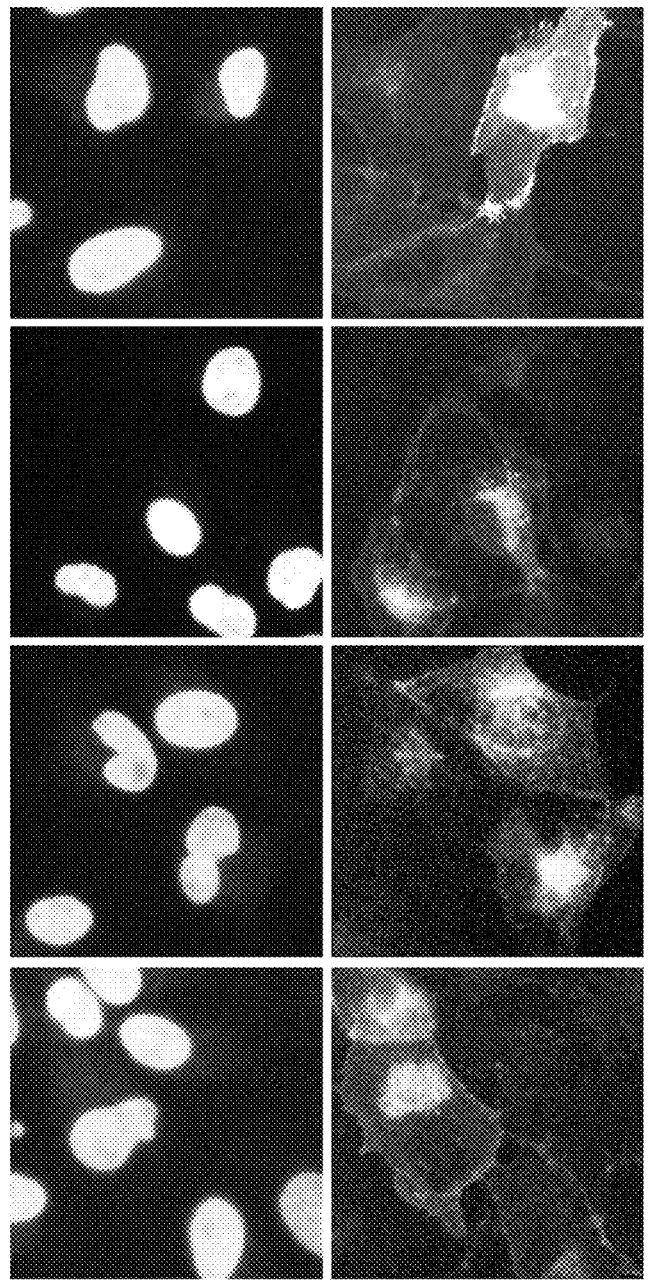

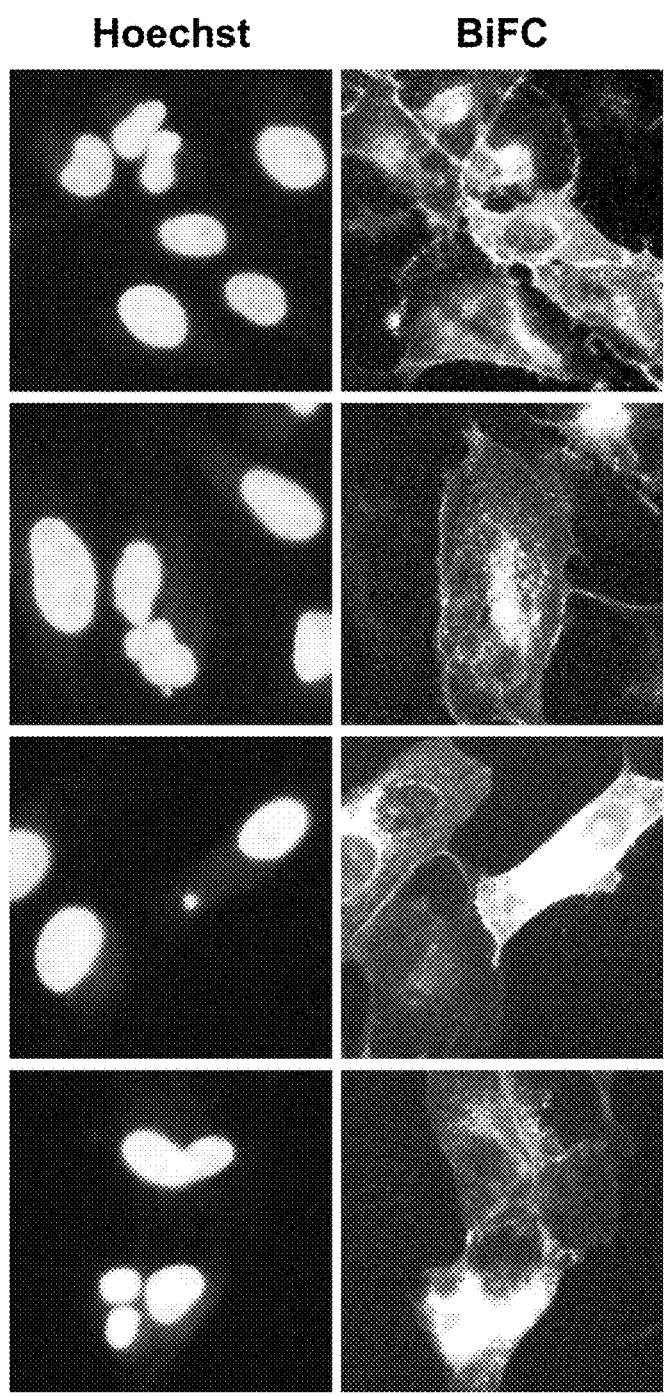

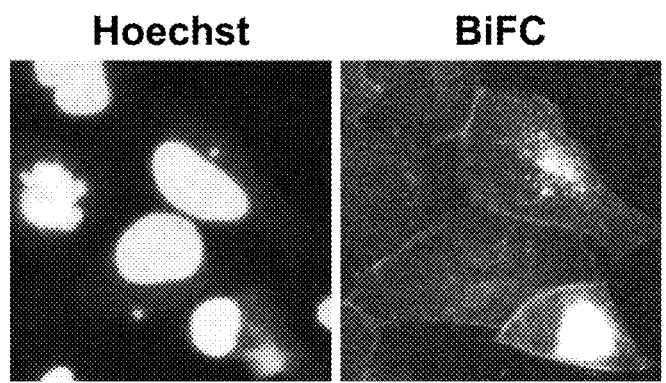
FIG. 2L — CXCR4-VN & CHRM1-VC
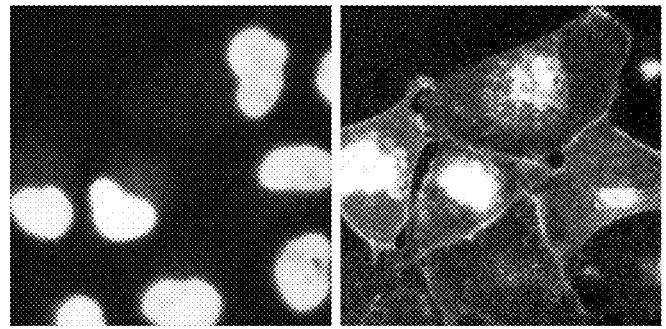
FIG. 2M — CXCR4-VN & GALR1-VC
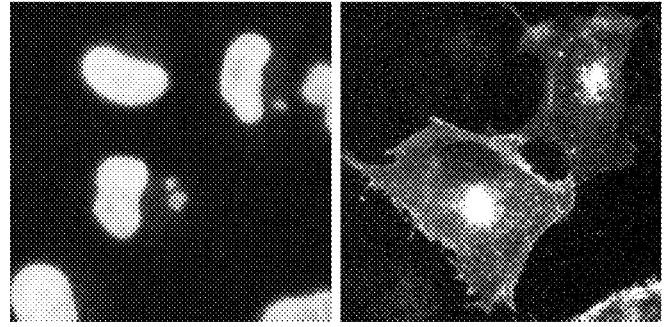
FIG. 2N — CXCR4-VN & EDNRB-VC
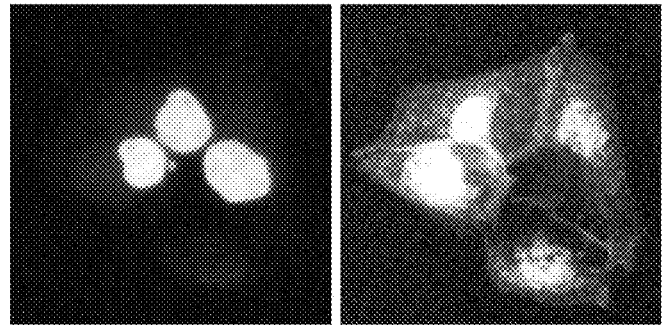
FIG. 2O — CXCR4-VN & HRH1-VC

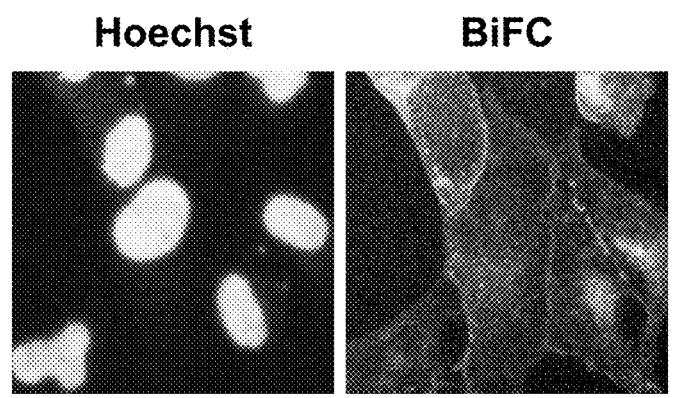
FIG. 2P  CXCR4-VN & MLNR-VC
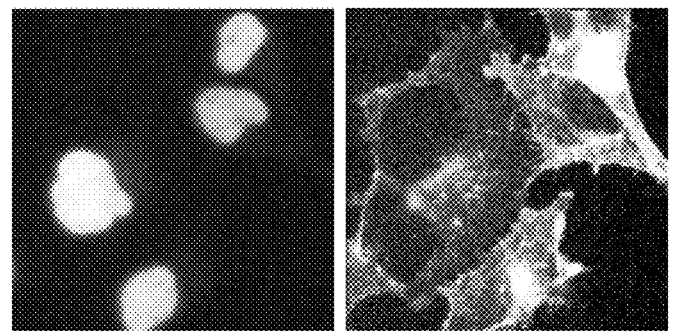
FIG. 2Q  CXCR4-VN & NTSR1-VC
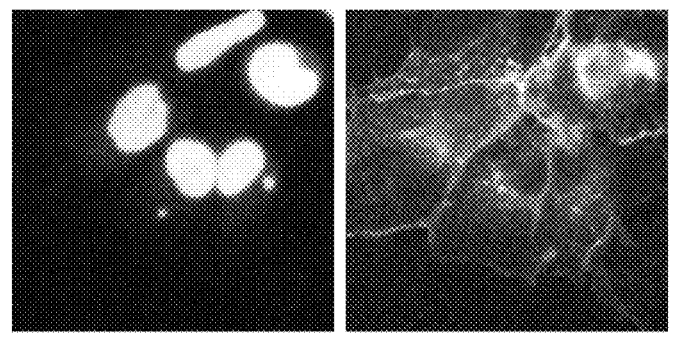
FIG. 2R  CXCR4-VN & PTGER2-VC
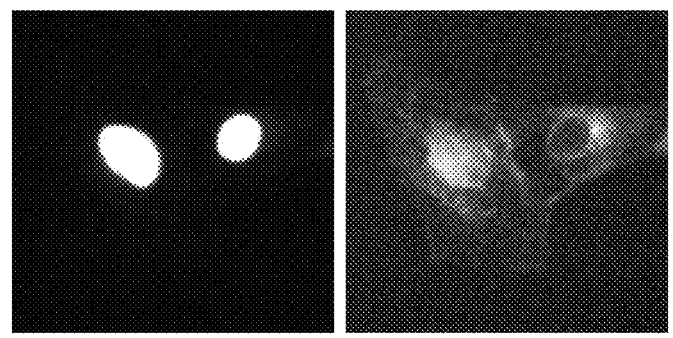
FIG. 2S  CXCR4-VC & PTGER3-VN

|  | Hoechst | BiFC |
|---|---|---|
| FIG. 2T  CXCR4-VN & SSTR2-VC | 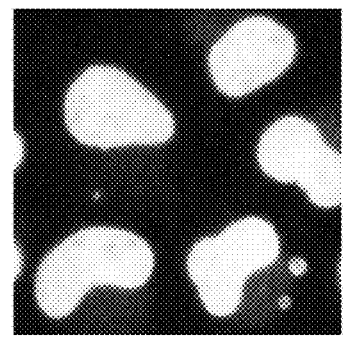 | 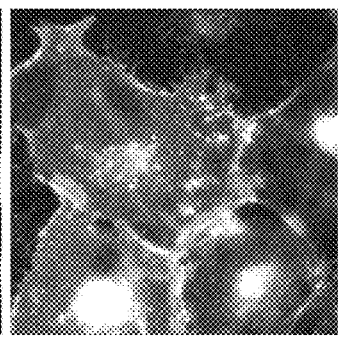 |
| FIG. 2U  CXCR4-VN & TACR3-VC | 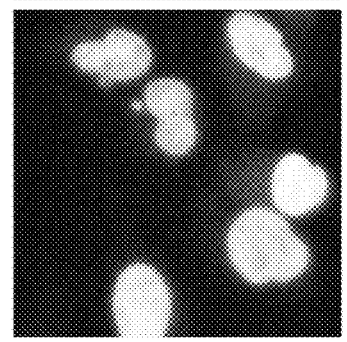 | 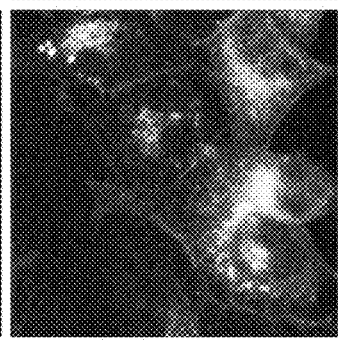 |

CXCR4-GFP
Pre-stimulation | CXCL12
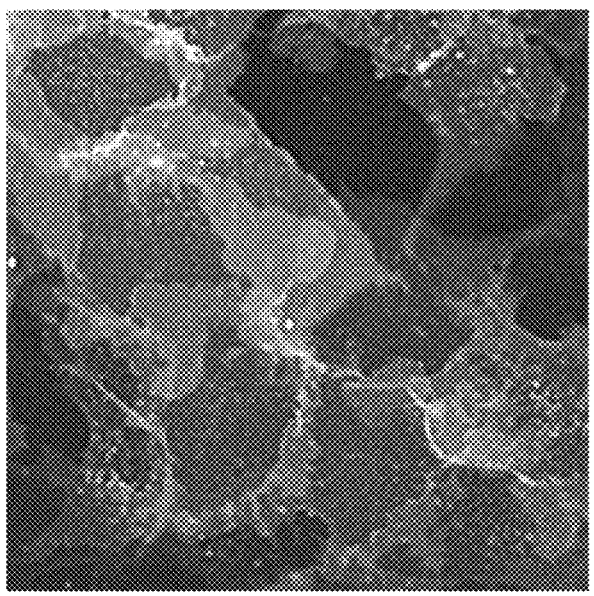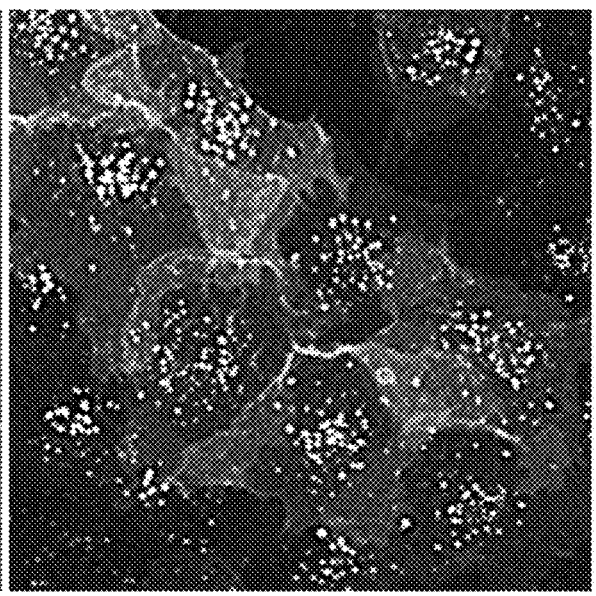
FIG. 4A
CXCR4-GFP & ADCYAP1R1
Pre-stimulation | VIP
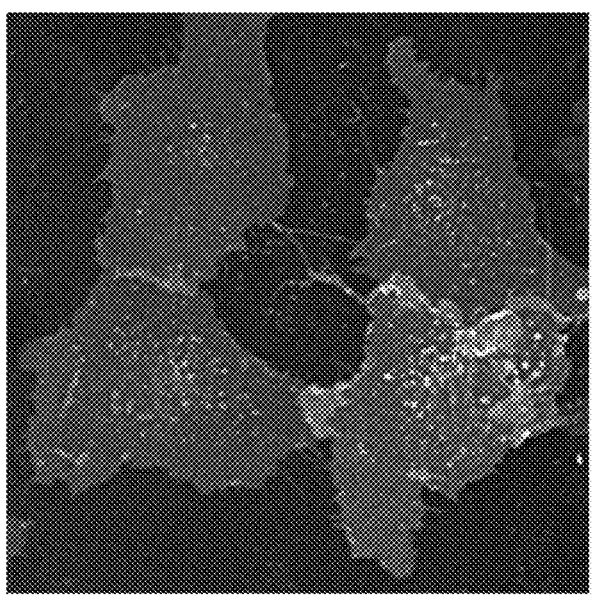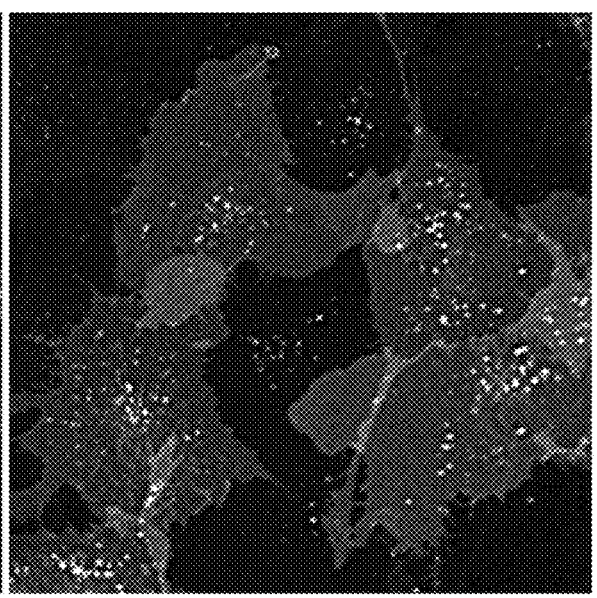
FIG. 4B

CXCR4-GFP & ADORA2B

CXCR4-GFP & ADORA3

CXCR4-GFP & ADRB2
Pre-stimulation | Formoterol
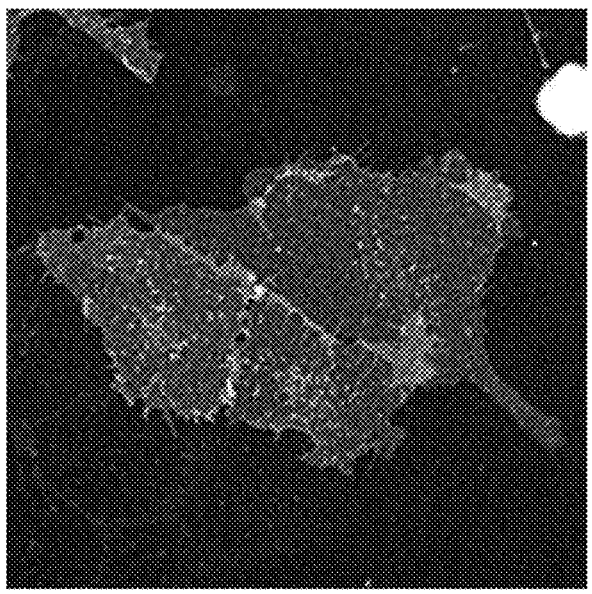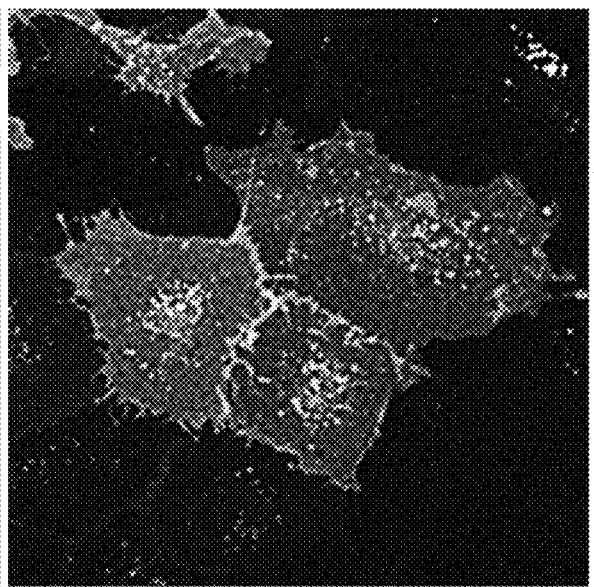
FIG. 4E
CXCR4-GFP & APLNR
Pre-stimulation | Apelin-13
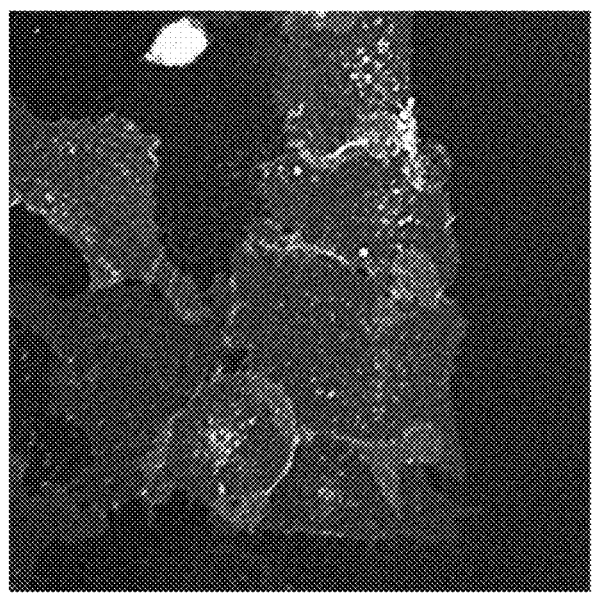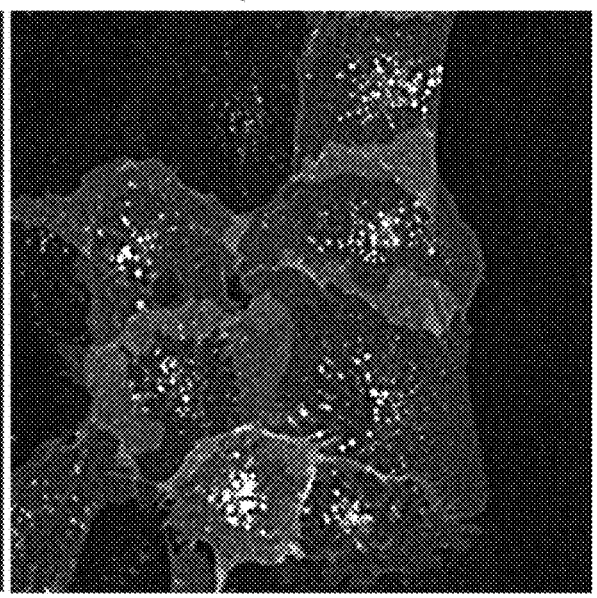
FIG. 4F

CXCR4-GFP & C5AR1
Pre-stimulation | C5a
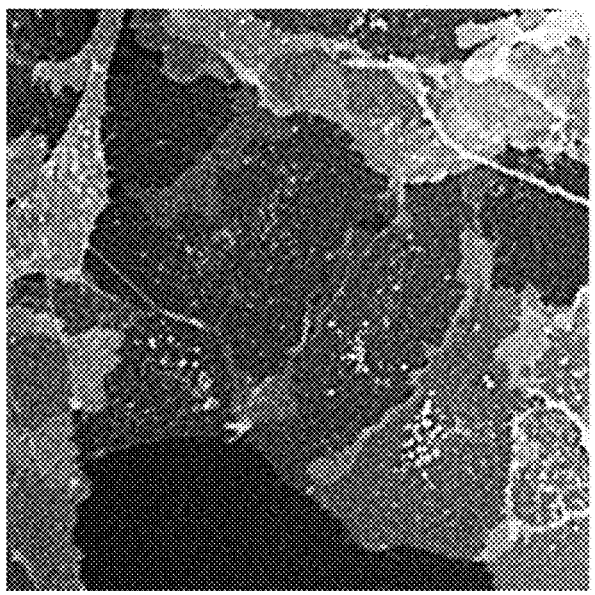 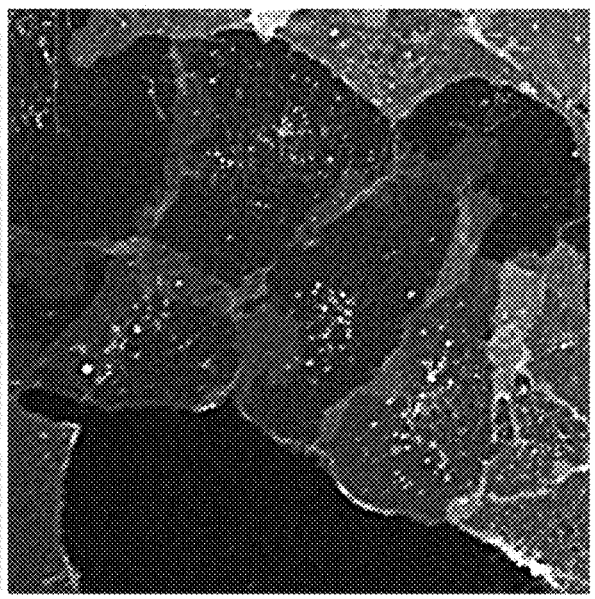
FIG. 4G
CXCR4-GFP & CCR5
Pre-stimulation | CCL2
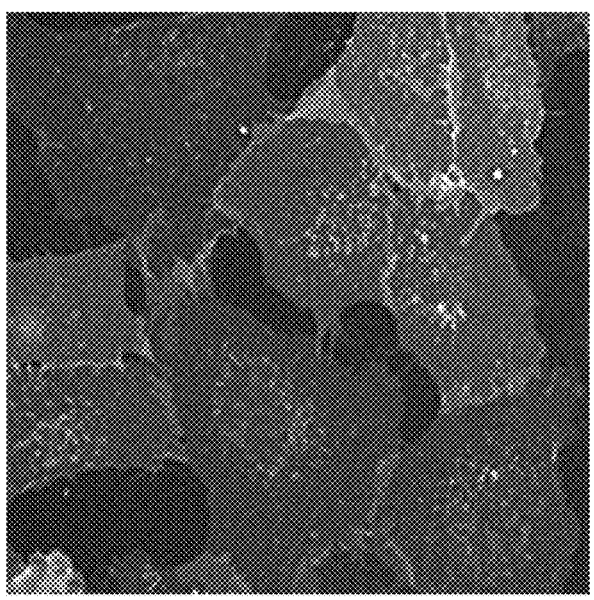 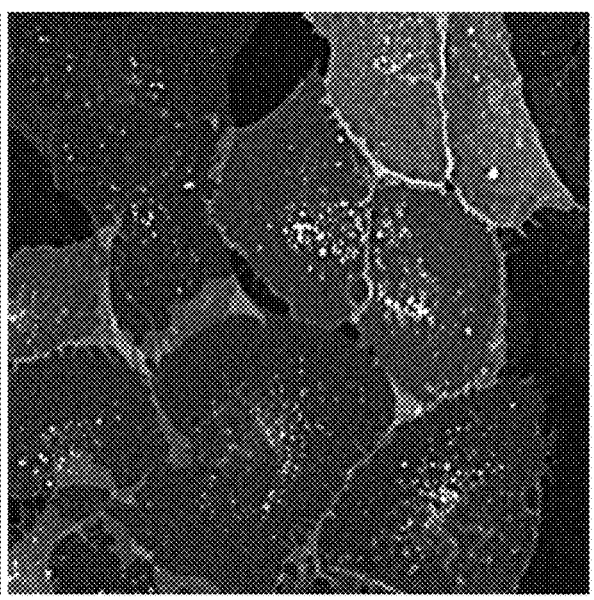
FIG. 4H

CXCR4-GFP & CHRM1
Pre-stimulation | Acetylcholine
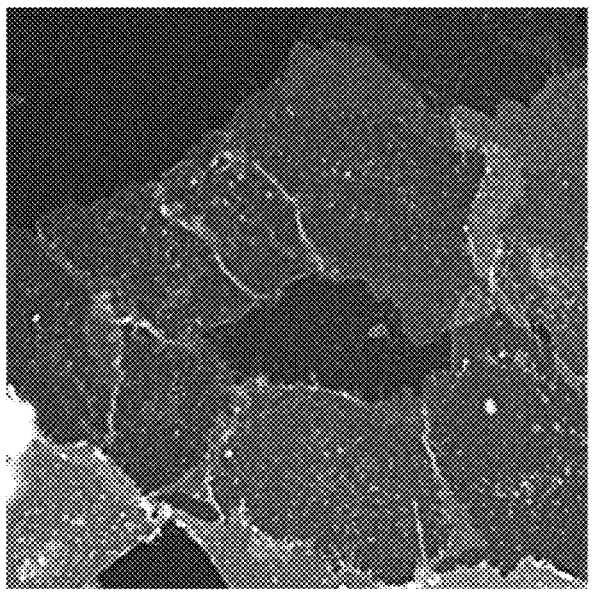 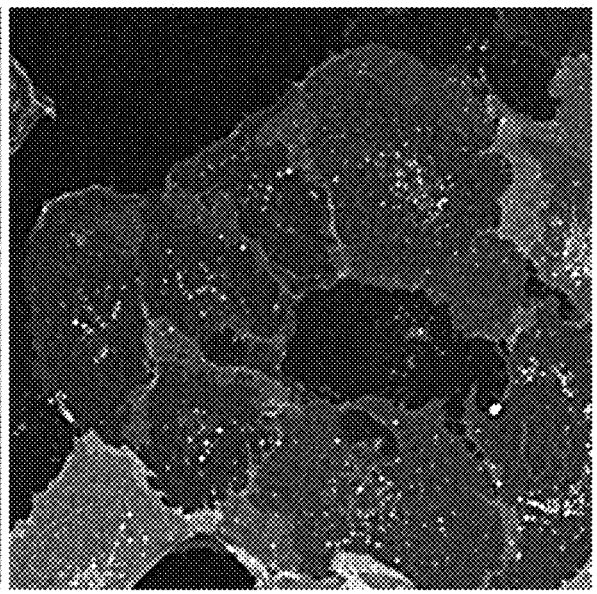
FIG. 4I
CXCR4-GFP & GALR1
Pre-stimulation | galanin
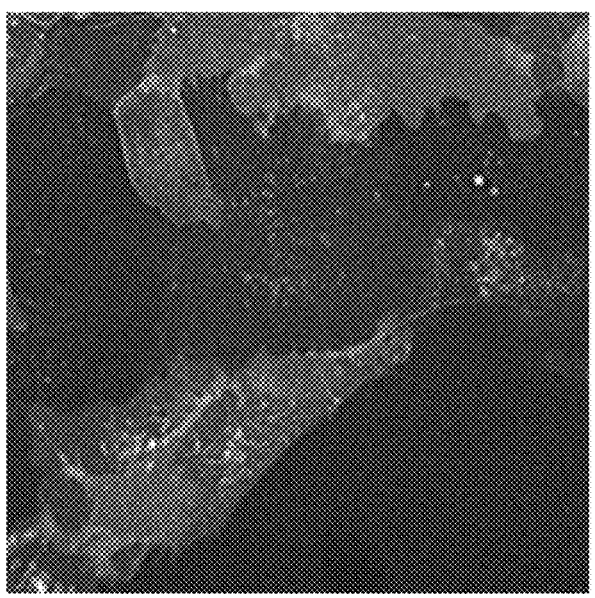 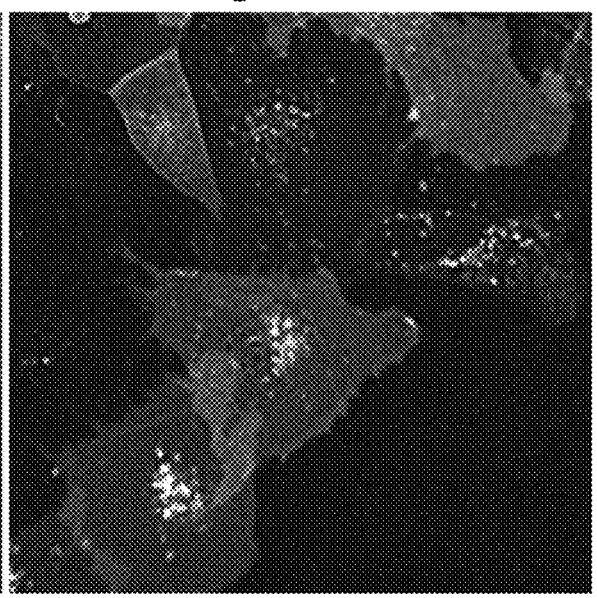
FIG. 4J

CXCR4-GFP & EDNRB

Pre-stimulation | Endothelin 1

CXCR4-GFP & HRH1

Pre-stimulation | Histamine

CXCR4-GFP & MLNR
Pre-stimulation | Motilin
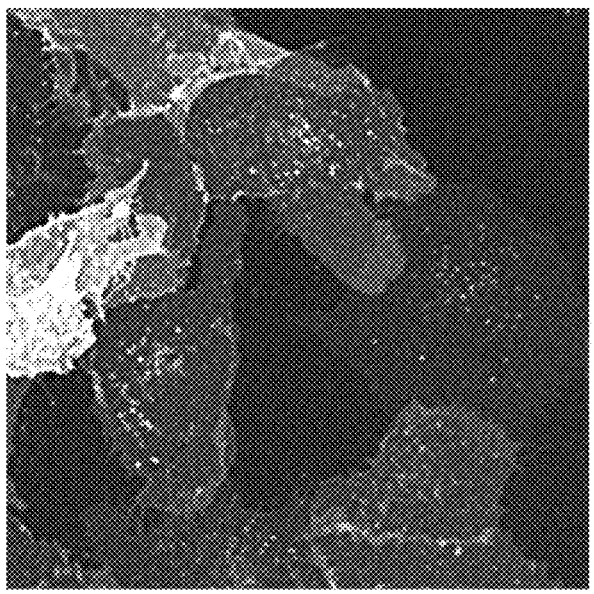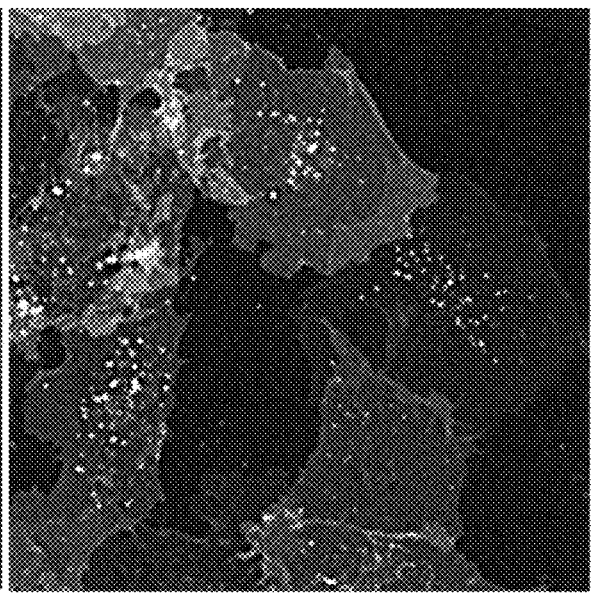
FIG. 4M
CXCR4-GFP & NTSR1
Pre-stimulation | Neurotensin
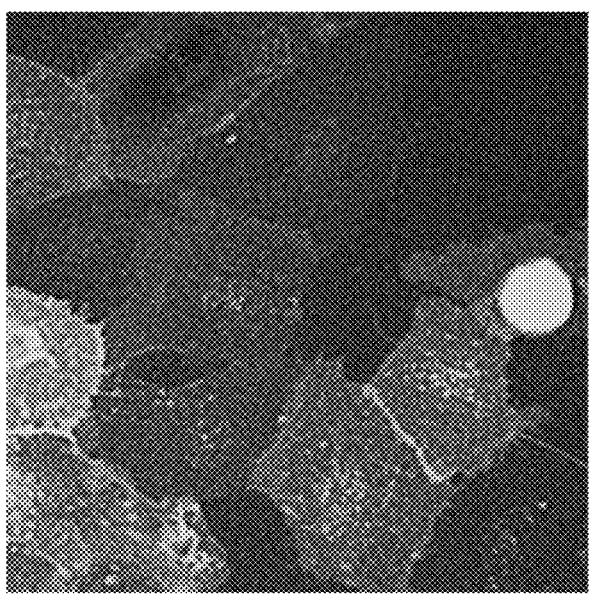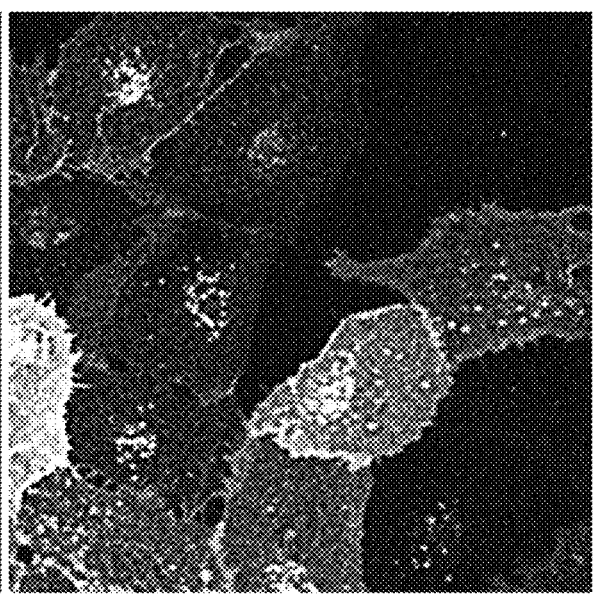
FIG. 4N

CXCR4-GFP & PTGER3

CXCR4-GFP & SSTR2

CXCR4-GFP & TACR3
Pre-stimulation 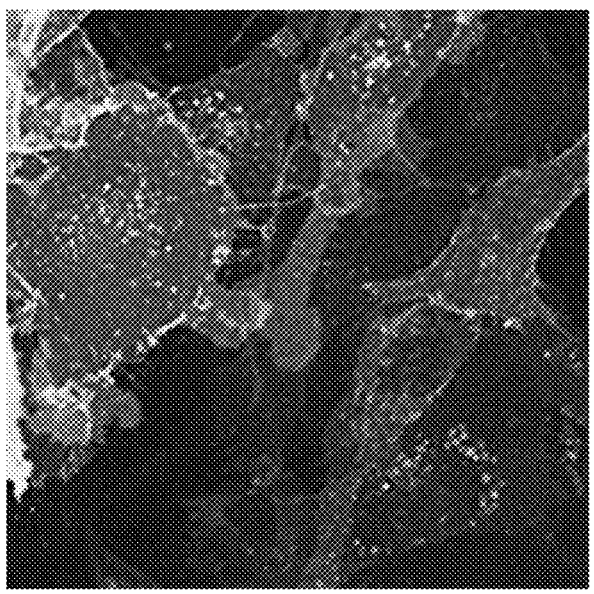 Senktide 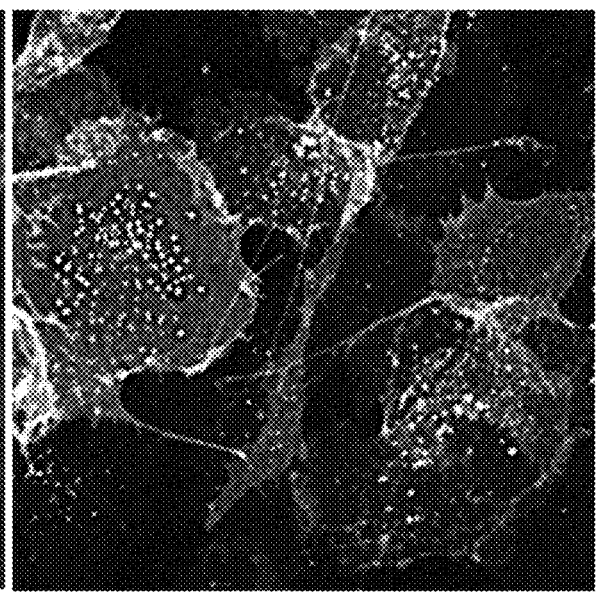
FIG. 4Q

CXCR4-ADRB2
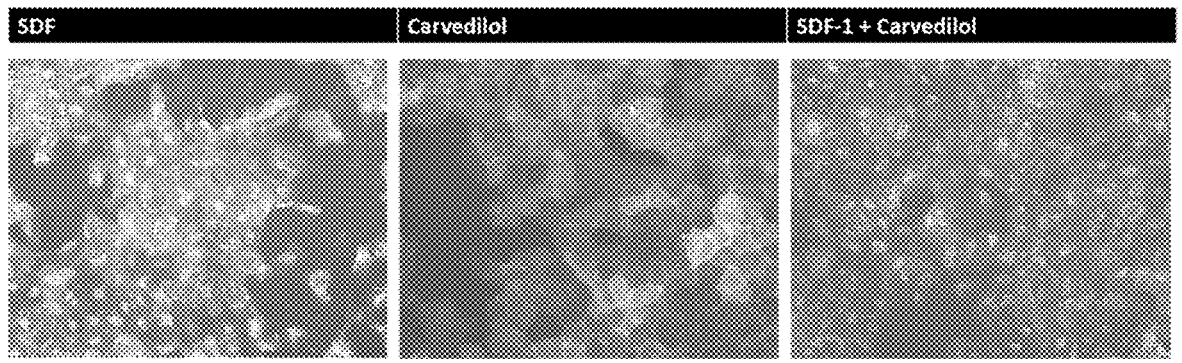
FIG. 10A
CXCR4-CHRM1
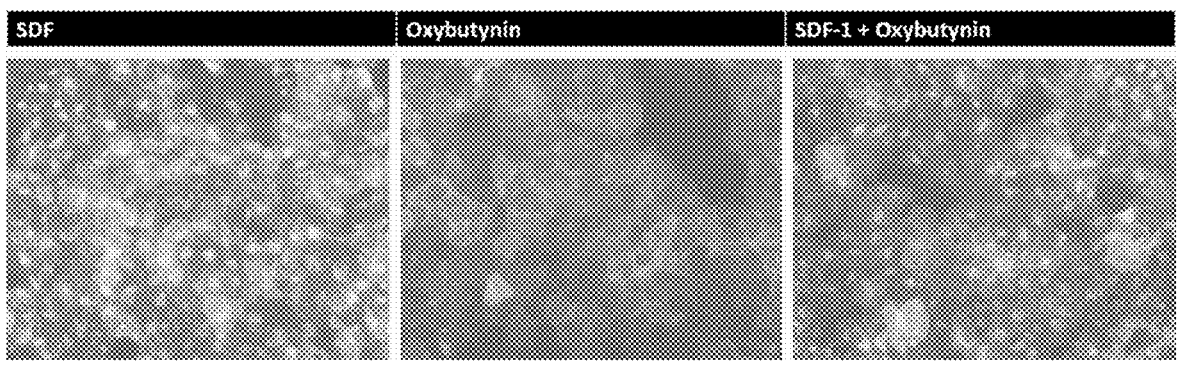
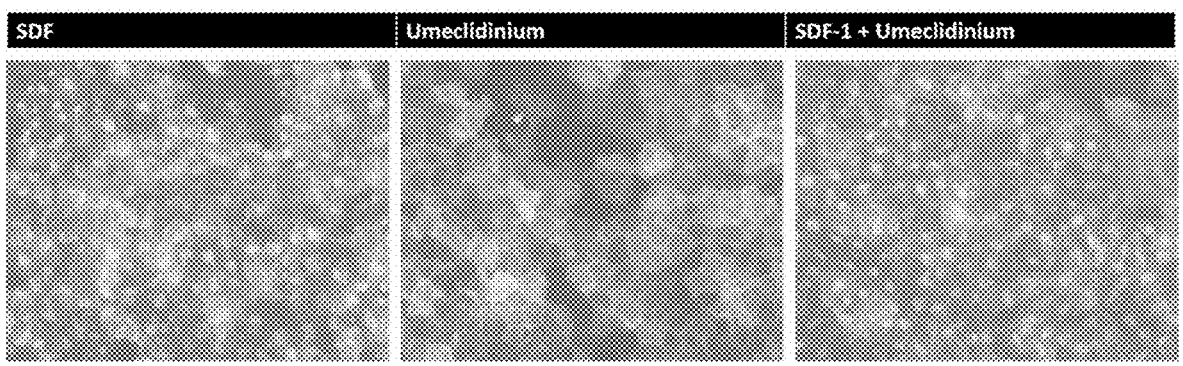
FIG. 10B

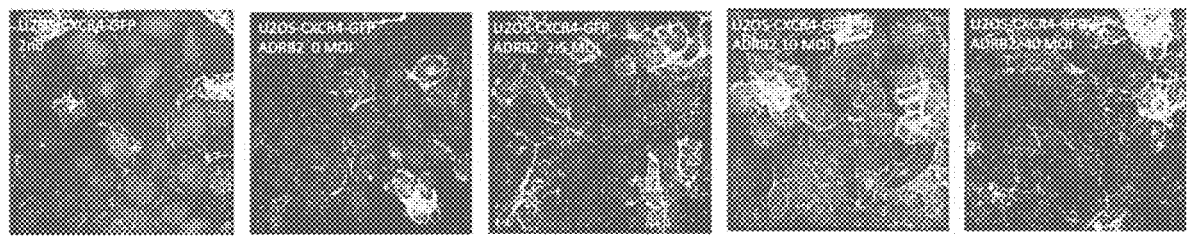
FIG. 12A
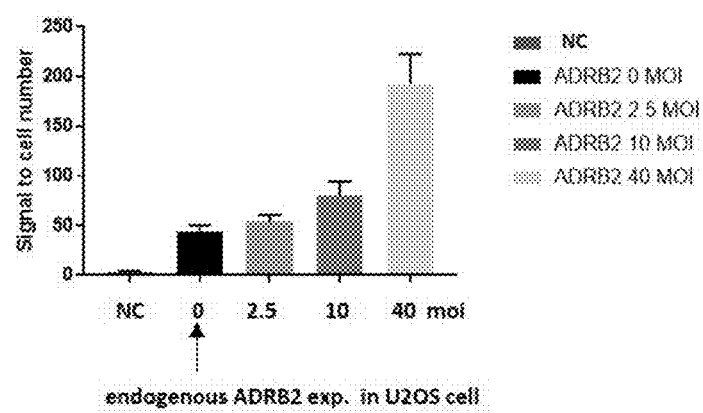
FIG. 12B
| sample | actin | ADRB2 |
|--------|-------|-------|
| U2OS   | *14.2 | *22.3 |
*qPCR (Ct value)
FIG. 12C

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Primer DNA sequence of ADRB2-F

<400> SEQUENCE: 1
ctcttccatc gtgtccttct ac                                            22

<210> SEQ ID NO 2
<211> LENGTH: 20

```
<212> TYPE: DNA
<213> ORGANISM: Artificial Sequence
<220> FEATURE:
<223> OTHER INFORMATION: Primer DNA sequence of ADRB2-R

<400> SEQUENCE: 2
aatcttctgg agctgccttt                                              20

<210> SEQ ID NO 3
<211> LENGTH: 22
<212> TYPE: DNA
<213> ORGANISM: Artificial Sequence
<220> FEATURE:
<223> OTHER INFORMATION: Primer DNA sequence of HRH1-F

<400> SEQUENCE: 3
cctctgctgg atcccttatt tc                                           22

<210> SEQ ID NO 4
<211> LENGTH: 22
<212> TYPE: DNA
<213> ORGANISM: Artificial Sequence
<220> FEATURE:
<223> OTHER INFORMATION: Primer DNA sequence of HRH1-R

<400> SEQUENCE: 4
ggttcagtgt ggagttgatg ta                                           22

<210> SEQ ID NO 5
<211> LENGTH: 23
<212> TYPE: DNA
<213> ORGANISM: Artificial Sequence
<220> FEATURE:
<223> OTHER INFORMATION: Primer DNA sequence of CXCR4-F

<400> SEQUENCE: 5
ccaccatcta ctccatcatc ttc                                          23

<210> SEQ ID NO 6
<211> LENGTH: 20
<212> TYPE: DNA
<213> ORGANISM: Artificial Sequence
<220> FEATURE:
<223> OTHER INFORMATION: Primer DNA sequence of CXCR4-R

<400> SEQUENCE: 6
acttgtccgt catgcttctc                                              20

<210> SEQ ID NO 7
<211> LENGTH: 22
<212> TYPE: DNA
<213> ORGANISM: Artificial Sequence
<220> FEATURE:
<223> OTHER INFORMATION: Primer DNA sequence of Beta-actin-F

<400> SEQUENCE: 7
ggaaatcgtg cgtgacatta ag                                           22

<210> SEQ ID NO 8
<211> LENGTH: 19
<212> TYPE: DNA
<213> ORGANISM: Artificial Sequence
<220> FEATURE:
<223> OTHER INFORMATION: Primer DNA sequence of Beta-actin-R

<400> SEQUENCE: 8
```

```
<210> SEQ ID NO 9
<211> LENGTH: 22
<212> TYPE: DNA
<213> ORGANISM: Artificial Sequence
<220> FEATURE:
<223> OTHER INFORMATION: Primer DNA sequence of GAPDH-F

<400> SEQUENCE: 9
atgacatcaa gaaggtggtg aa                                              22

<210> SEQ ID NO 10
<211> LENGTH: 21
<212> TYPE: DNA
<213> ORGANISM: Artificial Sequence
<220> FEATURE:
<223> OTHER INFORMATION: Primer DNA sequence of GAPDH-R

<400> SEQUENCE: 10
gctgttgaag tcagaggaga c                                               21

<210> SEQ ID NO 11
<211> LENGTH: 20
<212> TYPE: DNA
<213> ORGANISM: Artificial Sequence
<220> FEATURE:
<223> OTHER INFORMATION: Guide RNA sequence of CXCR4 gRNA no 1

<400> SEQUENCE: 11
tgttggctgc cttactacat                                                 20

<210> SEQ ID NO 12
<211> LENGTH: 20
<212> TYPE: DNA
<213> ORGANISM: Artificial Sequence
<220> FEATURE:
<223> OTHER INFORMATION: Guide RNA sequence of HRH gRNA no 3

<400> SEQUENCE: 12
cgatcaagtc cgccaccgag                                                 20

<210> SEQ ID NO 13
<211> LENGTH: 20
<212> TYPE: DNA
<213> ORGANISM: Artificial Sequence
<220> FEATURE:
<223> OTHER INFORMATION: Guide RNA sequence of non-targeting gRNA

<400> SEQUENCE: 13
acggaggcta agcgtcgcaa                                                 20
```

GPCR HETEROMER INHIBITORS AND USES THEREOF

CROSS REFERENCE

This application claims the benefit of priority from U.S. Provisional Application No. 62/607,876, filed Dec. 19, 2017, and further claims the benefit of priority from U.S. Provisional Application No. 62/679,598, filed Jun. 1, 2018, and further claims the benefit of priority from U.S. Provisional Application No. 62/732,946, filed Sep. 18, 2018. Each of the foregoing related applications, in their entirety, are incorporated herein by reference.

In addition, each of the references identified herein, in their entirety, are incorporated herein by reference.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14462-009-999_SEQ_LISTING.txt, was created on Dec. 17, 2018, and is 3,018 bytes in size.

BACKGROUND OF THE INVENTION

The invention disclosed herein relates generally to inhibitors of novel, functional GPCR heteromers, and more specifically to inhibitors of CXC receptor 4 (CXCR4)-G protein-coupled receptor (GPCR) heteromers that display enhanced signaling downstream of CXCR4 as a result of functional heteromer formation and that are associated with cancers and other diseases.

G protein-coupled receptors (GPCRs) are seven-transmembrane domain cell surface receptors that are coupled to G proteins. GPCRs mediate diverse sensory and physiological responses by perceiving stimuli including light, odorants, hormones, neurotransmitters, chemokines, small lipid molecules, and nucleotides. There are approximately 800 GPCR genes in human genome, and more than half of them are predicted to encode sensory receptors such as olfactory, visual, and taste receptors (Bjarnadottir, et al., 2006). The remaining 350 GPCRs have physiologically important roles in embryonic development, behavior, mood, cognition, regulation of blood pressure, heart rate, and digestive processes, regulation of immune system and inflammation, maintenance of homeostasis, and growth and metastasis of cancers (Filmore 2004, Overington, et al., 2006). GPCRs are associated with many diseases and are the targets of approximately 40% of all prescription drugs (Filmore 2004).

CXC receptor 4 (CXCR4) is a member of the chemokine receptor family GPCR. CXCR4 is expressed on most of the hematopoietic cell types, bone marrow stem cells, endothelial progenitor cells, vascular endothelial cells, neurons and neuronal stem cells, microglia and astrocytes (Klein and Rubin 2004, Griffith, et al., 2014). CXCR4 responds to its ligand C-X-C Motif Chemokine ligand 12 (CXCL12), also known as Stromal cell-derived factor 1 (SDF-1), and has essential roles in the embryonic development of the hematopoietic, cardiovascular, and nervous systems (Griffith, et al., 2014). CXCR4 was discovered as a co-receptor for human immunodeficiency virus (HIV), and has important roles in the homing of hematopoietic stem cells (HSCs) to the bone marrow, inflammation, immune surveillance of tissues, and tissue regeneration in adult (Chatterjee, et al. 2014). Mutations in the C-terminus of CXCR4 cause persistent CXCR4 activation, leading to a congenital immune deficiency called WHIM syndrome (Warts, Hypogammaglobulinemia, Infections, and Myelokathexis) characterized by neutropenia and B cell lymphopenia (Hernandez, et al., 2003; Kawai, 2009). CXCR4 also has essential roles in T and B lymphocyte development within lymphoid organs and the thymus during development and in adult (Allen, et al., 2004; Ara, et al., 2003).

CXCR4 is implicated in various immune and autoimmune diseases, such as HIV infection, ischaemia, wound healing, rheumatoid arthritis, systemic lupus erythematosus (SLE), interstitial pneumonias, vascular disease, multiple sclerosis, pulmonary fibrosis, and allergic airway disease (Chu et al., 2017; Debnath, et al., 2013; Domanska, et al., 2013). The involvement of CXCR4 in rheumatoid arthritis was demonstrated by the increased accumulation of CXCR4-positive T-cells in arthritic joints, and a reduction in collagen-induced arthritis in CXCR4-deficient mice (Buckley et al., 2000; Chung et al., 2010). Moreover, CXCR4 antagonist, AMD3100, alleviated collagen-induced arthritis significantly in a mouse model (De Klerck et al., 2005). CXCR4 also regulates pulmonary fibrosis by recruiting circulatory fibroblasts and bone marrow-derived progenitor cells during lung injury, and AMD3100 demonstrated a preventive effect in bleomycin-induced mouse pulmonary fibrosis (Song et al., 2010). CXCR4/CXCL12 axis is also implicated in the pathogenesis of SLE. In mouse models of lupus and patients with SLE, inflammatory cells such as monocytes, neutrophils, and B-cells showed increased expression of CXCR4 and migrated toward skin and lung that overexpress CXCL12 predominantly (Chong and Mohan, 2009; Wang et al., 2009; Wang et al., 2010). CXCR4 antagonist, CTCE-9908, prolonged survival and greatly improved disease conditions and nephritis in a mouse model of lupus (Wang et al., 2009). Furthermore, CXCR4 is also involved in brain and cardiac diseases including brain injury, stroke, myocardial infarction, atherosclerosis and injury-induced vascular restenosis (Cheng et al., 2017; Domanska, et al., 2013; Doring, et al., 2014).

The involvement of CXCR4 in cancer was first noticed when B cells from patients with chronic lymphocytic leukemia (B-CCL) express high levels of functional CXCR4 on the surface, showing enhanced calcium mobilization and actin polymerization upon CXCL12 exposure, and migration towards bone marrow stromal cells that secret CXCL12 (Burger, et al., 1999).

CXCR4 is subsequently characterized to be responsible for breast cancer metastasis to organs that express higher levels of CXCL12 such as lymph nodes, bone marrow, lung, and liver (Muller, et al., 2001). After initial discovery, increasing evidence indicates that CXCR4 is associated with a variety of different cancers and has multiple potential roles in malignancy. CXCR4 is overexpressed in more than 23 human cancers, including breast cancer, lung cancer, brain cancer, kidney cancer (or renal cell carcinoma), pancreatic cancer, ovarian cancer, prostate cancer, melanoma, leukemia, multiple myeloma, gastrointestinal cancers, and soft tissue sarcomas, and regarded as a poor prognosis marker (Domanska, et al., 2013; Chatterjee, et al., 2014; Furusato et al., 2010). CXCR4 is the only chemokine receptor that is expressed by the majority of cancer types (Liang et al., 2015), and stimulates tumor cell growth, survival, and invasiveness in response to CXCL12 secreted by the cancer cells and the surrounding cancer-associated cells (Burger and Kipps, 2006; Chatterjee et al., 2014; Domanska et al., 2013).

Systematic meta-analyses using databases including PubMed, EMBASE, and Cochrane library indicate significant association between CXCR4 over-expression and poorer progression-free survival and overall survival in various cancers including hematological malignancy, breast cancer, colorectal cancer, esophageal cancer, head and neck cancer, renal cancer, lung cancer, gynecologic cancer, liver cancer, prostate cancer, and gallbladder cancer (Du et al., 2015; Hu et al., 2015; Li et al., 2017; Wang et al., 2016; Zhao et al., 2015).

CXCR4/CXCL12 axis plays a central role in tumor growth, invasion, angiogenesis, vasculogenesis, metastasis, drug resistance, and cancer cell-tumor microenvironment interaction (D'Alterio et al., 2012; Domanska et al., 2013; Guo et al., 2016)

The critical role of CXCR4 in cancer cell proliferation and tumor growth was demonstrated in various experimental models in vitro and in vivo such as orthotopic, subcutaneous human xenograft, and transgenic mouse models using CXCR4 antagonists (Domanska et al., 2013). The Daoy medulloblastoma cells and U87 glioblastoma cells showed CXCR4 expression and exhibited dose-dependent increase in proliferation to a gradient of CXCL12 in vitro, and systemic administration of AMD3100 inhibited the growth of intracranial U87 and Daoy cell xenografts (Rubin et al., 2003).

Involvement of CXCR4 in the metastasis of cancer cells towards CXCL12 expressing organs was also demonstrated in pancreatic, thyroid, melanoma, prostate, and colon cancer xenograft models (Bartolome et al., 2009; De Falco et al., 2007; Taichman et al., 2002; Wang et al., 2008; Zeelenberg et al., 2003).

The main mechanism of action described for the small molecules or peptides antagonists of CXCR4 is centered on their ability to mobilize malignant cells from the BM, thereby sensitizing them to chemotherapy. These agents have shown limitations regarding short half-lives, making their adequate management over long periods of time difficult (Hendrix et al., 2000). In contrast, therapeutic monoclonal antibodies have the advantage of having more prolonged half-lives, and are suitable for less frequent dosing. Additionally, human IgG antibodies have the ability to induce cell death upon binding to their target protein on cancer cells, via interaction with Fc-receptor on effector cells, including antibody-dependent cell mediated cytotoxicity/phagocytosis (ADCC/ADCP) (Jiang et al., 2011). Such cytotoxic mechanism of action are not inherent to small molecules or peptides, and have been demonstrated to play a key role in the clinical activity of several therapeutic antibodies (Wang et al., 2015).

Targeting CXCR4 using a neutralizing anti-CXCR4 antibody or CXCR4 specific antagonists inhibited primary tumor growth as well as metastasis to secondary organs in breast cancer, colon cancer, hepatocellular carcinoma, osteosarcoma, and melanoma (De Falco et al., 2007; Hassan et al., 2011; Huang et al., 2009; Kim et al., 2008; Muller et al., 2001; Schimanski et al., 2006; Smith et al., 2004; Zeelenberg et al., 2003). In a transgenic breast cancer mouse model, inhibition of CXCR4 with CTCE-9908 reduced not only the growth of primary tumor but also the expression of vascular endothelial growth factor (VEGF) and AKT phosphorylation (Hassan et al., 2011).

Cancer stem cells (CSCs) are a population of cancer cells with properties such as infinite self-renewal, potential to differentiate into multiple cancer lineages, ability to adopt a quiescent state, and intrinsic high resistance to chemo- and radio-therapy. CSCs are considered as the major cause of cancer relapse and recurrence after standard anti-proliferative therapy. Therefore, targeting cancer stem cells are expected to provide more effective therapeutic interventions to eradicate the cancer and prevent relapse (Batlle and Clevers, 2017; Reya et al., 2001; Wurth, 2016). Interestingly, CSCs also express CXCR4, and CXCR4 directs the trafficking and metastasis of these cells to the CXCL12-rich microenvironments such as bone marrow and subventricular zone in the brain that favor cancer stem cell maintenance, survival and growth. CXCR4 antagonists have been shown to mobilize CSCs from these protective microenvironments, and sensitize them to conventional chemo- and radiotherapy, and anti-angiogenic therapy (Burger and Kipps, 2006; Burger and Peled, 2009; Furusato et al., 2010; Redondo-Munoz et al., 2006; Walenkamp et al., 2017; Wurth, 2016).

Increasing evidence showed that tumor mass contains various cell types such as stromal fibroblasts, immune cells, endothelial cells, connective tissue, and extracellular matrix in addition to cancer cells that constitute tumor microenvironment (TME) or cancer cell niches. CXCR4/CXCL12 axis plays pivotal roles in tumor cell-microenvironment interaction that support tumor structure, growth, angiogenesis, and evasion of immune surveillance in various cancers of both the hematopoietic and nonhematopoietic system (Burger and Kipps, 2006; Burger and Peled, 2009; Walenkamp et al., 2017). CXCL12 can promote tumor angiogenesis by recruiting endothelial cells to the TME directly, or indirectly by attracting CXCR4-positive inflammatory cells to the tumor mass, and making them to secret proangiogenic factors (Owen and Mohamadzadeh, 2013; Walenkamp et al., 2017).

Growing evidence indicates that CXCR4/CXCL12 axis contributes to the lack of tumor responsiveness to angiogenesis inhibitors. Vascular endothelial growth factor (VEGF) was considered as the major pro-angiogenic factor in cancer, and was targeted for anti-angiogenic therapy in patients with rectal carcinoma using an anti-VEGF antibody bevacizumab (Genentech). Surprisingly, bevacizumab increased the expression of CXCL12 and CXCR4 in cancer cells, and increased plasma levels of CXCL12 in these patients were associated with rapid disease progression and metastasis (Owen and Mohamadzadeh, 2013; Xu et al., 2009). Therefore, the efficacy of a combination therapy using bevacizumab and plerixafor was evaluated for recurrent glioma (ClinicalTrials.gov identifier: NCT01339039). However, the study was terminated due to a low accrual rate (Walenkamp et al., 2017).

Inhibition of CXCR4/CXCL12 axis has been demonstrated to disrupt the tumor microenvironment (TME) and expose the tumor cells to immune attack by decreasing the infiltration of myeloid-derived suppressor cells, by increasing the ratio of CD8+ cytotoxic T cells to Treg cells, or eliminating tumor re-vascularization (Burger et al., 2011; Domanska et al., 2013; Walenkamp et al., 2017). Administration of CXCR4 antagonists, AMD3100 or T22, acted synergistically with immune checkpoint inhibitors such as cytotoxic T-lymphocyte-associated antigen 4 (CTLA-4) antibodies, programmed cell death protein 1 (PD-1), and programmed cell death ligand 1 (PD-L1) antibodies and greatly increased their antitumor activity in a model of pancreatic ductal adenocarcinoma, advanced hepatocellular carcinoma (HCC), and CXCR4-transduced B16 melanoma (Chen et al., 2015; Feig et al., 2013; Lee et al., 2006; Scala, 2015; Walenkamp et al., 2017). These results indicate that targeting CXCR4/CXCL12 axis offers benefit to the conventional immune checkpoint inhibitors.

Various drugs targeting CXCR4 have been developed (Peled, et al., 2012; Debnath, et al., 2013; Walenkamp, et al., 2017). CXCR4 inhibitors can be divided into 5 categories:

(1) non-peptide small molecule antagonists, such as AMD3100 (plerixafor, Mozobil™, Genzyme (MA, USA); (Cashen et al., 2007; Donzella et al., 1998), AMD070 (AMD11070; Crawford and Alan Kaller, 2008; Stone et al., 2007), AMD3465 (Genzyme Corp., Biochem Pharmacol. 2009 Oct. 15; 78(8):993-1000; Bodart et al., 2009; Ling et al., 2013), GSK812397 (Jenkinson et al., 2010; Planesas et al., 2015), KRH-3955 (Murakami et al., 2009; Nakasone et al., 2013), KRH-1636 (Ichiyama et al., 2003), D-[Lys3] GHRP-6 (Patel et al., 2012), TG-0054 (Burixafor, TaiGen Biotechnology Co., Ltd.; de Nigris et al., 2012; Hsu et al., 2015), WZ811 (Zhan et al., 2007), MSX-122 (Metastatix, Inc.; Liang et al., 2012), and 508MCl (Compound 26; Zhu et al., 2010);

(2) small-peptide antagonists, such as anti-HIV peptides T22 (Masuda et al., 1992), T134 and T140 (Tamamura et al., 1998), BKT140 (a/k/a BL-8040; TF14016; 4F-Benzoyl-TN14003, Biokine Therapeutics Ltd. (Rehovot, Israel); Fahham et al., 2012; Otani et al., 2012), ALX40-4C (Canadian company Allelix Biopharmaceuticals (ON, Canada); Doranz et al., 2001), GST-NT21MP (Yang et al., 2014), FC131 (Tanaka et al., 2009; Tanaka et al., 2008), FC122 (Inokuchi et al., 2011), POL6326 (de Nigris et al., 2012), and LY2510924 (Lilly) (Peng et al., 2015);

(3) antibodies to CXCR4, such as ulocuplumab (MDX1338/BMS-936564; Kuhne et al., 2013), PF-06747143 (Pfizer; Liu et al., 2017), 12G5 (Endres et al., 1996), i-bodies (AD-114, AD-114-6H, AD-114-Im7-FH, and AD-114-PA600-6H; AdAlta; Griffiths et al., 2016; Griffiths et al., 2018), nanobodies (238D2 and 238D4; Jahnichen et al., 2010; Proc. Natl Acad. Sci. 2010, USA 107(47), 20565-20570), and ALX-0651 (Ablynx, biparatopic nanobody, ClinicalTrials.gov Identifier: NCT01374503);

(4) ligand (CXCL12) analogs with suppressive activity, such as CTCE-9908 (Chemokine Therapeutics (BC, Canada); Wong et al., 2014); and (5) radiolabeled CXCR4 ligands, such as [99mTc]O2-AMD3100 (Hartimath et al., 2013), [68Ga]pentixafor (Demmer et al., 2011; Gourni et al., 2011), [177Lu] pentixather, and [90Y]pentixather (Herrmann et al., 2016).

AMD3100 (JM 3100, plerixafor, marketed as Mozobil) is a CXCR4-specific small molecule antagonist that inhibits CXCL12-mediated calcium mobilization and chemotaxis in various cell types (Hatse, Princen et al. 2002), and prevents tumor growth in mouse xenograft models (Rubin, Kung et al. 2003, Cho, Yoon et al. 2013, Liao, Fu et al. 2015). AMD3100 was originally developed for HIV therapy (as an HIV entry blocker that specifically antagonizes CXCR4, one of the HIV entry co-receptors), but was approved by the U.S. Food and Drug Administration only for stem cell mobilization in patients with lymphoma and multiple myeloma in 2008 (Keating 2011). During the initial clinical trial of AMD3100 for HIV infection, this compound was noted to cause hematopoietic stem cell (HSC, CD34$^+$) mobilization from bone marrow to peripheral blood (Broxmeyer et al., 2005; De Clercq, 2003; Liles et al., 2003).

Development of AMD3100 for HIV therapy was suspended due to significant side effects including thrombocytopenia, premature ventricular contractions, and leukocytosis following long-term inhibition of CXCR4/CXCL12 axis (Hendrix, et al., 2004; Peled, et al., 2012). Although investigating the possibility of the use of AMD3100 as an anticancer drug is underway, lack of oral availability and some severe side effects accompanying with long-term use need to be overcome (Peled, et al., 2012). Instead, subcutaneous AMD3100 was approved in combination with G-CSF for autologous stem cell mobilization and transplantation for patients in the US with non-Hodgkin lymphoma (NHL) or multiple mylenoma for up to 4 consecutive days, and for patients in Europe with multiple mylenoma or lymphoma for 2-4 consecutive days and for up to 7 consecutive days, respectively (DiPersio et al., 2009a; DiPersio et al., 2009b; Keating, 2011). So far, AMD3100 is the only CXCR4 antagonist approved by the FDA.

AMD3100 has been shown to inhibit CXCL12-mediated calcium mobilization and chemotaxis in various cancer cell types expressing CXCR4 (Hatse et al., 2002), and has demonstrated significant anti-tumor activity with decreased metastasis and increased overall survival in various mouse xenograft models (Burger et al., 2011; Chatterjee et al., 2014; Cho et al., 2013; Debnath et al., 2013; Domanska et al., 2013; Liao et al., 2015; Rubin et al., 2003; Walenkamp et al., 2017).

However, AMD3100 exhibits partial agonism for CXCR4 in vitro and increases the proliferation of meloma cells (Kim et al., 2010; Zhang et al., 2002). AMD3100 also acts as a positive allosteric modulator of CXCR7, an alternative chemokine receptor for CXCL12, and increases CXCL12 binding to CXCR7 (Kalatskaya et al., 2009). Like CXCR4, CXCR7 is also highly expressed by many types of cancers and is associated with tumor metastasis (Decaillot et al., 2011; Zabel et al., 2011). Due to the complex properties of AMD3100, the exact role of AMD3100 on cancer needs to be investigated carefully.

AMD3100 has been clinically evaluated as anticancer drug in combination with conventional cytotoxic drugs such as mitoxantrone, etoposide, cytarabine, daunorubicin, azacitidine, lenalidomide, decitabine, clofarabine, fludarabine, and/or idarubicin; receptor tyrosine kinase inhibitors AC220 and sorafenib; HSP90 inhibitor (Ganetespib); G-CSF; proteasome inhibitor (bortezomib); or monoclonal antibody (rituximab) in hematological malignancies including acute myeloid leukemia (AML), MM, Myelodysplastic Syndromes (MDS), CLL, and small lymphocytic lymphoma (SLL) (ClinicalTrials.gov Identifier: NCT00512252, NCT00694590, NCT00903968, NCT00990054, NCT01065129, NCT01373229, NCT01352650, NCT01236144, NCT01301963, NCT01160354, NCT01027923, NCT00943943, and NCT01435343). AMD3100 was examined for interrupting lymphoid tumor microenvironment communication (NCT01610999) and for chemosensitization in combination with other anti-cancer drugs in patients with relapsed or refractory AML, ALL, and MDS (ClinicalTrials.gov identifier: NCT00906945 and NCT01319864).

AMD3100 has been or is also being evaluated in solid tumors including high grade glioma, Ewing's sarcoma, neuroblastoma, pancreatic, ovarian, and colorectal cancers alone or in combination with angiogenesis inhibitor bevacizumab (ClinicalTrials.gov identifier: NCT01339039, NCT01977677, NCT01288573, NCT02179970, and NCT03277209).

AMD3100 has been tested or is currently being evaluated for the mobilization of the hematopoietic stem/progenitor/precursor cells in patients with various hematological malignancies and diseases including AML, MDS, neutropenia, beta-thalassemia, sickle cell disease, WHIMS, Fanconi anemia, Wiskott-Aldrich Syndrome, systemic mastocytosis ((Domanska et al., 2013), NCT01058993, NCT01206075, NCT03226691, NCT00967785, NCT02678533, NCT03019809, and NCT00001756). It has been or currently being evaluated for recruiting CD34+ cells, endothelial progenitor cells (EPC), and/or CD117+ progenitor cells in patients with diabetes, wounds, critical limb ischemia, chronic obstructive pulmonary disease (COPD), cystic fibrosis, pulmonary fibrosis (ClinicalTrials.gov identifier: NCT02056210, NCT02790957, NCT01916577, NCT03182426).

Although investigating the possibility of the use of AMD3100 as an anticancer drug is underway, lack of oral availability and some severe side effects accompanying with long-term use need to be overcome (Peled et al., 2012).

The orally available CXCR4 antagonist, AMD070 (also referred to herein as AMD-070, AMD11070, AMD-11070, or X4P-001; X4 Pharmaceuticals) has demonstrate antitumor activity in various tumor models (Morimoto et al., 2016; O'Boyle et al., 2013; Parameswaran et al., 2011) and has been studied in a phase I/II clinical trial in HIV infected subjects (ClinicalTrials.gov identifier: NCT00089466, (Debnath et al., 2013). AMD070 is now in Phase II/III clinical trial in patients with WHIM syndrome, advanced melanoma, and renal cell carcinoma alone or together with pembrolizumab, nivolumab, or axitinib (ClinicalTrials.gov identifier: NCT03005327, NCT02823405, NCT02923531, and NCT02667886).

The efficacy of small peptide antagonists of CXCR4, T140 and its analogs TN14003, TC14012, and BKT140 (also referred to herein as BL-8040, TF14016, 4F-Benzoyl-TN14003, BioLineRx, Ltd.) for blocking CXCR4 has been demonstrated in numerous preclinical studies including stem cell mobilization, small-cell lung cancer (SCLC), breast cancer, melanoma, AML, chronic myeloid leukemia, MM, pancreatic cancer, and rheumatoid arthritis (Burger et al., 2011). Currently, BKT140 is under clinical development for hematopoietic stem and progenitor cell mobilization in various hematopoietic malignancies (ClinicalTrials.gov identifier: NCT02502968, NCT03154827, NCT02763384, NCT02639559, and NCT02462252). In addition, BKT140 is in Phase II clinical trials for interfering tumor microenvironment interaction in subjects with AML in combination with cytarabine (ClinicalTrials.gov identifier: NCT02502968). It is also investigated in various cancers such as AML, gastric cancer, non-small-cell lung cancer (NSCLC), and metastatic pancreatic cancers together with immune checkpoint inhibitors such as Pembrolizumab (Keytruda, Merck) and Atezolizumab (Tecentriq, Genentech/Roche) (ClinicalTrials.gov Identifier: NCT03154827, NCT03281369, NCT03337698, NCT02907099, NCT03193190, and NCT02826486).

Similarly, CTCE-9908 (Chemokine Therapeutics Corp., Canada), a peptide inhibitor of CXCR4, reduced metastases in mouse models of osteosarcoma and melanoma (Kim et al., 2008). After phase I study in patients with advanced solid cancers, CTCE-9908 was designated as an orphan drug for the treatment of osteosarcoma by the FDA in 2005. There is no further development after phase I/II clinical trial has been completed in 2008 (Debnath, et al., 2013).

MSX-122 (Altiris Therapeutics), a small molecule CXCR4 antagonist, has been abandoned after clinical trial in patients with solid tumors (ClinicalTrials.gov identifier: NCT00591682). Two major setbacks have been reported in 2017 in the field of developing CXCR4 antagonists as anti-cancer drugs. Bristol-Myers Squibb (BMS) discontinued a phase I/II study of ulocuplumab (BMS-936564/MDX1338, (Kuhne et al., 2013), a fully human anti-CXCR4 antibody, in patients with solid tumors for lack of efficacy (https://seekingalpha.com/article/4057548-bristol-failure-makes-small-dent-cxcr4-blocking-approach?page=2). Also, Eli Lilly decided to abandon a few anti-cancer programs including LY2510924, which is a CXCR4 peptide antagonist (http://www.fiercebiotech.com/biotech/lilly-puts-two-thirds-mid-phase-cancer-pipeline-up-for-sale-major-shake-up-r-d-priorities) after a series of clinical trials in solid tumors (ClinicalTrials.gov identifier: NCT02737072, NCT01391130, and NCT01439568). These events indicate that development of CXCR4 antagonists as anti-cancer drugs, especially for solid tumors, is an ongoing challenge.

Other small molecule antagonists that are currently under clinical investigation, include:

USL311 (Upsher-Smith) is under phase I and phase II in patients with solid tumors and glioblastoma multiforme (GBM), respectively (ClinicalTrials.gov identifier: NCT02765165); GMI-1359 (Glycomimetics) is in phase I trial (ClinicalTrials.gov identifier: NCT02931214).

PF-06747143 (Pfizer), a humanized anti-CXCR4 antibody, is in phase I clinical trial in patients with AML either alone or combined with chemotherapy (ClinicalTrials.gov identifier: NCT02954653, (Liu et al., 2017)).

AD-114 (i-body, AdAlta; (Griffiths et al., 2018) is a humanized shark anti-CXCR4 antibody and received orphan drug designation from united states FDA for a drug candidate used for treatment of Idiopathic Pulmonary Fibrosis in 2017 (https://www.reuters.com/article/idUSFWN1F70Y0). AD-114 study is mainly focused on fibrotic conditions, including wet age-related macular degeneration and non-alcoholic fatty liver disease (https://lungdiseasenews.com/2017/08/23/adalta-present-research-on-investigative-therapy-ad-114-at-ipf-summit/).

POL6326 (balixafortide, Polyphor), a peptide CXCR4 antagonist, has been under clinical evaluation in subjects with breast cancer (ClinicalTrials.gov identifier: NCT01837095), hematologic malignancies (ClinicalTrials.gov identifier: NCT01413568), and stem cell mobilization and healing in patients with acute myocardial infarction (ClinicalTrials.gov identifier: NCT01905475).

Radiolabeled CXCR4 ligands such as [99mTc]O2-AMD3100 and [68Ga]Pentixafor has been used for preclinical or clinical SPECT or PET imaging of CXCR4 expression (Demmer et al., 2011; Gourni et al., 2011; Hartimath et al., 2013; Walenkamp et al., 2017). PET imaging with [68Ga] Pentixafor has demonstrated increased expression of CXCR4 not only in hematologic and solid tumors such as leukemia, lymphoma, MM, adrenocortical carcinoma, and SCLC, but also in other pathological conditions such as splenosis, stroke, atherosclerosis, and myocardial infarction (Walenkamp et al., 2017).

A peptide CXCR4 ligand labeled with α- or β-emitters ([177Lu]pentixather and [90Y]pentixather) has been tested in more than 30 therapies as CXCR4-directed endoradio-therapy together with standard chemotherapy in patients with hematologic malignancies (Walenkamp et al., 2017).

Although various drugs antagonizing CXCR4 or antibody targeting CXCR4 have been developed and are under investigation, be it alone, in combination with conventional anticancer therapies, or with an immune checkpoint inhibitor, success has been limited so far (Peled, et al., 2012, Debnath, et al., 2013, Walenkamp, et al., 2017). Due to the pivotal roles of CXCR4 in B and T lymphocyte development and immune surveillance, long-term or persistent inhibition of CXCR4 with CXCR4 antagonist would potentially evoke immune system and hematopoietic dysfunctions and expose cancer patients to risk of immune suppression (Burger, 2009). Hematopoietic stem cells (HSCs) are normally protected in bone marrow niches. If CXCR4 antagonists are administered with cytotoxic drugs or radiotherapy, HSCs mobilized into periphery would be exposed to the effects of cytotoxic treatment which could exacerbate cytopenias. Cardiac complications observed in patients treated with AMD3100 also raised general concern in prolonged use of CXCR4 antagonists as anticancer drugs.

To avoid potential side effects associated with conventional CXCR4 antagonists and to develop more efficient anti-cancer drugs targeting CXCR4, new paradigm for designing CXCR4 inhibitor is urgently required.

Recently, GPCR heteromers offer new possibilities for developing more specific and disease-restricted therapeutics. Traditionally, GPCRs were considered to be monomeric since monomeric GPCRs can activate G proteins by inducing conformational changes of the heptahelical domain upon ligand binding (Pin et al., 2008; Okada et al., 2001). However, increasing evidence demonstrates that GPCRs may form oligomers, either homo- or hetero-oligomers, and GPCR heteromers can exhibit specific properties that clearly distinguish them from existing well-defined monomers, such as signaling pathways, ligand binding affinities, internalization, and recycling (De Falco et al., 2007; Ferre et al., 2010; Gomes et al., 2016). Therefore, GPCR oligomerization may provide a way to increase the diversity of GPCR entities with a limited number of genes (Park and Palczewski, 2005). Thus, identification of novel GPCR heteromers would offer new possibilities for understanding the roles of GPCR heteromers in specific tissues and in specific diseases, as well as providing new opportunities for developing more efficient therapeutics with less side effects. (Milligan 2008; Rozenfeld and Devi 2010; Gomes et al., 2016; Farran 2017).

CXCR4 also forms heteromers with different GPCRs. So far CXCR4 is known to interact with GPCRs in the chemokine receptor family (CCR2 (Rodriguez-Frade et al., 2004; Sohy et al., 2007; Sohy et al., 2009; Armando et al., 2014), CCR5 (Agrawal et al., 2004; Rodriguez-Frade et al., 2004; Sohy et al., 2007, Sohy et al., 2009; Martinez-Munoz et al., 2014), CXCR3 (Watts et al., 2013), and CXCR7 (Sierro et al., 2007; Levoye et al., 2009; Decaillot et al., 2011)), chemerin chemokine-like receptor 1 (CMKLR1) (de Poorter et al., 2013), δ-opioid receptor (OPRD) (Pello et al. 2008; Burbassi et al., 2010), and adrenergic receptor family (ADRA1A (Tripathi et al., 2015), ADRA1B (Tripathi et al., 2015), and ADRB2 (LaRocca et al. 2010; Nakai et al., 2014)).

The existence of CXCR4-CCR2 and CXCR4-CCR5 heteromers was first noticed by studying HIV infection. Rodriguez-Frade et al. showed that CCR2-01, a CCR2-specific monoclonal antibody, did not compete with CCL2 for binding to CCR2 or trigger CCR2 signaling, but blocked replication of monotropic (R5) and T-tropic (X4) HIV strains by inducing oligomerization of CCR2 with CCR5 or CXCR4 (Rodriguez-Frade et al., 2004). Agrawal et al. also showed that CCR5Δ32 specifically inhibited CCR5 and CXCR4 cell surface expression by heteromerization with CCR5 and CXCR4, thereby inhibiting HIV coreceptor activity of CCR5 and CXCR4 in CD4+ cells (Agrawal et al., 2004). Co-expression of CCR5 was shown to prevent HIV-1 gp120 binding to the cell surface and to reduce X4 HIV-1 infectivity by inducing CCR5-CD4-CXCR4 oligomerization and conformational changes in CD4 and CXCR4 (Martinez-Munoz et al., 2014).

Sohy et al. reported the existence of negative binding cooperativity between the subunits of CXCR4-CCR2 and CXCR4-CCR5 heteromers, i.e. the ligands of one receptor competed for the binding of a specific tracer of the other, in recombinant cell lines and primary leukocytes (Sohy et al., 2007; Sohy et al., 2009). They also demonstrated that TAK-779, the CCR2 and CCR5 antagonist, prevented calcium mobilization and chemotaxis initiated by the CXCR4 agonist CXCL12 in cells co-expressing CCR2 and CXCR4 or CCR5 and CXCR4 (Sohy et al., 2007; Sohy et al., 2009). Armando et al. showed that CXCR4 and CCR2 can form homo- and hetero-oligomers, and co-activation of CCR2 and CXCR4 with the human monocyte chemotactic protein 1 (MCP-1) and CXCL12 caused a synergistic increase in calcium mobilization (Armando et al., 2014).

Watts et al. identified CXCR4-CXCR3 heteromers in HEK293T cells and showed negative binding cooperativity for endogenous agonists and small CXCR3 agonist VUF10661, but not for CXCR3 antagonists VUF10085 nor CXCR4 antagonist AMD3100 (Watts et al., 2013).

CXCR4 also interacts with ACKR3, also known as CXCR7, a chemokine family GPCR that binds the CXCL12 and CXCL11, but is unable to couple with G proteins upon agonist binding. Sierro et al. identified CXCR4-ACKR3 heteromers as functional heteromers that displayed enhanced CXCL12-induced calcium signaling and altered ERK1/2 signaling in HEK293 cells (Sierro et al., 2007). Lovoye et al., reported an opposite result showing that CXCR4-ACKR3 heteromers exhibited reduced Gai and calcium responses upon exposure to CXCL12 in CHO-K1 cells (Levoye et al., 2009). Decaillot et al. noticed that co-expression of CXCR4 and ACKR3 constitutively recruited β-arrestin to CXCR4/ACKR3 heteromers and potentiated CXCL12-mediated β-arrestin-dependent downstream signaling pathways, including ERK1/2, p38 MAPK, and enhanced cell migration upon exposure to CXCL12 (Decaillot et al., 2011).

CXCR4 also interacts with the chemerin chemokine-like receptor 1 (CMKLR1, also known as ChemR23) (de Poorter et al., 2013). Although CXCR4-CMKLR1 heteromers display negative agonist binding cooperativity similar to CXCR4-CCR2 and CXCR4-CCR5 heteromers reported by Sohy et al. (Sohy et al., 2007; Sohy et al., 2009), AMD3100 did not cross inhibit chemerin binding or inhibit calcium mobilization induced by CXCL12 (de Poorter et al., 2013).

CXCR4 and the δ-opioid receptor (DOR) are widely distributed in brain tissues and immune cells. Pello et al. reported that CXCR4 and DOR can form heteromers, and simultaneous stimulation with both agonists suppressed the activation of Gai signaling, and prevented cell migration toward CXCL12, although individual agonist elicit robust Gai signaling (Pello et al., 2008). Burbassi et al. also noticed increased CXCR4-DOR heteromers and reduced coupling of CXCR4 to G-proteins in brain tissue and cultured glia from μ-opioid receptor (MOR)-deficient mice (Burbassi et al., 2010). CXCR4 function was rescued with a DOR antagonist, indicating that DOR is involved in the suppression of CXCR4 in glia by forming CXCR4-DOR heteromers (Burbassi et al., 2010).

CXCR4 is also known to interact with α- and β-adrenergic receptors (α-AR and β-AR). LaRocca et al. reported that stimulation of CXCR4 with CXCL12 negatively regulates β-AR-induced cAMP accumulation and PKA-dependent phosphorylation of phospholamban in adult rat ventricular myocytes using non-selective β-AR agonist, isoproterenol (LaRocca et al., 2010). They showed the co-expression of CXCR4 and ADRB2 (β2-AR) on the cardiac myocytes, and physical association of CXCR4 with ADRB2 using co-immunoprecipitation and bioluminescence resonance energy transfer, suggesting the CXCR4-ADRB2 heteromer as a novel cardiac modulator.

Nakai et al. studied the function of ADRB2 on lymphocytes. Stimulation of lymphocytes with ADRB2-selective agonists suppressed egress of lymphocytes from lymph nodes and produced lymphopenia in mice (Nakai et al., 2014). ADRB2 physically interacted with CCR7 and CXCR4, and activation of ADRB2 enhanced retention-promoting signals through CCR7-ADRB2 and CXCR4-ADRB2 heteromers, and subsequently reduced lymphocyte egress from lymph nodes.

Tripathi et al. revealed the presence of CXCR4-ADRA1A ($\alpha$1A-AR) and CXCR4-ADRA1B ($\alpha$1B-AR) heteromers on the surface of vascular smooth muscle cells (VSMC) (Tripathi et al., 2015). A peptide derived from the second transmembrane helix of CXCR4 disrupted the interaction between ADRA1A/B and CXCR4, inhibited calcium mobilization and contraction of VSMC upon $\alpha$1-AR stimulation. Activation of CXCR4 with CXCL12 increased the potency of $\alpha$1-AR agonists on blood pressure response in rats, suggesting that CXCR4-ADRA1A/B heteromers could be a novel pharmacological target for blood pressure regulation.

CXCR4 was reported to interact with CNR2 (Cannabinoid Receptor 2, aka CB2) (Coke et al., 2016; Scarlett et al., 2018). Simultaneous activation of CXCR4 and CB2 with both agonists resulted in reduction of ERK1/2 activation, calcium mobilization and cellular chemotaxis. These results show that cannabinoid system can negatively modulate CXCR4 function and tumor progression.

As described above, GPCRs forming heteromers with CXCR4 have been studied within a limited number of GPCR families, such as chemokine, adrenergic, and opioid receptor families. Considering the major role and increased expression of CXCR4 in a variety of pathological conditions, there is a great potential for the existence of different CXCR4-GPCRx heteromers that confer unique features to a specific disease. However, due to the large number of GPCR genes (about 800) and difficulties in establishing high-throughput proximity-based screening techniques and functional assays, the identification of new CXCR4-GPCRx heteromers has been a major challenge.

Thus, there exists in the art a need for identifying functional GPCR heteromers, such as CXCR4-GPCRx, and developing their inhibitors for use as GPCR heteromer-targeting cancer therapeutics with higher efficacy and lower side effects. This invention satisfies this need and provides related advantages.

SUMMARY OF THE INVENTION

By the use of adenovirus high-throughput system (AdHTS) that allows rapid and efficient generation of multiple recombinant adenoviruses simultaneously (Choi, et al., 2012), and the adenovirus-based bimolecular fluorescence complementation (BiFC) assay (patent; Song, 2014), inventors screened large number of GPCRs for their association with CXCR4 in U-2 OS cells.

In one aspect, provided herein is a method for treatment, amelioration, prevention, or diagnosis, of a cancer in a subject having CXCR4-GPCRx heteromer, the method comprising: administering to the subject a therapeutically effective amount of an inhibitor of a CXCR4-GPCRx heteromer, wherein: GPCRx heteromerizes with CXCR4 in the subject, the heteromerization of GPCRx with CXCR4 is accompanied by enhancement of signaling downstream of CXCR4; and the enhancement of signaling downstream of CXCR4 is suppressed by the inhibitor of the CXCR4-GPCRx heteromer.

In another aspect, provided herein, is a method for treating cancer in a patient having a cell containing a CXCR4-GPCRx heteromer, the method comprising: administering to the patient an inhibitor or a combination of inhibitors selected from the group consisting of: an inhibitor of CXCR4, an inhibitor of GPCRx, and an inhibitor of the CXCR4-GPCRx heteromer; wherein:
  i) the CXCR4-GPCRx heteromer has enhanced downstream signaling; and
  ii) the administered inhibitor or combination of inhibitors suppresses the enhanced downstream signaling from said CXCR4-GPCRx heteromer in the cancer patient.

In another aspect, provided herein, is a method of suppressing enhanced downstream signaling from a CXCR4-GPCRx heteromer in a cell of a patient suffering from cancer, the method comprising: administering to the patient an inhibitor or a combination of inhibitors selected from the group consisting of: an inhibitor of CXCR4, an inhibitor of GPCRx, and an inhibitor of the CXCR4-GPCRx heteromer; wherein:
  i) the CXCR4-GPCRx heteromer has enhanced downstream signaling; and
  ii) the administered inhibitor or combination of inhibitors suppresses the enhanced downstream signaling from said CXCR4-GPCRx heteromer in the cancer patient.

In another aspect, provided herein, is a pharmaceutical kit for use in treating cancer in a patient having a cell containing a CXCR4-GPCRx heteromer, the pharmaceutical kit comprising: an inhibitor or a combination of inhibitors selected from the group consisting of: an inhibitor of CXCR4, an inhibitor of GPCRx, and an inhibitor of the CXCR4-GPCRx heteromer; wherein the CXCR4-GPCRx heteromer has enhanced downstream signaling.

In another aspect, provided herein, is a pharmaceutical composition for use in treating cancer in a patient having a cell containing a CXCR4-GPCRx heteromer, the pharmaceutical composition comprising:
  i) an inhibitor or a combination of inhibitors selected from the group consisting of: an inhibitor of CXCR4, an inhibitor of GPCRx, and an inhibitor of the CXCR4-GPCRx heteromer; and
  ii) a pharmaceutically acceptable carrier;
wherein the CXCR4-GPCRx heteromer has enhanced downstream signaling.

In another aspect, provided herein, is a method for treating cancer in a patient having a cancer cell containing a CXCR4-GPCRx heteromer, wherein the CXCR4-GPCRx heteromer has enhanced downstream signaling, the method comprising:
  1) determining whether the patient has the cancer cell containing the CXCR4-GPCRx heteromer having enhanced downstream signaling by: obtaining or having obtained a biological sample from the patient; and performing or having performed an assay on the biological sample to determine if:
    i) the patient's cancer cell containing said CXCR4-GPCRx heteromer; or
    ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing the CXCR4-GP- CRx heteromer; or decreases cell proliferation of a patient derived cell(s) containing the CXCR4-GP-CRx heteromer; and 2) if the patient has a cancer cell containing said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the cancer patient.

In another aspect, provided herein, is a method for treating cancer in a patient having a cancer cell containing a CXCR4-GPCRx heteromer, the method comprising:
1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein:
   a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NT SR1, and TACR3; and
   b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, or a fluorescent animal assay; and
2) if the patient's cancer cell contains said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the patient.

In another aspect, provided herein, is a method for treating cancer in a patient having a cancer cell containing a CXCR4-GPCRx heteromer having enhanced downstream signaling, the method comprising:
1) determining whether the patient has the cancer cell containing the CXCR4-GPCRx heteromer having enhanced downstream signaling by: obtaining or having obtained a biological sample from the patient; and performing or having performed an assay on the biological sample to determine if:
   i) the patient's cancer cell contains said CXCR4-GPCRx heteromer; or
   ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing said CXCR4-GPCRx heteromer; or decreases cell proliferation of a patient derived cell(s) containing said CXCR4-GPCRx heteromer; and
2) if the patient has a cancer cell containing said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
3) if the patient does not have a cancer cell containing said CXCR4-GPCRx heteromer, then internally administering to the cancer patient either the CXCR4 inhibitor or the GPCRx inhibitor as a single inhibitor.

In another aspect, provided herein, is a method for treating cancer in a patient having a cancer cell containing a CXCR4-GPCRx heteromer, the method comprising:
1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein:
   a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; and
   b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay; and
2) if the patient's cancer cell contains said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
3) if the patient's cancer cell does not contain said CXCR4-GPCRx heteromer, then internally administering to the cancer patient either the CXCR4 inhibitor or the GPCRx inhibitor as a single inhibitor.

In certain embodiments of the method of treating, method of suppressing, pharmaceutical composition, or pharmaceutical kit, disclosed herein, the heteromerization of CXCR4 with GPCRx is evaluated by a proximity-based assay.

In certain embodiments of the method of treating, method of suppressing, pharmaceutical composition, or pharmaceutical kit, disclosed herein, the proximity-based assay is selected from the group consisting of bimolecular fluorescence complementation (BiFC), proximity ligation assay (PLA), fluorescence resonance energy transfer (FRET), bioluminescence resonance energy transfer (BRET), cysteine crosslinking, co-immunoprecipitation, and a combination of TR-FRET and SNAP-tag (Comps-Agrar et al., 2011).

In certain embodiments of the method of treating, method of suppressing, pharmaceutical composition, or pharmaceutical kit, disclosed herein, the heteromerization of CXCR4 with GPCRx is evaluated by a co-internalization assay.

In certain embodiments of the method of treating, method of suppressing, pharmaceutical composition, or pharmaceutical kit, disclosed herein, the enhancement of cell signaling downstream of CXCR4 is evaluated by an intracellular $Ca^{2+}$ assay.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, APLNR, C5AR1, CALCR, CCR5, CHRM1, GALR1, EDNRB, HRH1, MLNR, NTSR1, PTGER2, PTGER3, SSTR2, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, C5AR1, CALCR, CHRM1, EDNRB, HRH1, MLNR, NTSR1, PTGER2, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, C5AR1, CALCR, CHRM1, EDNRB, HRH1, MLNR, NTSR1, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, C5AR1, CHRM1, EDNRB, HRH1, MLNR, NTSR1, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, CHRM1, EDNRB, HRH1, MLNR, NTSR1, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, CHRM1, EDNRB, HRH1, NTSR1, and TACR3.

In certain embodiments of the method of treating, method of suppressing, pharmaceutical composition, or pharmaceutical kit, disclosed herein, GPCRx is selected from the group consisting of ADCYAP1R1, ADORA2B, ADORA3, ADRB2, CHRM1, HRH1, NTSR1, and TACR3.

In certain embodiments of the method of treating, method of suppressing, pharmaceutical composition, or pharmaceutical kit, disclosed herein, GPCRx is selected from the group consisting of ADORA2B, ADORA3, ADRB2, CHRM1, EDNRB, HRH1, NTSR1, and TACR3.

In certain embodiments of the method of treating, method of suppressing, pharmaceutical composition, or pharmaceutical kit, disclosed herein, GPCRx is selected from the group consisting of ADRB2, CHRM1, EDNRB, HRH1, NTSR1, and TACR3.

In certain embodiments of the method of treating, method of suppressing, pharmaceutical composition, or pharmaceutical kit, disclosed herein, GPCRx is selected from the group consisting of ADRB2, CHRM1, EDNRB, HRH1, and TACR3.

In certain embodiments of the method of treating, method of suppressing, pharmaceutical composition, or pharmaceutical kit, disclosed herein, GPCRx is selected from the group consisting of ADRB2, CHRM1, HRH1, and TACR3.

In certain embodiments of the method of treating, method of suppressing, pharmaceutical composition, or pharmaceutical kit, disclosed herein, GPCRx is selected from the group consisting of ADRB2, EDNRB, HRH1, and TACR3.

In certain embodiments of the method of treating, method of suppressing, pharmaceutical composition, or pharmaceutical kit, disclosed herein, GPCRx is selected from the group consisting of ADRB2, EDNRB, and HRH1.

In certain embodiments of the method of treating, method of suppressing, pharmaceutical composition, or pharmaceutical kit, disclosed herein, GPCRx is selected from the group consisting of ADRB2, CHRM1, and HRH1.

In certain embodiments of the method of treating, method of suppressing, pharmaceutical composition, or pharmaceutical kit, disclosed herein, GPCRx is selected from the group consisting of ADRB2, HRH1, and TACR3.

In certain embodiments of the method of treating, method of suppressing, pharmaceutical composition, or pharmaceutical kit, disclosed herein, GPCRx is selected from the group consisting of ADRB2 and HRH1.

In certain embodiments of the method of treating, method of suppressing, pharmaceutical composition, or pharmaceutical kit, disclosed herein, the inhibitor of the CXCR4-GPCRx heteromer is, or comprises, an inhibitor of the CXCR4.

In certain embodiments of the method of treating, method of suppressing, pharmaceutical composition, or pharmaceutical kit, disclosed herein, the inhibitor of CXCR4 is selected from the group consisting of: AD-114, AD-114-6H, AD-114-Im7-FH, AD-114-PA600-6H, ALX-0651, ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMI-1359, GSK812397, GST-NT21MP, isothiourea-1a, isothiourea-1t (IT1t), KRH-1636, KRH-3955, LY2510924, LY2624587, MSX-122, N-[$^{11}$C]Methyl-AMD3465, PF-06747143, POL6326, SDF-1 1-9 [P2G] dimer, SDF1 P2G, T134, T140, T22, TC 14012, TG-0054 (Burixafor), USL311, ulocuplumab (MDX1338/BMS-936564), viral macrophage inflammatory protein-II (vMIP-II), WZ811, 12G5, 238D2, 238D4, [$^{64}$Cu]-AMD3100, [$^{64}$Cu]-AMD3465, [$^{68}$Ga]pentixafor, [$^{90}$Y]pentixather, [$^{99m}$Tc]O$_2$-AMD3100, [$^{177}$Lu]pentixather, and 508MCl (Compound 26).

In certain embodiments of the method of treating, method of suppressing, pharmaceutical composition, or pharmaceutical kit, disclosed herein, the inhibitor of the CXCR4-GPCRx heteromer is, or comprises, an antagonist of the CXCR4.

In certain embodiments of the method of treating, method of suppressing, pharmaceutical composition, or pharmaceutical kit, disclosed herein, the antagonist of CXCR4 is selected from the group consisting of ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMI-1359, GSK812397, GST-NT21MP, isothiourea-1a, isothiourea-1t (IT1t), KRH-1636, KRH-3955, LY2510924, MSX-122, N-[11C]Methyl-AMD3465, POL6326, SDF-1 1-9[P2G] dimer, SDF1 P2G, T134, T140, T22, TC 14012, TG-0054 (Burixafor), USL311, viral macrophage inflammatory protein-II (vMIP-II), WZ 811, [64Cu]-AMD3100, [64Cu]-AMD3465, [68Ga] pentixafor, [90Y]pentixather, [99mTc]O2-AMD3100, [177Lu]pentixather, and 508MCl (Compound 26).

In certain embodiments of the method of treating, method of suppressing, pharmaceutical composition, or pharmaceutical kit, disclosed herein, the inhibitor of the CXCR4-GPCRx heteromer is, or comprises, an antibody of the CXCR4.

In certain embodiments of the method of treating, method of suppressing, pharmaceutical composition, or pharmaceutical kit, disclosed herein, the antibody of CXCR4 is selected from the group consisting of AD-114, AD-114-6H, AD-114-Im7-FH, AD-114-PA600-6H, ALX-0651, LY2624587, PF-06747143, ulocuplumab (MDX1338/BMS-936564), 12G5, 238D2, and 238D4.

In certain embodiments of the method of treating, method of suppressing, pharmaceutical composition, or pharmaceutical kit, disclosed herein, the inhibitor of the CXCR4-GPCRx heteromer is, or further comprises, an inhibitor of the GPCRx.

In certain embodiments of the method of treating, method of suppressing, pharmaceutical composition, or pharmaceutical kit, disclosed herein, the inhibitor of the GPCRx is concurrently or sequentially administered with the inhibitor of the CXCR4.

In certain embodiments of the method of treating, method of suppressing, pharmaceutical composition, or pharmaceutical kit, disclosed herein, the inhibitor of the CXCR4-GPCRx heteromer is, or comprises, an antagonist, an inverse agonist, an allosteric modulator, an antibody or binding portion thereof, a ligand, or any combinations, of GPCRx.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, C5AR1, CALCR, CHRM1, EDNRB, HRH1, MLNR, NTSR1, PTGER2, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, C5AR1, CALCR, CHRM1, EDNRB, HRH1, MLNR, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, C5AR1, CHRM1, EDNRB, HRH1, MLNR, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, CHRM1, EDNRB, HRH1, MLNR, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, CHRM1, EDNRB, HRH1, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADCYAP1R1, ADORA2B, ADORA3, ADRB2, CHRM1, HRH1, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADORA2B, ADORA3, ADRB2, CHRM1, EDNRB, HRH1, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, CHRM1, EDNRB, HRH1, NTSR1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, CHRM1, EDNRB, HRH1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, CHRM1, HRH1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, EDNRB, HRH1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, EDNRB, and HRH1.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, CHRM1, and HRH1.

In certain embodiments of the method of treating, method of suppressing, pharmaceutical composition, or pharmaceutical kit, disclosed herein, the inhibitor of GPCRx is an inhibitor of a molecule selected from the group consisting of ADRB2, HRH1, and TACR3.

In certain embodiments of the method of treating, method of suppressing, pharmaceutical composition, or pharmaceutical kit, disclosed herein, the inhibitor of GPCRx is an inhibitor of a molecule selected from the group consisting of ADRB2 and HRH1.

In certain embodiments of the method of treating, method of suppressing, pharmaceutical composition, or pharmaceutical kit, disclosed herein, the inhibitor of GPCRx is an inhibitor of ADCYAP1R1 selected from the group consisting of: M65, Max.d.4, MK-0893, N-stearyl-[Nle$^{17}$] neurotensin-(6-11)/VIP-(7-28), PACAP-(6-38), and PG 97-269.

In certain embodiments of the method of treating, method of suppressing, pharmaceutical composition, or pharmaceutical kit, disclosed herein, the inhibitor of GPCRx is an inhibitor of ADORA2B selected from the group consisting of: 3-isobutyl-8-pyrrolidinoxanthine, alloxazine, AS16, AS70, AS74, AS94, AS95, AS96, AS99, AS100, AS101, ATL802, BW-A1433, caffeine, CGS 15943, CPX, CSC, CVT-6883, DAX, DEPX, derenofylline, DPCPX, FK-453, I-ABOPX, istradefylline, KF26777, LAS38096, LUF5981, MRE 2029F20, MRE 3008F20, MRS1191, MRS1220, MRS1523, MRS1706, MRS1754, MSX-2, OSIP339391, pentoxifylline, preladenant, PSB-10, PSB-11, PSB36, PSB603, PSB-0788, PSB1115, rolofylline, SCH 58261, SCH442416, ST-1535, theophylline, tonapofylline, vipadenant, xanthine amine congener, XCC, and ZM-241385.

In certain embodiments of the method of treating, method of suppressing, pharmaceutical composition, or pharmaceutical kit, disclosed herein, the inhibitor of GPCRx is an inhibitor of ADORA3 selected from the group consisting of: ATL802, BW-A1433, caffeine, CGS 15943, CSC, CVT-6883, derenofylline, dexniguldipine, DPCPX, FK-453, flavanone, flavone, galangin, I-ABOPX, istradefylline, KF26777, LAS38096, LUF5981, MRE 2029F20, MRE 3008F20, MRE 3010F20, MRS1041, MRS1042, MRS1067, MRS1088, MRS1093, MRS1097, MRS1177, MRS1186, MRS1191, MRS1191, MRS1220, MRS1476, MRS1486, MRS1505, MRS1523, MRS1754, MRS928, MSX-2, nicardipine, preladenant, PSB-10, PSB-11, PSB36, PSB603, PSB1115, rolofylline, sakuranetin, SCH 58261, SCH442416, ST-1535, theophylline, tonapofylline, vipadenant, visnagin, VUF5574, VUF8504, VUF8507, xanthine amine congener, and ZM-241385.

In certain embodiments of the method of treating, method of suppressing, pharmaceutical composition, or pharmaceutical kit, disclosed herein, the inhibitor of GPCRx is an inhibitor of ADRB2 selected from the group consisting of: Alprenolol, atenolol, betaxolol, bupranolol, butoxamine, carazolol, carvedilol, CGP 12177, cicloprolol, ICI 118551, ICYP, labetalol, levobetaxolol, levobunolol, LK 204-545, metoprolol, nadolol, NIHP, NIP, propafenone, propranolol, sotalol, SR59230A, and timolol.

In certain embodiments of the method of treating, method of suppressing, pharmaceutical composition, or pharmaceutical kit, disclosed herein, the inhibitor of ADRB2 is Carvedilol.

In certain embodiments of the method of treating, method of suppressing, pharmaceutical composition, or pharmaceutical kit, disclosed herein, the inhibitor of GPCRx is an inhibitor of C5AR1 inhibitor is selected from the group consisting of: $A8^{\Delta71-73}$, AcPhe-Orn-Pro-D-Cha-Trp-Arg, avacopan, C089, CHIPS, DF2593A, JPE1375, L-156,602, NDT9520492, N-methyl-Phe-Lys-Pro-D-Cha-Trp-D-Arg-$CO_2H$, PMX205, PMX53, RPR121154, and W54011.

In certain embodiments of the method of treating, method of suppressing, pharmaceutical composition, or pharmaceutical kit, disclosed herein, the inhibitor of GPCRx is an inhibitor of CALCR selected from the group consisting of α-CGRP-(8-37) (human), AC187, CT-(8-32) (salmon), and olcegepant.

In certain embodiments of the method of treating, method of suppressing, pharmaceutical composition, or pharmaceutical kit, disclosed herein, the inhibitor of CALCR is AC187.

In certain embodiments of the method of treating, method of suppressing, pharmaceutical composition, or pharmaceutical kit, disclosed herein, the inhibitor of GPCRx is an inhibitor of CHRM1 selected from the group consisting of 3-Quinuclidinyl benzilate (QNB), 4-DAMP, aclidinium, AE9C9OCB, AFDX384, amitriptyline, AQ-RA 741, atropine, benzatropine, biperiden, darifenacin, dicyclomine, dosulepin, ethopropazine, glycopyrrolate, guanylpirenzepine, hexahydrodifenidol, hexahydrosiladifenidol, hexocyclium, himbacine, ipratropium, lithocholylcholine, methoctramine, ML381, muscarinic toxin 1, muscarinic toxin 2, muscarinic toxin 3, N-methyl scopolamine, otenzepad, oxybutynin, pirenzepine, propantheline, (R,R)-quinuclidinyl-4-fluoromethyl-benzilate, scopolamine, silahexocyclium, solifenacin, telenzepine, tiotropium, tolterodine, trihexyphenidyl, tripitramine, UH-AH 37, umeclidinium, and VU0255035.

In certain embodiments of the method of treating, method of suppressing, pharmaceutical composition, or pharmaceutical kit, disclosed herein, the inhibitor of CHRM1 is Oxybutynin, umeclidinium, and VU0255035.

In certain embodiments of the method of treating, method of suppressing, pharmaceutical composition, or pharmaceutical kit, disclosed herein, the inhibitor of GPCRx is an inhibitor of EDNRB selected from the group consisting of A192621, ambrisentan, atrasentan, bosentan (RO 470203, Tracleer); BQ788, IRL 2500, K-8794, macitentan, RES7011, Ro 46-8443, SB209670, SB217242 (enrasentan), TAK 044, and tezosentan (RO610612).

In certain embodiments of the method of treating, method of suppressing, pharmaceutical composition, or pharmaceutical kit, disclosed herein, the inhibitor of EDNRB is bosentan.

In certain embodiments of the method of treating, method of suppressing, pharmaceutical composition, or pharmaceutical kit, disclosed herein, the inhibitor of GPCRx is an inhibitor of HRH1 selected from the group consisting of (−)-chlorpheniramine, (+)-chlorpheniramine, (−)-trans-$H_2$-PAT, (+)-cis-$H_2$-PAT, (+)-trans-$H_2$-PAT, (±)-cis-$H_2$-PAT, (±)-trans-$H_2$-PAT, (R)-cetirizine, (S)-cetirizine, 9-OH-risperidone, A-317920, A-349821, ABT-239, alimemazine, amitriptyline, aripiprazole, arpromidine, asenapine, astemizole, AZD3778, azelastine, BU-E 47, cetirizine, chlorpheniramine, chlorpromazine, ciproxifan, clemastine, clobenpropit, clozapine, conessine, cyclizine, cyproheptadine, desloratadine, diphenhydramine, dosulepin, doxepin, epinastine, fexofenadine, fluphenazine, fluspirilene, haloperidol, hydroxyzine, impromidine, INCB-38579, JNJ-39758979, ketotifen, loratadine, loxapine, MK-0249, molindone, olanzapine, perphenazine, pimozide, pipamperone, pitolisant, promethazine, pyrilamine, quetiapine, risperidone, sertindole, terfenadine, thioridazine, thiothixene, trifluoperazine, tripelennamine, triprolidine, ziprasidone, and zotepine.

In certain embodiments of the method of treating, method of suppressing, pharmaceutical composition, or pharmaceutical kit, disclosed herein, the inhibitor of HRH1 is cetirizine, pyrilamine, hydroxyzine, or loratadine.

In certain embodiments of the method of treating, method of suppressing, pharmaceutical composition, or pharmaceutical kit, disclosed herein, the inhibitor of GPCRx is an inhibitor of MLNR selected from the group consisting of GM-109, MA-2029, and OHM-11526.

In certain embodiments of the method of treating, method of suppressing, pharmaceutical composition, or pharmaceutical kit, disclosed herein, the inhibitor of MLNR is MA-2029.

In certain embodiments of the method of treating, method of suppressing, pharmaceutical composition, or pharmaceutical kit, disclosed herein, the inhibitor of GPCRx is an inhibitor of NTSR1 selected from the group consisting of Meclinertant, SR48527, SR48692, and SR142948A.

In certain embodiments of the method of treating, method of suppressing, pharmaceutical composition, or pharmaceutical kit, disclosed herein, the inhibitor of NTSR1 is Meclinertant.

In certain embodiments of the method of treating, method of suppressing, pharmaceutical composition, or pharmaceutical kit, disclosed herein, the inhibitor of GPCRx is an inhibitor of TACR3 selected from the group consisting of [$Trp^7$, $\beta$-$Ala^8$] neurokinin A-(4-10), AZD2624, FK 224, GR138676, GSK 172981, GSK 256471, N',2-diphenylquinoline-4-carbohydrazide 8m, N',2-diphenylquinoline-4-carbohydrazide, osanetant, PD 154740, PD 161182, PD157672, saredutant, SB 218795, SB 222200, SB 235375, SCH 206272, SSR 146977, and talnetant.

In certain embodiments of the method of treating, method of suppressing, pharmaceutical composition, or pharmaceutical kit, disclosed herein, the inhibitor of TACR3 is SSR146977.

In certain embodiments of the method of treating, method of suppressing, pharmaceutical composition, or pharmaceutical kit, disclosed herein, the inhibitor of the CXCR4-GPCRx heteromer is a protein-protein interaction (PPI) inhibitor.

In certain embodiments of the method of treating, method of suppressing, pharmaceutical composition, or pharmaceutical kit, disclosed herein, the cancer is selected from the group consisting of breast cancer, lung cancer, brain cancer, kidney cancer, pancreatic cancer, ovarian cancer, prostate cancer, melanoma, multiple myeloma, gastrointestinal cancers, renal cell carcinoma, soft tissue sarcomas, hepatocellular carcinoma, stomach cancer, colorectal cancer, esophageal cancer, and leukemia.

In certain embodiments of the method of treating, method of suppressing, pharmaceutical composition, or pharmaceutical kit, disclosed herein, the inhibitor of CXCR4-GPCRx heteromer is administered to the subject in a pharmaceutical composition.

Further disclosed herein is a method for assessing response, or potential response, of a subject having CXCR4-GPCRx heteromer, to treatment, amelioration, or prevention of a cancer, the method comprising: obtaining a sample from the subject; detecting heteromerization of CXCR4 and GPCRx in the sample; and based at least in part on detection of the heteromerization of CXCR4 and GPCRx, assessing the subject's response, or potential response, to the treatment, amelioration, or prevention of a cancer.

In certain embodiments of the method of treating, method of suppressing, pharmaceutical composition, or pharmaceutical kit, disclosed herein, the heteromerization of CXCR4 and GPCRx is accompanied by enhancement of signaling downstream of CXCR4.

In certain embodiments of the method of treating, method of suppressing, pharmaceutical composition, or pharmaceutical kit, disclosed herein, the enhancement of cell signaling downstream of CXCR4 is evaluated by an intracellular Ca2+ assay.

In certain embodiments of the method of treating, method of suppressing, pharmaceutical composition, or pharmaceutical kit, disclosed herein, the heteromerization of CXCR4 with GPCRx is evaluated by a proximity-based assay.

In certain embodiments of the method of treating, method of suppressing, pharmaceutical composition, or pharmaceutical kit, disclosed herein, the proximity-based assay is selected from the group consisting of bimolecular fluorescence complementation (BiFC), proximity ligation assay (PLA), fluorescence resonance energy transfer (FRET), bioluminescence resonance energy transfer (BRET), cysteine crosslinking, and co-immunoprecipitation.

In certain embodiments of the method of treating, method of suppressing, pharmaceutical composition, or pharmaceutical kit, disclosed herein, the heteromerization of CXCR4 with GPCRx is evaluated by a co-internalization assay.

In certain embodiments of the method of treating, method of suppressing, pharmaceutical composition, or pharmaceutical kit, disclosed herein, the CXCR4-GPCRx heteromer has, causes, or produces, the enhanced downstream signaling.

In certain embodiments of the method of treating, method of suppressing, pharmaceutical composition, or pharmaceutical kit, disclosed herein, the enhanced downstream signaling results from the CXCR4-GPCRx heteromer, such as results from agonism of the CXCR4-GPCRx heteromer, results from CXCR4 agonism of the CXCR4-GPCRx heteromer, or results from GPCRx agonism of the CXCR4-GPCRx heteromer.

In certain embodiments of the method of treating, method of suppressing, pharmaceutical composition, or pharmaceutical kit, disclosed herein, the enhanced downstream signaling is downstream of the CXCR4, the respective GPCRx, or the CXCR4-GPCRx heteromer.

In certain embodiments of the method of treating, method of suppressing, pharmaceutical composition, or pharmaceutical kit, disclosed herein, the inhibitor or combination of inhibitors suppresses the enhanced downstream signaling from said CXCR4-GPCRx heteromer in the cancer patient, such as suppresses the enhanced downstream signaling from said CXCR4-GPCRx heteromer in the patient's cancer cells.

In certain embodiments of the method of treating, method of suppressing, pharmaceutical composition, or pharmaceutical kit, disclosed herein, the enhanced downstream signaling from the CXCR4-GPCRx heteromer is determined by an intracellular Ca2+ assay.

In certain embodiments of the method of treating, method of suppressing, pharmaceutical composition, or pharmaceutical kit, disclosed herein, the enhanced downstream signaling is an enhanced amount of calcium mobilization.

In certain embodiments of the method of treating, method of suppressing, pharmaceutical composition, or pharmaceutical kit, disclosed herein, the enhanced amount of calcium mobilization is a synergistic amount of calcium mobilization.

In certain embodiments of the method of treating, method of suppressing, pharmaceutical composition, or pharmaceutical kit, disclosed herein, the CXCR4-GPCRx heteromer has two or more of the following characteristics:

1) the CXCR4-GPCRx heteromer components in a cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, or a fluorescent animal assay;

2) an enhanced amount of calcium mobilization, such that: a) either CXCR4 or the respective GPCRx in an individual protomer context in a cell, upon co-stimulation with CXCL12 and a respective selective GPCRx agonist, results in a calcium mobilization amount that is equal to or less than the sum of calcium mobilization amounts resulting from single agonist stimulation with either the CXCL12 or the respective selective GPCRx agonist; and b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist; as determined via a calcium mobilization assay; or 3) a CXCR4-GPCRx heteromer-selective reagent: i) alters heteromer-specific properties of the CXCR4-GPCRx heteromer in a patient derived cell, ii) alters heteromer-specific function of the CXCR4-GPCRx heteromer in a patient derived cell; iii) alters heteromer-specific properties of a patient derived cell containing the CXCR4-GPCRx heteromer; or iv) decreases cell proliferation of a patient derived cell(s) containing the CXCR4-GPCRx heteromer.

In certain embodiments of the method of treating, method of suppressing, pharmaceutical composition, or pharmaceutical kit, disclosed herein, the CXCR4-GPCRx heteromer components in the cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, or a fluorescent animal assay.

In certain embodiments of the method of treating, method of suppressing, pharmaceutical composition, or pharmaceutical kit, disclosed herein, the proximity-based assay is, or comprises, resonance energy transfer (RET), bioluminescence RET (BRET), fluorescence RET (FRET), time-resolved fluorescence RET (TR-FRET), antibody-aided FRET, ligand-aided FRET, bimolecular fluorescence complementation (BiFC), or a proximity ligation assay (PLA).

In certain embodiments of the method of treating, method of suppressing, pharmaceutical composition, or pharmaceutical kit, disclosed herein, the CXCR4-GPCRx heteromer exhibits the enhanced amount of calcium mobilization, such that:

a) either the CXCR4 or the respective GPCRx in an individual protomer context in the cell upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist; and b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist;

as determined via a calcium mobilization assay.

In certain embodiments of the method of treating, method of suppressing, pharmaceutical composition, or pharmaceutical kit, disclosed herein, the CXCR4-GPCRx heteromer-selective reagent: i) alters heteromer-specific properties of the CXCR4-GPCRx heteromer in the patient derived cell; ii) alters heteromer-specific function of the CXCR4-GPCRx heteromer in the patient derived cell; iii) alters heteromer-specific properties of the patient derived cell containing the CXCR4-GPCRx heteromer; or iv) decreases cell proliferation of the patient derived cell containing the CXCR4-GPCRx heteromer.

In certain embodiments of the method of treating, method of suppressing, pharmaceutical composition, or pharmaceutical kit, disclosed herein, the CXCR4-GPCRx heteromer-selective reagent is a CXCR4 inhibitor, a GPCRx inhibitor, or a CXCR4-GPCRx heteromer inhibitor.

In certain embodiments of the method of treating, method of suppressing, pharmaceutical composition, or pharmaceutical kit, disclosed herein, the CXCR4-GPCRx heteromer-selective reagent is a CXCR4 antagonist, a GPCRx antagonist, or a CXCR4-GPCRx heteromer antagonist.

In certain embodiments of the method of treating, method of suppressing, pharmaceutical composition, or pharmaceutical kit, disclosed herein, the method administers an inhibitor selected from the group consisting of: the CXCR4 inhibitor, the GPCRx inhibitor, or the CXCR4-GPCRx heteromer inhibitor.

In certain embodiments of the method of treating, method of suppressing, pharmaceutical composition, or pharmaceutical kit, disclosed herein, the inhibitor is administered as a pharmaceutical composition.

In certain embodiments of the method of treating, method of suppressing, pharmaceutical composition, or pharmaceutical kit, disclosed herein, the administered inhibitor is the CXCR4 inhibitor.

In certain embodiments of the method of treating, method of suppressing, pharmaceutical composition, or pharmaceutical kit, disclosed herein, the administered inhibitor is the GPCRx inhibitor.

In certain embodiments of the method of treating, method of suppressing, pharmaceutical composition, or pharmaceutical kit, disclosed herein, the administered inhibitor is the inhibitor of the CXCR4-GPCRx heteromer.

In certain embodiments of the method of treating, method of suppressing, pharmaceutical composition, or pharmaceutical kit, disclosed herein, the method administers the combination of inhibitors selected from the group consisting of: the CXCR4 inhibitor, the GPCRx inhibitor, and the inhibitor of the CXCR4-GPCRx heteromer.

In certain embodiments of the method of treating, method of suppressing, pharmaceutical composition, or pharmaceutical kit, disclosed herein, the combination of inhibitors are administered sequentially, concurrently, or simultaneously.

In certain embodiments of the method of treating, method of suppressing, pharmaceutical composition, or pharmaceutical kit, disclosed herein, the CXCR4 inhibitor is an antagonist of CXCR4, an inverse agonist of CXCR4, a partial antagonist of CXCR4, an allosteric modulator of CXCR4, an antibody of CXCR4, an antibody fragment of CXCR4, a ligand of CXCR4, or an antibody-drug conjugate of CXCR4.

In certain embodiments of the method of treating, method of suppressing, pharmaceutical composition, or pharmaceutical kit, disclosed herein, the GPCRx inhibitor is an antagonist of GPCRx, an inverse agonist of GPCRx, a partial antagonist of GPCRx, an allosteric modulator of GPCRx, an antibody of GPCRx, an antibody fragment of GPCRx, a ligand of GPCRx, or an antibody-drug conjugate of GPCRx.

In certain embodiments of the method of treating, method of suppressing, pharmaceutical composition, or pharmaceutical kit, disclosed herein, the inhibitor of the CXCR4-GPCRx heteromer is an antagonist of the CXCR4-GPCRx heteromer, an inverse agonist of the CXCR4-GPCRx heteromer, a partial antagonist of the CXCR4-GPCRx heteromer, an allosteric modulator of the CXCR4-GPCRx heteromer, an antibody of the CXCR4-GPCRx heteromer, an antibody fragment of the CXCR4-GPCRx heteromer, a ligand of the CXCR4-GPCRx heteromer, a protein-protein interaction (PPI) inhibitor of the CXCR4-GPCRx heteromer, or an antibody-drug conjugate of the CXCR4-GPCRx heteromer.

In certain embodiments of the method of treating or method of suppressing, disclosed herein, the method further comprises detecting the CXCR4-GPCRx heteromer in the cancer patient.

In certain embodiments of the method of treating or method of suppressing, disclosed herein, the method further comprises identifying the CXCR4-GPCRx heteromer in the cancer patient.

In certain embodiments of the method of treating, method of suppressing, pharmaceutical composition, or pharmaceutical kit, disclosed herein, the method further comprises:

i) obtaining or having obtained a biological sample from the cancer patient;

ii) conducting or having conducted a diagnostic assay to determine presence, identity, or presence and identity, of a CXCR4-GPCRx heteromer in the obtained biological sample from the cancer patient; and iii) selecting the inhibitor or combination of inhibitors to suppress enhanced downstream signaling from the CXCR4-GPCRx heteromer.

In certain embodiments of the method of treating or method of suppressing, disclosed herein, the patient's biological sample is a biological fluid sample or a biological tissue sample.

In certain embodiments of the method of treating or method of suppressing, disclosed herein, a liquid biopsy is performed on the biological fluid sample or the biological tissue sample.

In certain embodiments, the biological fluid sample includes circulating tumor cells (CTCs), tumor-derived cell-free DNA (cfDNA), circulating small RNAs, and extracellular vesicles including exosomes, from bodily fluids as disclosed, for example, in Campos C D M et al., "Molecular Profiling of Liquid Biopsy Samples for Precision Medicine,"

Cancer J. 2018 March/April; 24(2):93-103, which is incorporated hereby in its entirety.

In certain embodiments of the method of treating or method of suppressing, disclosed herein, the biological fluid sample is a blood sample, a plasma sample, a saliva sample, a cerebral fluid sample, an eye fluid sample, or a urine sample.

In certain embodiments of the method of treating or method of suppressing, disclosed herein, the biological tissue sample is an organ tissue sample, a bone tissue sample, or a tumor tissue sample.

In certain embodiments of the method of treating, method of suppressing, pharmaceutical composition, or pharmaceutical kit, disclosed herein, the cancer cell contains the CXCR4-GPCRx heteromer.

In certain embodiments of the method of treating, method of suppressing, pharmaceutical composition, or pharmaceutical kit, disclosed herein, a normal, non-cancerous cell, does not contain the CXCR4-GPCRx heteromer.

In certain embodiments of the method of treating, method of suppressing, pharmaceutical composition, or pharmaceutical kit, disclosed herein, the progression of the cancer in the patient having said cancer cell containing the CXCR4-GPCRx heteromer is decreased in the range of 5-100% more upon administration of the combination of inhibitors, relative to administering the CXCR4 inhibitor or GPCRx inhibitor as the single inhibitor to said patient.

In certain embodiments of the method of treating, method of suppressing, pharmaceutical composition, or pharmaceutical kit, disclosed herein, the efficacy of a CXCR4 inhibitor is increased in the range of 5-2000% when administered in combination with the GPCRx inhibitor to the patient having said cancer cell containing the CXCR4-GPCRx heteromer, relative to efficacy of the CXCR4 inhibitor when administered as a single inhibitor.

In certain embodiments of the method of treating, method of suppressing, pharmaceutical composition, or pharmaceutical kit, disclosed herein, the efficacy of a GPCRx inhibitor is increased in the range of 5-2000% when administered in combination with the CXCR4 inhibitor to the patient having said cancer cell containing the CXCR4-GPCRx heteromer, relative to efficacy of the GPCRx inhibitor when administered as a single inhibitor.

In certain embodiments of the method of treating, method of suppressing, pharmaceutical composition, or pharmaceutical kit, disclosed herein, the progression of the cancer in the patient having said cancer cell containing the CXCR4-GPCRx heteromer is decreased in the range of 5-100% more upon administration of the combination of inhibitors, relative to administering the CXCR4 inhibitor or GPCRx inhibitor as the single inhibitor to said patient.

In certain embodiments of the method of treating, method of suppressing, pharmaceutical composition, or pharmaceutical kit, disclosed herein, the efficacy of a CXCR4 inhibitor is increased in the range of 5-2000% when administered in combination with the GPCRx inhibitor to the patient having said cancer cell containing the CXCR4-GPCRx heteromer, relative to efficacy of the CXCR4 inhibitor when administered as a single inhibitor.

In certain embodiments of the method of treating, method of suppressing, pharmaceutical composition, or pharmaceutical kit, disclosed herein, the efficacy of a GPCRx inhibitor is increased in the range of 5-2000% when administered in combination with the CXCR4 inhibitor to the patient having said cancer cell containing the CXCR4-GPCRx heteromer, relative to efficacy of the GPCRx inhibitor when administered as a single inhibitor.

In certain embodiments of the method of treating, method of suppressing, pharmaceutical composition, or pharmaceutical kit, disclosed herein, the method administers a combination of inhibitors selected from the group consisting of: an inhibitor of CXCR4, an inhibitor of GPCRx, and an inhibitor of the CXCR4-GPCRx heteromer.

In certain embodiments of the method of treating, method of suppressing, pharmaceutical composition, or pharmaceutical kit, disclosed herein, the method administers a combination of a CXCR4 inhibitor and a GPCRx inhibitor.

In certain embodiments of the method of treating, method of suppressing, pharmaceutical composition, or pharmaceutical kit, disclosed herein, the method administers a CXCR4-GPCRx heteromer inhibitor.

In certain embodiments of the method of treating, method of suppressing, pharmaceutical composition, or pharmaceutical kit, disclosed herein, the administering of the combination of inhibitors suppresses the enhanced downstream signaling from said CXCR4-GPCRx heteromer in the cancer patient in the range of between 5-2000 fold, relative to single inhibitor administration.

In certain embodiments of the method of treating, method of suppressing, pharmaceutical composition, or pharmaceutical kit, disclosed herein, the administering of the combination of inhibitors suppresses the enhanced downstream signaling from said CXCR4-GPCRx heteromer in the cancer patient in the range of between 5-1500 fold, relative to single inhibitor administration.

In certain embodiments of the method of treating, method of suppressing, pharmaceutical composition, or pharmaceutical kit, disclosed herein, the administering of the combination of inhibitors suppresses the enhanced downstream signaling from said CXCR4-GPCRx heteromer in the cancer patient in the range of between 500-1500 fold, relative to single inhibitor administration.

In certain embodiments of the method of treating, method of suppressing, pharmaceutical composition, or pharmaceutical kit, disclosed herein, the administering of the inhibitor or combination of inhibitors suppresses the enhanced downstream signaling from said CXCR4-GPCRx heteromer in the cancer patient in the range of between 5-2000 fold, relative to suppression of downstream signaling from either a CXCR4 protomer or a GPCRx protomer in their respective individual protomer context.

In certain embodiments of the method of treating, method of suppressing, pharmaceutical composition, or pharmaceutical kit, disclosed herein, the administering of the inhibitor or combination of inhibitors suppresses the enhanced downstream signaling from said CXCR4-GPCRx heteromer in the cancer patient in the range of between 5-1500 fold, relative to suppression of downstream signaling from either a CXCR4 protomer or a GPCRx protomer in their respective individual protomer context.

In certain embodiments of the method of treating, method of suppressing, pharmaceutical composition, or pharmaceutical kit, disclosed herein, the administering of the inhibitor or combination of inhibitors suppresses the enhanced downstream signaling from said CXCR4-GPCRx heteromer in the cancer patient in the range of between 500-1500 fold, relative to suppression of downstream signaling from either a CXCR4 protomer or a GPCRx protomer in their respective individual protomer context.

In certain embodiments of the method of treating, method of suppressing, pharmaceutical composition, or pharmaceutical kit, disclosed herein, the cancer cell of the patient contains the CXCR4-GPCRx heteromer in a greater concentration than a normal, non-cancerous cell from said patient, In certain embodiments of the method of treating, method of suppressing, pharmaceutical composition, or pharmaceutical kit, disclosed herein, the presence of the CXCR4-GPCRx heteromer in the cancer cell of the patient identifies a sub-population of CXCR4-mediated cancer patients.

In certain embodiments of the method of treating, method of suppressing, pharmaceutical composition, or pharmaceutical kit, disclosed herein, the presence of the CXCR4-GPCRx heteromer in the cancer cell of the patient is a biomarker of a sub-population of CXCR4-mediated cancer patients.

In certain embodiments of the method of treating, method of suppressing, pharmaceutical composition, or pharmaceutical kit, disclosed herein, the biomarker of the sub-population of CXCR4-mediated cancer patients allows for precision medicine, patient stratification, or patient classification.

In certain embodiments of the method of treating, method of suppressing, pharmaceutical composition, or pharmaceutical kit, disclosed herein, the biomarker of the sub-population of CXCR4-mediated cancer patients allows for GPCR-based precision cancer therapeutics.

In certain embodiments of the method of treating, method of suppressing, pharmaceutical composition, or pharmaceutical kit, disclosed herein, the inhibitor is an antibody.

In certain embodiments of the method of treating, method of suppressing, pharmaceutical composition, or pharmaceutical kit, disclosed herein, the CXCR4-GPCRx heteromer-selective reagent is an antibody.

In certain embodiments of the method of treating, method of suppressing, pharmaceutical composition, or pharmaceutical kit, disclosed herein, the antibody is a bi-specific antibody of the CXCR4-GPCRx heteromer.

In certain embodiments of the method of treating, method of suppressing, pharmaceutical composition, or pharmaceutical kit, disclosed herein, the antibody is a heteromer-specific antibody of the CXCR4-GPCRx heteromer.

In certain embodiments of the method of treating, method of suppressing, pharmaceutical composition, or pharmaceutical kit, disclosed herein, the inhibitor is a bi-specific ligand(s) of the CXCR4-GPCRx heteromer.

In certain embodiments of the method of treating, method of suppressing, pharmaceutical composition, or pharmaceutical kit, disclosed herein, the antibody is an antibody-drug conjugate (ADC), as disclosed in, for example, Beck a et al., "Strategies and challenges for the next generation of antibody-drug conjugates", Nature Reviews Drug Discovery, 16:315-337, (2017) and Lambert, et al., "Antibody-Drug Conjugates for Cancer Treatment", Annual Review of Medicine, 69:191-207 (2018), each of which are incorporated hereby in its entirety.

BRIEF DESCRIPTION OF THE DRAWINGS

FIGS. 2A-2U: Shows identification of CXCR4-interacting GPCRs using BiFC assay. Representative images that showed negative BiFC signal; CXCR4-VN and HA-VC (FIG. 2A), and CXCR4-VN and GCGR-VC (FIG. 2C). Representative images of CXCR4 and GPCRx that showed positive BiFC signal; CXCR4-VN and CXCR4-VC (FIG. 2B), CXCR4-VN and ADCYAP1R1-VC (FIG. 2D), CXCR4-VC and ADORA2B-VN (FIG. 2E), CXCR4-VN and ADORA3-VC (FIG. 2F), CXCR4-VN and ADRB2-VC (FIG. 2G), CXCR4-VN and APLNR-VC (FIG. 2H), CXCR4-VN and C5AR1-VC (FIG. 2I), CXCR4-VN and CALCR-VC (FIG. 2J), CXCR4-VN and CCRS-VC (FIG. 2K), CXCR4-VN and CHRM1-VC (FIG. 2L), CXCR4-VN and GALR1-VC (FIG. 2M), CXCR4-VN and EDNRB-VC (FIG. 2N), CXCR4-VN and HRH1-VC (FIG. 2O), CXCR4-VN and MLNR-VC (FIG. 2P), CXCR4-VN and NTSR1-VC (FIG. 2Q), CXCR4-VN and PTGER2-VC (FIG. 2R), CXCR4-VC and PTGER3-VN (FIG. 2S), CXCR4-VN and SSTR2-VC (FIG. 2T), and CXCR4-VN and TACR3-VC (FIG. 2U).

(FIG. 3A) CXCR4 and GPCRx does not physically interact with each other. GPCRx agonist induces internalization of GPCRx, but not CXCR4-GFP. (FIG. 3B) CXCR4 and GPCRx physically interact and forms heteromer. GPCRx agonist induces internalization of GPCRx, and CXCR4-GFP is co-internalized with GPCRx.

(FIG. 5D) Calcium mobilization was quantified by calculating the area-under-the-curve (AUC) of each graph in A-C. Data were normalized to CXCL12-stimulated calcium response in cells expressing CXCR4 alone. Sum represents the calculated additive effect of the responses obtained after stimulation of CXCL12 and salmeterol individually in cells co-expressing CXCR4 and ADRB2, to allow the visualization of the potentiation. ***$P<0.001$; Student's t test.

FIGS. 10A-10C: Shows inhibition of internalization by GPCRx antagonist for heteromers. (FIG. 10A) CXCR4-ADRB2; (FIG. 10B) CXCR4-CHRM1; and (FIG. 10C) CXCR4-HRH1. (FIG. 10A) CXCR4-GFP expressing U-2 OS cells were transduced with adenovirus encoding ADRB2. Treatment by CXCL12 (SDF-1), a CXCR4 agonist, induced CXCR4-ADRB2 internalization. But Carvedilol, an ADRB2 antagonist, did not induce internalization. Co-treatment with CXCL12 and Carvedilol partially inhibited CXCL12 induced CXCR4-ADRB2 internalization. (FIG. 10B) CXCR4-GFP expressing U-2 OS cells were transduced with adenovirus encoding CHRM1. Treatment by CXCL12 induced CXCR4-CHRM1 internalization. But Oxybutynin or Umeclidinium, CHRM1 antagonists, did not induce internalization. Co-treatment with CXCL12 and Oxybutynin or Umeclidinium inhibited CXCL12 induced CXCR4-CHRM1 internalization. (FIG. 10C) CXCR4-GFP expressing U-2 OS cells were transduced with adenovirus encoding HRH1. Treatment by CXCL12 induced CXCR4-HRH1 internalization. But Promethazine, Hydroxyzine, or Loratadine, HRH1 antagonists, did not induce internalization. Co-treatment with CXCL12 and Promethazine, Hydroxyzine, or Loratadine inhibited CXCL12 induced CXCR4-HRH1 internalization.

(FIG. 11A) Effect of ADRB2 antagonist (Carvedilol) on the survival of PDC. Carvedilol induced significantly decreased survival of cells. (IC50=11.69 µM) (FIG. 11B) Effect of CHRM1 antagonists (Oxybutynin, Umeclidinium) on the survival of PDC. Oxybutynin and Umeclidinium each showed significantly decreased survival of cells at IC50=3.04 µM and 4.03 µM respectively. (FIG. 11C) Effect of HRH1 antagonists (Promethazine, Hydroxyzine, and Loratadine) on the survival of PDC. Promethazine, Hydroxyzine, and Loratadine each showed decreased survival of PDC at IC50=18.39 µM, 12.79 µM and 5.29 µM, respectively.

FIGS. 12A-12C: Shows CXCR4-ADRB2 heterodimer detection by PLA and qRT-PCR in U-2 OS cells overexpressing CXCR4 and ADRB2. CXCR4-GFP expressing U-2 OS cells were transduced with adenovirus encoding ADRB2 at different MOIs for 2 days. Then CXCR4-ADRB2 co-expressing U-2 OS cells were performed PLA. (FIG. 12A) Image of CXCR4-ADRB2 heteromer detection by PLA. (FIG. 12B) Increase of the PLA signal proportionate to the expression level of ADRB2 in a dose dependent manner. (FIG. 12C) Data from qRT-PCR showing endogenous ADRB2 expression level of U-2 OS cells.

(FIG. 13A) Image of CXCR4-ADRB2 heteromer detection. Nuclei were visualized with DAPI staining and CXCR4-ADRB2 heteromers were shown as small dots. (FIG. 13B) Ratio of CXCR4-ADRB2 heteromer in PDC.

(FIG. 14A) Image of CXCR4-CHRM1 heteromer detection. Nuclei were visualized with DAPI staining and CXCR4-ADRB2 heteromers were shown as small dots. (FIG. 14B) Ratio of CXCR4-CHRM1 heteromer in PDC.

(FIG. 15A) Image of CXCR4-ADRB2 heteromer detection. Nuclei were visualized with DAPI staining and CXCR4-ADRB2 heteromers were shown as small dots. (FIG. 15B) Ratio of CXCR4-ADRB2 heteromer in PDX.

Figure 17A:
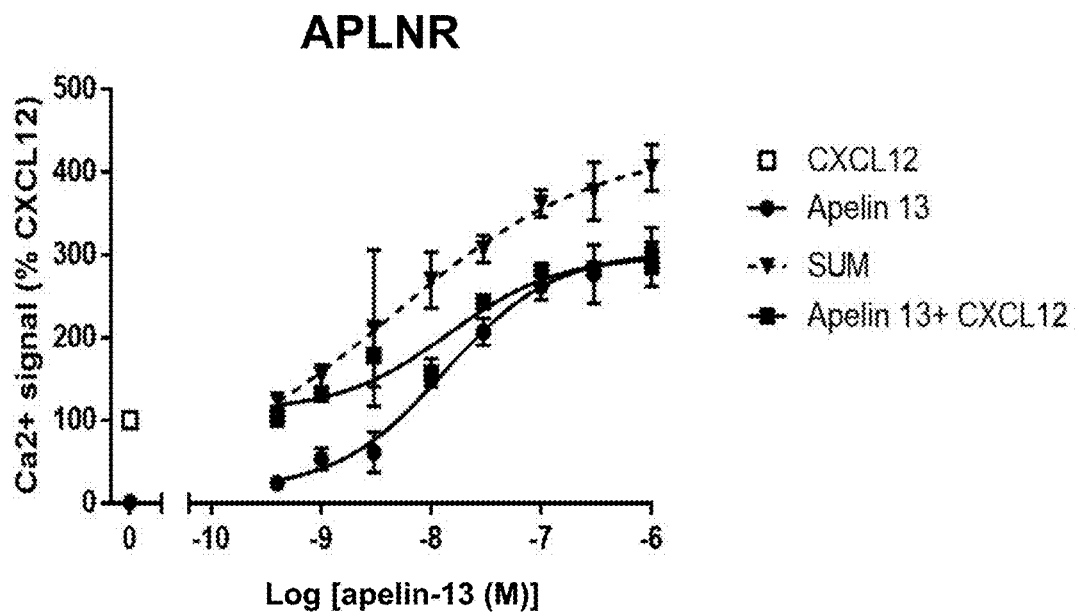
Figure 17B:
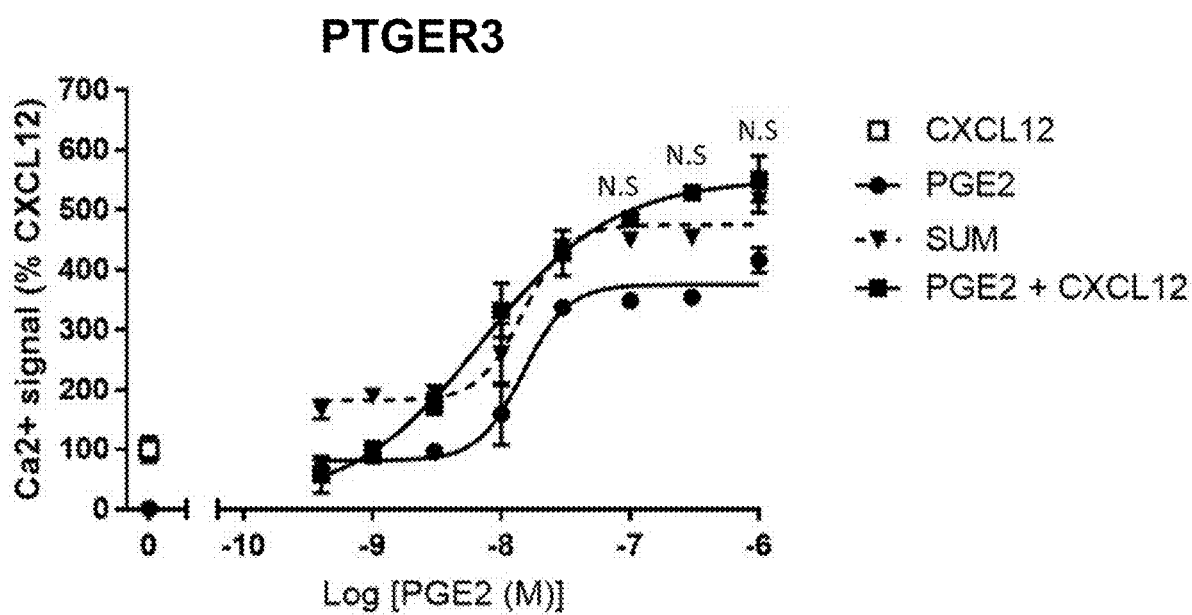
Figure 17C:
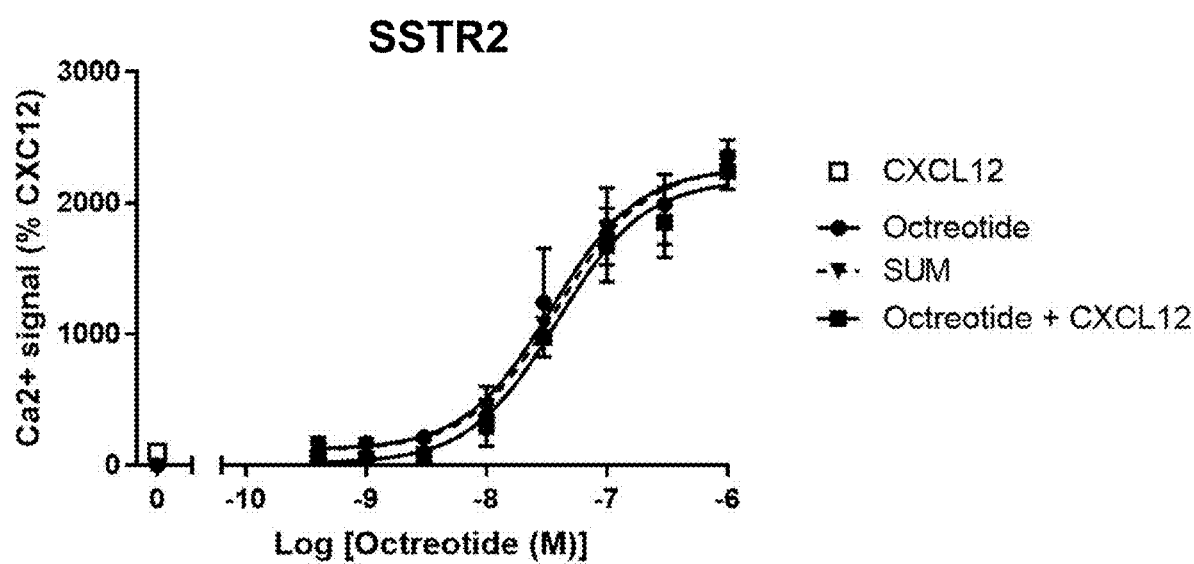

FIGS. 17A-17C: Shows no enhancement of the calcium response in cells co-expressing CXCR4 and GPCRx upon co-stimulation with their respective agonists. MDA-MB-231 cells were transduced with adenoviruses encoding CXCR4 and APLNR (FIG. 17A), CXCR4 and PTGER3 (FIG. 17B), or CXCR4 and SSTR2 (FIG. 17C). Cells were cultured for 3 days, stained with Cal 6 dye, and were treated with either CXCL12 alone (20 nM), increasing doses of Apelin-13, PGE2, or octreotide alone, or increasing doses of Apelin-13, PGE2 or octreotide in combination with 20 nM of CXCL12. Calcium mobilization was measured using FlexStation 3. Sum represents the calculated additive value of the responses evoked by 20 nM of CXCL12 alone (open square) and GPCRx ligand alone at indicated doses (filled circle). Sum graph was depicted as a broken line with inverted triangles. Statistically significant differences between the sum (inverted triangle) and co-treatment (filled square) at each point were determined by Student's t test. No statistical difference was observed at any point. Data represent mean±SD (n=3).

Figure 18A:
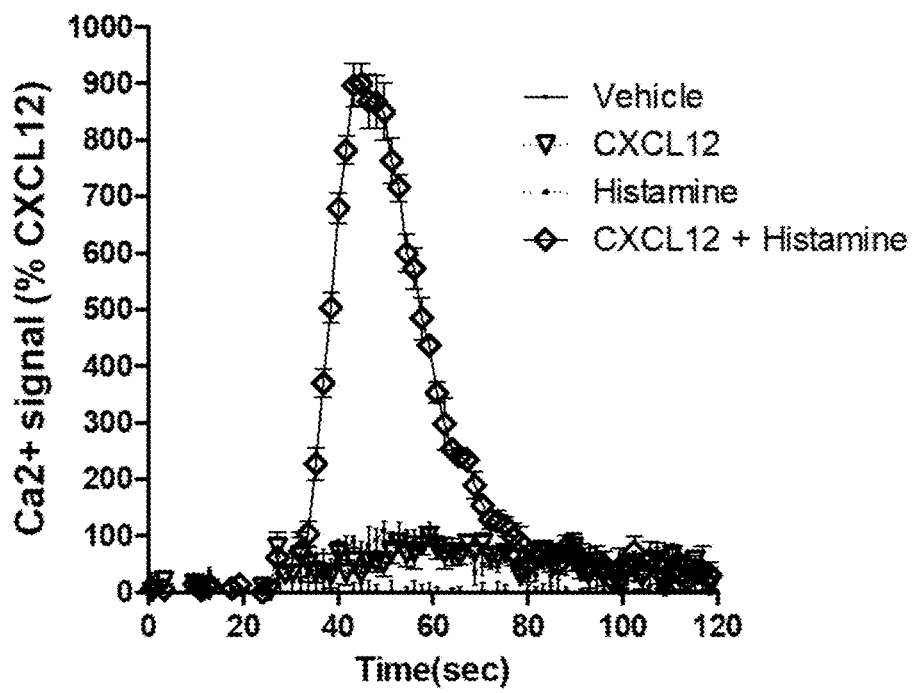
Figure 18B:
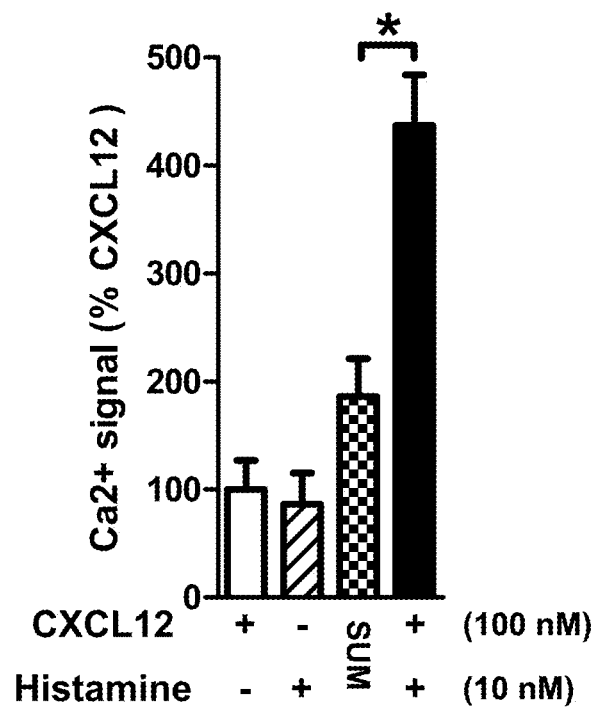

FIGS. 18A-18B: Shows the enhancement of the calcium response in wild-type MDA-MB-231 cells upon co-stimulation with CXCL12 and histamine. (FIG. 18A) MDA-MB-231 cells were stimulated with CXCL12 (100 nM), histamine (10 nM), or CXCL12 and histamine together, and Ca2+ responses elicited by endogenous CXCR4 and HRH1 were measured. (FIG. 18B) Calcium mobilization was quantified by calculating the area-under-the-curve (AUC) of each graph. Sum represents the calculated additive value of the responses evoked by each agonist. The data represent three independent experiments done in triplicates (mean±SEM). Statistically significant difference between the sum and co-treatment was determined by Student's t test. *P<0.05.

Figure 19A:
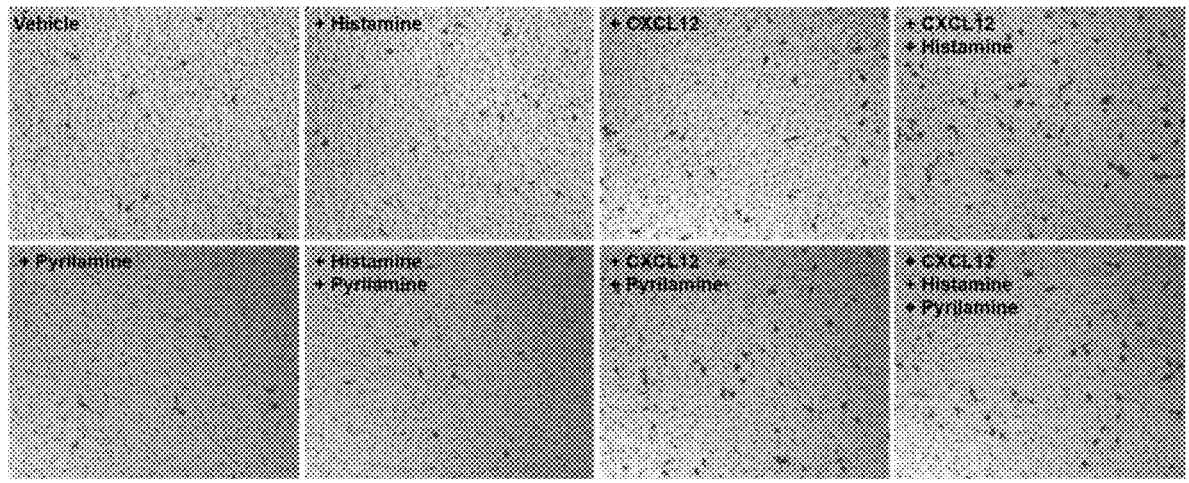
Figure 19B:
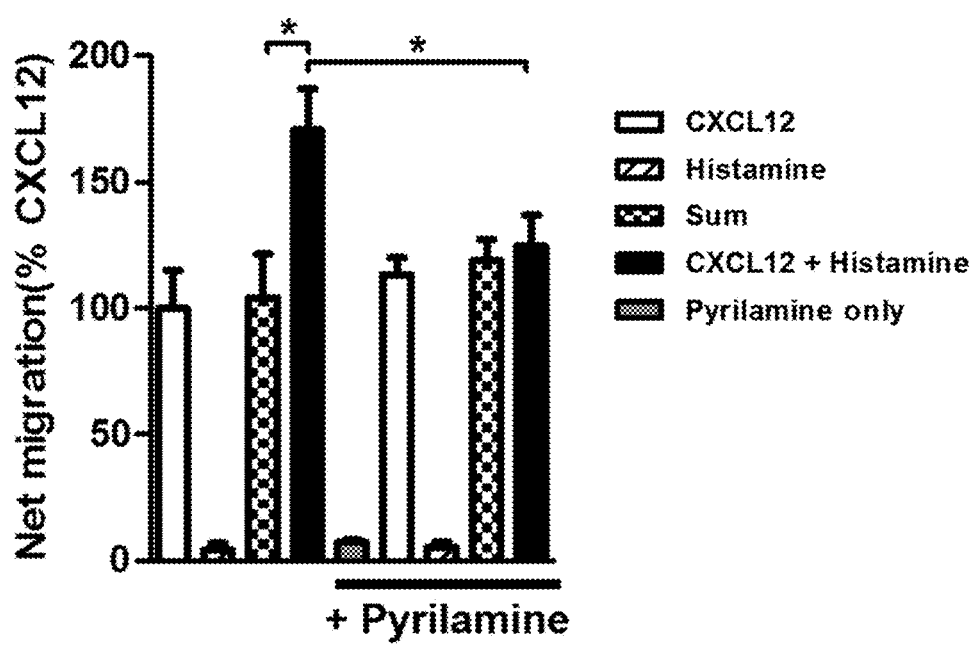

FIGS. 19A-19B: Shows enhanced migration of MDA-MB-231 cells in response to a co-stimulation with CXCL12 (30 nM) and histamine (50 nM). MDA-MB-231 cells were transduced with 1 MOI of lentivirus encoding CXCR4, and chemotactic migration of the cells toward CXCL12, histamine, CXCL12 and histamine together in the presence or absence of pyrilamine (1 µM), a HRH1-selective inverse agonist, was evaluated. Chemotaxis was quantified by counting the migrated cells on the lower surface of the membrane of 10 fields per chamber. (FIG. 19A) A representative picture of each group. (FIG. 19B) Although histamine itself did not induce migration of the MDA-MB-231 cells, it significantly increased the migration of the cells upon co-stimulation with CXCL12. The enhanced migration of MDA-MB-231 cells was due to endogenous HRH1 since the addition of pyrilamine (1 µM), a HRH1-selective inverse agonist, completely abolished the enhanced response. The data represent mean±SEM (n=3 or 5). Statistically significant differences were determined by Student's t test. *P<0.05.

Figure 20:
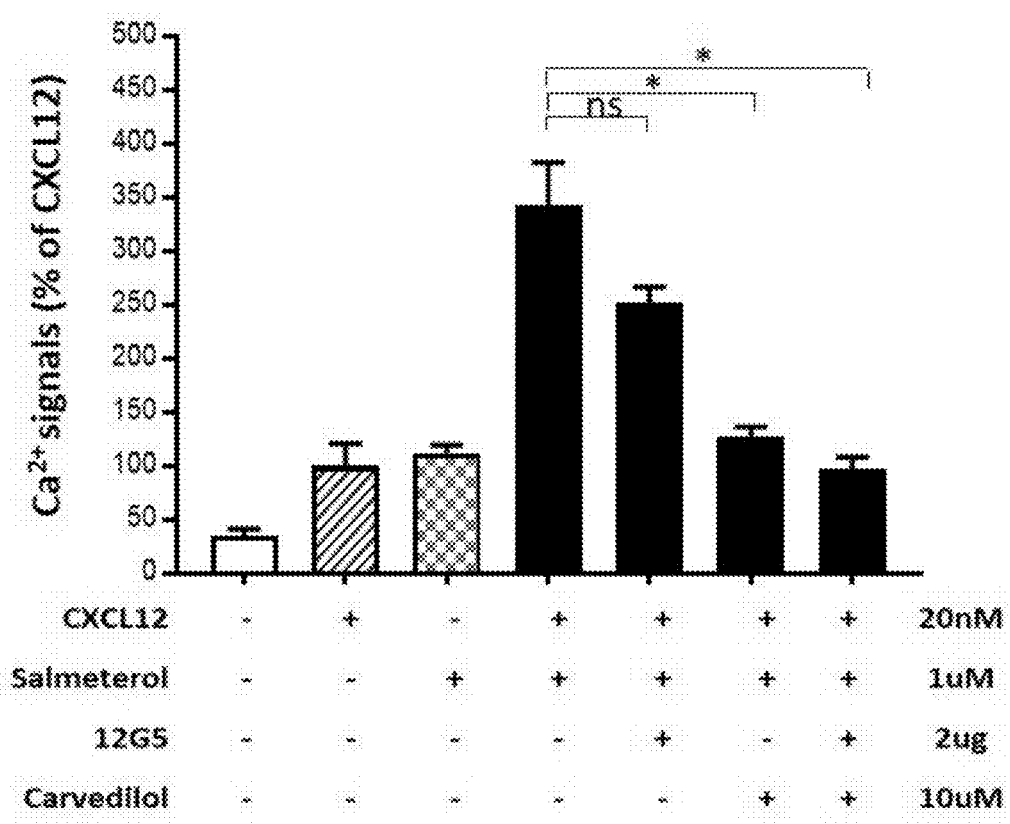

FIG. 20: Shows efficient suppression of the enhanced calcium response by co-treatment of anti-CXCR4 antibody and ADRB2 antagonist when cells expressing CXCR4-ADRB2 heteromer were simultaneously stimulated with CXCL12 and ADRB2 agonist. MDA-MB-231 cells were co-transduced with adenoviruses encoding CXCR4 and ADRB2. Cells were treated with ADRB2 antagonist (Carvedilol), anti-CXCR4 antibody (12G5), or vehicle of indicated concentration and incubated with Cal 6 for 2 hours. Cells were subsequently stimulated with indicated amounts of CXCL12, ADRB2 agonist (Salmeterol), or CXCL12 and ADRB2 agonist.

Figure 21A:
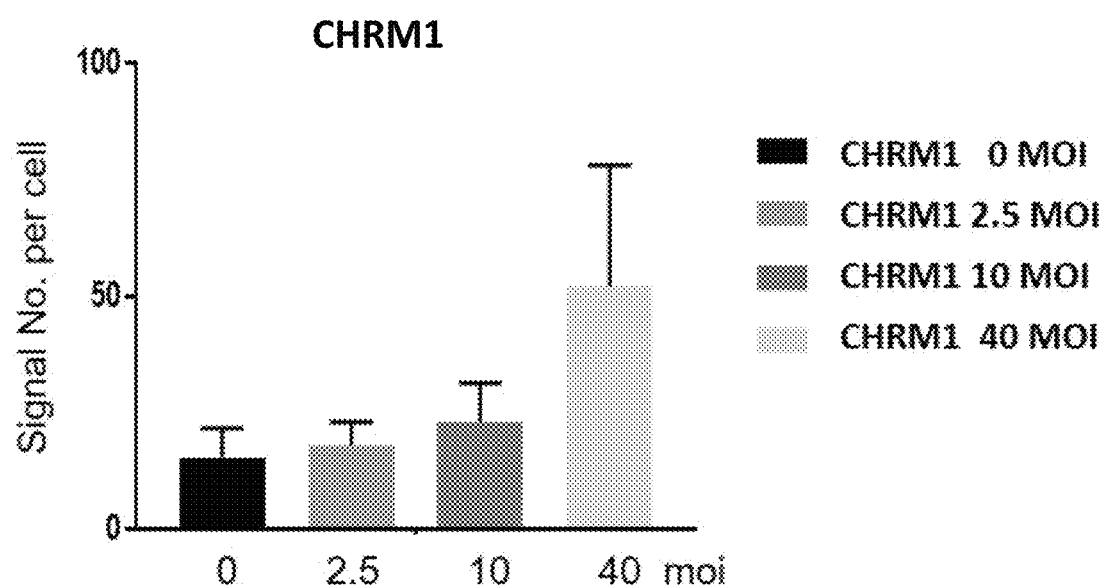
Figure 21B:
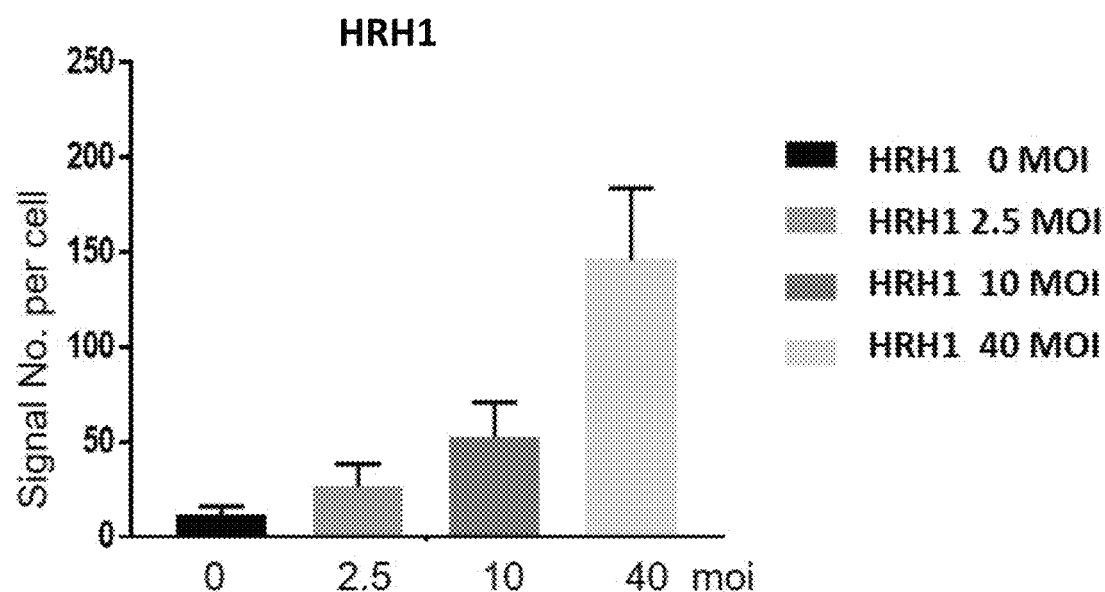

FIGS. 21A-21B: Shows detection of CXCR4-GPCR heteromer by PLA in U-2 OS cells over-expressing CXCR4 and GPCRx. U-2 OS cells expressing CXCR4-GFP were transduced with adenovirus encoding CHRM1 or HRH1 at different MOIs for 2 days. Subsequently, PLA was performed on U-2 OS cells co-expressing CXCR4-GPCRx using CXCR4- and GPCRx-specific antibodies. The PLA signal increased in proportion to the expression level of CHRM1 (FIG. 21A) and HRH1(FIG. 21B) in a dose-dependent manner.

Figure 22A:
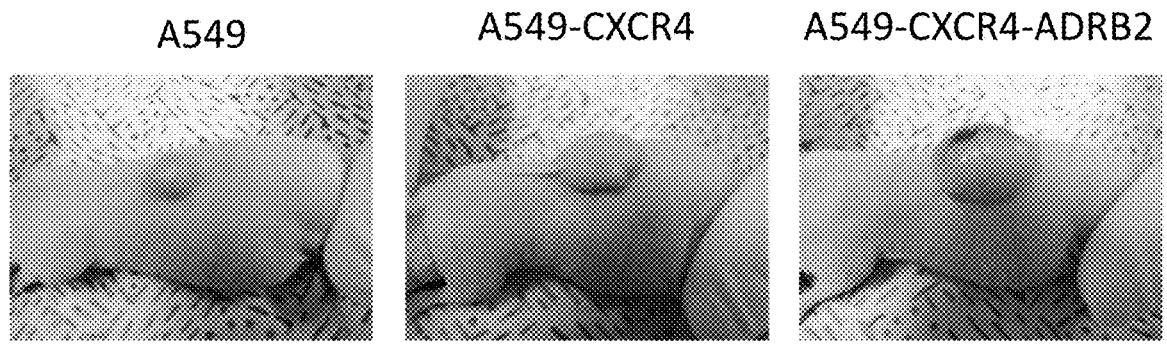
Figure 22B:
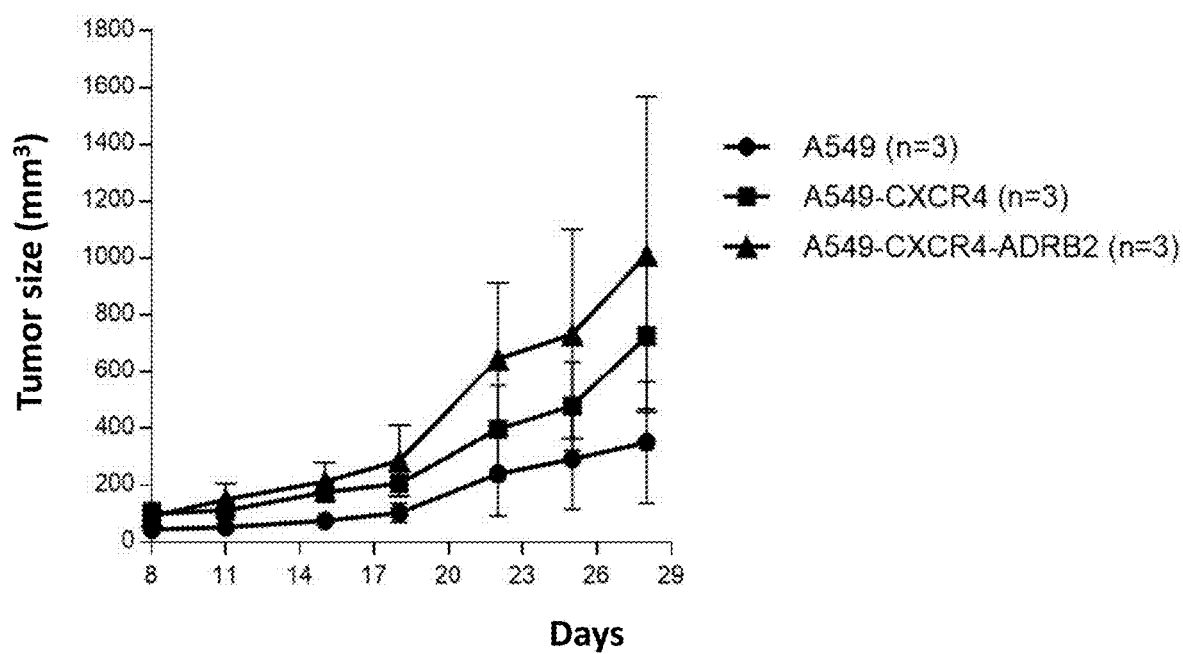

FIGS. 22A-22B: (FIG. 22A) Shows images of three mice that were transplanted with a parental cell A549, A549-CXCR4 overexpressing CXCR4 stably and A549-CXCR4-ADRB2 stably overexpressing CXCR4-ADRB2 heteromer, respectively, at 28 days after transplantation; (FIG. 22B) Shows graph comparing tumor growth between transplanted cells from FIG. 22A; tumor growth was monitored every third or fourth day by measuring the length (L) and width (W) of the tumor and calculating tumor volume in the basis of the following formula: Volume=0.5 $LW^2$. The results are presented as the mean±standard deviation of 3 individuals.

Figure 23A:
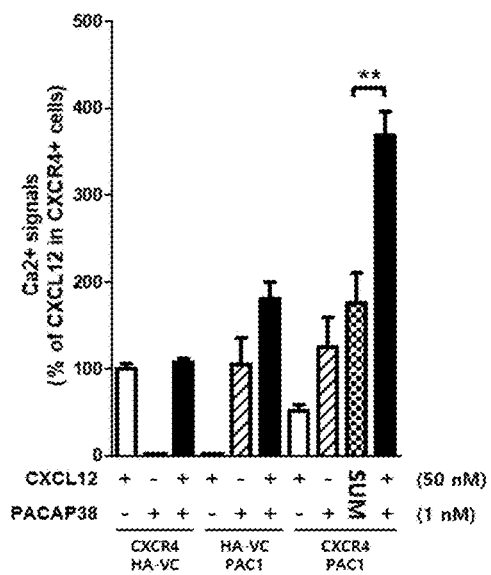
Figure 23B:
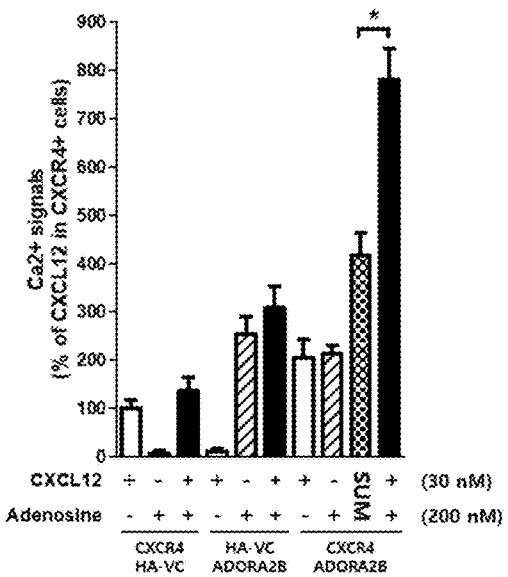
Figure 23C:
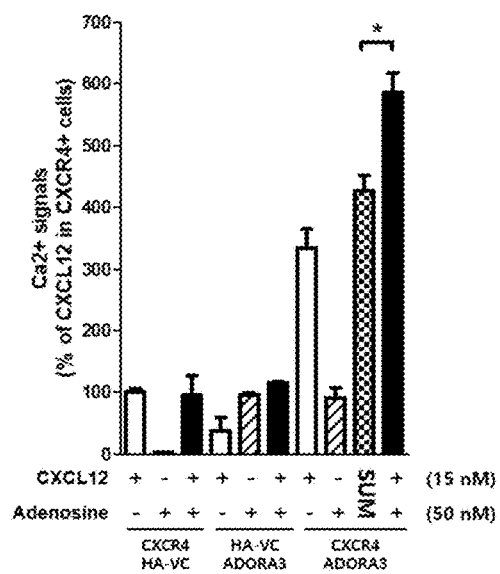
Figure 23D:
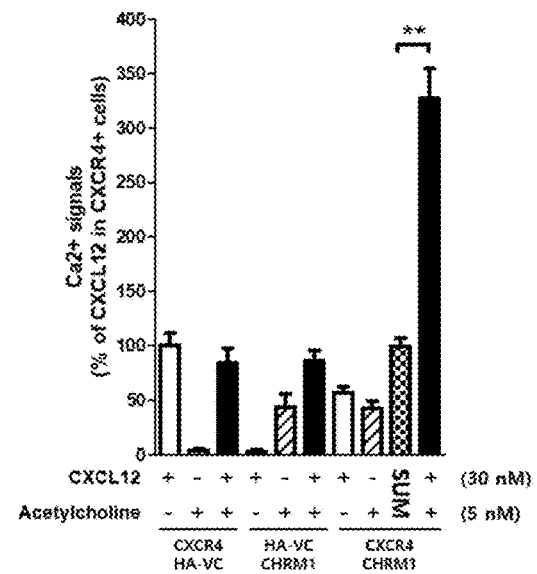
Figure 23E:
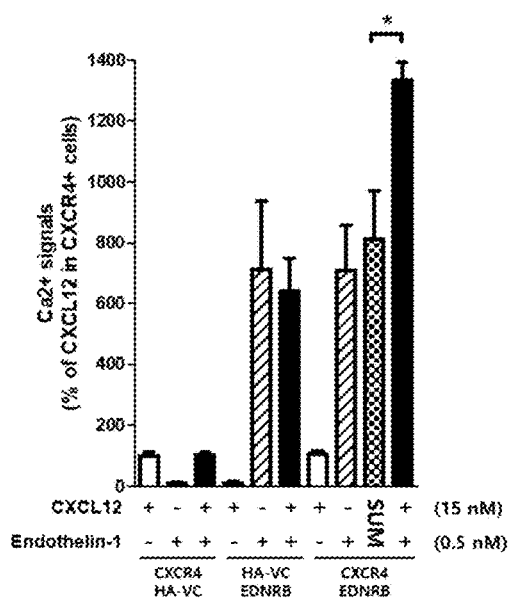
Figure 23F:
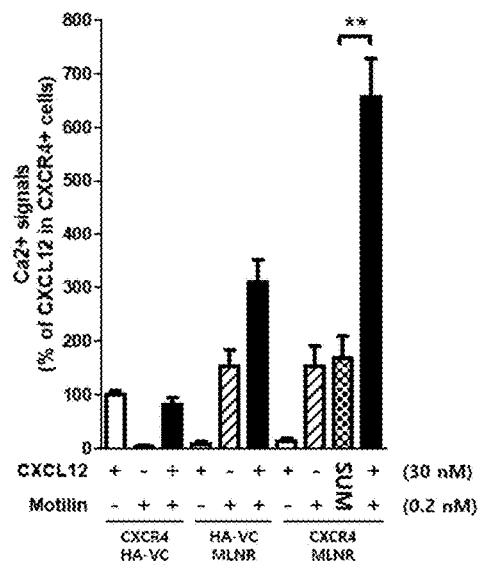
Figure 23G:
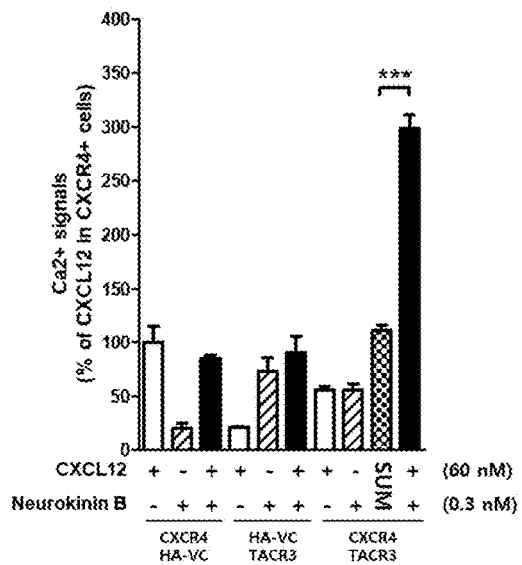

FIGS. 23A-23G: Shows calcium response in MDA-MB-231 cells co-expressing CXCR4 and GPCRx upon co-stimulation with CXCL12 and endogenous ligand for GPCRx. MDA-MB-231 cells were transduced with adenoviruses encoding CXCR4 and HA-VC, GPCRx and HA-VC, or CXCR4 and GPCRx where GPCRx represents ADCYAP1R1 (PAC1) (FIG. 23A), ADORA2B (FIG. 23B), ADORA3 (FIG. 23C), CHRM1 (FIG. 23D), EDNRB (FIG. 23E), MLNR (FIG. 23F), and TACR3 (FIG. 23G).

Figure 24A:
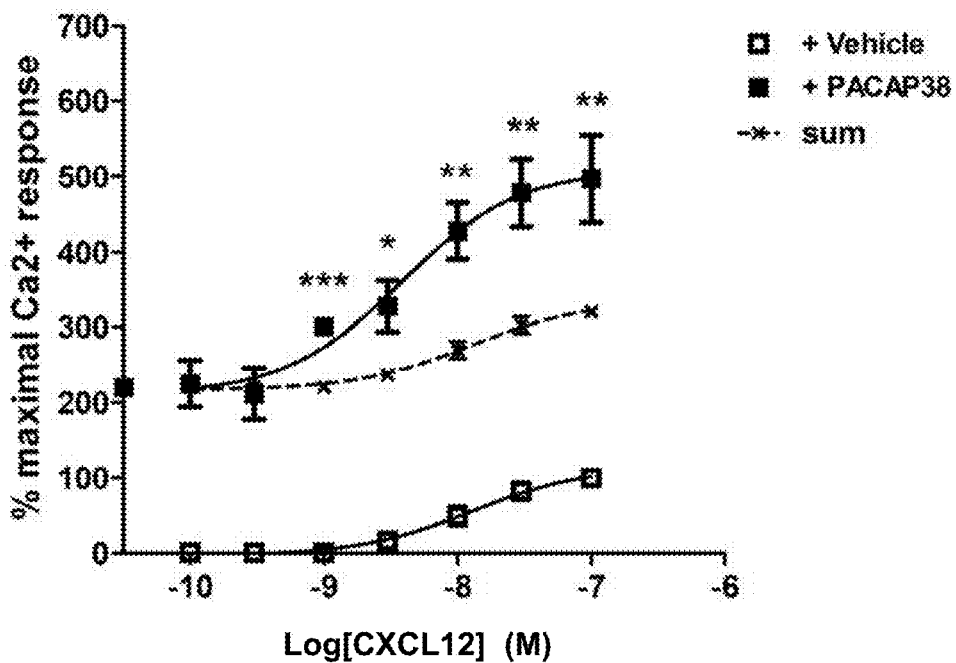
Figure 24B:
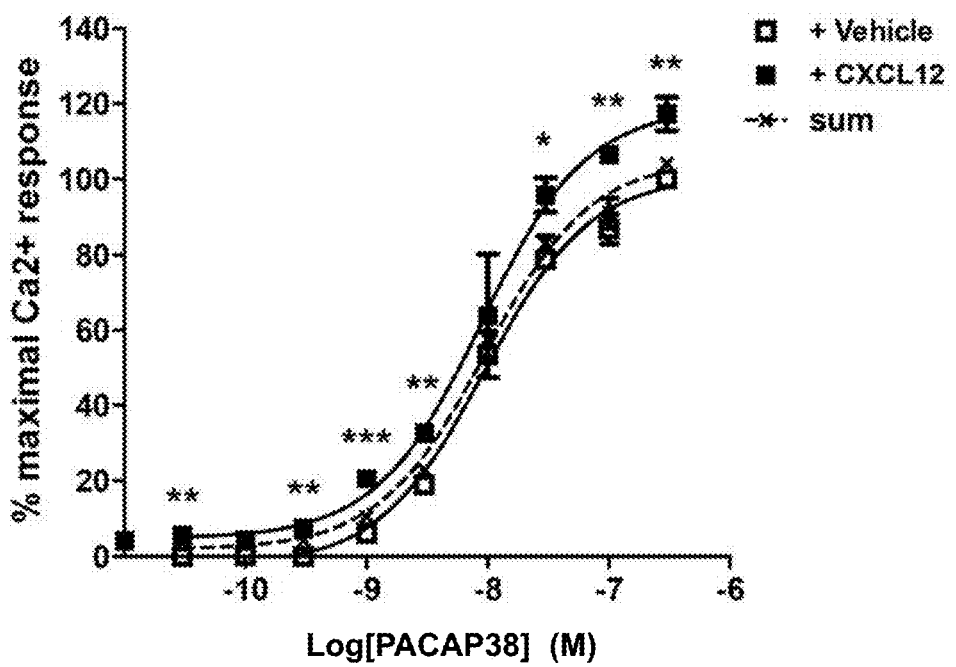

FIGS. 24A-24B: Shows calcium response in MDA-MB-231 cells co-expressing CXCR4 and ADCYAP1R1 upon co-stimulation with their selective endogenous ligands. MDA-MB-231 cells were transduced with adenoviruses encoding CXCR4 and ADCYAP1R1. (FIG. 24A) Cells were treated with PACAP38 (1 nM, ADCYAP1R1 selective endogenous ligand) alone, increasing doses of CXCL12 alone, or increasing doses of CXCL12 in combination with 1 nM of PACAP38. (FIG. 24B) Cells were treated with CXCL12 alone, increasing doses of PACAP38 alone, or increasing doses of PACAP38 in combination with 15 nM of CXCL12.

Figure 25A:
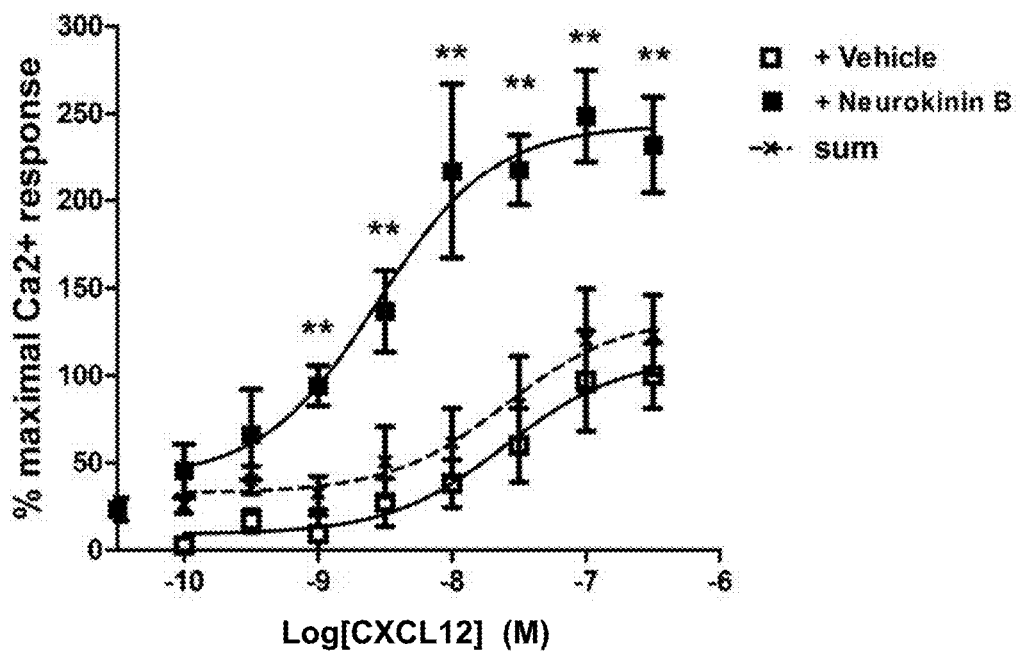
Figure 25B:
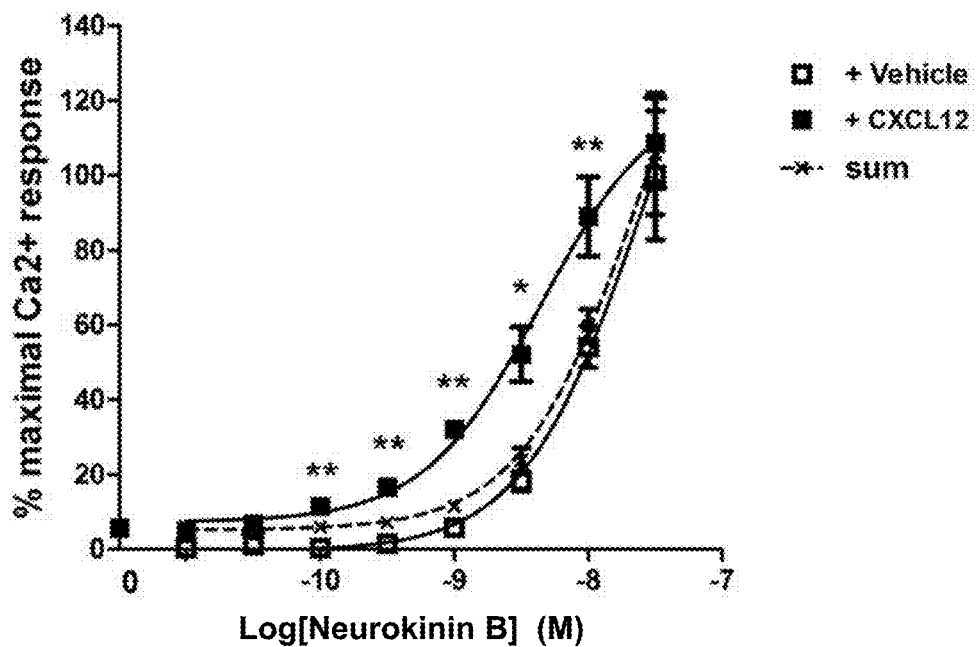

FIGS. 25A-25B: Shows calcium response in MDA-MB-231 cells co-expressing CXCR4 and TACR3 upon co-stimulation with their selective endogenous ligands. MDA-MB-231 cells were transduced with adenoviruses encoding CXCR4 and TACR3. (FIG. 25A) Cells were treated with Neurokinin B (0.4 nM, TACR3 selective endogenous ligand) alone, increasing doses of CXCL12 alone, or increasing doses of CXCL12 in combination with 0.4 nM of Neurokinin B. (FIG. 25B) Cells were treated with CXCL12 alone (30 nM), increasing doses of Neurokinin B alone, or increasing doses of Neurokinin B in combination with 30 nM of CXCL12.

Figure 26A:
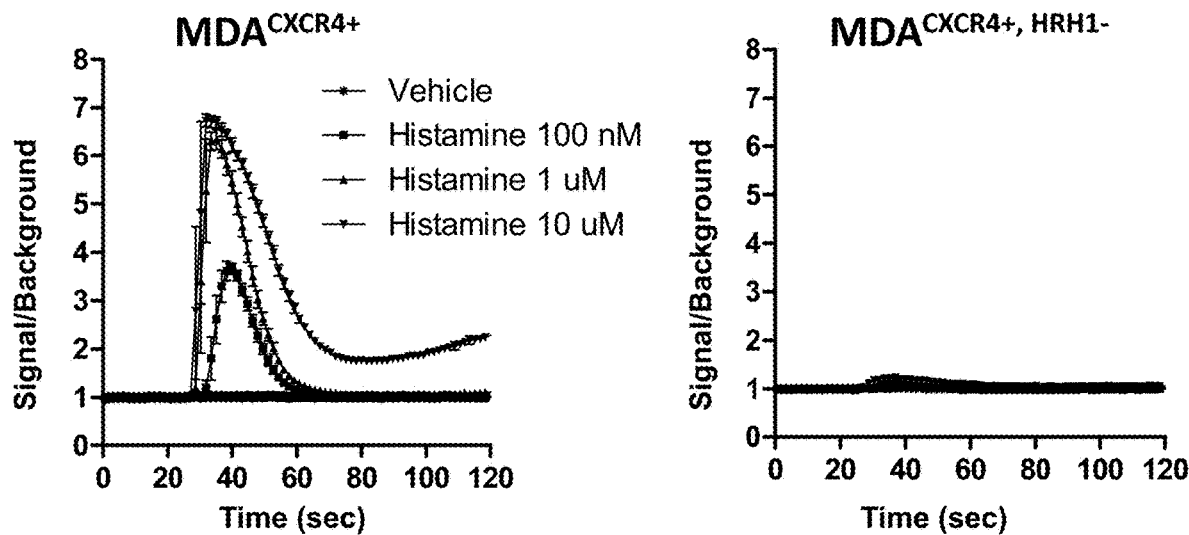
Figure 26B:
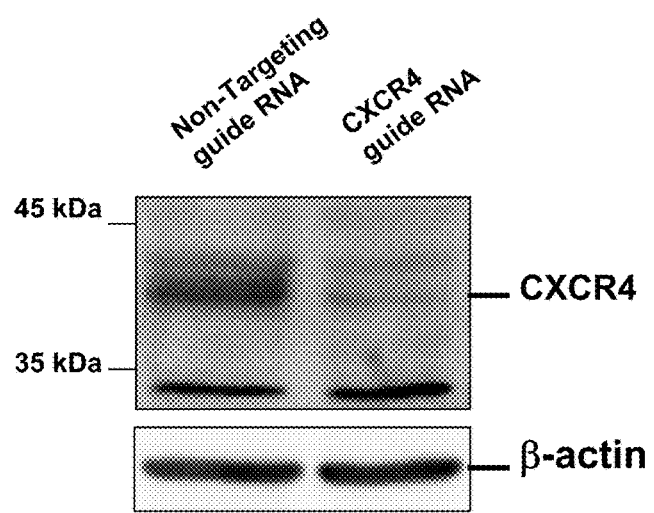

FIGS. 26A-26B: Shows validation of CRISPR/Cas9-mediated CXCR4 and HRH1 gene editing in MDA-MB-231 cells. (FIG. 26A) MDA$^{CXCR4+, HRH-}$ cells were generated by disrupting HRH1 gene in MDA-MB-231 cells stably expressing CXCR4 (MDA$^{CXCR4+}$), by transducing lentiviruses encoding Cas9 and guide RNA targeting HRH1. The absence of functional HRH1 was confirmed by measuring calcium responses upon exposure to histamine. (FIG. 26B) CXCR4 gene was edited in MDA-MB-231 cells using CRISPR/Cas-9 system and expression of CXCR4 was detected using immunoblotting.

Figure 27A:
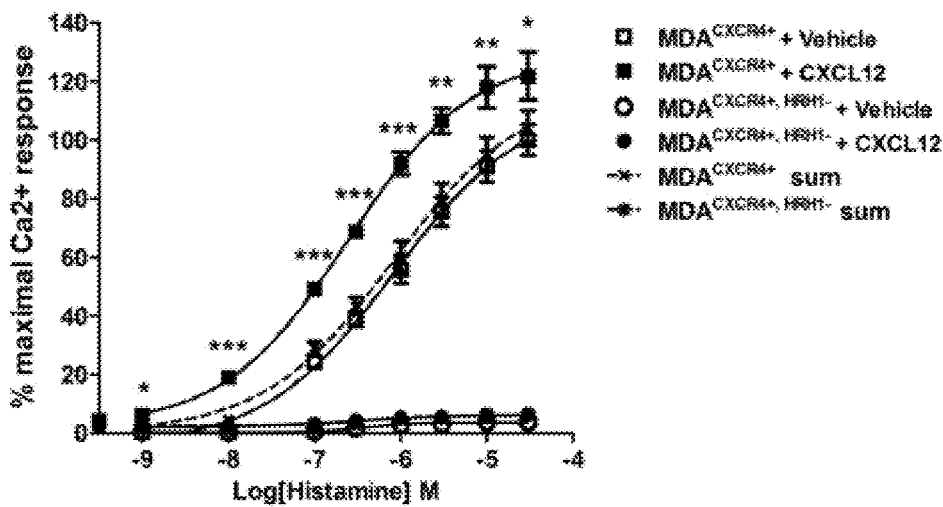
Figure 27B:
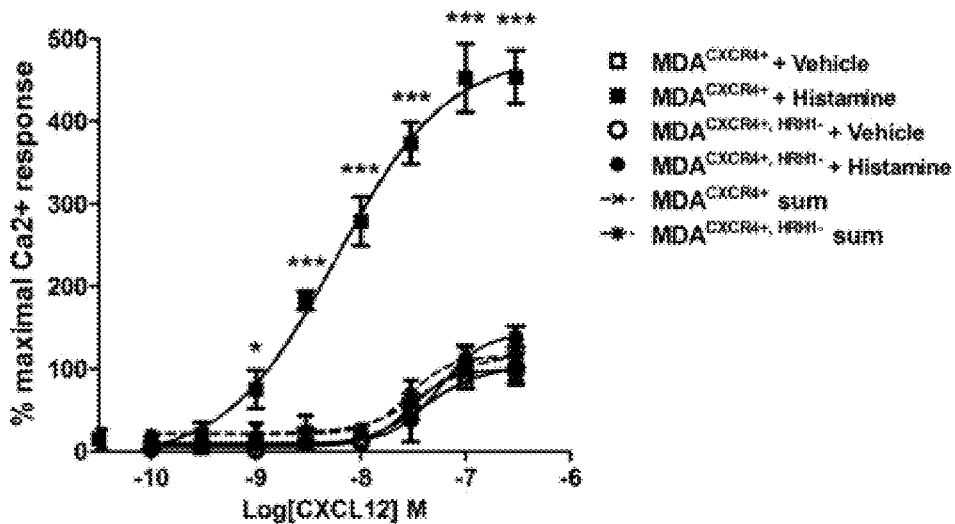

FIGS. 27A-27B: Shows enhanced calcium response in MDA-MB-231 cells upon co-treatment with CXCL12 and histamine is abrogated in the absence of HRH1. (FIG. 27A) MDA-MB-231 cells stably overexpressing CXCR4 (MDA$^{CXCR4+}$) or MDA$^{CXCR4+}$ cells depleted with HRH1 using CRISPR/Cas9 system (MDA$^{CXCR4+, HRH1-}$) were treated with CXCL12 alone (50 nM), increasing concentrations of histamine, or histamine and CXCL12 together. (FIG. 27B) MDA$^{CXCR4+}$ cells or MDA$^{CXCR4+, HRH1-}$ cells were treated with histamine alone (15 nM), increasing concentrations of CXCL12, or CXCL12 and histamine together.

Figure 28A:
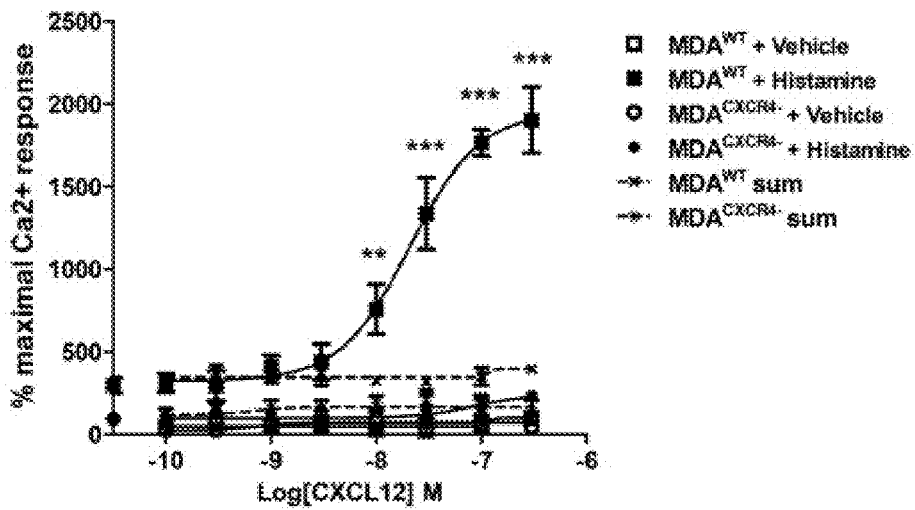
Figure 28B:
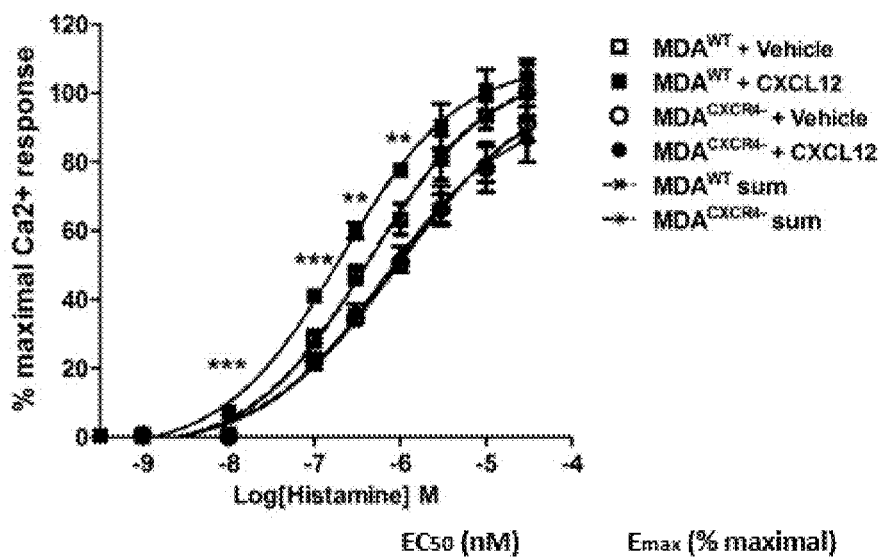

FIGS. 28A-28B: Shows enhanced calcium response in MDA-MB-231 cells upon co-treatment with CXCL12 and histamine is abrogated in the absence of CXCR4. (FIG. 28A) MDA-MB-231 cells (MDA$^{WT}$) or MDA$^{WT}$ cells depleted with CXCR4 using CRISPR/Cas9 system (MDA$^{CXCR4-}$) were treated with histamine alone (15 nM), increasing concentrations of CXCL12, or histamine and CXCL12 together. (FIG. 28B) MDA-MB-231 cells or MDA$^{CXCR4-}$ cells were treated with CXCL12 alone (100 nM), increasing concentrations of histamine alone, or CXCL12 and histamine together, and Ca2+ responses were measured.

Figure 29A:
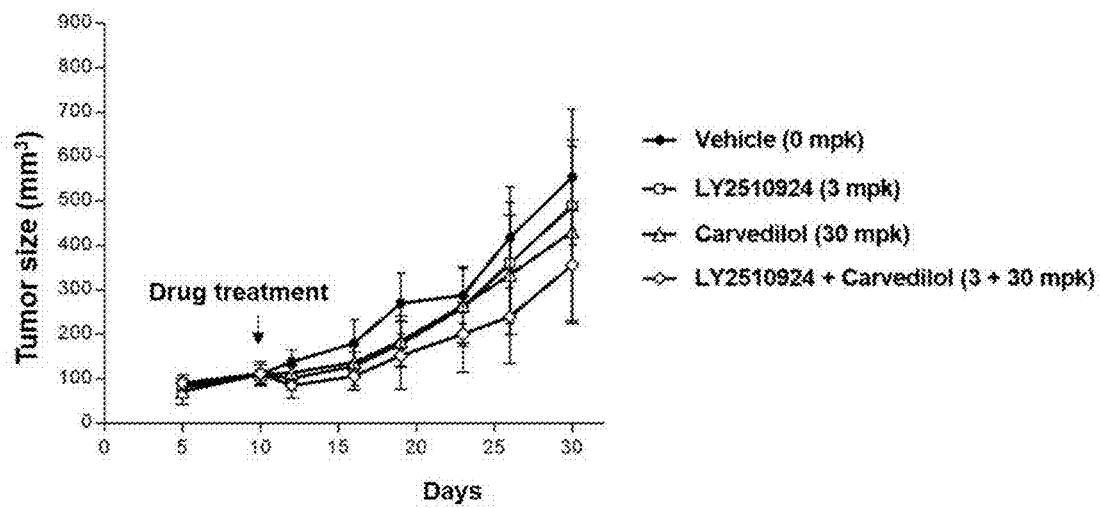
Figure 29B:
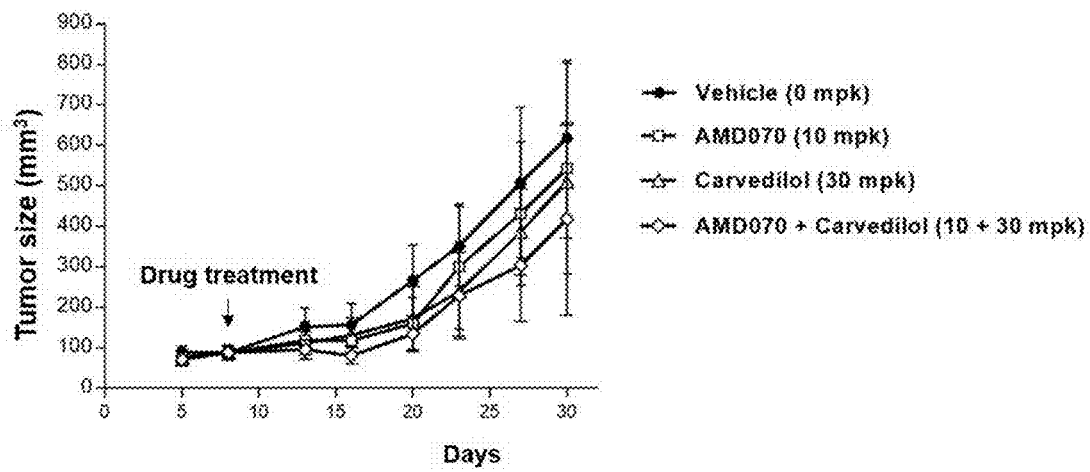

FIGS. 29A-29B: Shows anti-tumor effect of CXCR4 inhibitor, ADRB2 inhibitor, or CXCR4 and ADRB2 inhibitor in mice transplanted with A549-CXCR4-ADRB2 cell line stably overexpressing CXCR4-ADRB2 heteromer. FIG. 29A is a graph comparing tumor growth rates for the in vivo antitumor effect of CXCR4 inhibitor LY2510924, ADRB2 inhibitor Carvedilol, or combination of LY2510924 and Carvedilol. FIG. 29B is a graph comparing tumor growth rates for the antitumor effect of CXCR4 inhibitor AMD070, ADRB2 inhibitor Carvedilol, or combination of AMD070 and Carvedilol. Tumor growth was monitored every third or fourth day by measuring the length (L) and width (W) of the tumor and calculating tumor volume in the basis of the following formula: Volume=0.5 LW$^2$. The results are presented as the mean±standard deviation of 10 individuals.

ABBREVIATIONS

Unless indicated otherwise, the following includes abbreviations for terms disclosed herein: acute myeloid leukemia (AML), Adenosine A3 Receptor (ADORA3), Adenosine Receptor A2b (ADORA2B), adenovirus high-throughput system (AdHTS), Adenylate Cyclase Activating Polypeptide 1 (Pituitary) Receptor Type I (ADCYAP1R1), Adrenoceptor Alpha 1A (ADRA1A), Adrenoceptor Beta 2 (ADRB2), Apelin Receptor (APLNR), Atypical chemokine receptor 3 (ACKR3), bimolecular fluorescence complementation (BiFC), Bioluminescence Resonance Energy Transfer (BRET), bovine serum albumin (BSA), Calcitonin Receptor (CALCR), Cancer stem cells (CSCs), C-C chemokine receptor type 2 (CCR2), chemerin chemokine-like receptor 1 (CMKLR1), Cholinergic Receptor Muscarinic 1 (CHRM1), chronic lymphocytic leukemia (CLL), chronic myeloid leukemia (CML), chronic obstructive pulmonary disease (COPD), Complement C5a Receptor 1 (C5AR1), C-terminal fragment of Venus (VC), C-X-C Motif Chemokine ligand 12 (CXCL12), CXC receptor 4 (CXCR4), cytotoxic T-lymphocyte-associated antigen 4 (CTLA-4), δ-opioid receptor (OPRD), Endothelin Receptor Type B (EDNRB), enzyme-linked immunosorbent assay (ELISA), formalin-fixed paraffin-embedded (FFPE), fluorescence resonance energy transfer (FRET), G protein-coupled receptor (GPCR), Galanin Receptor 1 (GALR1), glioblastoma multiforme (GBM), Glucagon receptor (GCGR), GPCR heteromer identification technology (GPCR-HIT), Granulocyte-colony stimulating factor (G-CSF), hematopoietic stem cells (HSCs), hepatocellular carcinoma (HCC), Histamine Receptor H1 (HRH1), human immunodeficiency virus (HIV), International Union of Basic and Clinical Pharmacology Committee on Receptor Nomenclature and Drug Classification (NC-IUPHAR), μ-opioid receptor (MOR), Motilin Receptor (MLNR), Multiple myeloma (MM), multiplicity of infection (MOI), Myelodysplastic Syndromes (MDS), Neurotensin Receptor 1 (NTSR1), non-Hodgkin lymphoma (NHL), non-small-cell lung cancer (NSCLC), N-terminal fragments of Venus (VN), patient derived cell (PDC), Patient-Derived Xenograft (PDX), positron emission tomography (PET), Computed Tomography (CT), programmed cell death ligand 1 (PD-L1), programmed cell death protein 1(PD-1), Prostaglandin E Receptor 2 (PTGER2), Prostaglandin E Receptor 3 (PTGER3), proximity ligation assay (PLA), reverse transcription-quantitative polymerase chain reaction (RT-qPCR), Single-photon emission computed tomography (SPECT), small lymphocytic lymphoma (SLL), small-cell lung cancer (SCLC), Somatostatin Receptor 2 (SSTR2), Stromal cell-derived factor 1 (SDF-1), systemic lupus erythematosus (SLE), Tachykinin Receptor 3 (TACR3), Threshold cycles (Ct), time-resolved FRET (TR-FRET), tumor microenvironment (TME), Vascular endothelial growth factor (VEGF), vascular smooth muscle cells (VSMC), WHIM syndrome (Warts, Hypogammaglobulinemia, Infections, and Myelokathexis), green fluorescence protein (GFP), and yellow fluorescence protein (YFP).

DETAILED DESCRIPTION OF THE INVENTION

CXCR4 plays important roles in tumor formation and progression, but the development of CXCR4 antagonists as anticancer drugs has not been successful possibly due to side effects and lack of efficacy within acceptable dose ranges. Recently, various CXCR4-GPCR heteromers with distinct physiological and pharmacological properties were reported, but their roles in cancer biology or possibilities for developing anti-cancer therapeutics targeting CXCR4-GPCR heteromers have not been clearly understood.

Traditionally GPCRs were believed to function as monomers that interact with heterotrimeric G proteins upon ligand binding, and drugs were developed based on monomeric or homomeric GPCRs (Milligan 2008). This view has changed drastically by the discoveries that GPCRs can form heteromers, and heteromerization is obligatory for some GPCRs. GPCR heteromerization is known to alter GPCR maturation and cell surface delivery, ligand binding affinity, signaling intensity and pathways, as well as receptor desensitization and recycling (Terrillon and Bouvier 2004; Ferre et al., 2010; Rozenfeld and Devi 2010; Gomes et al., 2016; Farran 2017). Different GPCR heteromers display distinct functional and pharmacological properties, and GPCR heteromerization can vary depending on cell types, tissues, and diseases or pathological conditions (Terrillon and Bouvier 2004; Ferre et al., 2010; Rozenfeld and Devi 2010; Gomes et al., 2016; Farran 2017). Now GPCR heteromerization is regarded as a general phenomenon, and deciphering GPCR heteromerization opens new avenues for understanding receptor function, physiology, roles in diseases and pathological conditions. Accordingly, identification of GPCR heteromers and their functional properties offers new opportunity for developing new pharmaceuticals or finding new use of old drugs with fewer side effects, higher efficacy, and increased tissue selectivity (Ferre et al., 2010; Rozenfeld and Devi 2010; Farran 2017).

The identification of bona fide GPCR heteromer requires intensive and critical evaluation. To distinguish GPCR heteromers from simple association of GPCRs, researchers in this field and the International Union of Basic and Clinical Pharmacology Committee on Receptor Nomenclature and Drug Classification (NC-IUPHAR) have declared GPCR heteromer as "macromolecular complex composed of at least two (functional) receptor units [protomers] with biochemical properties that are demonstrably different from those of its individual components" and these heteromers exist in native tissue (Ferre et al., 2009; Gomes et al., 2016; Pin et al., 2007). They proposed three criteria to demonstrate GPCR heteromers: (1) Heteromers should exhibit appropriate co-localization and interaction to enable allosterism using co-immunoprecipitation, in situ hybridization, or proximity-based techniques including proximity ligation assays in cells/tissues that express both receptors and not in cells/tissues that lack one of the receptors; (2) Heteromers should exhibit distinct properties such as changes in signaling, ligand binding, and/or trafficking, only in cells/tissues expressing both receptors but not in cells/tissues that lack one of the receptors; and (3) Heteromer-selective reagents should alter heteromer-specific properties. Heteromer-selective reagents include heteromer-selective antibodies, membrane-permeable peptides, and bivalent/bifunctional ligands (Gomes et al., 2016; Pin et al., 2007). Although many GPCR heteromers have been identified in vitro using recombinant receptors expressed in heterologous cells, only a few have demonstrated novel properties, and very few have shown evidence for GPCR heteromerization in native tissue due to technical problems (Gomes et al., 2016). NC-IUPHAR announced that one should provide evidence that satisfies at least two of the above three criteria for approval of new GPCR heteromers (Pin et al., 2007).

As disclosed herein, to establish whether criterion 1 of 3 is satisfied (relating to whether heteromer components colocalize and physically interact, either directly or via intermediate proteins acting as conduits for allosterism) in determining the presence/existence of a CXCR4-GPCRx heteromer, one or more of the following methods may be utilized to including, but not limited to: co-internalization assays; co-localization assays (determining co-localization of the receptor portomers within a cellular compartment) such as in situ hybridization, immunohistochemistry, or immunoelectron microscopy; proximity-based assays, such as proximity-based biophysical techniques, including resonance energy transfer (RET), bioluminescence RET (BRET), fluorescence RET (FRET), time-resolved fluorescence RET (TR-FRET), antibody-aided FRET, ligand-aided FRET, bimolecular fluorescence complementation (BiFC), and proximity ligation assays (PLA); co-immunoprecipitation assays; or fluorescent animals. For example, BiFC, co-internalization assay, or PLA, were utilized to evaluate whether a CXCR4-GPCRx heteromer satisfied criterion 1 of 3.

As disclosed herein, to establish whether criterion 2 of 3 is satisfied (relating to whether a heteromer exhibits properties distinct from those of the individual protomers), such as a CXCR4-GPCRx heteromer that results in an enhanced downstream signaling, for example an enhanced calcium mobilization (such as determined by a calcium mobilization assay), a two-tiered approach was utilized on those CXCR4-GPCRx heteromers that satisfied criterion 1 of 3 discussed above: (1) determine the presence/absence of an enhanced downstream signaling, for example an enhanced calcium mobilization (synergism) in the individual protomer context-comparing calcium mobilization in cells co-expressing HA-VC and one of the protomers (either CXCR4 or GPCRx) upon (a) co-stimulation with CXCL12 and the respective selective agonist, relative to (b) stimulation with either CXCL12 alone or the respective selective agonist alone; and (2) determine the presence/absence of an enhanced downstream signaling, for example an enhanced calcium mobilization (synergism) in the CXCR4-GPCRx heteromer context-comparing calcium mobilization in cells co-expressing CXCR4 and GPCRx upon (a) co-stimulation with CXCL12 and the respective selective agonist, relative to (b) the sum of stimulation with either CXCL12 alone or the respective selective agonist alone. As disclosed herein, to satisfy criterion 2 of 3 and be considered a CXCR4-GPCRx heteromer that results in an enhanced downstream signaling, for example an enhanced calcium mobilization, there must be (1) an absence of an enhanced downstream signaling, for example an enhanced calcium mobilization in either protomer context (i.e., the CXCR4 and HA-VC context or the GPCRx and HA-VC context), and (2) a presence of an enhanced downstream signaling, for example an enhanced calcium mobilization in the CXCR4-GPCRx heteromer context. In both the protomer context and the CXCR4-GPCRx heteromer context, the concentration of CXCL12 utilized to stimulate the cells (either as a single agent or in combination with the respective selective GPCRx agonist) and the concentration of the selective GPCRx agonist (either an endogenous agonist or a known selective agonist for the respective GPCRx) utilized to stimulate the cells (either as a single agent or in combination with CXCL12) are independently at a concentration of 100× the EC50 concentration or lower. For example, the concentration of CXCL12 utilized to stimulate the cells (either as a single agent or in combination with the respective selective GPCRx agonist) was at a concentration of 15 nM (which is approximately the EC50 concentration against CXCR4).

As disclosed herein, to establish whether criterion 3 of 3 is satisfied (relating to whether heteromer-selective reagents should alter heteromer-specific properties) in determining the presence/existence of a CXCR4-GPCRx heteromer, patient derived cells, having satisfied criterion 1 of 3 and 2 of 3, are effected in the presence of an antagonist (a CXCR4 antagonist, a GPCRx antagonist, or a CXCR4-GPCRx heteromer antagonist), such as effecting cell proliferation of the patient derived cells containing a CXCR4-GPCRx heteromer.

In some embodiments, the method of treating, method of suppressing, pharmaceutical composition, or pharmaceutical kit, as disclosed herein, include or rely upon establishing that an association of CXCR4 and a GPCRx in a cell satisfies at least two of the following criteria or characteristics to be considered a CXCR4-GPCRx heteromer, comprising: 1) the CXCR4-GPCRx heteromer components in a cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, or a fluorescent animal assay; 2) an enhanced amount of calcium mobilization, such that: a) either CXCR4 or the respective GPCRx in an individual protomer context in a cell, upon co-stimulation with CXCL12 and a respective selective GPCRx agonist, results in a calcium mobilization amount that is equal to or less than the sum of calcium mobilization amounts resulting from single agonist stimulation with either the CXCL12 or the respective selective GPCRx agonist; and b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist; as determined via a calcium mobilization assay; or 3) a CXCR4-GPCRx heteromer-selective reagent: i) alters heteromer-specific properties of the CXCR4-GPCRx heteromer in a patient derived cell; ii) alters heteromer-specific function of the CXCR4-GPCRx heteromer in a patient derived cell; iii) alters heteromer-specific properties of a patient derived cell containing the CXCR4-GPCRx heteromer; or iv) decreases cell proliferation of a patient derived cell(s) containing the CXCR4-GPCRx heteromer. In some embodiments, the CXCR4-GPCRx heteromer-selective reagent alters heteromer-specific properties of the CXCR4-GPCRx heteromer in a patient derived cell, as determined by at least one of the following methods: PLA, radioligand binding assays, [35S]GTP-γS Binding assays, Calcium assay, cAMP assay, GTPase assay, PKA activation, ERK1/2 and/or Akt/PKB Phosphorylation assays, Src and STAT3 phosphorylation assays, CRE-reporter assay, NFAT-RE-reporter assay, SRE-reporter assay, SRF-RE reporter assay, NF-kB-RE reporter assay, Secreted alkaline phosphatase Assay, Inositol 1-Phosphate Production assay, Adenylyl Cyclase Activity assay, analysis of target gene expression by RT-PCR, RT-qPCR, RNAseq, next generation sequencing (NGS), or microarray. In some embodiments, the CXCR4-GPCRx heteromer-selective reagent alters heteromer-specific function of the CXCR4-GPCRx heteromer in a patient derived cell, as determined by at least one of the following methods: PLA, radioligand binding assays, [35S] GTP-γS Binding assays, Calcium assay, cAMP assay, GTPase assay, PKA activation, ERK1/2 and/or Akt/PKB Phosphorylation assays, Src and STAT3 phosphorylation assays, CRE-reporter assay, NFAT-RE-reporter assay, SRE-reporter assay, SRF-RE reporter assay, NF-kB-RE reporter assay, Secreted alkaline phosphatase Assay, Inositol 1-Phosphate Production assay, Adenylyl Cyclase Activity assay, analysis of target gene expression by RT-PCR, RT-qPCR, RNAseq, or microarray. In some embodiments, the CXCR4-GPCRx heteromer-selective reagent alters heteromer-specific properties of a patient derived cell containing the CXCR4-GPCRx heteromer, as determined by at least one of the following methods: assays on proliferation, migration, invasion, and drug resistance (survival) of cancer cells, modulation of immune cell function, angiogenesis, vasculogenesis, metastasis, drug resistance, tissue microarray (TMA), and cancer cell-tumor microenvironment (TME) interaction. For example, in some embodiments, the method of treating, method of suppressing, pharmaceutical composition, or pharmaceutical kit, as disclosed herein, include or rely upon establishing that an association of CXCR4 and a GPCRx in a cell satisfies at least two of the following criteria or characteristics to be considered a CXCR4-GPCRx heteromer, comprising: 1) the CXCR4-GPCRx heteromer components in a cell colocalize and physically interact, either directly or via intermediate proteins acting as conduits for allosterism, as determined via one or more of the following: a co-internalization assay, bimolecular fluorescence complementation (BiFC), or a proximity ligation assay (PLA); 2) an enhanced amount of calcium mobilization, such that: a) either CXCR4 or the respective GPCRx in an individual protomer context in a cell, upon co-stimulation with CXCL12 and a respective selective GPCRx agonist, results in a calcium mobilization amount that is equal to or less than the sum of calcium mobilization amounts resulting from single agonist stimulation with either the CXCL12 or the respective selective GPCRx agonist; and b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist; as determined via a calcium mobilization assay; or 3) a CXCR4-GPCRx heteromer-selective reagent: i) alters heteromer-specific properties of the CXCR4-GPCRx heteromer in a patient derived cell; ii) alters heteromer-specific function of the CXCR4-GPCRx heteromer in a patient derived cell; iii) alters heteromer-specific properties of a patient derived cell containing the CXCR4-GPCRx heteromer; or iv) decreases cell proliferation of a patient derived cell(s) containing the CXCR4-GPCRx heteromer. In some embodiments, the method of treating, method of suppressing, pharmaceutical composition, or pharmaceutical kit, as disclosed herein, include or rely upon establishing that an association of CXCR4 and a GPCRx in a cell satisfies criteria 1 and 2 to be considered a CXCR4-GPCRx heteromer. In some embodiments, the method of treating, method of suppressing, pharmaceutical composition, or pharmaceutical kit, as disclosed herein, include or rely upon establishing that an association of CXCR4 and a GPCRx in a cell satisfies criteria 1 and 3 to be considered a CXCR4-GPCRx heteromer. In some embodiments, the method of treating, method of suppressing, pharmaceutical composition, or pharmaceutical kit, as disclosed herein, include or rely upon establishing that an association of CXCR4 and a GPCRx in a cell satisfies criteria 2 and 3 to be considered a CXCR4-GPCRx heteromer. In some embodiments, the method of treating, method of suppressing, pharmaceutical composition, or pharmaceutical kit, as disclosed herein, include or rely upon establishing that an association of CXCR4 and a GPCRx in a cell satisfies criteria 1, 2, and 3, to be considered a CXCR4-GPCRx heteromer.

As disclosed herein, the CXCR4-GPCRx heteromer satisfying at least two of the three criteria may have, cause, or produce an enhanced downstream signaling. The enhanced downstream signaling may be the result from the CXCR4-GPCRx heteromer, such as from agonism of the CXCR4-GPCRx heteromer, from CXCR4 agonism of the CXCR4-GPCRx heteromer, from GPCRx agonism of the CXCR4-GPCRx heteromer, and/or from CXCR4 agonism and GPCRx agonism of the CXCR4-GPCRx heteromer. In some embodiments, the enhanced downstream signaling may be downstream of the CXCR4, the respective GPCRx, or the CXCR4-GPCRx heteromer. In some embodiments, the enhanced downstream signaling may be from the CXCR4-GPCRx heteromer, relative to downstream signaling from a CXCR4 protomer or a respective GPCRx protomer in their respective individual protomer context. In some embodiments, the enhanced downstream signaling may be from the CXCR4-GPCRx heteromer, relative to downstream signaling from a CXCR4 protomer in an individual protomer context. In some embodiments, the enhanced downstream signaling may be from the CXCR4-GPCRx heteromer, relative to downstream signaling from a respective GPCRx protomer in an individual protomer context. In some embodiments, the enhanced downstream signaling may be from the CXCR4-GPCRx heteromer, relative to downstream signaling from a CXCR4 protomer and a respective GPCRx protomer in their respective individual protomer context. The enhanced downstream signaling from said CXCR4-GPCRx heteromer, may in some embodiments, be suppressed in the cancer patient, such as suppressed in the patient's cancer cells. In some embodiments, the enhanced downstream signaling from said CXCR4-GPCRx heteromer, may be an enhanced amount of calcium mobilization (or synergistic amount of calcium mobilization), which may be determined by an intracellular Ca2+ assay, such as a calcium mobilization assay.

As disclosed herein, the CXCR4-GPCRx heteromer satisfying at least two of the three criteria may have, cause, or produce an enhanced downstream signaling, wherein the enhanced downstream signaling is an enhanced amount of calcium mobilization. The enhanced amount of calcium mobilization from the CXCR4-GPCRx heteromer may be a calcium mobilization amount that, upon co-stimulation with the CXCL12 and the respective selective GPCRx agonist, is at least 10% greater, than the sum of calcium mobilization amounts resulting from single agonist stimulation of said cells with either the CXCL12 or the respective selective GPCRx agonist, as determined via a calcium mobilization assay. In some embodiments, the enhanced amount of calcium mobilization from the CXCR4-GPCRx heteromer may be a synergistic amount of calcium mobilization that, upon co-stimulation with the CXCL12 and the respective selective GPCRx agonist, is at least 10% greater, than the sum of calcium mobilization amounts resulting from single agonist stimulation of said cells with either the CXCL12 or the respective selective GPCRx agonist, as determined via a calcium mobilization assay. For example, the enhanced amount of calcium mobilization (or synergistic amount of calcium mobilization) from the CXCR4-GPCRx heteromer may be a calcium mobilization amount that, upon co-stimulation with the CXCL12 and the respective selective GPCRx agonist, is at least 20% greater, at least 30% greater, at least 40% greater, at least 50% greater, at least 75% greater, at least 90% greater, at least 100% greater, at least 150% greater, or at least 200% greater, than the sum of calcium mobilization amounts resulting from single agonist stimulation of said cells with either the CXCL12 or the respective selective GPCRx agonist, as determined via a calcium mobilization assay. In some embodiments, the enhanced amount of calcium mobilization (or synergistic amount of calcium mobilization) from the CXCR4-GPCRx heteromer may be a calcium mobilization amount that, upon co-stimulation with the CXCL12 and the respective selective GPCRx agonist, may be between 10-100% greater than the sum of calcium mobilization amounts resulting from single agonist stimulation of said cells with either the CXCL12 or the respective selective GPCRx agonist, as determined via a calcium mobilization assay, for example, may be a calcium mobilization amount that, upon co-stimulation with the CXCL12 and the respective selective GPCRx agonist, may be between 25-100% greater, 50-100% greater, 75-100% greater, or 100-200% greater, than the sum of calcium mobilization amounts resulting from single agonist stimulation of said cells with either the CXCL12 or the respective selective GPCRx agonist, as determined via a calcium mobilization assay.

In some embodiments, according to the method of treating, method of suppressing, pharmaceutical composition, or pharmaceutical kit, as disclosed herein, the CXCR4-GPCRx heteromer satisfies at least two of the three criteria, thereby having, causing, or producing, an enhanced downstream signaling, wherein the enhanced downstream signaling is an enhanced amount of calcium mobilization, such that: a) either the CXCR4 or the respective GPCRx in an individual protomer context in the cell upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist; and b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist; as determined via a calcium mobilization assay. For example, in some embodiments, the enhanced downstream signaling from the CXCR4-GPCRx heteromer is an enhanced amount of calcium mobilization, such that: i) the calcium mobilization from the protomer CXCR4 or GPCRx, in the individual protomer context in the cell, is non-synergistic, as determined via calcium mobilization assay; and ii) the calcium mobilization from the CXCR4-GPCRx heteromer in the cell is synergistic, as determined via a calcium mobilization assay. In some embodiments, the individual protomer context may be: a) the individual protomer CXCR4 in the cell, in the absence of the respective individual protomer GPCRx; or b) the respective individual protomer GPCRx in the cell, in the absence of the individual protomer CXCR4; upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist, as determined via a calcium mobilization assay. In some embodiments, the individual protomer context may be, independently: a) the individual protomer CXCR4 in the cell, in the absence of the respective individual protomer GPCRx; and b) the respective individual protomer GPCRx in the cell, in the absence of the individual protomer CXCR4; upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist, as determined via a calcium mobilization assay. For example, in some embodiments, the CXCR4-GPCRx heteromer, upon co-stimulation with the CXCL12 and the respective selective GPCRx agonist, may result in a calcium mobilization amount that is greater than the sum of calcium mobilization amounts resulting from single agonist stimulation of said cells with either the CXCL12 or the respective selective GPCRx agonist, as determined via a calcium mobilization assay.

The term "CXCR4" as used herein refers to C-X-C Motif Chemokine Receptor 4, also identified by unique database identifiers (IDs) and alternate names as shown in Table 1 (Chatterjee et al., 2014; Debnath et al., 2013; Domanska et al., 2013; Guo et al., 2016; Peled et al., 2012; Roccaro et al., 2014; Walenkamp et al., 2017).

The terms "GPCRx" as used herein refers to GPCRs that were used in this study to investigate if these GPCRs interact with CXCR4 and show properties distinct from those of individual protomers, including ADCYAP1R1 (ADCYAP Receptor Type I), ADORA2B (Adenosine A2b Receptor), ADORA3 (Adenosine A3 Receptor), ADRB2 (Adrenoceptor Beta 2), APLNR (Apelin Receptor), C5AR1 (Complement C5a Receptor 1), CALCR (Calcitonin Receptor), CCR5 (Chemokine (C-C Motif) Receptor 5), CHRM1 (Cholinergic Receptor Muscarinic 1), GALR1 (Galanin Receptor 1), EDNRB (Endothelin Receptor Type B), HRH1 (Histamine Receptor H1), MLNR (Motilin Receptor), NTSR1 (Neurotensin Receptor 1), PTGER2 (Prostaglandin E Receptor 2), PTGER3 (Prostaglandin E Receptor 3), SSTR2 (Somatostatin Receptor 2), and TACR3 (Tachykinin Receptor 3), also identified by unique database identifiers (IDs) and alternate names as shown in Table 1 and Table 2.

Table 1 shown below provides the nomenclature of GPCRx that form heteromers with CXCR4 and synergistically enhance Ca2+ response upon co-stimulation with both agonists, and Table 2 shown below provides the nomenclature of GPCRx that form heteromers with CXCR4, but do not synergistically enhance Ca2+ response upon co-stimulation with both agonists.

TABLE 1

| Gene name | Full name | Other names | IDs |
| --- | --- | --- | --- |
| CXCR4 | C-X-C Motif Chemokine Receptor 4 | Leukocyte-Derived Seven Transmembrane Domain Receptor; Lipopolysaccharide-Associated Protein 3; Stromal Cell-Derived Factor 1 Receptor; Chemokine (C-X-C Motif) Receptor 4; LPS-Associated Protein 3 Seven Transmembrane Helix Receptor; C-X-C Chemokine Receptor Type 4; Neuropeptide Y Receptor Y3; Neuropeptide Y3 Receptor; Chemokine Receptor; Seven-Transmembrane-Segment Receptor, Spleen; Chemokine (C-X-C Motif), Receptor 4 (Fusin); SDF-1 Receptor; CD184 Antigen; Fusin; LAP-3; LESTR; NPYRL; FB22; HM89; LCR1; D2S201E; HSY3RR; NPYY3R; CXC-R4; CXCR-4; CD184; NPY3R; WHIMS; LAP3; NPYR; WHIM | GCID: GC02M136114<br>HGNC: 2561<br>Entrez Gene: 7852<br>Ensembl: ENSG00000121966<br>OMIM: 162643<br>UniProtKB: P61073 |
| ADCYAP1R1 | ADCYAP Receptor Type I | Adenylate Cyclase Activating Polypeptide 1 (Pituitary) Receptor Type I; Pituitary Adenylate Cyclase-Activating Polypeptide Type 1 Receptor; PACAP Type I Receptor; PACAP Receptor 1; PACAP-R1; Pituitary Adenylate Cyclase Activating Polypeptide 1 Receptor Type I Hiphop; Pituitary Adenylate Cyclase-Activating Polypeptide Type I Receptor; PACAP-R-1; PACAPRI; PACAPR; PAC1R; PAC1 | GCID: GC07P031058<br>HGNC: 242<br>Entrez Gene: 117<br>Ensembl: ENSG00000078549<br>OMIM: 102981<br>UniProtKB: P41586 |
| ADORA2B | Adenosine A2b Receptor | Adenosine Receptor A2b; ADORA2 | GCID: GC17P015927<br>HGNC: 264<br>Entrez Gene: 136<br>Ensembl: ENSG00000170425<br>OMIM: 600446<br>UniProtKB: P29275 |
| ADORA3 | Adenosine A3 Receptor | Adenosine Receptor A3; A3AR | GCID: GC01M111499<br>HGNC: 268<br>Entrez Gene: 140<br>Ensembl: ENSG00000282608<br>OMIM: 600445<br>UniProtKB: P0DMS8 |
| ADRB2 | Adrenoceptor Beta 2 | Adrenergic, Beta-2-, Receptor, Surface; Beta-2 Adrenoreceptor; Beta-2 Adrenoceptor; ADRB2R; B2AR; Adrenoceptor Beta 2, Surface; Adrenoceptor Beta 2 Surface; Beta-2 Adrenergic Receptor; Catecholamine Receptor; BETA2AR; ADRBR; BAR | GCID: GC05P148825<br>HGNC: 286<br>Entrez Gene: 154<br>Ensembl: ENSG00000169252<br>OMIM: 109690<br>UniProtKB: P07550 |
| C5AR1 | Complement C5a Receptor 1 | Complement Component 5a Receptor 1; Complement Component 5 Receptor 1 (C5a Ligand); C5a Anaphylatoxin Chemotactic Receptor 1; C5a Anaphylatoxin | GCID: GC19P047290<br>HGNC: 1338<br>Entrez Gene: 728<br>Ensembl: ENSG00000197405<br>OMIM: 113995<br>UniProtKB: P21730 |

TABLE 1-continued

| Gene name | Full name | Other names | IDs |
|---|---|---|---|
| | | Chemotactic Receptor; Complement Component 5 Receptor 1; C5a Anaphylatoxin Receptor; C5a-R; C5R1; C5AR; CD88 Antigen; C5a Ligand; CD88; C5a | |
| CALCR | Calcitonin Receptor | CT-R; CTR1; CRT; CTR | GCID: GC07M093424<br>HGNC: 1440<br>Entrez Gene: 799<br>Ensembl: ENSG00000004948<br>OMIM: 114131<br>UniProtKB: P30988 |
| CHRM1 | Cholinergic Receptor Muscarinic 1 | Acetylcholine Receptor, Muscarinic 1; Muscarinic Acetylcholine Receptor M1; HM1; M1R; M1 | GCID: GC11M062927<br>HGNC: 1950<br>Entrez Gene: 1128<br>Ensembl: ENSG00000168539<br>OMIM: 118510<br>UniProtKB: P11229 |
| EDNRB | Endothelin Receptor Type B | Endothelin Receptor Non-Selective Type; ET-BR; ET-B; ETRB; Endothelin Receptor Subtype B1; ABCDS; HSCR2; ETB1; ETBR; WS4A; HSCR; ETB | GCID: GC13M077895<br>HGNC: 3180<br>Entrez Gene: 1910<br>Ensembl: ENSG00000136160<br>OMIM: 131244<br>UniProtKB: P24530 |
| HRH1 | Histamine Receptor H1 | HH1R; H1R; Histamine Receptor, Subclass H1; Histamine H1 Receptor; HisH1; H1-R | GCID: GC03P011113<br>HGNC: 5182<br>Entrez Gene: 3269<br>Ensembl: ENSG00000196639<br>OMIM: 600167<br>UniProtKB: P35367 |
| MLNR | Motilin Receptor | G Protein-Coupled Receptor 38; GPR38; MTLR1; G-Protein Coupled Receptor 38; MTLR | GCID: GC13P049220<br>HGNC: 4495<br>Entrez Gene: 2862<br>Ensembl: ENSG00000102539<br>OMIM: 602885<br>UniProtKB: O43193 |
| NTSR1 | Neurotensin Receptor 1 | High-Affinity Levocabastine-Insensitive Neurotensin Receptor; Neurotensin Receptor 1 (High Affinity); NT-R-1; NTR1; NTRH; Neurotensin Receptor Type 1; NTRR; NTR | GCID: GC20P062708<br>HGNC: 8039<br>Entrez Gene: 4923<br>Ensembl: ENSG00000101188<br>OMIM: 162651<br>UniProtKB: P30989 |
| TACR3 | Tachykinin Receptor 3 | Neurokinin Beta Receptor; Neurokinin B Receptor; NK-3 Receptor; NK-3R; NK3R NKR; Neuromedin-K Receptor; TAC3RL; TAC3R; HH11 | GCID: GC04M103586<br>HGNC: 11528<br>Entrez Gene: 6870<br>Ensembl: ENSG00000169836<br>OMIM: 162332<br>UniProtKB: P29371 |

*GCID: Genecards identification
HGNC: HUGO Gene Nomenclature Committee

TABLE 2

| Gene name | Full name | Other names | IDs |
|---|---|---|---|
| APLNR | Apelin Receptor | G-Protein Coupled Receptor HG11; Angiotensin II Receptor-Like 1; Angiotensin Receptor-Like 1; APJ (Apelin) Receptor; G Protein-Coupled Receptor APJ; G-Protein Coupled Receptor APJ; HG11 Orphan Receptor; APJ Receptor; AGTRL1; APJ; APJR; HG11 | GCID: GC11M057233<br>HGNC: 339<br>Entrez Gene: 187<br>Ensembl: ENSG00000134817<br>OMIM: 600052<br>UniProtKB: P35414 |
| CCR5 | Chemokine (C-C Motif) Receptor 5 | C-C Chemokine Receptor Type 5; Chemokine Receptor CCR5; Chemokine (C-C Motif) Receptor 5 (Gene/Pseudogene); C-C Motif Chemokine Receptor 5 A159A; Chemokine Receptor CCR5 Delta32; CD195 Antigen; HIV-1 Fusion Coreceptor; CC-CKR-5; ChemR13; CMKBR5; CCR-5; C-C CKR-5; CCCKR5; IDDM22; CD195; CKR-5; CKR5 | GCID: GC03P046382<br>HGNC: 1606<br>Entrez Gene: 1234<br>Ensembl: ENSG00000160791<br>OMIM: 601373<br>UniProtKB: P51681 |

TABLE 2-continued

| Gene name | Full name | Other names | IDs |
|---|---|---|---|
| GALR1 | Galanin Receptor 1 | GALNR1; GAL1-R; GALR-1; GALNR; Galanin Receptor Type 1 | GCID: GC18P077250<br>HGNC: 4132<br>Entrez Gene: 2587<br>Ensembl: ENSG00000166573<br>OMIM: 600377<br>UniProtKB: P47211 |
| PTGER2 | Prostaglandin E Receptor 2 | Prostaglandin E Receptor 2 (Subtype EP2), 53 kDa; Prostaglandin E Receptor 2 (Subtype EP2), 53 kD; PGE2 Receptor EP2 Subtype; PGE Receptor EP2 Subtype; Prostanoid EP2 Receptor; Prostaglandin E2 Receptor EP2 Subtype; EP2 | GCID: GC14P052314<br>HGNC: 9594<br>Entrez Gene: 5732<br>Ensembl: ENSG00000125384<br>OMIM: 176804<br>UniProtKB: P43116 |
| PTGER3 | Prostaglandin E Receptor 3 | Prostaglandin E Receptor 3 (Subtype EP3); PGE2 Receptor EP3 Subtype; Prostanoid EP3 Receptor; PGE2-R; Prostaglandin E Receotor EP3 Subtype 3 Isoform; Prostaglandin E2 Receptor EP3 Subtype; Prostaglandin Receptor (PGE-2); PGE Receptor, EP3 Subtype; PGE Receptor EP3 Subtype; EP3-III; EP3-II; EP3-IV; EP3-VI; EP3-I; EP3e; EP3 | GCID: GC01M070852<br>HGNC: 9595<br>Entrez Gene: 5733<br>Ensembl: ENSG00000050628<br>OMIM: 176806<br>UniProtKB: P43115 |
| SSTR2 | Somatostatin Receptor 2 | SRIF-1; SS2R; Somatostatin Receptor Type 2; SS-2-R; SS2-R | GCID: GC17P073165<br>HGNC: 11331<br>Entrez Gene: 6752<br>Ensembl: ENSG00000180616<br>OMIM: 182452<br>UniProtKB: P30874 |

*GCID: Genecards identification
HGNC: HUGO Gene Nomenclature Committee

Further information regarding the GPCRs evaluated herein as heteromers with CXCR4 are detailed below:

(1) ADCYAP1R1—Pituitary adenylate cyclase-activating polypeptide type I receptor also known as PAC1, is a protein that in humans is encoded by the ADCYAP1R1 gene. This receptor binds pituitary adenylate cyclase activating peptide. ADCYAP1R1 is a membrane-associated protein and shares significant homology with members of the G-protein coupled class B glucagon/secretin receptor family. This receptor mediates diverse biological actions of adenylate cyclase activating polypeptide 1 and is positively coupled to adenylate cyclase (Vaudry et al., 2000). This is a receptor for PACAP-27 and PACAP-38. The activity of this receptor is mediated by G proteins which activate adenylyl cyclase. ADCYAP1R1 may regulate the release of adrenocorticotropin, luteinizing hormone, growth hormone, prolactin, epinephrine, and catecholamine. ADCYAP1R1 may play a role in spermatogenesis and sperm motility. ADCYAP1R1 causes smooth muscle relaxation and secretion in the gastrointestinal tract (Ogi et al., 1993).

ADCYAP1R1 is expressed in the adrenal medulla, pancreatic acini, uterus, myenteric plexus and brain (Reubi, 2000; Reubi et al., 2000). It is also expressed in the trigeminal, otic and superior cervical ganglia (prejunctional) and cerebral arteries (postjunctional) (Knutsson and Edvinsson, 2002). Diseases associated with ADCYAP1R1 include post-traumatic stress disorder (Lowe et al., 2015) and anxiety disorder. Among its related pathways are G alpha(s) signalling events and RET signaling (Cooper et al., 2013).

(2) ADORA2B—The adenosine A2B receptor, also known as ADORA2B, is a G-protein coupled adenosine receptor, and also denotes the human adenosine A2b receptor gene which encodes it. Adenosine functions as a signaling molecule through the activation of four distinct adenosine receptors—ADORA1, ADORA2A, ADORA2B, and ADORA3, also called as A1, A2A, A2B, and A3, respectively. This integral membrane protein stimulates adenylate cyclase activity in the presence of adenosine. This protein also interacts with netrin-1, which is involved in axon elongation. These receptors are widely expressed and have been implicated in several biological functions, both physiological and pathological. Both ADORA2A and ADORA2B receptors are important in cancer immunology. The tumor microenvironment is hypoxic, which promotes the expression of CD39 and CD73 by immune cells. CD39 and CD73 are ectonucleotidases that convert ATP to adenosine, elevating concentrations of adenosine locally. Adenosine is a crucial mediator of altered immune function in cancer as it binds ADORA2A and ADORA2B receptors on lymphocytes silencing the antitumor immune response (Chen et al., 2013).

ADORA2B has a role in regulating CXCR4 expression in vivo and in protecting against vascular lesion formation (Yang et al., 2008) and promotes progression of human oral cancer (Kasama et al., 2015). Identification of a pharmacologically tractable Fra-1/ADORA2B axis promoting breast cancer metastasis (Desmet et al., 2013). ADORA2B receptors display high expression levels in the cecum, colon and bladder, with lower levels in the lung, blood vessels and eye (Fagerberg et al., 2014).

(3) ADORA3—The adenosine A3 receptor, also known as ADORA3, is an adenosine receptor, but also denotes the human gene encoding it. ADORA3 receptors are G-protein coupled receptors that couple to Gi/Gq and are involved in a variety of intracellular signaling pathways and physiological functions. It mediates a sustained cardioprotective function during cardiac ischemia, it is involved in the inhibition of neutrophil degranulation in neutrophil-mediated tissue injury, it has been implicated in both neuroprotective and neurodegenerative effects, and it may also mediate both cell proliferation and cell death (Gao et al., 2008; Miwatashi et al., 2008).

Cordycepin induces apoptosis in human bladder cancer cells via activation of ADORA3 receptors (Cao et al., 2017). Jafari et al. showed that ADORA3 receptor agonist inhibited survival of breast cancer stem cells via GLI-1 and ERK1/2 pathway (Jafari et al., 2017). ADORA3 is broadly expressed in adrenal (RPKM 4.4), small intestine (RPKM 2.9) and 20 other tissues containing brain, bladder, lymph node and colon (Fagerberg et al., 2014).

(4) ADRB2—The beta-2 adrenergic receptor (β2 adrenoreceptor), also known as ADRB2, is a cell membrane-spanning beta-adrenergic receptor that interacts with epinephrine, a hormone and neurotransmitter (ligand synonym, adrenaline) whose signaling, via a downstream L-type calcium channel interaction, mediates physiologic responses such as smooth muscle relaxation and bronchodilation (Gregorio et al., 2017). ADRB2 functions in muscular system such as smooth muscle relaxation, motor nerve terminals, glycogenolysis and in circulatory system such as heart muscle contraction, cardiac output increase. In the normal eye, beta-2 stimulation by salbutamol increases intraocular pressure via net. In digestive system, the ADRB2 induces glycogenolysis and gluconeogenesis in liver and insulin secretion from pancreas (Fitzpatrick, 2004).

ADRB2 signaling in the cardiac myocyte is modulated by interactions with CXCR4 (LaRocca et al., 2010). Norepinephrine attenuates CXCR4 expression and the corresponding invasion of MDA-MB-231 breast cancer cells via ADRB2 (Wang et al., 2015a). ADRB2 is expressed in several cancers such as pancreatic, prostate (Braadland et al., 2014; Xu et al., 2017), renal and breast cancer (Choy et al., 2016).

(5) C5AR1—The C5a receptor also known as complement component 5a receptor 1 (C5AR1) or CD88 (Cluster of Differentiation 88) is a G protein-coupled receptor for C5a. It functions as a complement receptor. C5AR1 modulates inflammatory responses, obesity, development and cancers. (Gerard and Gerard, 1994).

The C5AR1 is expressed on granulocytes, monocytes, dendritic cells, hepatoma-derived cell line HepG2, astrocytes, microglia (Klos et al., 2013). C5AR1 is related in several diseases such as inflammatory bowel disease, rheumatoid arthritis, psoriasis, experimental allergic encephalomyelitis, multiple sclerosis, meningitis, and brain trauma (Lee et al., 2008).

(6) CALCR—The calcitonin receptor (CT) is a G protein-coupled receptor that binds the peptide hormone calcitonin and is involved in maintenance of calcium homeostasis, particularly with respect to bone formation and metabolism (Dacquin et al., 2004; Davey et al., 2008). CT works by activating the G-proteins Gs and Gq often found on osteoclasts, on cells in the kidney, and on cells in a number of regions of the brain. It may also affect the ovaries in women and the testes in men. The activity of this receptor is mediated by G proteins which activate adenylyl cyclase. The calcitonin receptor is thought to couple to the heterotrimeric guanosine triphosphate-binding protein that is sensitive to cholera toxin. The physiological effects of CT such as inhibition of osteoclast mediated bone resorption or increased Ca2+ excretion by the kidney are mediated by high affinity CTs (Albrandt et al., 1995).

Loss of function mutation in CT identifies highly aggressive glioblastoma with poor outcome (Pal et al., 2018). Expression of CTRs in mammary gland, cartilage, nose and ear has been reported. The developmental regulation of CALCR gene expression in a variety of the above tissues suggests a role for CTRs in the morphogenesis of these tissues (Pondel, 2000).

(7) CHRM1—The muscarinic cholinergic receptors belong to a larger family of G protein-coupled receptors. The functional diversity of these receptors is defined by the binding of acetylcholine and includes cellular responses such as adenylate cyclase inhibition, phosphoinositide degeneration, and potassium channel mediation. Muscarinic receptors influence many effects of acetylcholine in the central and peripheral nervous system (Rang, 2003). The muscarinic cholinergic receptor 1 is involved in mediation of vagally-induced bronchoconstriction and in the acid secretion of the gastrointestinal tract. It is predominantly found bound to G proteins of class Gq that use upregulation of phospholipase C and, therefore, inositol trisphosphate and intracellular calcium as a signaling pathway (Qin et al., 2011).

Muscarinic receptors are widely distributed throughout the body and control distinct functions according to location and subtype (CHRM1-CHRM5). They are predominantly expressed in the parasympathetic nervous system where they exert both inhibitory and excitatory effects. This receptor is found mediating slow excitatory postsynaptic potential at the ganglion in the postganglionic nerve, is common in exocrine glands and in the CNS (Johnson, 2002). Diseases associated with CHRM1 include asthma and heart block, congenital and Pelizaeus-Merzbacher disease. Activators of CHRM1 muscarinic acetylcholine receptors (mAChRs) may provide novel treatments for schizophrenia and Alzheimer's disease (Mario et al., 2009).

(8) EDNRB—Endothelin receptor type B (ETB) receptor was cloned shortly after the ETA receptor (EDBRA). Similarly to the EDNRA, it belongs to class A of G protein-coupled heptahelical receptors with an external amino terminus and internal carboxy terminus and binding sites intrinsic to the heptahelical portions of the receptor. Similar to the EDNRA, the endogenous agonist ET-1 has a high affinity for the EDNRB. The pharmacology of the EDNRB receptor is somewhat richer than that of the EDNRA in that multiple agonists of the EDNRB are recognized, including sarafotoxin 6c (S6c) and IRL1620. Selective antagonists of the EDNRB include BQ788, A192621, RES7011, and IRL2500. The EDNRB has been localized to cardiovascular tissues, the pulmonary system, neurons, bone, pancreas, and kidney (Watts, 2010).

EDNRB is a G protein-coupled receptor which activates a phosphatidylinositol-calcium second messenger system. Its ligand, endothelin, consists of a family of three potent vasoactive peptides: ET1, ET2, and ET3. In melanocytic cells the EDNRB gene is regulated by the microphthalmia-associated transcription factor. Mutations in either gene are links to Waardenburg syndrome (Sato-Jin et al., 2008). The multigenic disorder, Hirschsprung disease type 2, is due to mutation in EDNRB gene (Tanaka et al., 1998). Diseases associated with EDNRB include Waardenburg syndrome, Type 4A and Abcd syndrome. Among its related pathways are calcium signaling pathway and prostaglandin synthesis and regulation of Waardenburg Syndrome (Sato-Jin et al., 2008).

(9) HRH1—The H1 receptor is a histamine receptor belonging to the family of rhodopsin-like G-protein-coupled receptors. This receptor is activated by the biogenic amine histamine. The HRH1 is linked to an intracellular G-protein (Gq) that activates phospholipase C and the inositol triphosphate (IP3) signaling pathway. Antihistamines, which act on this receptor, are used as anti-allergy drugs. The crystal structure of the receptor has been determined and used to discover new HRH1 ligands in structure-based virtual screening studies (de Graaf et al., 2011). A subunit of the G-protein subsequently dissociates and affects intracellular messaging including downstream signaling accomplished through various intermediaries such as cyclic AMP, cyclic GMP, calcium, and nuclear factor kappa B. It functions in immune-cell chemotaxis, pro-inflammatory cytokine production, expression of cell adhesion molecules, and other allergic and inflammatory conditions (Canonica and Blaiss, 2011).

In peripheral tissues, the HRH1 mediates the contraction of smooth muscles, increase in capillary permeability due to contraction of terminal venules, and catecholamine release from adrenal medulla, as well as mediating neurotransmission in the central nervous system. It is also known to contribute to the pathophysiology of allergic diseases such as atopic dermatitis, asthma, anaphylaxis and allergic rhinitis (Xie and He, 2005). It is expressed in smooth muscles, on vascular endothelial cells, in the heart, and in the central nervous system (de Graaf et al., 2011).

(10) MLNR—Motilin receptor is a G protein-coupled receptor that binds motilin. Motilin in turn is an intestinal peptide that stimulates contraction of gut smooth muscle. Also, the MLNR mediates progastrokinetic effects. MLNR is an important therapeutic target for the treatment of hypomotility disorders (Depoortere, 2001).

It is found at its highest concentrations in the nerves of the antral wall of the stomach and is also found at significant levels throughout the smooth muscle of the upper gastrointestinal tract (Kitazawa et al., 1995). Diseases associated with MLNR include gastroparesis and diabetic autonomic neuropathy (Kitazawa et al., 1997).

(11) NTSR1—Neurotensin receptor 1 belongs to the large superfamily of G-protein coupled receptors. Neurotensin is a 13-amino acid peptide originally isolated from hypothalamic and later from intestines of bovine. In the brain, neurotensin is exclusively found in nerve cells, fibers, and terminals, whereas the majority of peripheral neurotensin is found in the endocrine N-cells located in the intestinal. Central or peripheral injections of neurotensin produce completely different pharmacological effects indicating that the peptide does not cross the blood-brain barrier. NTSR1 mediates the multiple functions of neurotensin, such as hypotension, hyperglycemia, hypothermia, antinociception, and regulation of intestinal motility and secretion (Vincent, 1995).

Signaling is effected via G proteins that activate a phosphatidylinositol-calcium second messenger system. Signaling leads to the activation of downstream MAP kinases and protects cells against apoptosis (Heakal et al., 2011). Swift et al. showed altered expression of neurotensin receptors is associated with the differentiation state of prostate cancer (Swift et al., 2010).

(12) PTGER2—Prostaglandin E2 receptor 2, also known as EP2, is a prostaglandin receptor for prostaglandin E2 (PGE2) encoded by the human gene PTGER2. PTGER2 is classified as a relaxant type of prostanoid receptor based on its ability, upon activation, to relax certain types of smooth muscle. When initially bound to PGE2 or any other of its agonists, it mobilizes G proteins containing the $G\alpha s$-$G\beta\gamma$ complex. The $G\alpha s$-$G\beta\gamma$ complexes dissociate into their $G\alpha s$ and $G\beta\gamma$ subunits which in turn regulate cell signaling pathways. In particular, $G\alpha s$ stimulates adenylyl cyclase to raise cellular levels of cAMP thereby activating PKA; PKA activates various types of signaling molecules such as the transcription factor CREB which lead to different types of functional responses depending on cell type (Markovic et al., 2017; Woodward et al., 2011). PTGER2 also activates the GSK-3 pathway which regulates cell migratory responses and innate immune responsesincluding pro-inflammatory cytokine and interleukin production and Beta-catenin pathway which regulates not only cell-cell adhesion but also activates the Wnt signaling pathway which, in turn, stimulates the transcription of genes responsible for regulating cell migration and proliferation (Woodward et al., 2011).

The PTGER2 receptor can act as a tumor promoter. PTGER2 gene knockout mice have less lung, breast, skin, and colon cancers following exposure to carcinogens. Knockout of this gene in mice with the adenomatous polyposis coli mutation also causes a decrease in the size and number of pre-cancerous intestinal polyps that the animals develop. These effects are commonly ascribed to the loss of PTGER2-mediated: vascular endothelial growth factor production and thereby of tumor vascularization; regulation of endothelial cell motility and survival; interference with transforming growth factor-β's anti-cell proliferation activity; and, more recently, regulation of host anti-tumor immune responses (O'Callaghan and Houston, 2015).

PTGER2 is widely distributed in humans. Its protein is expressed in human small intestine, lung, media of arteries and arterioles of the kidney, thymus, uterus, brain cerebral cortex, brain striatum, brain hippocampus, corneal epithelium, corneal choriocapillaries, Myometriuml cells, eosinophiles, sclera of the eye, articular cartilage, the corpus cavernosum of the penis, and airway smooth muscle cells; its mRNA is expressed in gingival fibroblasts, monocyte-derived dendritic cells, aorta, corpus cavernosum of the penis, articular cartilage, airway smooth muscle, and airway epithelial cells. In rats, the receptor protein and/or mRNA has been found in lung, spleen, intestine, skin, kidney, liver, long bones, and rather extensively throughout the brain and other parts of the central nervous system (Yagami et al., 2016).

Pre-clinical studies indicate that PTGER2 may be a target for treating and/or preventing particular human disorders involving: allergic diseases such as asthma (particular aspirin and nonsteroidal inflammatory drug-induced asthma syndromes) and rhinitis (Machado-Carvalho et al., 2014); glaucoma (Doucette and Walter, 2017); various diseases of the nervous system (Yagami et al., 2016); fractures, osteoporosis, and other bone abnormalities (Li et al., 2007); pulmonary fibrosis; certain forms of malignant disease such as colon cancer including those that arise from Adenomatous polyposis coli mutations (O'Callaghan and Houston, 2015); and salt-sensitive forms of hypertension (Yang and Du, 2012); This receptor has also been suggested to be a target for contraception (Sugimoto et al., 2015).

(13) TACR3—Tachykinin receptor 3, also known as TACR3, function as receptors for tachykinins. The tachykinins are a family of peptides that comprise substance P (SP), neurokinin A (NKA), neurokinin B (NKB) and the species divergent endokinins including endokinin B (EKB) in humans. These tachykinins are encoded on three different genes, preprotachykinin 1 (TAC1) encoding SP and NKA, TAC3 encoding NKB and TAC4 encoding EKB. Three tachykinin receptors have been identified, which interact with these tachykinins: TACR1, TACR2, and TACR3, also called as NK1, NK2 and NK3, respectively, whereby SP and EKB show the greatest potency for TACR1, NKA for TACR2 and NKB for TACR3. Receptor affinities are specified by variations in the 5'-end of the sequence. Tachykinin receptor-3 (TACR3) is the mediator of biologic actions encoded by the C-terminal sequence of tachykinins, for which neurokinin B is a more potent agonist than neurokinin A or substance P (Page et al., 2003).

It is reported that four human pedigrees with severe congenital gonadotropin deficiency and pubertal failure in which all affected individuals are homozygous for loss-of-function mutations in TAC3 (encoding Neurokinin B) or its receptor TACR3 (encoding NK3R) (Topaloglu et al., 2009). NKB, a member of the substance P-related tachykinin family, is known to be highly expressed in hypothalamic neurons that also express kisspeptin (Goodman et al., 2007), a recently identified regulator of gonadotropin-releasing hormone secretion (Gianetti and Seminara, 2008).

(14) APLNR—The apelin receptor (also known as the APJ receptor) is a G protein-coupled receptor which binds apelin and Apela/ELABELA/Toddler (Medhurst et al., 2003). Receptor for apelin receptor early endogenous ligand (APELA) and apelin (APLN) hormones coupled to G proteins that inhibit adenylate cyclase activity. APLNR plays a key role in early development such as gastrulation and heart morphogenesis by acting as a receptor for APELA hormone. APLNR plays also a role in various processes in adults such as regulation of blood vessel formation, blood pressure, heart contractility, and heart failure by acting as a receptor for APLN hormone. A decade of investigations has shown that the apelinergic system has a broad range of biological functions, playing an important role particularly in maintaining homeostasis of the cardiovascular system and fluid metabolism. The activation of APLNR causes a broad spectrum of biochemical changes including cAMP suppression, phosphorylation of protein kinase B (Akt), ERK1/25 and p70S6K, calcium mobilization7 and nitric oxide synthase (NOS). However, the specificity linking these biochemical activities to a certain biological function is yet to be determined (Wang et al., 2015c).

Also, It functions in embryonic and tumor angiogenesis (Wu et al., 2017) and as a human immunodeficiency virus (HIV-1) coreceptor (Zhou et al., 2003). Both APLNR and apelin are expressed in many tissues including heart, lung, endothelium, kidney and brain (Wang et al., 2015c).

(15) CCR5—C-C chemokine receptor type 5, also known as CCR5 or CD195, is a protein on the surface of white blood cells that is involved in the immune system as it acts as a receptor for chemokines. This is the process by which T cells are attracted to specific tissue and organ targets. Many forms of HIV, the virus that causes AIDS, initially use CCR5 to enter and infect host cells. Certain individuals carry a mutation known as CCR5-Δ32 in the CCR5 gene, protecting them against these strains of HIV. Certain populations have inherited the Delta 32 mutation resulting in the genetic deletion of a portion of the CCR5 gene. Homozygous carriers of this mutation are resistant to M-tropic strains of HIV-1 infection (Hutter et al., 2009). CCR5's cognate ligands include CCL3, CCL4 (also known as MIP 1α and 1β, respectively), and CCL3L1. CCR5 furthermore interacts with CCL5 (Struyf et al., 2001).

It is likely that CCR5 plays a role in inflammatory responses to infection, though its exact role in normal immune function is unclear. Regions of this protein are also crucial for chemokine ligand binding, functional response of the receptor, and HIV co-receptor activity (Barmania and Pepper, 2013). CCR5 is predominantly expressed on T cells, macrophages, dendritic cells, eosinophils, microglia and a subpopulation of either breast or prostate cancer cells (Sicoli et al., 2014; Velasco-Velazquez et al., 2012).

(16) GALR1—Galanin receptor 1 (GAL1) is a G-protein coupled receptor encoded by the GALR1 gene. The ubiquitous neuropeptide galanin controls numerous functions such as endocrine secretions, intestinal motility, and behavioral activities. These regulatory effects of galanin are mediated through the interaction with specific membrane receptors and involve the pertussis toxin-sensitive guanine nucleotide binding proteins Gi/Go as transducing elements (Habert-Ortoli et al., 1994).

GALR1 has anti-proliferative effects in oral squamous cell carcinoma. GALR1 protein and mRNA expression and GAL secretion were detected at variable levels in immortalized human oral keratinocytes and human oropharyngeal squamous cell carcinoma cell lines. Upon competitive inhibition of GALR1, proliferation was up-regulated in immortalized and malignant keratinocytes (Henson et al., 2005)

Stevenson et al. report the stem cell marker and regulator, galanin and GALR1 as key determinants of drug resistance and potential therapeutic targets for combating drug resistance. Mechanistically, they identify a novel role for the GALR1-galanin receptor-ligand axis as an important upstream regulator of expression of the anti-apoptotic protein FLIPL. Clinically, galanin mRNA was found to be overexpressed in colorectal tumours, and notably, high galanin mRNA expression correlated with poor disease-free survival in early stage disease (Stevenson et al., 2012). GALR1 is widely expressed in the brain and spinal cord, as well as in peripheral sites such as the small intestine and heart (Fagerberg et al., 2014)

(17) PTGER3—Prostaglandin EP3 receptor (53 kDa), also known as EP3, is a prostaglandin receptor for prostaglandin E2 (PGE2) encoded by the human gene PTGER3; it is one of four identified EP receptors, the others being PTGER1, PTGER2, and PTGER4, also called as EP1, EP2, and EP4, respectively, all of which bind with and mediate cellular responses to PGE2 and also, but generally with lesser affinity and responsiveness, certain other prostanoids. PTGER3 activation promotes duodenal secretion in mice; this function is mediated by PTGER3 activation in humans. EP receptor functions can vary with species and most of the functional studies cited here have not translated their animal and tissue models to humans (Moreno, 2017).

Studies of the direct effects of PTGER3 activation on cancer in animal and tissue models give contradictory results suggesting that this receptor does not play an important role in carcinogenesis. However, some studies suggest an indirect pro-carcinogenic function for the PTGER3: The growth and metastasis of implanted Lewis lung carcinoma cells, a mouse lung cancer cell line, is suppressed in PTGER3-deficient mice. This effect was associated with a reduction in the levels of Vascular endothelial growth factor and matrix metalloproteinase-9 expression in the tumor's stroma; expression of the pro-lymphangiogenic growth factor, VEGF-C and its receptor, VEGFR3; and a tumor-associated angiogenesis and lymphangiogenesis (O'Callaghan and Houston, 2015).

PTGER3 is widely distributed in humans. Its protein and/or mRNA is expressed in kidney (i.e. glomeruli, Tamm-Horsfall protein negative late distal convoluted tubules, connecting segments, cortical and medullary collecting ducts, media and endothelial cells of arteries and arterioles); stomach (vascular smooth muscle and gastric fundus mucosal cells); thalamus (anterior, ventromedial, laterodorsal, paraventricular and central medial nuclei); intestinal mucosal epithelia at the apex of crypts; myometrium (stromal cells, endothelial cells, and, in pregnancy, placenta, chorion, and amnion); mouth gingival fibroblasts; and eye (corneal endothelium and keratocytes, trabecular cells, ciliary epithelium, and conjunctival and iridal stroma cells, and retinal Muller cells) (Morel, 2016).

(18) SSTR2—Somatostatin receptor type 2 is a protein that in humans is encoded by the SSTR2 gene. Somatostatin acts at many sites to inhibit the release of many hormones and other secretory proteins. The biologic effects of somatostatin are probably mediated by a family of G protein-coupled receptors that are expressed in a tissue-specific manner. SSTR2 has been shown to interact with shank2 (Zitzer et al., 1999).

SSTR2 encodes somatostatin receptor that can inhibit the cell proliferation of solid tumors. SSTR2 promoter hypermethylation is associated with the risk and progression of laryngeal squamous cell carcinoma in males (Shen et al., 2016). Most pituitary adenomas express SSTR2, but other somatostatin receptors are also found (Miller et al., 1995). Somatostatin analogs (i.e. Octreotide, Lanreotide) are used to stimulate this receptors, and thus to inhibit further tumor proliferation (Zatelli et al., 2007). SSTR2 is expressed in highest levels in cerebrum and kidney (Fagerberg et al., 2014).

The term "inhibitor" as used herein refers to molecule that inhibits or suppresses the enhanced function of CXCR4-GPCRx heteromer. Non-limiting examples of the inhibitor of the invention that can be used for treatment, amelioration, or prevention of a cancer or related symptoms include GPCRx antagonist, GPCRx inverse agonist, GPCRx positive and negative allosteric modulator, CXCR4-GPCRx heteromer-specific antibody or its antigen biding portions including single-domain antibody-like scaffolds, bivalent ligands which have a pharmacophore selective for CXCR4 joined by a spacer arm to a pharmacophore selective for GPCRx, bispecific antibody against CXCR4 and GPCRx, radiolabeled CXCR4 ligand linked with GPCRx ligand, and small molecule ligands that inhibit heteromer-selective signaling. Certain examples of inhibitors against GPCRx that form heteromers with CXCR4 and enhance Ca2+ response upon co-stimulation with both agonists are listed in Table 3.

The term "antagonist" as used herein refers to a type of receptor ligand or drug that blocks or dampens a biological response by binding to and blocking a receptor, also called blockers. Antagonists have affinity but no efficacy for their cognate receptors, and their binding disrupts the interaction and inhibit the function of an agonist or inverse agonist at the cognate receptors. Certain examples of antagonists against GPCRx that form heteromers with CXCR4 and enhance Ca2+ response upon co-stimulation with both agonists are listed in Table 3.

TABLE 3

Examples of inhibitors against GPCRx that form heteromers with CXCR4 and enhances Ca2+ response upon co-stimulation with both agonists.

| Gene name | Antagonists/Inverse agonists | Antibodies/nanobodies/i-bodies/others |
|---|---|---|
| CXCR4 | ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMI-1359, GSK812397, GST-NT21MP, isothiourea-1a, isothiourea-1t (IT1t), KRH-1636, KRH-3955, LY2510924, MSX-122, N-[$^{11}$C]Methyl-AMD3465, POL6326, SDF-1 1-9[P2G] dimer, SDF1 P2G, T134, T140, T22, TC 14012, TG-0054 (Burixafor), USL311, viral macrophage inflammatory protein-II (vMIP-II), WZ811, [$^{64}$Cu]-AMD3100, [$^{64}$Cu]-AMD3465, [$^{68}$Ga]pentixafor, [$^{90}$Y]pentixather, [$^{99m}$Tc]O$_2$-AMD3100, [$^{177}$Lu]pentixather, and 508MCl (Compound 26). | AD-114, AD-114-6H, AD-114-Im7-FH, AD-114-PA600-6H, ALX-0651, LY2624587, PF-06747143, ulocuplumab (MDX1338/BMS-936564), 12G5, 238D2, and 238D4 |
| ADCYAP1R1 | M65, Max.d.4, MK-0893, N-stearyl-[Nle$^{17}$] neurotensin-(6-11)/VIP-(7-28), PACAP-(6-38), and PG 97-269 | |
| ADORA2B | 3-isobutyl-8-pyrrolidinoxanthine, alloxazine, AS16, AS70, AS74, AS94, AS95, AS96, AS99, AS100, AS101, ATL802, BW-A1433, caffeine, CGS 15943, CPX, CSC, CVT-6883, DAX, DEPX, derenofylline, DPCPX, FK-453, I-ABOPX, istradefylline, KF26777, LAS38096, LUF5981, MRE 2029F20, MRE 3008F20, MRS1191, MRS1220, MRS1523, MRS1706, MRS1754, MSX-2, OSIP339391, pentoxifylline, preladenant, PSB-10, PSB-11, PSB36, PSB603, PSB-0788, PSB1115, rolofylline, SCH 58261, SCH442416, ST-1535, theophylline, tonapofylline, vipadenant, xanthine amine congener, XCC, and ZM-241385. | |
| ADORA3 | ATL802, BW-A1433, caffeine, CGS 15943, CSC, CVT-6883, derenofylline, dexniguldipine, DPCPX, FK-453, flavanone, flavone, galangin, I-ABOPX, istradefylline, KF26777, LAS38096, LUF5981, MRE 2029F20, MRE 3008F20, MRE 3010F20, MRS1041, MRS1042, MRS1067, MRS1088, MRS1093, MRS1097, MRS1177, MRS1186, MRS1191, MRS1191, MRS1220, MRS1476, MRS1486, MRS1505, MRS1523, MRS1754, MRS928, MSX-2, nicardipine, preladenant, PSB-10, PSB-11, PSB36, PSB603, PSB1115, rolofylline, sakuranetin, SCH 58261, SCH442416, ST-1535, theophylline, tonapofylline, vipadenant, visnagin, VUF5574, VUF8504, VUF8507, xanthine amine congener, and ZM-241385 | |
| ADRB2 | Alprenolol, atenolol, betaxolol, bupranolol, butoxamine, carazolol, carvedilol, CGP 12177, cicloprolol, ICI 118551, ICYP, labetalol, levobetaxolol, levobunolol, LK 204-545, metoprolol, nadolol, NIHP, NIP, propafenone, propranolol, sotalol, SR59230A, and timolol. | |
| C5AR1 | A8$^{Δ71-73}$, AcPhe-Orn-Pro-D-Cha-Trp-Arg, avacopan, C089, CHIPS, DF2593A, JPE1375, L-156,602, NDT9520492, N-methyl-Phe-Lys-Pro-D-Cha-Trp-D-Arg-CO$_2$H, PMX205, PMX53, RPR121154, and W54011. | |
| CALCR | α-CGRP-(8-37) (human), AC187, CT-(8-32) (salmon), and olcegepant. | |
| CHRM1 | 3-Quinuclidinyl benzilate (QNB), 4-DAMP, aclidinium, AE9C90CB, AFDX384, amitriptyline, AQ-RA 741, atropine, benzatropine, biperiden, | |

TABLE 3-continued

Examples of inhibitors against GPCRx that form heteromers with CXCR4
and enhances Ca2+ response upon co-stimulation with both agonists.

| Gene name | Antagonists/Inverse agonists | Antibodies/ nanobodies/ i-bodies/others |
|---|---|---|
|  | darifenacin, dicyclomine, dosulepin, ethopropazine, glycopyrrolate, guanylpirenzepine, hexahydrodifenidol, hexahydrosiladifenidol, hexocyclium, himbacine, ipratropium, lithocholylcholine, methoctramine, ML381, muscarinic toxin 1, muscarinic toxin 2, muscarinic toxin 3, N-methyl scopolamine, otenzepad, oxybutynin, p-F-HHSiD, pirenzepine, propantheline, (R,R)-quinuclidinyl-4-fluoromethyl-benzilate, scopolamine, silahexocyclium, solifenacin, telenzepine, tiotropium, tolterodine, trihexyphenidyl, tripitramine, UH-AH 37, umeclidinium, and VU0255035. |  |
| EDNRB | A192621, ambrisentan, atrasentan, bosentan (RO 470203, Tracleer);, BQ788, IRL 2500, K-8794, macitentan, RES7011, Ro 46-8443, SB209670, SB217242 (enrasentan), TAK 044, and tezosentan (RO610612). |  |
| HRH1 | (−)-chlorpheniramine, (+)-chlorpheniramine, (−)-trans-$H_2$-PAT, (+)-cis-$H_2$-PAT, (+)-trans-$H_2$-PAT, (±)-cis-$H_2$-PAT, (±)-trans-$H_2$-PAT, (R)-cetirizine, (S)-cetirizine, 9-OH-risperidone, A-317920, A-349821, ABT-239, alimemazine, amitriptyline, aripiprazole, arpromidine, asenapine, astemizole, AZD3778, azelastine, BU-E 47, cetirizine, chlorpheniramine, chlorpromazine, ciproxifan, clemastine, clobenpropit, clozapine, conessine, cyclizine, cyproheptadine, desloratadine, diphenhydramine, dosulepin, doxepin, epinastine, fexofenadine, fluphenazine, fluspirilene, haloperidol, hydroxyzine, impromidine, INCB-38579, JNJ-39758979, ketotifen, loratadine, loxapine, MK-0249, molindone, olanzapine, perphenazine, pimozide, pipamperone, pitolisant, promethazine, pyrilamine, quetiapine, risperidone, sertindole, terfenadine, thioridazine, thiothixene, trifluoperazine, tripelennamine, triprolidine, ziprasidone, and zotepine. |  |
| MLNR | GM-109, MA-2029, and OHM-11526. |  |
| NTSR1 | Meclinertant, SR48527, SR48692, and SR142948A |  |
| TACR3 | [Trp$^7$, β-Ala$^8$] neurokinin A-(4-10), AZD2624, FK 224, GR138676, GSK 172981, GSK 256471, N',2-diphenylquinoline-4-carbohydrazide 8m, N',2-diphenylquinoline-4-carbohydrazide, osanetant, PD 154740, PD 161182, PD157672, saredutant, SB 218795, SB 222200, SB 235375, SCH 206272, SSR 146977, and talnetant. |  |

In some embodiments, the method for treating cancer in a patient having a cell containing a CXCR4-GPCRx heteromer, or the method of suppressing enhanced downstream signaling from a CXCR4-GPCRx heteromer in a cell of a patient suffering from cancer, as disclosed herein, may comprise administering, or the pharmaceutical kit or pharmaceutical kit, comprise, administering to the patient an inhibitor or a combination of inhibitors selected from the group consisting of: an inhibitor of CXCR4, an inhibitor of GPCRx, and an inhibitor of the CXCR4-GPCRx heteromer; wherein: i) the CXCR4-GPCRx heteromer has enhanced downstream signaling; and ii) the administered inhibitor or combination of inhibitors suppresses the enhanced downstream signaling from said CXCR4-GPCRx heteromer in the cancer patient. In some embodiments, the pharmaceutical kit or pharmaceutical composition for use in treating cancer in a patient having a cell containing a CXCR4-GPCRx heteromer, as disclosed herein, may comprise an inhibitor or a combination of inhibitors selected from the group consisting of: an inhibitor of CXCR4, an inhibitor of GPCRx, and an inhibitor of the CXCR4-GPCRx heteromer; wherein the CXCR4-GPCRx heteromer has enhanced downstream signaling. For example, in some embodiments, the CXCR4 inhibitor is an antagonist of CXCR4, an inverse agonist of CXCR4, a partial antagonist of CXCR4, an allosteric modulator of CXCR4, an antibody of CXCR4, an antibody fragment of CXCR4, a ligand of CXCR4, or an antibody-drug conjugate of CXCR4. For example, in some embodiments, the GPCRx inhibitor is an antagonist of GPCRx, an inverse agonist of GPCRx, a partial antagonist of GPCRx, an allosteric modulator of GPCRx, an antibody of GPCRx, an antibody fragment of GPCRx, a ligand of GPCRx, or an antibody-drug conjugate of GPCRx. For example, in some embodiments, the inhibitor of the CXCR4-GPCRx heteromer is an antagonist of the CXCR4-GPCRx heteromer, an inverse agonist of the CXCR4-GPCRx heteromer, a partial antagonist of the CXCR4-GPCRx heteromer, an allosteric modulator of the CXCR4-GPCRx heteromer, an antibody of the CXCR4-GPCRx heteromer, an antibody fragment of the CXCR4-GPCRx heteromer, a ligand of the CXCR4-GPCRx heteromer, a protein-protein interaction (PPI) inhibitor of the CXCR4-GPCRx heteromer, or an antibody-drug conjugate of the CXCR4-GPCRx heteromer.

In some embodiments, the method for treating, method of suppressing, pharmaceutical kit, or pharmaceutical composition, as disclosed herein, includes a combination of inhibitors selected from the group consisting of: the CXCR4 inhibitor, the GPCRx inhibitor, and the inhibitor of the CXCR4-GPCRx heteromer, wherein the combination may be in a single pharmaceutical composition or a plurality of separate pharmaceutical compositions for each respective inhibitor. In some embodiments, the combination of inhibitors comprises the CXCR4 inhibitor and the GPCRx inhibitor. In some embodiments, the combination of inhibitors comprises the CXCR4 inhibitor and the inhibitor of the CXCR4-GPCRx heteromer. In some embodiments, the combination of inhibitors comprises the GPCRx inhibitor and the inhibitor of the CXCR4-GPCRx heteromer. In some embodiments, the combination of inhibitors are administered sequentially, concurrently, or simultaneously. In some embodiments, the combination of inhibitors are administered as a pharmaceutical composition further comprising a pharmaceutically acceptable carrier. In some embodiments, the combination of inhibitors are administered as separate pharmaceutical compositions, wherein the separate pharmaceutical compositions independently further comprise a pharmaceutically acceptable carrier. In some embodiments, the method for treating, method of suppressing, pharmaceutical kit, or pharmaceutical composition, as disclosed herein, comprises a therapeutically effective amount or a sub-therapeutically effective amount of the CXCR4 inhibitor, such as administering a therapeutically effective amount of the CXCR4 inhibitor to the patient. In some embodiments, the method for treating, method of suppressing, pharmaceutical kit, or pharmaceutical composition, as disclosed herein, comprises a therapeutically effective amount or a sub-therapeutically effective amount of the GPCRx inhibitor, such as administering a therapeutically effective amount of the GPCRx inhibitor to the patient. In some embodiments, the method for treating, method of suppressing, pharmaceutical kit, or pharmaceutical composition, as disclosed herein, comprises a therapeutically effective amount or a sub-therapeutically effective amount of the inhibitor of the CXCR4-GPCRx heteromer, such as administering a therapeutically effective amount of the inhibitor of the CXCR4-GPCRx heteromer to the patient.

In some embodiments, the method for treating cancer in a patient having a cancer cell containing a CXCR4-GPCRx heteromer, as disclosed herein, may comprise: 1) determining whether the patient has the cancer cell containing the CXCR4-GPCRx heteromer having enhanced downstream signaling by: obtaining or having obtained a biological sample from the patient; and performing or having performed an assay on the biological sample to determine if: i) the patient's cancer cell containing said CXCR4-GPCRx heteromer; or ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing the CXCR4-GPCRx heteromer; or decreases cell proliferation of a patient derived cell(s) containing the CXCR4-GPCRx heteromer; and 2) if the patient has a cancer cell containing said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the cancer patient. In some embodiments, the method for treating cancer in a patient having a cancer cell containing a CXCR4-GPCRx heteromer, as disclosed herein, may comprise: 1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein: a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; and b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, or a fluorescent animal assay, such as via a co-internalization assay, bimolecular fluorescence complementation (BiFC), or a proximity ligation assay (PLA); and 2) if the patient's cancer cell contains said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the patient. In some embodiments, the patient's biological sample is a biological fluid sample or is a biological tissue sample. In some embodiments, a liquid biopsy is performed on the biological fluid sample or performed on the biological tissue sample. In some embodiments, the biological fluid sample is a blood sample, a plasma sample, a saliva sample, a cerebral fluid sample, an eye fluid sample, or a urine sample. In certain embodiments, the biological fluid sample includes circulating tumor cells (CTCs), tumor-derived cell-free DNA (cfDNA), circulating small RNAs, and extracellular vesicles including exosomes, from bodily fluids as disclosed, for example, in Campos C D M et al., "Molecular Profiling of Liquid Biopsy Samples for Precision Medicine," Cancer J. 2018 March/April; 24(2):93-103, which is incorporated hereby in its entirety. In some embodiments, the biological tissue sample is an organ tissue sample, a bone tissue sample, or a tumor tissue sample.

The term "heteromer" as used herein refers to macromolecular complex composed of at least two GPCR units [protomers] with biochemical properties that are demonstrably different from those of its individual components. Heteromerization can be evaluated by in situ hybridization, immunohistochemistry, RNAseq, Reverse transcription-quantitative PCR (RT-qPCR, realtime PCR), microarray, proximity ligation assay (PLA), time-resolved FRET (TR-FRET), whole-body Single-photon emission computed tomography (SPECT) or Positron Emission Tomography/Computed Tomography (PET/CT).

The phrase "effective amount" as used herein refers to an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc.

The phrase "therapeutically effective amount" as used herein refers to the amount of a therapeutic agent (e.g., an inhibitor, an antagonist, or any other therapeutic agent provided herein) which is sufficient to reduce, ameliorate, and/or prevent the severity and/or duration of a cancer and/or a symptom related thereto. A therapeutically effective amount of a therapeutic agent can be an amount necessary for the reduction, amelioration, or prevention of the advancement or progression of a cancer, reduction, amelioration, or prevention of the recurrence, development or onset of a cancer, and/or to improve or enhance the prophylactic or therapeutic effect of another therapy (e.g., a therapy other than the administration of a inhibitor, an antagonist, or any other therapeutic agent provided herein).

The phrase "therapeutic agent" refers to any agent that can be used in the treatment, amelioration, prevention, or management of a cancer and/or a symptom related thereto. In certain embodiments, a therapeutic agent refers to an inhibitor of CXCR4-GPCRx heteromer of the invention. A therapeutic agent can be an agent which is well known to be useful for, or has been or is currently being used for the treatment, amelioration, prevention, or management of a cancer and/or a symptom related thereto.

The phrase "intracellular Ca2+ assay," "calcium mobilization assay," or their variants as used herein refer to cell-based assay to measure the calcium flux associated with GPCR activation or inhibition. The method utilizes a calcium sensitive fluorescent dye that is taken up into the cytoplasm of most cells. The dye binds the calcium released from intracellular store and its fluorescence increases. The change in the fluorescence intensity is directly correlated to the amount of intracellular calcium that is released into cytoplasm in response to ligand activation of the receptor of interest.

The phrase "proximity-based assay" as used herein refers to biophysical and biochemical techniques that are able to monitor proximity and/or binding of two protein molecules in vitro (in cell lysates) and in live cells, including bioluminescence resonance energy transfer (BRET), fluorescence resonance energy transfer (FRET), bimolecular fluorescence complementation (BiFC), Proximity ligation assay (PLA), cysteine crosslinking, and co-immunoprecipitation (Ferre et al., 2009; Gomes et al., 2016).

Alternative methods for detecting heteromer formation include, but are not limited to: immunostaining (Bushlin et al., 2012; Decaillot et al., 2008); immunoelectron microscopy (Fernandez-Duenas et al., 2015); BRET (Pfleger and Eidne, 2006); Time-resolved FRET assays (Fernandez-Duenas et al., 2015); In Situ Hybridization (He et al., 2011); FRET (Lohse et al., 2012); β-arrestin recruitment assay using GPCR heteromer identification technology (GPCR-HIT, Dimerix Bioscience) (Mustafa and Pfleger, 2011) using BRET, FRET, BiFC, Bimolecular Luminescence Complementation, enzyme fragmentation assay, and Tango Tango GPCR assay system (Thermo Fisher Scientific) (Mustafa, 2010); PRESTO-Tango system (Kroeze et al., 2015); regulated secretion/aggregation technology (ARIAD Pharmaceuticals) (Hansen et al., 2009); Receptor Selection and Amplification Technology (ACADIA Pharmaceuticals) (Hansen et al., 2009); DimerScreen (Cara Therapeutics) (Mustafa, 2010); Dimer/interacting protein translocation assay (Patobios) (Mustafa, 2010); Co-immunoprecipitation (Abd Alla et al., 2009); GPCR internalization assays using surface enzyme-linked immunosorbent assay (ELISA) (Decaillot et al., 2008) or Flow Cytometry (Law et al., 2005); Whole Cell Phosphorylation Assays (Pfeiffer et al., 2002); and Proximity-ligation assay (PLA) (Frederick et al., 2015).

Alternative methods for detecting changes in pharmacological properties, signaling properties, and/or trafficking properties, in cells expressing both CXCR4 and GPCRx include, but are not limited to: Radioligand Binding Assays (Bushlin et al., 2012; Pfeiffer et al., 2002); Cell Surface Biotinylation and Immunoblotting (He et al., 2011); immunostaing (Bushlin et al., 2012; Decaillot et al., 2008); immunoelectron microscopy (Fernandez-Duenas et al., 2015); [35S]GTP-γS Binding assays (Bushlin et al., 2012); Calcuim imaging or assays using dyes such as Fura 2-acetomethoxy ester (Molecular Probes), Fluo-4 NW calcium dye (Thermo Fisher Scientific), or FLIPRS dye (Molecular Devices); cAMP assays using radioimmunoassay kit (Amersham Biosciences); AlphaScreen (PerkinElmer Life Sciences); Parameter Cyclic AMP Assay (R&D Systems); femto cAMP kit (Cisbio); cAMP Direct Immunoassay Kit (Calbiochem) or GloSensor cAMP assay (Promega); GTPase assay (Pello et al., 2008); PKA activation (Stefan et al., 2007); ERK1/2 and/or Akt/PKB Phosphorylation Assays (Callen et al., 2012); Src and STAT3 phosphorylation assays (Rios et al., 2006); reporter assays such as cAMP response element (CRE); nuclear factor of activated T-cells response element (NFAT-RE); serum response element (SRE); serum response factor response element (SRF-RE); and NF-KB-response element luciferase reporter assays; Secreted alkaline phosphatase Assay (Decaillot et al., 2011); Measurement of Inositol 1-Phosphate Production Using TR-FRET or [3H]myo-Inositol (Mustafa et al., 2012); RT-qPCR for measuring downstream target gene expression (Mustafa et al., 2012); and Adenylyl Cyclase Activity (George et al., 2000); next generation sequencing (NGS); and any other assay that can detect a change in receptor function as a result of receptor heterodimerization.

The phrase "protein-protein interaction inhibitor," "PPI inhibitor," or their variants as used herein refer to any molecules that can interfere with protein-protein interactions. Protein-protein interaction, unlike enzyme-substrate interaction involving well-defined binding pockets, is a transient interaction or association between proteins over relatively large areas and is often driven by electrostatic interactions, hydrophobic interactions, hydrogen bonds, and/or Van der Waals forces. PPI inhibitors may include, but not limited to, membrane-permeable peptides or lipid fused to a peptide sequence that disrupts the GPCR heteromeric interface, for example, transmembrane helix, intracellular loop, or C-terminal tail of GPCRx. The PPI inhibitor of the CXCR4-GPCRx heteromer, for example, may be a membrane-permeable peptide or cell-penetrating peptide (CPP) conjugated with peptide that targets the CXCR4-GPCRx heteromeric interface(s), or may be a cell-penetrating lipidated peptide targeting the CXCR4-GPCRx heteromeric interface(s).

For example, the membrane-permeable peptide or cell-penetrating peptide includes: HIV-1 TAT peptides, such as $TAT_{48-60}$ and $TAT_{49-57}$; Penetratins, such as pAntp(43-58); Polyarginines (Rn such as R5 to R12); Diatos peptide vector 1047 (DPV1047, Vectocell®); MPG (HIV gp41 fused to the nuclear localization signal (NLS) of the SV40 large T antigen); Pep-1 (tryptophan-rich cluster fused to the NLS of SV40 large T antigen); pVEC peptide (vascular endothelial cadherin); p14 alternative reading frame (ARF) protein-based ARF (1-22); N-terminus of the unprocessed bovine prion protein BPrPr(1-28); Model amphipathic peptide (MAP); Transportans; Azurin-derived p28 peptide; amphipathic β-sheet peptides, such as VT5; proline-rich CPPs, such as Bac 7 (Bac1-24); hydrophobic CPPs, such as C105Y derived from α1-Antitrypsin; PFVYLI derived from synthetic C105Y; Pep-7 peptide (CHL8 peptide phage clone); and modified hydrophobic CPPs, such as stapled peptides and prenylated peptides (Guidotti et al., 2017; Kristensen et al., 2016). The membrane-permeable peptide or cell-penetrating peptide can further include, for example, TAT-derived cell-penetrating peptides, signal sequence-based (e.g., NLS) cell-penetrating peptides, hydrophobic membrane translocating sequence (MTS) peptides, and arginine-rich molecular transporters. The cell-penetrating lapidated peptide includes, for example, pepducins, such as ICL1/2/3, C-tail-short palmitoylated peptides (Covic et al., 2002; O'Callaghan et al., 2012).

The peptide(s) that target the CXCR4-GPCRx heteromeric interface may be, for example, a transmembrane domain of CXCR4, transmembrane domain of GPCRx, intracellular loop of CXCR4, intracellular loop of GPCRx, C-terminal domain of CXCR4, or C-terminal domain of GPCRx, extracellular loop of CXCR4, extracellular loop of GPCRx, N-terminal region of CXCR4, or N-terminal region of GPCRx.

In some embodiments, the invention provides a pharmaceutical composition (sometimes referred to herein as "pharmaceutical formulations") having an inhibitor of a CXCR4-GPCRx heteromer of the invention and a pharmaceutically acceptable carrier. A pharmaceutically acceptable carrier that can be used in the pharmaceutical compositions of the invention include any of the standard pharmaceutical carriers known in the art, such as physiologically acceptable carriers, excipients or stabilizers, for example, phosphate buffered saline solution, water and emulsions such as an oil and water emulsion, and various types of wetting agents. These pharmaceutical compositions can be prepared in liquid unit dose forms or any other dosing form that is sufficient for delivery of the inhibitor of a CXCR4-GPCRx heteromer of the invention to the target area of the subject in need of treatment. For example, the pharmaceutical compositions can be prepared in any manner appropriate for the chosen mode of administration, e.g., intravascular, intramuscular, subcutaneous, intradermal, intrathecal, etc. Other optional components, e.g., pharmaceutical grade stabilizers, buffers, preservatives, excipients and the like can be readily selected by one of skill in the art. The preparation of a pharmaceutically composition, having due regard to pH, isotonicity, stability and the like, is within the level of skill in the art.

Pharmaceutical formulations containing one or more inhibitors of a CXCR4-GPCRx heteromer of the invention provided herein can be prepared for storage by mixing the inhibitors having the desired degree of purity with optional physiologically acceptable carriers, excipients or stabilizers (Remington's Pharmaceutical Sciences (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; low molecular weight polypeptides of less than about 10 residues; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes, e.g., Zn-protein complexes; and/or non-ionic surfactants such as TWEEN™, PLURONICS™, or polyethylene glycol (PEG).

Thus, in some embodiments, the invention provides a method for treatment, amelioration, or prevention of a disease in a subject in need thereof. The methods of the invention can include administering a therapeutically effective amount of a pharmaceutical composition provided herein to the subject. For example, the pharmaceutical composition can include one or more inhibitors of a CXCR4-GPCRx heteromer provided herein. Diseases that can be treated or prevented using the methods of the invention include cancer, tumor, metastasis, and/or angiogenesis. In particular, the methods of the invention are useful for treating cancers or related symptoms wherein the cells of cancer, tumor, and/or microenvironment expresses the CXCR4-GPCRx heteromer. Non-limiting examples of cancers or tumors that can be treated, ameliorated, or prevented using the methods of the invention include tumors of the gastrointestinal tract, for example, breast cancer, lung cancer, small cell carcinoma of the lung, hepatocellular carcinoma, brain cancer, kidney cancer, pancreatic cancer or pancreatic adenocarcinoma, ovarian cancer, prostate cancer, melanoma, lymphoma, leukemia, multiple myeloma, renal cell carcinoma, soft tissue sarcoma, gastrointestinal cancer, stomach cancer, colon cancer, colorectal cancer, colorectal adenocarcinoma, bladder adenocarcinoma, esophageal cancer, and adenocarcinoma of the stomach, esophagus, throat, and urogenital tract.

In some embodiments, the invention provides a method for treating cancer in a patient having a cell containing a CXCR4-GPCRx heteromer, or provides a method of suppressing enhanced downstream signaling from a CXCR4-GPCRx heteromer in a cell of a patient suffering from cancer, the method comprising: administering to the patient an inhibitor or a combination of inhibitors selected from the group consisting of: an inhibitor of CXCR4, an inhibitor of GPCRx, and an inhibitor of the CXCR4-GPCRx heteromer; wherein: i) the CXCR4-GPCRx heteromer has enhanced downstream signaling; and ii) the administered inhibitor or combination of inhibitors suppresses the enhanced downstream signaling from said CXCR4-GPCRx heteromer in the cancer patient.

In some embodiments, the invention provides a pharmaceutical kit for use in treating cancer in a patient having a cell containing a CXCR4-GPCRx heteromer, the pharmaceutical kit comprising: an inhibitor or a combination of inhibitors selected from the group consisting of: an inhibitor of CXCR4, an inhibitor of GPCRx, and an inhibitor of the CXCR4-GPCRx heteromer; wherein the CXCR4-GPCRx heteromer has enhanced downstream signaling. In some embodiments, the invention provides a pharmaceutical composition for use in treating cancer in a patient having a cell containing a CXCR4-GPCRx heteromer, the pharmaceutical composition comprising: i) an inhibitor or a combination of inhibitors selected from the group consisting of: an inhibitor of CXCR4, an inhibitor of GPCRx, and an inhibitor of the CXCR4-GPCRx heteromer; and ii) a pharmaceutically acceptable carrier; wherein the CXCR4-GPCRx heteromer has enhanced downstream signaling.

In some embodiments, according to the method of treating, method of suppressing, pharmaceutical kit, or pharmaceutical composition, provided herein, the progression of the cancer in the patient having said cancer cell containing the CXCR4-GPCRx heteromer is decreased in the range of 5-100% more upon administration of the combination of inhibitors, relative to administering the CXCR4 inhibitor or GPCRx inhibitor as the single inhibitor to said patient, such as decreased in the range of 5-100% more, 10-100% more, 20-100% more, 30-100% more, 40-100% more, 50-100% more, 60-100% more, 75-100% more, 5-75% more, 5-50% more, or 5-25% more, upon administration of the combination of inhibitors, relative to administering the CXCR4 inhibitor or GPCRx inhibitor as the single inhibitor to said patient. In some embodiments, the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3. In some embodiments, the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

In some embodiments, according to the method of treating, method of suppressing, pharmaceutical kit, or pharmaceutical composition, provided herein, the efficacy of a CXCR4 inhibitor is increased in the range of 5-2000% when administered in combination with the GPCRx inhibitor to the patient having said cancer cell containing the CXCR4-GPCRx heteromer, relative to efficacy of the CXCR4 inhibitor when administered as a single inhibitor, such as increased in the range of 5-1750%, 5-1500%, 5-1250%, 5-1000%, 5-900%, 5-800%, 5-700%, 5-500%, 5-400%, 5-250%, 5-200%, 5-100%, 5-75%, 5-50%, 5-40%, 5-30%, 5-25%, 100-2000%, 200-2000%, 300-2000%, 500-2000%, 750-2000%, 1000-2000%, 1250-2000%, 1500-2000%, 5-1500%, 25-1500%, 50-1500%, 75-1500%, 100-1500%, 200-1500%, 300-1500%, 500-1500%, 750-1500%, 1000-1500%, or 1250-1500%, when administered in combination with the GPCRx inhibitor to the patient having said cancer cell containing the CXCR4-GPCRx heteromer, relative to efficacy of the CXCR4 inhibitor when administered as a single inhibitor. In some embodiments, the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3. In some embodiments, the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

In some embodiments, according to the method of treating, method of suppressing, pharmaceutical kit, or pharmaceutical composition, provided herein, the efficacy of a GPCRx inhibitor is increased in the range of 5-2000% when administered in combination with the CXCR4 inhibitor to the patient having said cancer cell containing the CXCR4-GPCRx heteromer, relative to efficacy of the GPCRx inhibitor when administered as a single inhibitor, such as increased in the range of 5-1750%, 5-1500%, 5-1250%, 5-1000%, 5-900%, 5-800%, 5-700%, 5-500%, 5-400%, 5-250%, 5-200%, 5-100%, 5-75%, 5-50%, 5-40%, 5-30%, 5-25%, 100-2000%, 200-2000%, 300-2000%, 500-2000%, 750-2000%, 1000-2000%, 1250-2000%, 1500-2000%, 5-1500%, 25-1500%, 50-1500%, 75-1500%, 100-1500%, 200-1500%, 300-1500%, 500-1500%, 750-1500%, 1000-1500%, or 1250-1500%, when administered in combination with the CXCR4 inhibitor to the patient having said cancer cell containing the CXCR4-GPCRx heteromer, relative to efficacy of the GPCRx inhibitor when administered as a single inhibitor. In some embodiments, the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3. In some embodiments, the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

In some embodiments, according to the method of treating, method of suppressing, pharmaceutical kit, or pharmaceutical composition, provided herein, the method administers a combination of inhibitors selected from the group consisting of: an inhibitor of CXCR4, an inhibitor of GPCRx, and an inhibitor of the CXCR4-GPCRx heteromer; or the pharmaceutical kit or pharmaceutical composition comprises a combination of inhibitors selected from the group consisting of: an inhibitor of CXCR4, an inhibitor of GPCRx, and an inhibitor of the CXCR4-GPCRx heteromer. In some embodiments, the combination of inhibitors is a combination of two inhibitors selected from the group consisting of: an inhibitor of CXCR4, an inhibitor of GPCRx, and an inhibitor of the CXCR4-GPCRx heteromer. In some embodiments, according to the method of treating, method of suppressing, pharmaceutical kit, or pharmaceutical composition, provided herein, the method administers a combination of a CXCR4 inhibitor and a GPCRx inhibitor; or the pharmaceutical kit or pharmaceutical composition comprises a combination of a CXCR4 inhibitor and a GPCRx inhibitor. In some embodiments, according to the method of treating, method of suppressing, pharmaceutical kit, or pharmaceutical composition, provided herein, the method administers a CXCR4-GPCRx heteromer inhibitor; or the pharmaceutical kit or pharmaceutical composition comprises a CXCR4-GPCRx heteromer inhibitor.

In some embodiments, according to the method of treating or method of suppressing provided herein, or according to the use of the pharmaceutical kit or pharmaceutical composition provided herein, the administering of the combination of inhibitors suppresses the enhanced downstream signaling from said CXCR4-GPCRx heteromer in the cancer patient in the range of between 5-2000 fold, relative to single inhibitor administration, such as suppresses the enhanced downstream signaling from said CXCR4-GPCRx heteromer in the cancer patient in the range of between 5-1750 fold, 5-1500 fold, 5-1250 fold, 5-1000 fold, 5-900 fold, 5-800 fold, 5-700 fold, 5-500 fold, 5-400 fold, 5-250 fold, 5-200 fold, 5-100 fold, 5-75 fold, 5-50 fold, 5-40 fold, 5-30 fold, 5-25 fold, 100-2000 fold, 200-2000 fold, 300-2000 fold, 500-2000 fold, 750-2000 fold, 1000-2000 fold, 1250-2000 fold, 1500-2000 fold, 5-1500 fold, 25-1500 fold, 50-1500 fold, 75-1500 fold, 100-1500 fold, 200-1500 fold, 300-1500 fold, 500-1500 fold, 750-1500 fold, 1000-1500 fold, or 1250-1500 fold, relative to single inhibitor administration. In some embodiments, the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3. In some embodiments, the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

In some embodiments, according to the method of treating or method of suppressing provided herein, or according to the use of the pharmaceutical kit or pharmaceutical composition provided herein, the administering of the inhibitor or combination of inhibitors suppresses the enhanced downstream signaling from said CXCR4-GPCRx heteromer in the cancer patient in the range of between 5-2000 fold, relative to suppression of downstream signaling from either a CXCR4 protomer or a GPCRx protomer in their respective individual protomer context, such as suppresses the enhanced downstream signaling from said CXCR4-GPCRx heteromer in the cancer patient in the range of between 5-1750 fold, 5-1500 fold, 5-1250 fold, 5-1000 fold, 5-900 fold, 5-800 fold, 5-700 fold, 5-500 fold, 5-400 fold, 5-250 fold, 5-200 fold, 5-100 fold, 5-75 fold, 5-50 fold, 5-40 fold, 5-30 fold, 5-25 fold, 100-2000 fold, 200-2000 fold, 300-2000 fold, 500-2000 fold, 750-2000 fold, 1000-2000 fold, 1250-2000 fold, 1500-2000 fold, 5-1500 fold, 25-1500 fold, 50-1500 fold, 75-1500 fold, 100-1500 fold, 200-1500 fold, 300-1500 fold, 500-1500 fold, 750-1500 fold, 1000-1500 fold, or 1250-1500 fold, relative to suppression of downstream signaling from either a CXCR4 protomer or a GPCRx protomer in their respective individual protomer context. In some embodiments, the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3. In some embodiments, the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

Initial testing and evaluation of an inhibitor, or combination of inhibitors, regarding whether effective, or therapeutically effective, in suppressing an enhanced downstream signaling from a CXCR4-GPCRx heteromer, according to the methods disclosed herein, and/or in determining an IC50 value according to the assays disclosed herein, may utilize a concentration of the inhibitor in the range of between 1-10 µM (or each of the inhibitors of the combination at concentrations in the range of between 1-10 such as at a concentration of 1, 2, 3, 4, 5, 6, 7, 8, 9, or 10 µM. If suppression of the signal by the inhibitor is not appreciable enough for a determinable measurement, then a greater concentration of the inhibitor may be used to better evaluate a determinable measurement, such as an IC50 value. If suppression of the signal by the inhibitor is very strong, then a lower concentration of the inhibitor may be used to better evaluate a determinable measurement, such as an IC50 value.

It is understood that modifications which do not substantially affect the activity of the various embodiments of this invention are also provided within the definition of the invention provided herein. Accordingly, the following examples are intended to illustrate but not limit the invention disclosed herein.

EXAMPLES

Example 1. Evaluation of CXCR4-GPCRx Heteromer Formation by BiFC Assay

Figure 1:
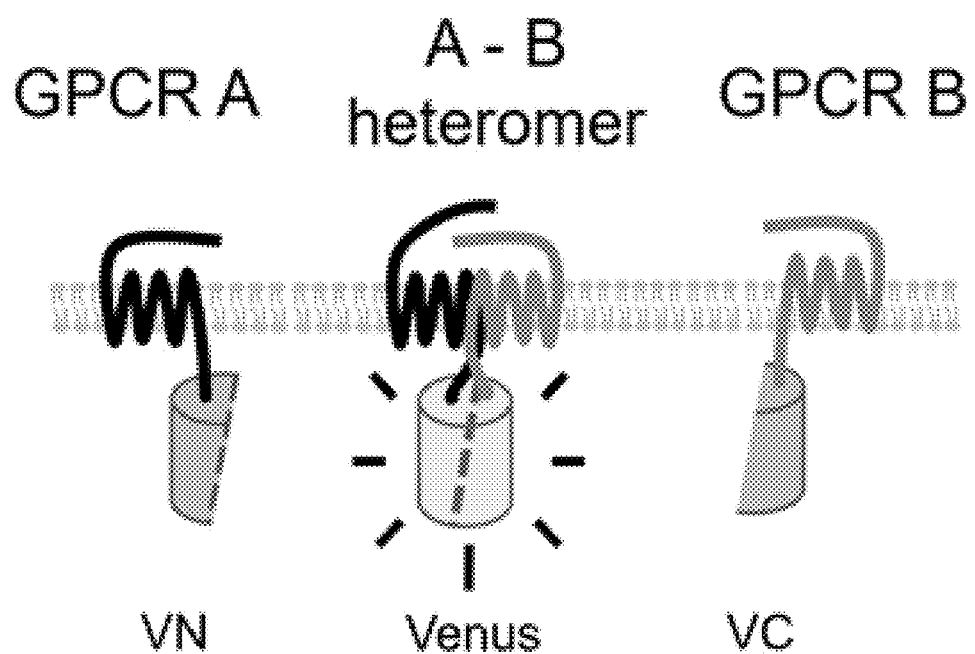
FIG. 1: Shows schematic drawing of bimolecular fluorescence complementation (BiFC) assay. GPCR A is fused with N-terminal fragment of yellow fluorescent protein (YFP) Venus (VN) and GPCR B is fused with C-terminal fragment of Venus (VC). When GPCR A and B form heteromer, the complementary VN and VC are close enough to form functional Venus.

To identify novel CXCR4-GPCRx heteromers, we made recombinant adenoviruses encoding 143 GPCRs fused with N-terminal fragments of yellow fluorescent protein Venus (VN) and 147 GPCRs fused with C-terminal fragment of Venus (VC) as described in Song et al. (Song et al., 2014; SNU patent; Song, thesis). CXCR4-GPCR heteromers were identified using bimolecular fluorescence complementation (BiFC) assay (FIG. 1), in which two complementary VN and VC fragments of Venus reconstitute a fluorescent signal only when both fragments are close enough through interaction between two different proteins to which they are fused (Hu et al., 2002).

U-2 OS cells were plated in 96-well plates, were co-transduced with 30 MOI each of adenoviruses encoding CXCR4-VN and GPCRx-VC or CXCR4-VC and GPCRx-VN, and were allowed to express GPCRs for 2 days. After staining the cells with Hoechst 33342, BiFC and nuclear images were obtained from three fields per well using IN Cell Analyzer 1000. Images of about 200 cells from each well were analyzed with Multi-target analysis software in IN Cell Developer ToolBox (GE Healthcare, Waukesha, Wis.). Cell boundary was marked based on Hoechst signal, and fluorescence intensity per cell was measured. Cells with fluorescence intensities higher than background level were considered as BiFC positive cells. Dead cells that showed extremely high intensities were excluded from the cell count. Positive cells were determined, and positive cell count ratio ("BiFC score") was calculated as (positive cells/total cells)×100 (see Table 4 below).

When CXCR4-VN was co-expressed with HA-VC (FIG. 2A) or GCGR-VC, a GPCR encoding glucagon receptor (FIG. 2C), no yellow fluorescence protein (YFP) signal (BiFC signal) was observed. In contrast, when CXCR4-VN was co-expressed with CXCR4-VC (FIG. 2B), BiFC signal was observed in the plasma membrane and in the cytoplasm. Strong BiFC signal was observed in the plasma membrane and in the cytoplasm when CXCR4-VN was co-transduced with ADCYAP1R1-VC (FIG. 2D), ADORA3-VC (FIG. 2F), ADRB2-VC (FIG. 2G), APLNR-VC (FIG. 2H), C5AR1-VC (FIG. 2I), CALCR-VC (FIG. 2J), CCR5-VC (FIG. 2K), CHRM1-VC (FIG. 2L), GALR1-VC (FIG. 2M), EDNRB-VC (FIG. 2N), HRH1-VC (FIG. 2O), MLNR-VC (FIG. 2P), NTSR1-VC (FIG. 2Q), PTGER2-VC (FIG. 2R), SSTR2-VC (FIG. 2T), and TACR3-VC (FIG. 2U). Robust BiFC signal was also observed when cells were co-transduced with CXCR4-VC and ADORA2B-VN (FIG. 2E) or PTGER3-VN (FIG. 2S). Cells that showed BiFC fluorescence signal higher than background level was counted as BiFC positive cells, and BiFC score was calculated.

Protein-protein interaction can be affected by fusion tags such as fluorescence protein fragments in BiFC or renilla luciferase in BRET through interfering with the expression, folding, or localization of the partner protein. Partner protein can also impair the expression or folding of the fusion tags, and affect proximity-based assay result. Thus, the absence of signal between two proteins in specific combination does not necessarily imply that the proteins do not interact, but simply that the attached donor and acceptor molecules are in particular conformation that does not allow interaction to occur (Eidne et al., 2002; Kerppola, 2006).

Therefore, CXCR4 and GPCRx that gave BiFC signal in either CXCR4-VN and GPCRx-VC or CXCR4-VC and GPCRx-VN combination were considered as interacting proteins. The BiFC score of CXCR4-VN and CXCR4-VC pair, a well-known homomer, was 9.9. Thus, CXCR4-GPCRx pairs that gave BiFC score equal or higher than 10 were selected as candidates for CXCR-GPCRx heteromer as shown in Table 4.

TABLE 4

GPCRs that exhibited BiFC score equal or higher than 10 when co-expressed with CXCR4.

|  | GPCRx | BiFC score CXCR4-VN & GPCRx-VC |
| --- | --- | --- |
| 1 | ADCYAP1R1 | 23 |
| 2 | ADORA2B | 11* |
| 3 | ADORA3 | 43 |
| 4 | ADRB2 | 24 |
| 5 | APLNR | 63 |
| 6 | C5AR1 | 42 |
| 7 | CALCR | 53 |
| 8 | CCR5 | 44 |
| 9 | CHRM1 | 24 |
| 10 | GALR1 | 60 |
| 11 | EDNRB | 41 |
| 12 | HRH1 | 45 |
| 13 | MLNR | 10 |
| 14 | NTSR1 | 48 |
| 15 | PTGER2 | 58 |

TABLE 4-continued

GPCRs that exhibited BiFC score equal or higher than 10 when co-expressed with CXCR4.

| | GPCRx | BiFC score CXCR4-VN & GPCRx-VC |
|---|---|---|
| 16 | PTGER3 | 13* |
| 17 | SSTR2 | 30 |
| 18 | TACR3 | 33 |

*CXCR4-VC and GPCRx-VN were used.

Sixteen GPCRs, ADCYAP1R1, ADORA3, ADRB2, APLNR, C5AR1, CALCR, CCR5, CHRM1, GALR1, EDNRB, HRH1, MLNR, NTSR1, PTGER2, SSTR2, and TACR3, were identified as CXCR4-interacting GPCRs in CXCR4-VN and GPCRx-VC combination and two GPCRs, ADORA2B and PTGER3, gave BiFC score higher than 10 in CXCR4-VC and GPCRx-VN combination as shown in Table 4. Among those, ADRB2 and CCR5 have been reported to form heteromers with CXCR4 (LaRocca 2010, Nakai 2014, (Agrawal et al., 2004; LaRocca et al., 2010; Rodriguez-Frade et al., 2004; Sohy et al., 2007; Sohy et al., 2009; Martinez-Munoz et al., 2014)), and the remaining 16 GPCRs were found to be novel CXCR4-GPCRx heteromers that have not been reported to the best of our knowledge.

Among GPCRs that have been known to interact with CXCR4, ADRA1A and CXCR3 were also included in our BiFC assay. These GPCRs were excluded from further investigation since they gave BiFC signal of less than 10 with CXCR4: ADRA1A (CXCR4-VN-ADRA1A-VC: BiFC score 7.85) and CXCR3 (BiFC score 1.16).

Cannabinoid Receptor 2 (CB2, sometimes referred to as CNR2) was identified as a CXCR4-interacting GPCR in our BiFC assay (CNR2-VN-CXCR4-VC configuration: BiFC score 4.25; CNR2-VC-CXCR4-VN configuration: BiFC score 38.1), and co-internalization assay as described in FIGS. 3A-3B and 4A-4Q. But CNR2 was not selected as the final candidate because it failed to exhibit an enhanced downstream signaling in the calcium mobilization assay (see Example 3 below).

Example 2. Evaluation of CXCR4-GPCRx Heteromer Formation by Co-Internalization Assay Some of the GPCR heteromers are known to exhibit, as a result of the heteromerization, altered trafficking properties such as maturation of the partner GPCR (GABA(B) receptor) (White, 1998), agonist-mediated internalization of the partner GPCR from the cell surface (DOR-GRPR, A2A-D2R) (Hillion et al., 2002; Liu et al., 2011; Torvinen et al., 2005), and changes in the localization of the partner GPCR from an intracellular compartment to the cell surface (DOR-CB1) (Rozenfeld et al., 2012).

Figure 3A:
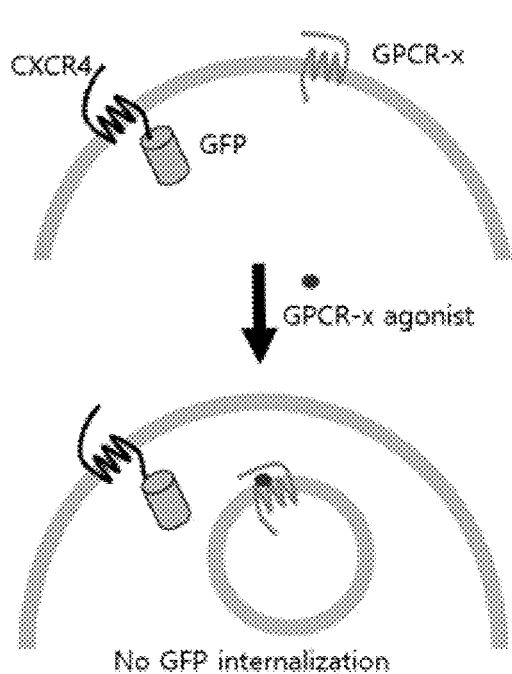
FIGS. 3A-3B: Shows principle of GPCR co-internalization study. Cells co-expressing CXCR4-GFP and GPCRx are treated with GPCRx specific agonist.
Figure 3B:
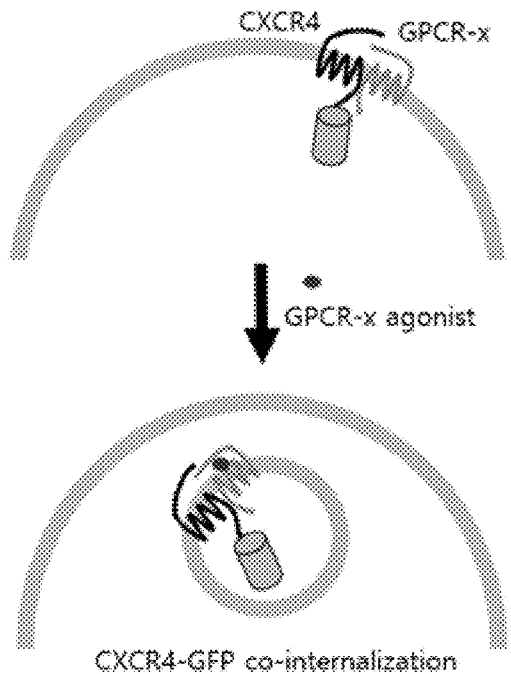

Co-internalization of pairs of co-expressed GPCRs in response to agonists selective for only one of the pair has been used to confirm GPCR heteromerization (Milligan, 2008). To examine if GPCRx modulates the trafficking of CXCR4 when co-expressed and forms CXCR4-GPCRx heteromer and also to confirm the physical interaction between CXCR4 and GPCRx identified using BiFC assay, cells were co-transduced with adenoviruses encoding CXCR4-GFP and GPCRx and GFP images were obtained before and 30 min after stimulation with GPCRx agonist. Loss of GFP expression on the cell surface or appearance of GFP granules inside the cells were considered as CXCR4-GFP co-internalization with GPCRx (FIGS. 3A-3B).

Figure 4C:
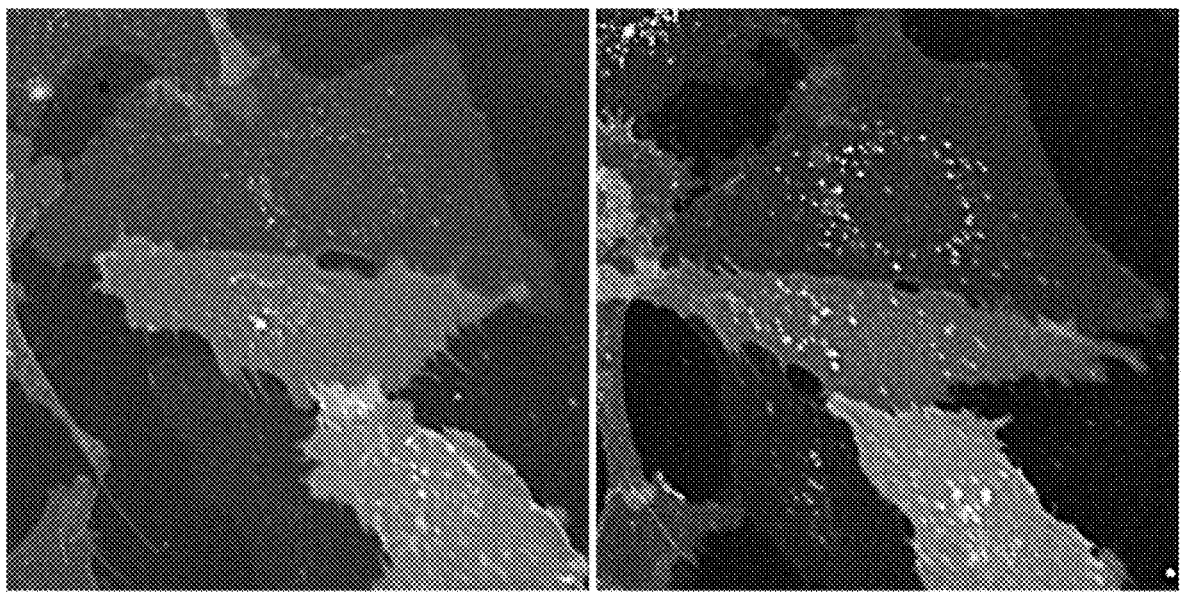
FIGS. 4A-4Q: Shows co-internalization of CXCR4-EGFP upon stimulation of GPCRx with its corresponding agonist (control: CXCR4-GFP (FIG. 4A)). U-2 OS cells were co-transduced with adenoviruses encoding CXCR-EGFP and GPCRx-VC, and the following GPCRx partners were examined to form heteromer with CXCR4-EGFP and to induce co-internalization of the CXCR4-EGFP: GPCRx represents ADCYAP1R1 (FIG. 4B), ADORA2B (FIG. 4C), ADORA3 (FIG. 4D), ADRB2 (FIG. 4E), APLNR (FIG. 4F), C5AR1 (FIG. 4G), CCR5 (FIG. 4H), CHRM1 (FIG. 4I), GALR1 (FIG. 4J), EDNRB (FIG. 4K), HRH1 (FIG. 4L), MLNR (FIG. 4M), NTSR1 (FIG. 4N), PTGER3 (FIG. 4O), SSTR2 (FIG. 4P), and TACR3 (FIG. 4Q).
Figure 4D:
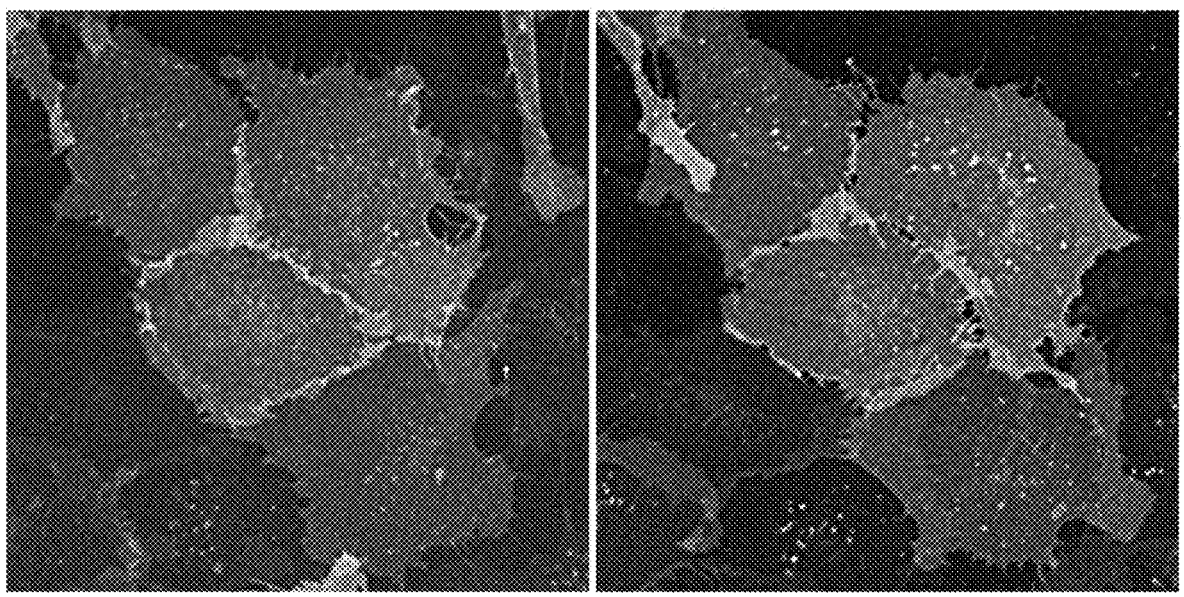
Figure 4K:
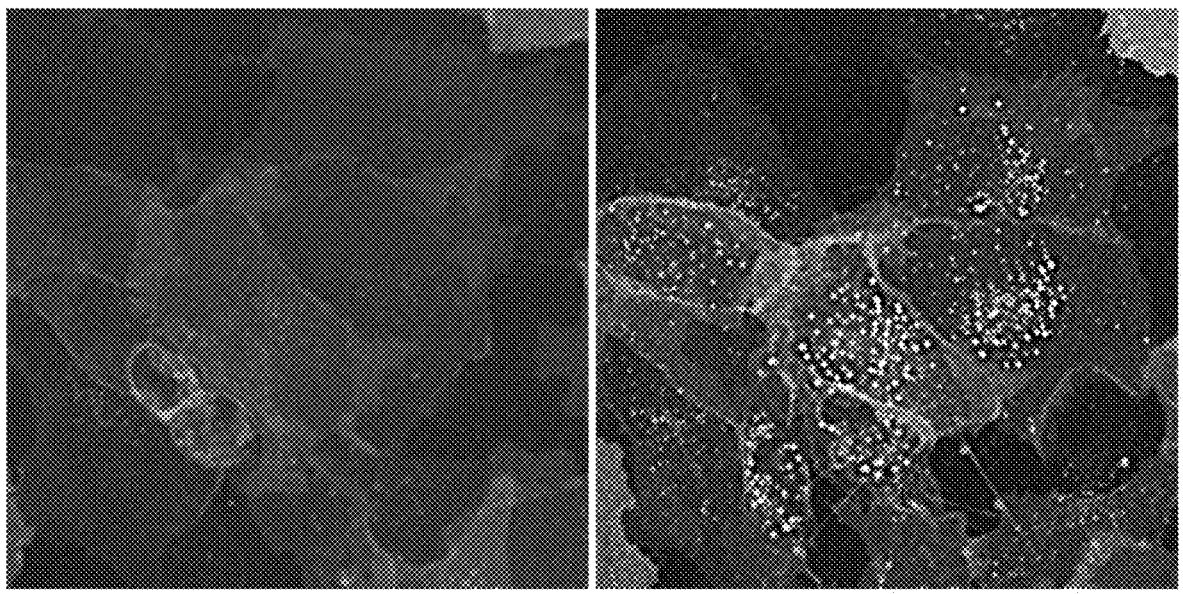
Figure 4L:
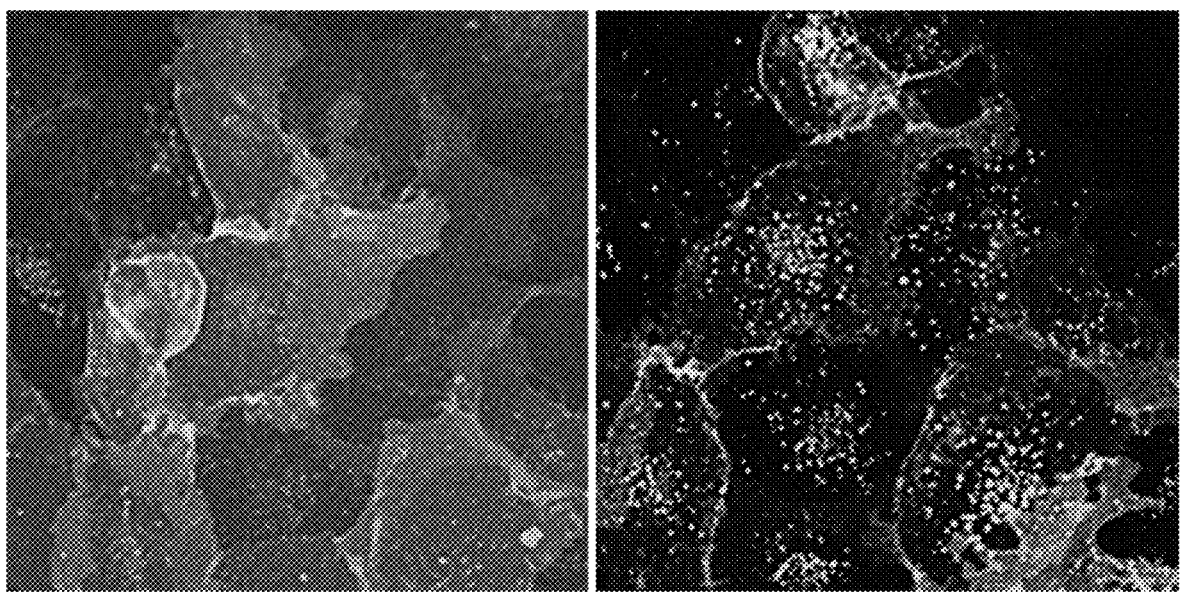
Figure 4O:
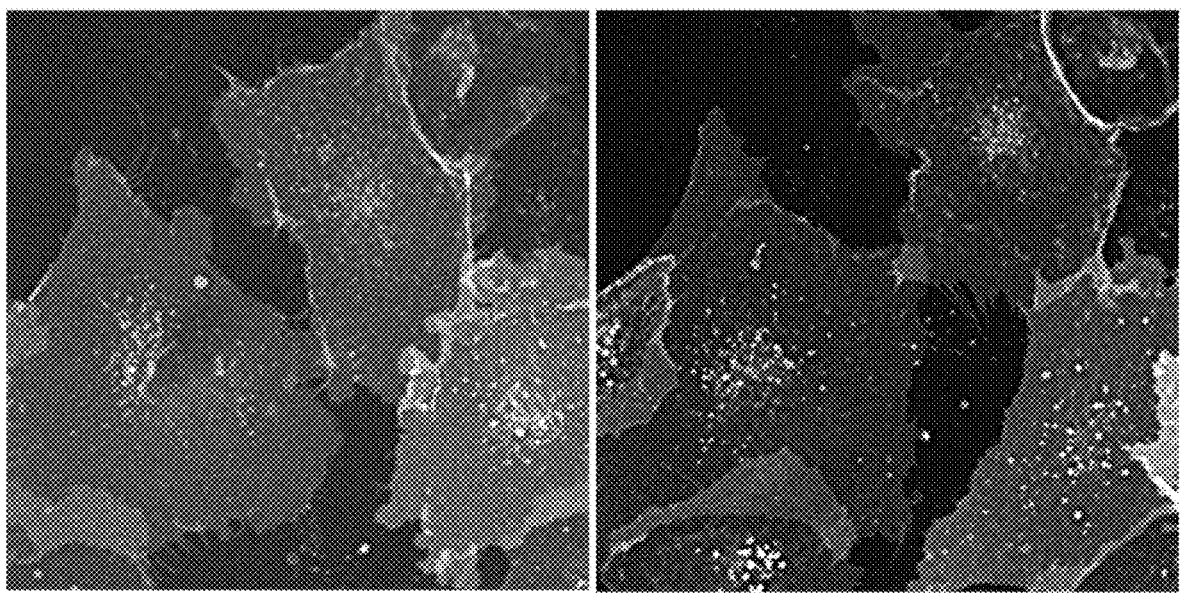
Figure 4P:
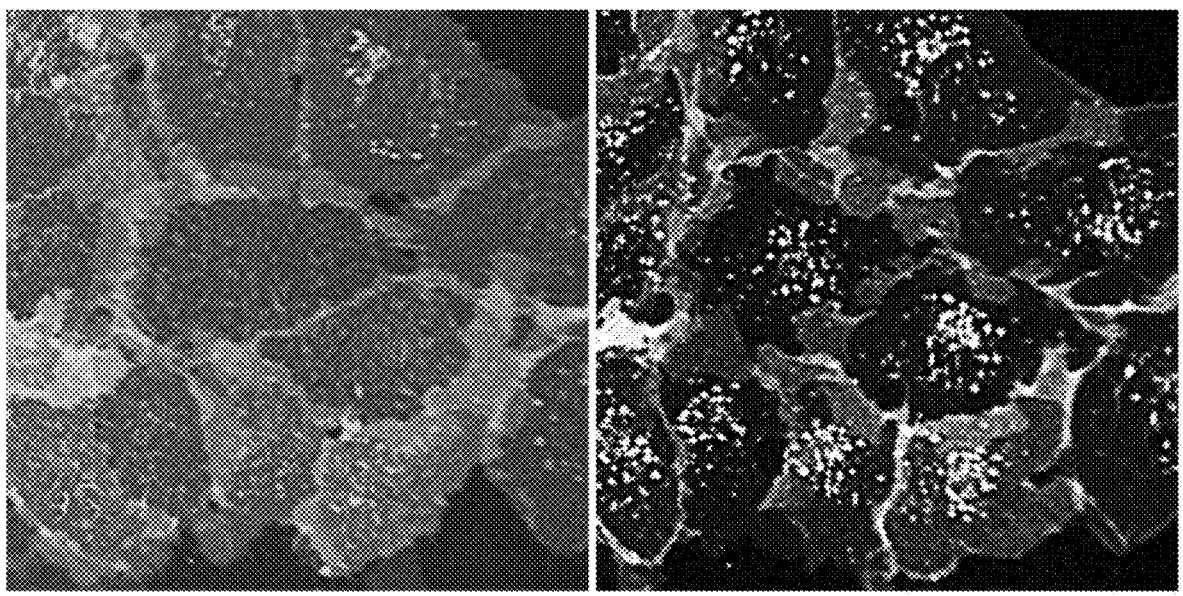

In FIGS. 4A-4Q, cells were stimulated with GPCRx agonists specific for CXCR4 (FIG. 4A), ADCYAP1R1 (FIG. 4B), ADORA2B (FIG. 4C), ADORA3 (FIG. 4D), ADRB2 (FIG. 4E), APLNR (FIG. 4F), C5AR1 (FIG. 4G), CCR5 (FIG. 4H), CHRM1 (FIG. 4I), GALR1 (FIG. 4J), EDNRB (FIG. 4K), HRH1 (FIG. 4L), MLNR (FIG. 4M), NTSR1 (FIG. 4N), PTGER3 (FIG. 4O), SSTR2 (FIG. 4P), and TACR3 (FIG. 4Q) as follows: 10 nM of CXCL12 (FIG. 4A), 1 µM of vasoactive intestinal peptide (VIP) (FIG. 4B), 1 µM of BAY 60-6583 (FIG. 4C), 1 µM of CGS21680 (FIG. 4D), 100 nM of formoterol (FIG. 4E), 1 µM of apelin-13 (FIG. 4F), 100 nM of C5a (FIG. 4G), 100 nM of CCL2 (FIG. 4H), 1 µM of acetylcholine (FIG. 4I), 100 nM of galanin (FIG. 4J), 1 µM of endothelin 1 (FIG. 4K), 1 µM of histamine (FIG. 4L), 100 nM of motilin (FIG. 4M), 1 µM of neurotensin (FIG. 4N), 1 µM of PGE2 (FIG. 4O), 1 µM of SRIF-14 (FIG. 4P), and 1 µM of senktide (FIG. 4Q), respectively. Images were obtained before and 30 min after agonist stimulation, and analyzed using IN Cell Analyzer 2000. The selection of the concentration of these GPCRx agonists was initially set at the EC50 concentration (or alternatively, the Ki or Kd concentration) for the respective specific GPCRx, and if the resulting signal was too intense, then the concertation was lowered below the EC50, and if the resulting signal was too weak, then the concertation was increased to no more than 10,000× the EC50 concentration.

Stimulation of cells expressing CXCR4-GFP with CXCL12 resulted in re-location of GFP from the plasma membrane to distinct intracellular granules, showing internalization of surface CXCR4-GFP into the cytoplasm (FIG. 4A). Among 18 CXCR4-GPCRx heteromers identified by BiFC assay, 16 heteromers containing the following GPCRx induced internalization of CXCR4 as revealed by increased intracellular GFP granules and reduced GFP signal in the plasma membrane in cells co-expressing CXCR4-GFP and GPCRx, confirming heteromer co-internalization: ADCYAP1R1, ADORA2B, ADORA3, ADRB2, APLNR, C5AR1, CCR5, CHRM1, GALR1, EDNRB, HRH1, MLNR, NTSR1, PTGER3, SSTR2, and TACR3 (FIG. 4B-Q). CXCR4-GPCRx heteromers containing CALCR and PTGER2, on the other hand, did not show co-internalization of the heteromer upon GPCRx agonist treatment. These results demonstrate that certain GPCRx partners identified in the BiFC assay do form CXCR4-GPCRx heteromers in cells co-expressing both GPCRs, as evidenced by altered cellular trafficking properties of the heteromer.

Example 3. Evaluation by Ca2+ Mobilization Assay of Enhanced CXCR4 Downstream Signaling Upon CXCR4-GPCRx Heteromer Formation and Inhibition of the Enhanced Signaling To further examine if these CXCR4-GPCRx heteromers exhibit properties distinct from those of the individual protomers (in cells lacking one of the receptors), we investigated calcium signaling in the presence of either or both agonists in cells expressing either GPCR or both GPCRs together. In this example, as noted in Example 2, the selection of the concentration of these GPCRx agonists was initially set at the EC50 concentration (or alternatively, the Ki or Kd concentration) for the respective specific GPCRx, and if the resulting Ca2+ signal was too intense, then the concentration was lowered below the EC50, and if the resulting Ca2+ signal was too weak, then the concentration was increased to no more than 100× the EC50 concentration.

Figure 5A:
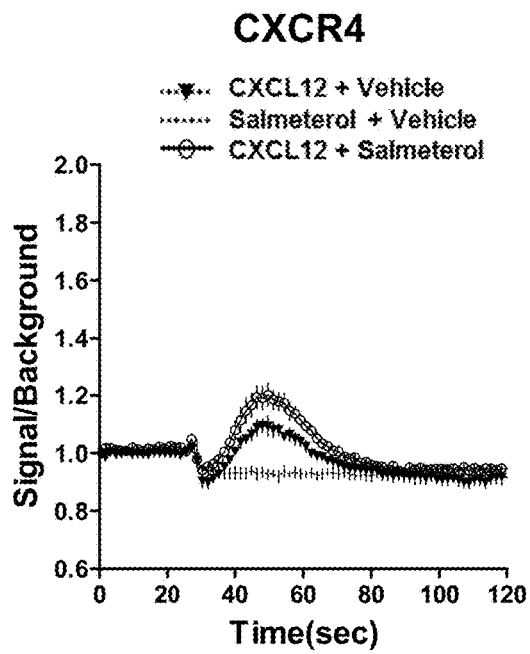
FIGS. 5A-5D: Shows enhancement of the calcium response in cells co-expressing CXCR4 and ADRB2 upon co-stimulation with their respective selective agonists. MDA-MB-231 human breast cancer cells were transduced with adenoviruses encoding CXCR4 and HA-VC (FIG. 5A), ADRB2 and HA-VC (FIG. 5B), or CXCR4 and ADRB2 (FIG. 5C). Adenoviruses encoding HA-VC were used to adjust the total amount of adenoviruses transduced. Cells were allowed to express GPCR for 2 days, incubated with Cal-520 AM for 2 hr, and were treated with 15 nM of CXCL12, 100 nM of salmeterol (ADRB2-selective agonist), or CXCL12 and salmeterol together. Calcium mobilization was measured using FlexStation 3 Multi-Mode Microplate Reader. The results were normalized for base-line activity. Data represent three independent experiments (mean±SEM).
Figure 5B:
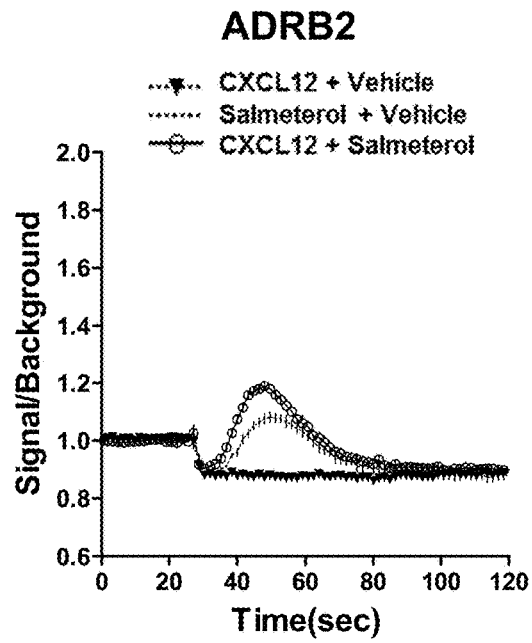

When MDA-MB-231 human breast cancer cells were transduced with adenoviruses encoding CXCR4, treatment of CXCL12 evoked intracellular calcium mobilization (FIG. 5A). Stimulation of the cells with salmeterol, an ADRB2-selective agonist, did not induce calcium response, demonstrating the calcium response evoked by CXCR4 was mediated by CXCR4. Co-treatment of the cells with CXCL12 and salmeterol induced similar calcium response compared to the one induced by CXCL12 alone. In cells overexpressing ADRB2 alone, CXCL12 did not induced calcium response while salmeterol induced calcium response, showing that salmeterol induces calcium response through ADRB2 (FIG. 5B). Co-treatment of both agonists induced similar calcium response to the one stimulated by salmeterol alone.

Figure 5C:
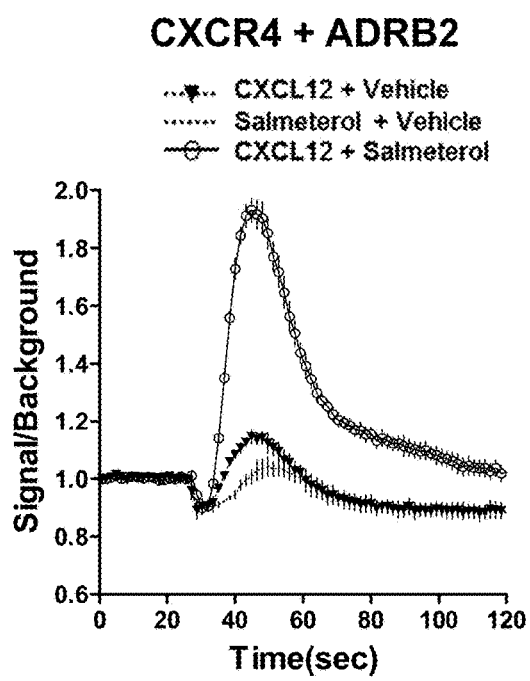
Figure 5D:
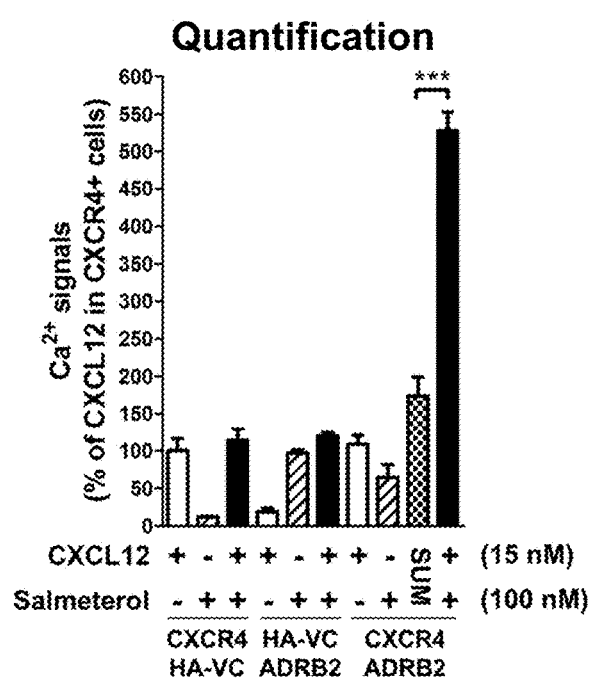

In cells overexpressing both CXCR4 and ADRB2, stimulation with each agonist induced calcium responses similar to the ones shown in cells expressing CXCR4 or ADRB2 alone (FIGS. 5C vs 5A and 5B). In contrast, co-treatment of both agonists together significantly increased the calcium response compared to the ones evoked by individual agonists (FIGS. 5C & 5D). The enhanced calcium signaling was observed only in cells expressing both CXCR4 and ADRB2, but not in cells expressing either CXCR4 or ADRB2 alone. These results clearly demonstrate that CXCR4-ADRB2 heteromer exhibit properties distinct from those of the individual GPCRs.

To examine if the other GPCRs identified to interact with CXCR4 in BiFC and co-internalization assay also show distinct properties in calcium signaling, experiments shown in FIGS. 5A-5D were performed for other identified GPCRx partners. In cells co-expressing CXCR4 and either ADCYAP1R1 (FIG. 6A), ADORA2B (FIG. 6B), ADORA3 (FIG. 6C), C5AR1 (FIG. 6D), CALCR (FIG. 6E), CHRM1 (FIG. 6F), EDNRB (FIG. 6G), HRH1 (FIG. 6H), MLNR (FIG. 6I), NTSR1 (FIG. 6J), PTGER2 (FIG. 6K), or TACR3 (FIG. 6L), co-treatment of CXCL12 and respective GPCRx agonist significantly increased calcium responses compared with the sum of calcium responses that were induced by individual agonists as shown in FIGS. 5C and 5D, and as shown in FIGS. 6A-6L. The cells co-expressing the CXCR4 and the GPCRx (either ADCYAP1R1 (FIG. 6A), ADORA2B (FIG. 6B), ADORA3 (FIG. 6C), C5AR1 (FIG. 6D), CALCR (FIG. 6E), CHRM1 (FIG. 6F), EDNRB (FIG. 6G), HRH1 (FIG. 6H), MLNR (FIG. 6I), NTSR1 (FIG. 6J), PTGER2 (FIG. 6K), or TACR3 (FIG. 6L)) exhibited an enhanced calcium mobilization upon co-stimulation (or co-treatment) with the CXCL12 and the respective selective GPCRx agonist relative to the sum of calcium mobilization amounts resulting from single agonist stimulation with either the CXCL12 or the respective selective GPCRx agonist, as determined by the calcium mobilization assay. Notably, in cells co-expressing CXCR4 and CNR2, CXCL12-induced calcium response was significantly reduced, rather than enhanced, upon addition of CXCL12 alone or together with JWH-133, a selective CNR2 agonist, compared with the CXCL12-mediated calcium response observed in cells expressing CXCR4 alone (data not shown).

Within the above set of co-expressed systems, it was also noted that an enhanced amount of calcium mobilization was observed in the individual protomer context in cells involving CXCR4 and PTGER2 (FIG. 6K) (an individual protomer context, e.g., either CXCR4 expressed in the absence of the respective GPCRx, or the respective GPCRx expressed in the absence of the CXCR4), upon co-stimulation with CXCL12 and the respective selective GPCRx agonist. Specifically, an enhanced amount of calcium mobilization was observed for PTGER2 (FIG. 6K), in the individual protomer context, in both situations where CXCR4 was expressed in the absence of the respective GPCRx, and where the respective GPCRx (PTGER2) was expressed in the absence of the CXCR4, upon co-stimulation with CXCL12 and the respective selective GPCRx agonist (5 μM of PGE2), the calcium mobilization amount resulting from the individual protomer context systems were greater than the sum of calcium mobilization amounts resulting from single agonist stimulations with either the CXCL12 or the respective selective GPCRx agonist (5 μM of PGE2).

Accordingly, from these observations, those systems co-expressing CXCR4 and the GPCRx selected from the group consisting of ADCYAP1R1 (FIG. 6A), ADORA2B (FIG. 6B), ADORA3 (FIG. 6C), C5AR1 (FIG. 6D), CALCR (FIG. 6E), CHRM1 (FIG. 6F), EDNRB (FIG. 6G), HRH1 (FIG. 6H), MLNR (FIG. 6I), NTSR1 (FIG. 6J), and TACR3 (FIG. 6L), are considered to have: (i) exhibited an enhanced calcium mobilization upon co-stimulation (or co-treatment) with the CXCL12 and the respective selective GPCRx agonist relative to the sum of calcium mobilization amounts resulting from single agonist stimulation with either the CXCL12 or the respective selective GPCRx agonist, as determined by the calcium mobilization assay; (ii) exhibited a calcium mobilization amount equal to or less than the sum of calcium mobilization amounts resulting from single agonist stimulation with either the CXCL12 or the respective selective GPCRx agonist in an individual protomer context; and thus (iii) constituted CXCR4-GPCRx heteromers exhibiting properties distinct from those of the individual GPCR. The enhanced calcium responses were not observed in cells expressing individual GPCRs, thereby demonstrating that these CXCR4-GPCRx heteromers exhibit properties distinct from those of the individual GPCR.

The enhanced calcium signaling induced by small amounts of individual agonists together clearly indicated that CXCR4-GPCRx heteromers would increase the sensitivity and dynamic range of these receptors at limiting ligand concentrations in vivo, and may be associated with poor prognosis. The enhanced calcium signaling by the CXCR4-GPCRx heteromers also indicates that the current diagnosis based on the level of CXCR4 expression alone needs to be changed to consider the expression levels of CXCR4 and GPCRx.

In contrast, GPCRs such as APLNR (FIG. 7A), CCR5 (FIG. 7B), GALR1 (FIG. 7C), PTGER3 (FIG. 7D), and SSTR2 (FIG. 7E) did not show enhanced calcium responses when cells expressing both receptors were co-treated with both agonists, although these GPCRs were shown to interact with CXCR4 in BiFC (Table 5) and CXCR4-GFP co-internalization assay. These results clearly demonstrate that the synergistic increase in calcium response shown in FIGS. 5A-5D and 6A-6L is a unique feature of CXCR4-GPCRx heteromers, that is not shared by other CXCR4-GPCRx heteromers such as CXCR4-APLNR, CXCR4-CCR5, CXCR4-GALR1, CXCR4-PTGER3, and CXCR4-SSTR2.

TABLE 5

GPCRs that exhibited BiFC score equal or higher than 10 when co-expressed with CXCR4 but did not show enhanced Ca2+ signaling upon co-treatment of both agonists. CXCR4-GPCRx heteromers that do not show enhanced $Ca^{2+}$ signaling upon co-treatment of both agonists

| | GPCRx | BiFC score CXCR4-VN & GPCRx-VC |
|---|---|---|
| 1 | APLNR | 63 |
| 2 | CCR5 | 44 |
| 3 | GALR1 | 60 |

TABLE 5-continued

GPCRs that exhibited BiFC score equal or higher than 10 when co-expressed with CXCR4 but did not show enhanced Ca2+ signaling upon co-treatment of both agonists.
CXCR4-GPCRx heteromers that do not show enhanced $Ca^{2+}$ signaling upon co-treatment of both agonists

| | GPCRx | BiFC score CXCR4-VN & GPCRx-VC |
|---|---|---|
| 4 | PTGER3* | 13 |
| 5 | SSTR2 | 30 |

*CXCR4-VC and GPCRx-VN were used.

It was further examined if enhanced calcium responses in cells co-expressing CXCR4 and GPCRx upon co-stimulation with CXCL12 and GPCRx ligands are inhibited by GPCRx antagonists. In cells co-expressing CXCR4 and either ADRB2 (FIG. 8A), CHRM1 (FIG. 8B & FIG. 8C), HRH1 (FIGS. 8F-8I), MLNR (FIG. 8J), or NTSR1 (FIG. 8K), treatment of 10 μM of ADRB2 antagonist carvedilol (FIG. 8A), 1 μM of CHRM1-selective antagonist VU0255035 (FIG. 8B), 10 μM of CHRM1 antagonist oxybutynin (FIG. 8C), 1 μM of HRH1-selective antagonist cetirizine (FIG. 8F), 1 μM of HRH1-selective antagonist pyrilamine (FIG. 8G), 10 μM of HRH1 antagonist hydroxyzine (FIG. 8H), 10 μM of HRH1-selective antagonist loratadine (FIG. 8I), 1 μM of MLNR-selective antagonist MA-2029 (FIG. 8J) and 1 μM of NTSR1-selective antagonist meclinertant (FIG. 8K), respectively, suppressed the enhanced calcium signaling significantly. And co-treatment of both antagonists together resulted in a more complete suppression (FIGS. 8A-8C, and 8F-8K). These results demonstrated that GPCRx antagonists could be used as an efficient therapeutics against CXCR4-GPCRx heteromers where GPCRx represents ADRB2, CHRM1, HRH1, MLNR, and NTSR1.

Figure 8A:
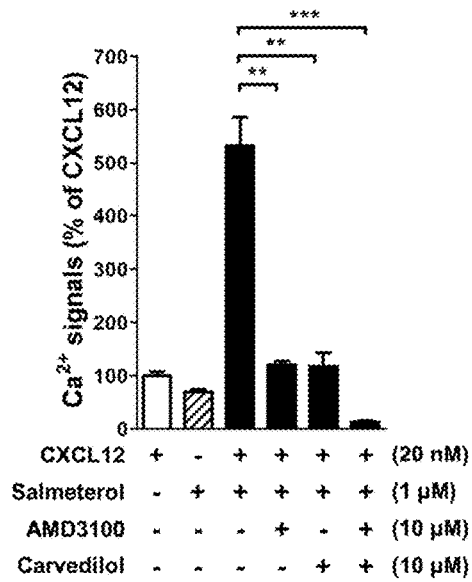
FIGS. 8A-8L: Shows co-treatment of both antagonists efficiently suppressed the enhanced calcium response when cells expressing CXCR4-GPCRx heteromer were stimulated with CXCL12 and GPCRx agonists simultaneously. MDA-MB-231 cells were co-transduced with adenoviruses encoding CXCR4 and GPCRx. GPCRx represents ADRB2 (FIG. 8A), CHRM1 (FIGS. 8B-8D), EDNRB (FIG. 8E), HRH1 (endo) (FIG. 8F and FIG. 8G), HRH1 (FIG. 8H and FIG. 8I), MLNR (FIG. 8J), NTSR1 (FIG. 8K), and TACR3 (FIG. 8L). In F &G, cells were transduced with adenoviruses encoding CXCR4, and endogenous HRH1 responses were examined with 50 nM of histamine. Cells were incubated with Cal-520 AM for 2 hr, GPCR antagonists or vehicle for 30 min, and stimulated with indicated amounts of CXCL12, GPCRx agonist, or CXCL12 and GPCRx agonist. Calcium mobilization was quantified as described in FIG. 5D. Data represent three independent experiments (mean±SEM). *P<0.05, P<0.01, *P<0.001; Student's t test.
Figure 8B:
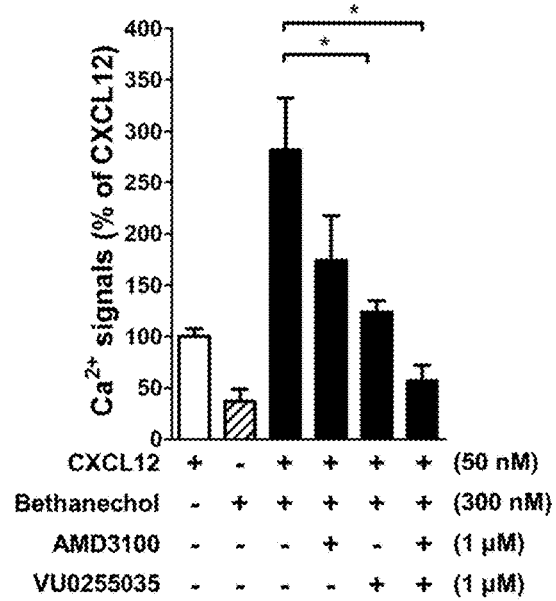
Figure 8C:
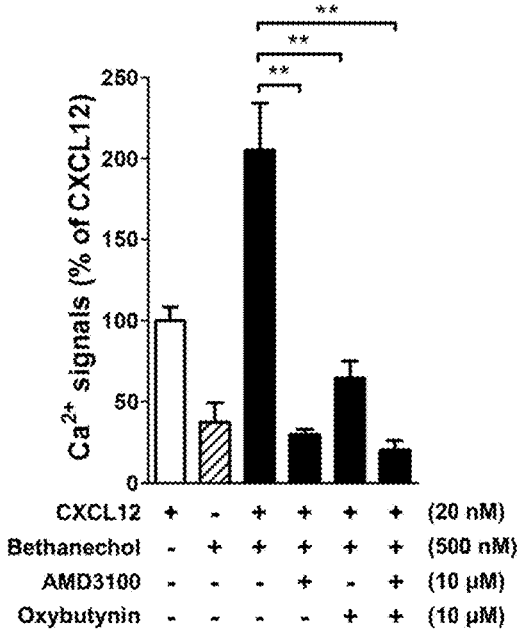
Figure 8D:
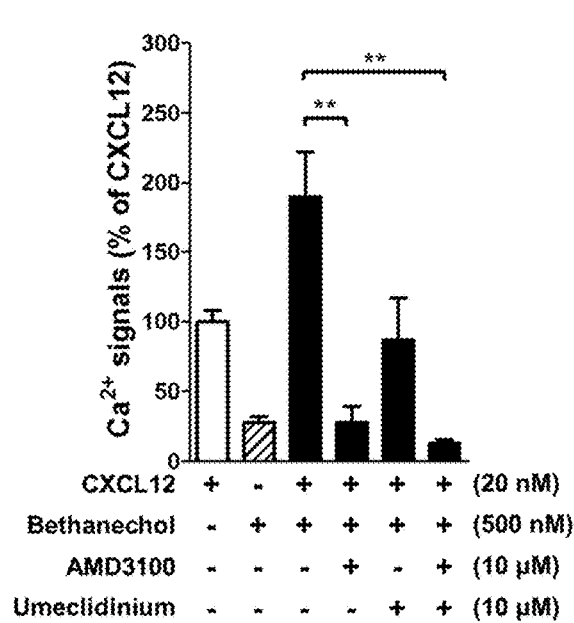

In cells co-expressing CXCR4 and CHRM1, 10 μM of muscarinic acetylcholine receptor antagonist umeclidinium reduced the enhanced calcium signaling, although not statistically significant (FIG. 8D). In these cells, co-treatment of AMD3100 and umeclidinium almost completely inhibited calcium response induced by simultaneous addition of CXCL12 and bethanechol.

Figure 8E:
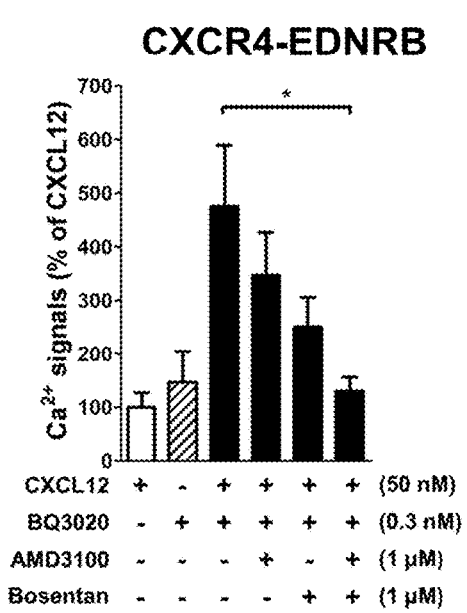

In cells co-expressing CXCR4 and either EDNRB (FIG. 8E) or TACR3 (FIG. 8L), treatment of either 1 μM of AMD3100 alone (FIG. 8E and FIG. 8L), or 1 μM of endothelin receptor antagonist bosentan (FIG. 8E) or 1 μM of TACR3-selective antagonist SSR 146977 alone (FIG. 8L) failed to inhibit enhanced calcium response significantly. But when the cells were co-treated with AMD3100 and bosentan (FIG. 8E) or AMD3100 and SSR 146977 together (FIG. 8L), the enhanced calcium responses were significantly inhibited.

In cells co-expressing CXCR4 and either CHRM1 (FIG. 8B), EDNRB (FIG. 8E), HRH1 (FIGS. 8F and 8G), or MLNR (FIG. 8J), although 1 μM of AMD3100 alone failed to inhibit enhanced calcium signaling, co-treatment of 1 μM of both antagonists together significantly suppressed the enhanced calcium signaling.

These results clearly demonstrate that co-treatment of small doses of antagonists targeting each protomer provides novel therapeutic tools to efficiently suppress CXCR4-GPCRx heteromer response while avoiding side effects associated with high doses of individual antagonists.

Example 4. Inhibition of Internalization by GPCRx Antagonists

Figure 9:
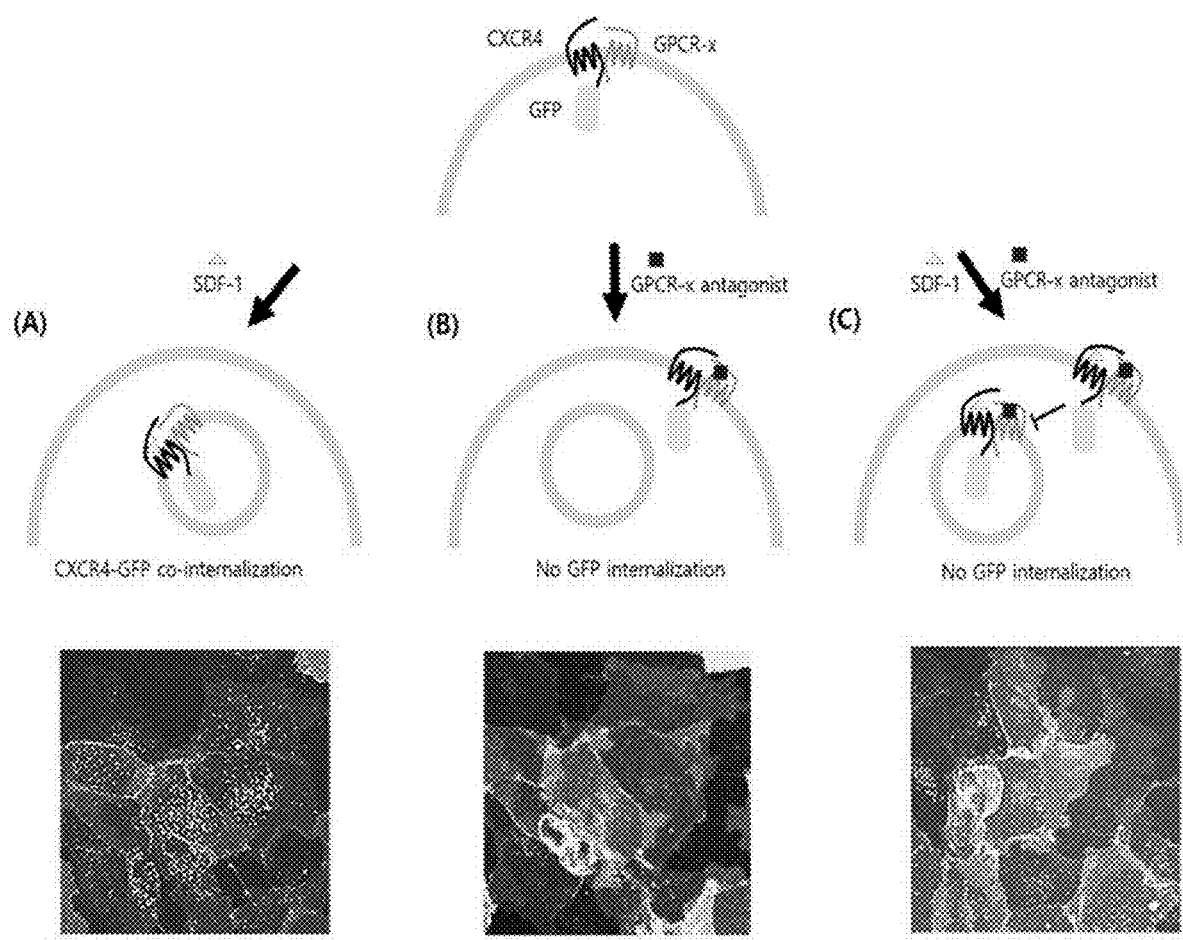
FIG. 9: Shows principle of internalization inhibition study. Cells co-expressing CXCR4-GFP and GPCRx are treated with CXCL12 (SDF-1) and/or GPCRx specific antagonist. (scenario A) CXCR4 and GPCRx forms heteromer. CXCR4 agonist, CXCL12 (SDF-1) induced internalization of CXCR4-GFP alone or CXCR4-GFP with GPCRx. (scenario B) GPCRx antagonist does not induce internalization of CXCR4-GFP. (scenario C) Internalization of CXCL12 (SDF-1) stimulated CXCR4-GFP is inhibited by GPCRx specific antagonist.

To further study if co-internalization of CXCR4 heterodimer was blocked by partner GPCRx antagonists, internalization inhibition assay was performed. As shown in FIGS. 4B-4Q, CXCR4-GFP expressing U-2 OS cells were co-internalized by partner GPCRx specific agonist when CXCR4 and GPCRx were simultaneously transduced to cells (control: CXCR4-GFP (FIG. 4A)). If CXCR4 formed heterodimer with GPCRx and co-internalized by partner GPCRx, it can be blocked by GPCRx specific antagonist (FIG. 9).

Figure 10C:
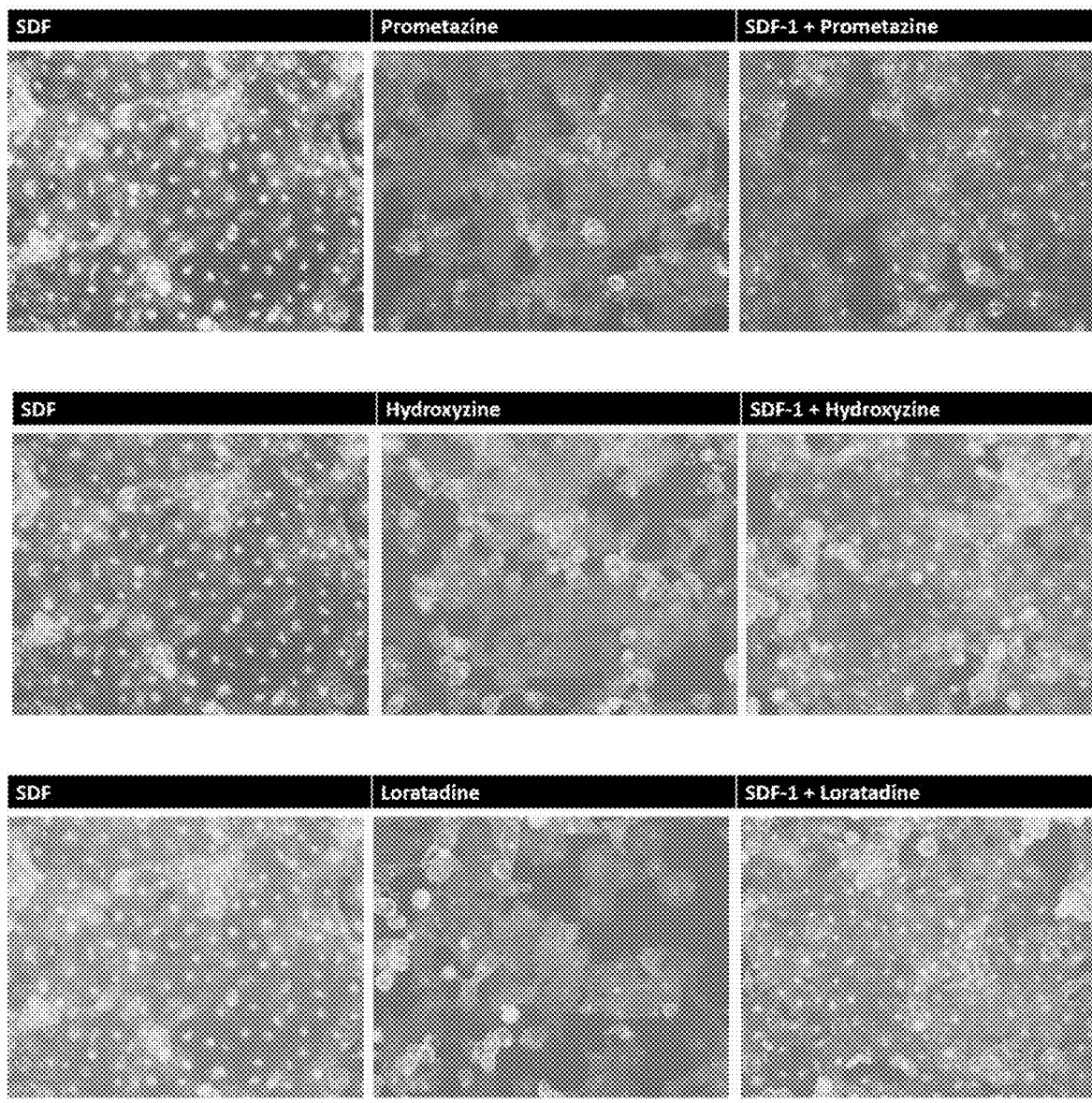

U-2 OS cells stably expressing CXCR4-GFP were transduced with Adenoviruses encoding GPCRx (ADRB2, CHRM1, HRH1). After 2 days, images were obtained before and 20 minutes after stimulating cells with CXCR4-specific agonist, CXCL12 (SDF-1) (20 nM), and/or GPCRx-specific antagonist (10 μM). Internalization of CXCR4-GFP was observed as GFP granules using IN Cell Analyzer 2500. Loss of GFP expression on the cell surface or appearance of GFP granules inside the cells were considered as CXCR4-GFP co-internalization. CXCR4 agonist, CXCL12 induced internalization of CXCR4-GFP with GPCRx (FIGS. 10A-C, first columns). GPCRx antagonists, treated as follows, had no effect on the internalization of the heteromer (FIGS. 10A-C, second columns): Carvedilol, an ADRB2 antagonist (FIG. 10A); Oxybutynin and Umeclidinium, CHRM1 antagonists (FIG. 10B); Promethazine, Hydroxyzine, and Loratadine, HRH1 antagonists (FIG. 10C). Internalization of CXCL12 stimulated CXCR4-GFP with GPCRx were inhibited by GPCRx specific antagonists (FIGS. 10A-C, third columns).

These data demonstrate that CXCR4-GPCRx co-internalization was heteromer specific event and CXCR4 and GPCRx formed heterodimer. These data further demonstrate that, by inhibition of internalization of CXCR4 heteromer, abnormal downstream signal in CXCR4-GPCRx heteromer overexpressed cells, such as cancers, can be blocked for therapeutics purposes.

Example 5. Evaluation by Cell Proliferation Assay of Phenotypic Effects of Inhibitor of CXCR4-GPCRx Heteromer Signaling on Tumor Growth Several CXCR4 antagonists have been developed, but none have been approved as anticancer drugs until now. To overcome the limitation of CXCR4 inhibitors and to develop CXCR4 heteromer-based therapeutic agent, we tested the effect of GPCRx antagonist on cell proliferation.

We prepared single cell suspensions of resected and dissociated glioblastoma tissues from patients (provided by Samsung Seoul hospital in Seoul, Korea). These cells were cultured under conditions optimal for propagation and non-differentiation of normal neuronal stem cell. Media were composed serum free Neurobasal media supplemented with basic FGF and EGF.

The effect of GPCRx antagonist on the survival of patient derived cells (PDCs) were assessed using ATPlite (PerkinElmer, Cat. No. 6016739 reagent. ATPlite is an Adenosine Triphospate monitoring system based on firefly luciferase. This luminescence assay is the alternative to colorimetric, fluorometric and radioisotopic assays for the quantitative evaluation of proliferation and cytotoxicity of cultured mammalian cells. Cells were seeded in 384-well plate at 500 cells/well in 40 μl culture media. After overnight growth, the cells were cultured for 7 days in the presence of several dose of GPCRx antagonist or DMSO alone. After the 7-day incubation, 15 µl ATPlite was added into the each well and the plate were shaken for 5 minutes in an orbital shaker at 700 rpm. The luminescent signal was detected within 30 minutes at PerkinElmer TopCount detection instrument. The cell viability was calculated using the equation: Cell viability (%)=(OD of antagonist treatment/OD of DMSO only treatment)×100%.

Figure 11A:
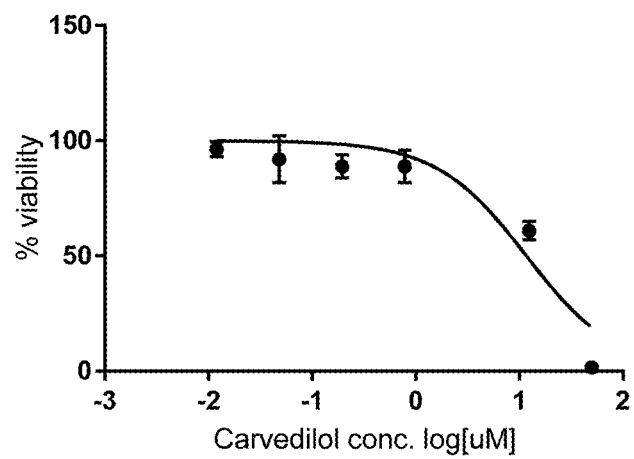
FIGS. 11A-11C: Shows the effect of GPCRx antagonist on the survival of patient derived cells (PDCs) from cancer patients.
Figure 11B:
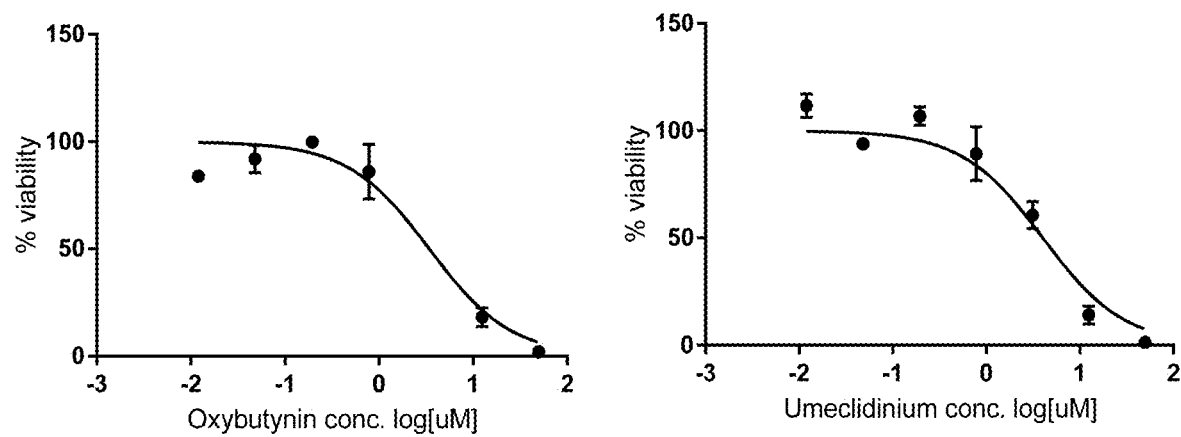
Figure 11C:
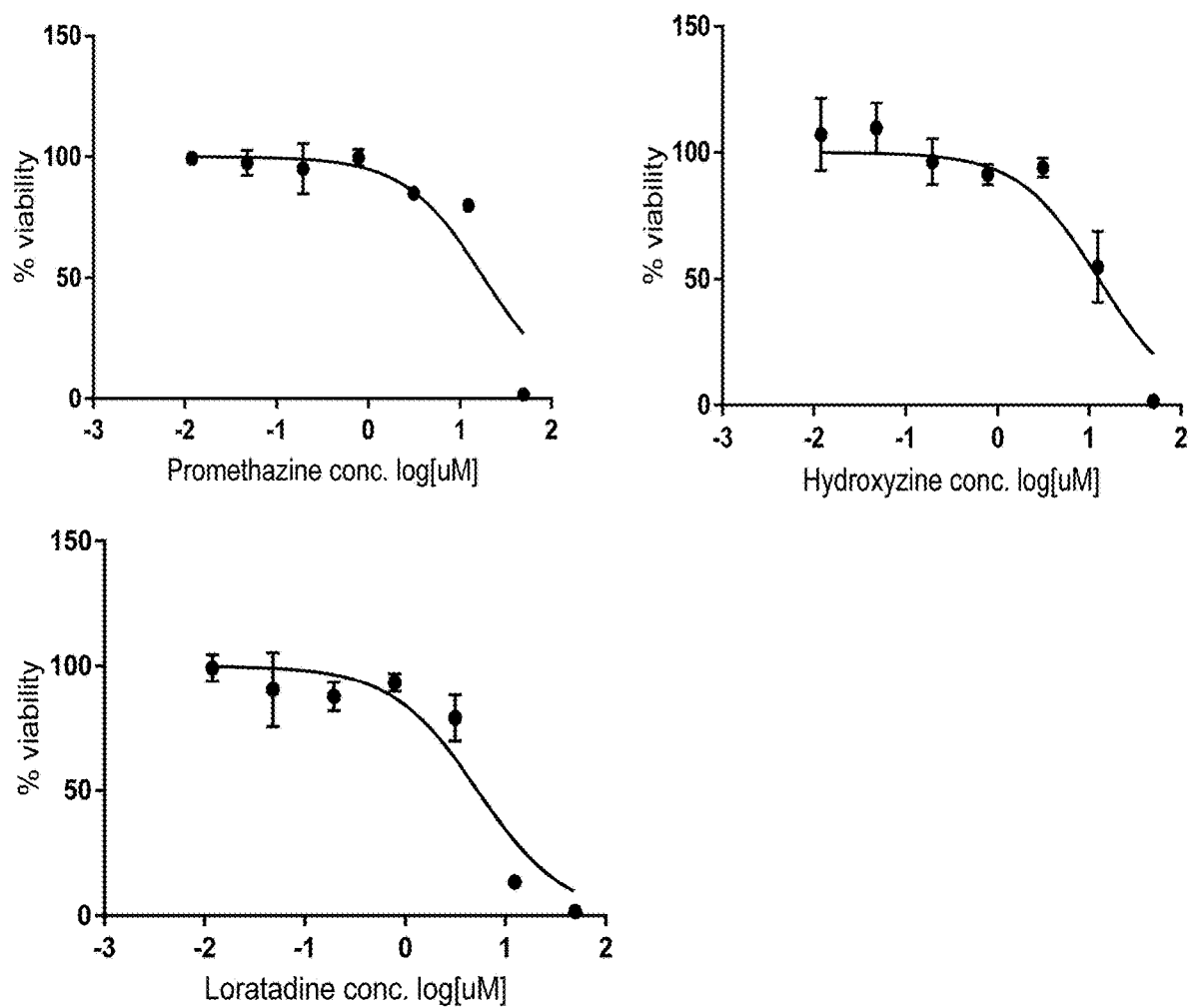
Figure 13A:
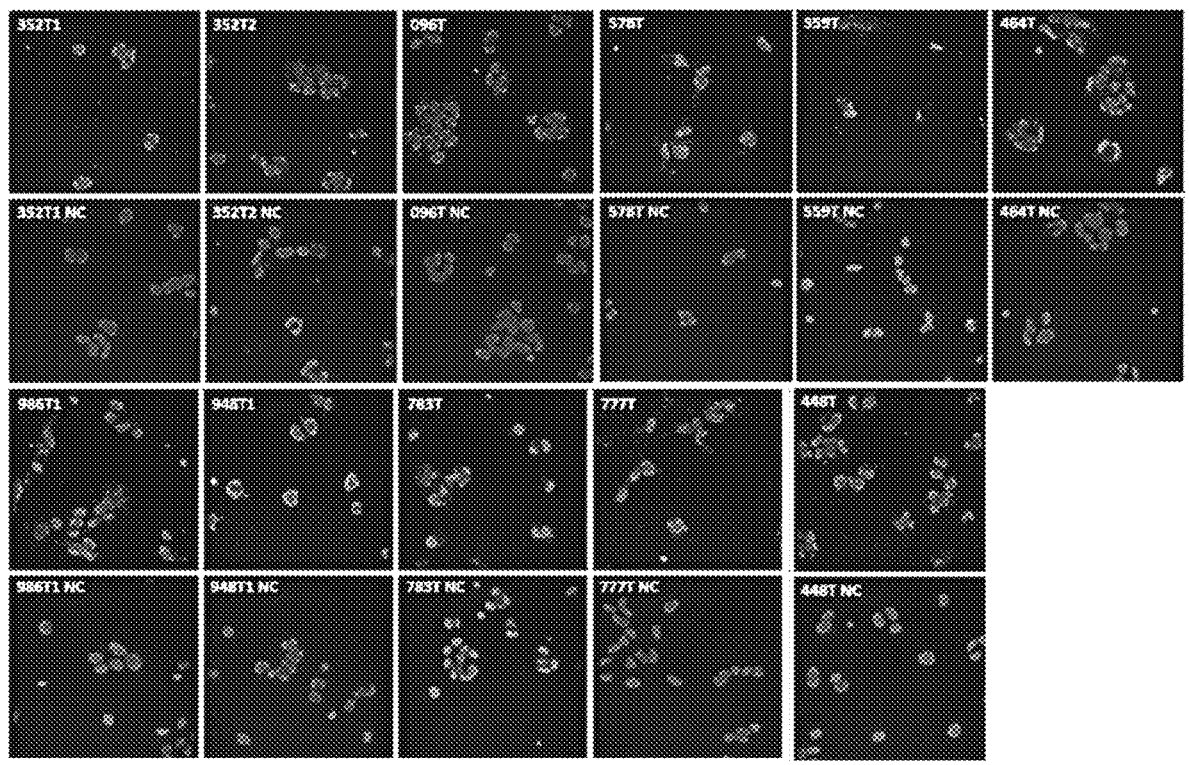
FIGS. 13A-13B: Shows CXCR4-ADRB2 heteromer detection in PDC by PLA. GBM originated PDCs (sample IDs: 986T, 948T, 783T, 777T, 352T1, 352T2, 578T, 559T, 464T, 448T, 096T) were plated at chamber slide and CXCR4-ADRB2 heteromer were detected by PLA with CXCR4 and ADRB2 specific antibodies.
Figure 13B:
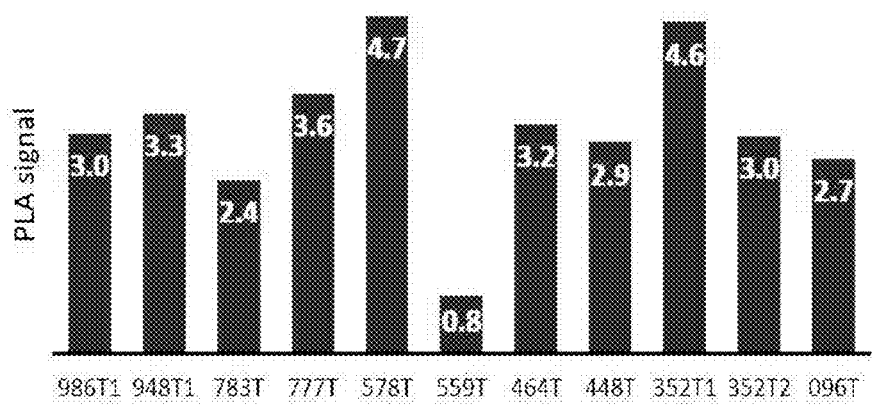
Figure 14A:
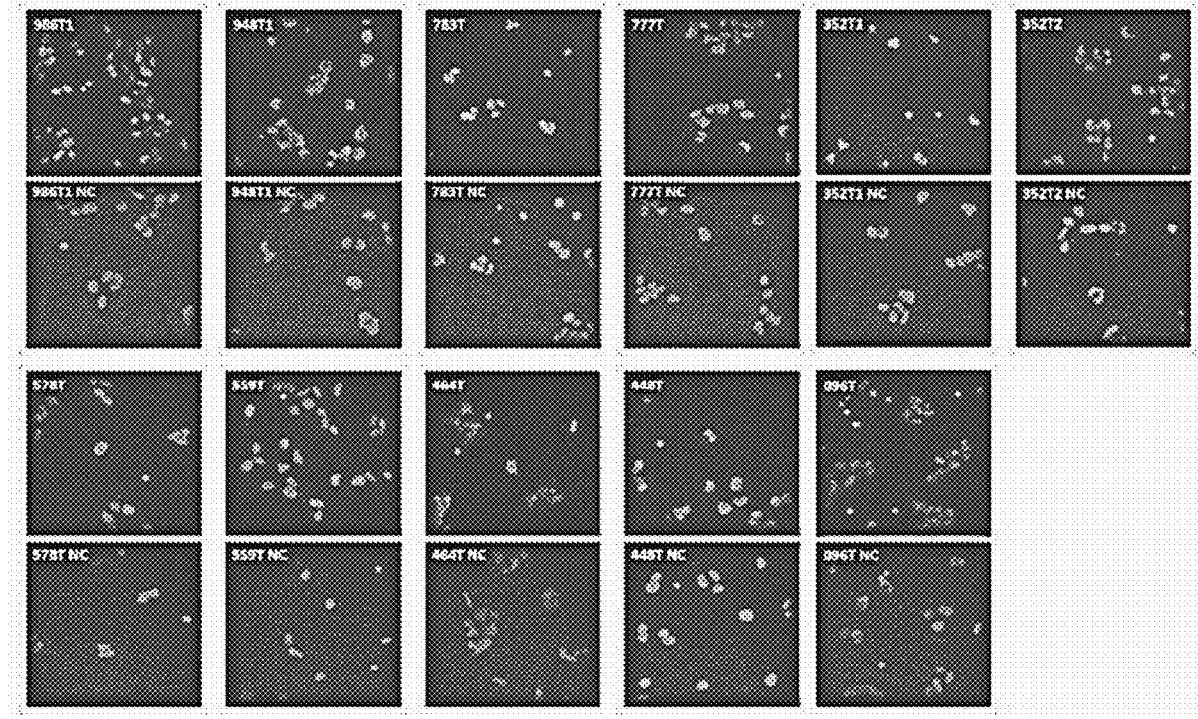
FIGS. 14A-14B: Shows CXCR4-CHRM1 heteromer detection in PDC by PLA. GBM originated PDCs (sample IDs: 986T, 948T, 783T, 777T, 352T1, 352T2, 578T, 559T, 464T, 448T, 096T) were plated at chamber slide and CXCR4-CHRM1 heteromer were detected by PLA with CXCR4 and CHRM1 specific antibodies.
Figure 14B:
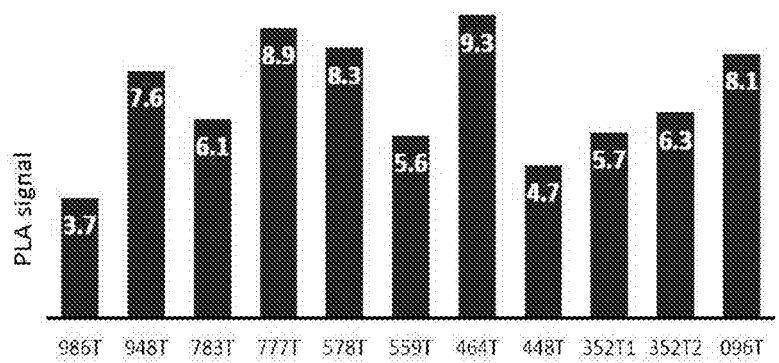

As shown in FIGS. 11A-C, when Carvedilol, ADRB2 specific antagonist, was treated in PDC expressing CXCR4 and ADRB2, growth of cells was inhibited significantly. (IC50=11.69 µM, FIG. 11A). Oxybutynin and Umeclidinium, CHRM1 antagonists also inhibited on the survival of PDc. Oxybutynin or Umeclidinium each showed significantly decreased survival of cells at IC50=3.04 µM or 4.03 µM, respectively. (FIG. 11B). Promethazine, Hydroxyzine, and or Loratadine as a HRH1 antagonist each showed decreased survival of PDc at IC50=18.39 uM, 12.79 µM or 5.29 µM, respectively. (FIG. 11C).

These results demonstrate that CXCR4 heteromer induced abnormal cell proliferation can be blocked by partner GPCRx specific antagonist in CXCR4-GPCRx heteromer expressing cells, indicating that inhibition of cancer cell growth using partner GPCRx antagonist in CXCR4-GPCRx heteromer bearing patients can overcome the limitations of CXCR4 inhibitors alone as cancer therapeutics.

Example 6. Evaluation of CXCR4-GPCRx Heteromer Formation in Patient Derived Cells (PDC) Using Proximity Ligation Assay (PLA)

To investigate the existence of GPCR complexes in native tissues, various approaches such as atomic force microscopy (Fotiadis et al., 2006), co-immunoprecipitation (Gomes et al., 2004) and binding or functional assays (Wreggett and Wells, 1995) have been used. The most convenient methods to monitor interactions are based on resonance energy transfer performed with labeled proteins. The labeling can be performed by selective probes such as antibodies or fluorescent ligands (Roess et al., 2000; Patel et al., 2002).

Bazin et al. employed a time-resolved fluorescence resonance energy transfer (TR-FRET)-based approach that offers a much higher signal-to-noise ratio (Bazin et al., 2002). FRET is based on the transfer of energy between two fluorophores, a donor and an acceptor, when in close proximity. Molecular interactions between biomolecules can be assessed by coupling each partner with a fluorescent label and by detecting the level of energy transfer. Introducing a time delay of approximately 50 to 150 µseconds between the system excitation and fluorescence measurement allows the signal to be cleared of all non-specific short-lived emissions.

Proximity ligation assay (PLA) is a technology that extends the capabilities of traditional immunoassays to include direct detection of proteins, protein interactions and modifications with high specificity and sensitivity (Gullberg et al., 2004). Two primary antibodies raised in different species recognize the target antigen on the proteins of interest. Secondary antibodies directed against the constant regions of the different primary antibodies, called PLA probes, bind to the primary antibodies. Each of the PLA probes has a unique short DNA strand attached to it, If the PLA probes are in close proximity (that is, if the two original proteins of interest are in close proximity, or part of a protein complex, as shown in the figures), the DNA strands can participate in rolling circle DNA synthesis when appropriate substrates and enzymes are added. The DNA synthesis reaction results in several-hundred fold amplification of the DNA circle. Next, fluorescent-labeled complementary oligonucleotide probes are added, and they bind to the amplified DNA. The resulting high concentration of fluorescence is easily visible as a distinct bright spot when viewed with a fluorescence microscope (Gustafsdottir et al., 2005).

CXCR4 overexpressing cell line, U2OS-CXCR4, was infected with ADRB2 expressing adenovirus, Ad-ADRB2 at the dose of 0, 2.5, 10, 40 MOIs for 2 days. PLA was performed as described previously (Brueggemann et al., 2014; Tripathi et al., 2014). To perform PLA, infected cells were fixed with 4% paraformaldehyde (PFA) on sixteen-well tissue culture slides. Slides were blocked with blocking solution provided by Duolink and incubated with mouse anti-CXCR4 (1:200, Santacruz, Sc-53534), Rabbit anti-ADRB2(1:200, Thermoscientific, PA5-33333), Rabbit anti-CHRM1(1:200, Ls bio, Ls-C313301) at 37° C. for 1 h in a humidifying chamber. Slides were then washed and incubated (1 h at 37° C.) with secondary anti-rabbit and anti-mouse antibodies conjugated with plus and minus Duolink II PLA probes. Slides were washed again and then incubated with ligation-ligase solution (30 min at 37° C.) followed by incubation with amplification-polymerase solution (2 h at 37° C.). Slides were then mounted with minimal volume of Duolink II mounting medium with 4',6-diamidino-2phenylindole (DAPI) for 15-30 min, and PLA signals [Duolink In Situ Detection Reagents Green (λ excitation/emission 495/527 nm) or Red (λ excitation/emission 575/623 nm)] were identified as fluorescent spots under a IN Cell analyzer 2500.

As shown in the FIGS. 12A-12B, the PLA signal increases in a dose dependent manner as the expression level of ADRB2. FIG. 12A: Images of PLA signal from U2OS cells expressing CXCR4-ADRB2 heteromer over a series of MOIs (multiplicity of infection). FIG. 12B: The red signal spots were counted and calculated by normalization against negative control. The PLA signal increased proportionate to the expression level of ADRB2 in a dose dependent manner. FIG. 12C: To investigate endogenous ADRB2 expression, qRT-PCR was performed with ADRB2 specific primers. As the results show, endogenous ADRB2 expression level of U2OS cell was quite high, indicating that the PLA signal is detected even in the section without virus infection (at 0 MOI for ADRB2).

Traditionally Glioblastoma (GBM) is the most common and lethal primary brain tumor. Preclinical cancer biology has largely relied on the use of human cancer cell lines in vitro and the xenograft process of established these cell lines. However, the process of establishing conventional cell lines results in irreversible loss of important biological properties and, as a result, the xenograft tumor models do not maintain genomic and phenotypic characteristics present in the original tumor.

Patient derived cell (PDC) derived directly from glioblastoma harbor extensive similarities to normal neural stem cells and recapitulate the genotype, gene expression patterns, and in vivo biology of human glioblastomas.

To perform PLA with PDC samples, the patient derived cells were plated and fixed with 4% PFA on sixteen-well tissue culture slides. Slides were blocked with blocking solution provided by Duolink and incubated with mouse anti-CXCR4 (1:200, Santa Cruz, Sc-53534), rabbit anti-ADRB2 (1:200, Thermo Scientific, PAS-33333), rabbit anti-CHRM1 (1:200, Lsbio, Ls-C313301) at 37° C. for 1 h in a humidifying chamber. Slides were then washed and incubated (1 h at 37° C.) with secondary anti-rabbit and anti-mouse antibodies conjugated with plus and minus Duolink II PLA probes. Slides were washed again and then incubated with ligation-ligase solution (30 min at 37° C.) followed by incubation with amplification-polymerase solution (2 h at 37° C.). Slides were then mounted with minimal volume of Duolink II mounting medium with 4',6'-diamidino-2-phenylindole (DAPI) for 15-30 min, and PLA signals [Duolink In Situ Detection Reagents Green (λ excitation/emission 495/527 nm) or Red (λ excitation/emission 575/623 nm)] were identified as fluorescent spots under the IN Cell analyzer 2500.

As shown in FIGS. 13A-13B and FIGS. 14A-14B, PLA ratio refers to the CXCR4 GPCRx heteromer, and the frequency of the heteromer formation varies depending on the patient. PLA ratio was calculated as: number of fluorescent spots in PDC sample/number of fluorescent spots in negative control. Negative control (NC) represents background fluorescence signal, indicated by the number of spots when only the secondary antibody conjugated with plus and minus Duolink II PLA probes is treated without primary antibody (mouse anti-CXCR4, rabbit anti-ADRB2, rabbit anti-CHRM1) treatment in PLA processing. These data demonstrate quantitative analysis of CXCR4-ADRB2 heterodimer in cancer patient samples.

Example 7. Evaluation of CXCR4-GPCRx Heteromer Formation In Vivo Using PDX Model To perform PLA with PDX samples, the glioblastoma patient derived FFPE samples were used (provided by Samsung Seoul hospital in Seoul, Korea). After FFPE sample were de-paraffinized and performed heat induced antigen retrieval for 15 minutes at 100° C. Slides were blocked with blocking solution provided by Duolink and incubated with rabbit anti-CXCR4 (1:200, Thermoscientific, PA3305), mouse anti-ADRB2 (1:200, Santacruz, Sc-271322), at 37° C. for 1 h in a humidifying chamber. The other process was same as described above (PLA with PDC).

Figure 15A:
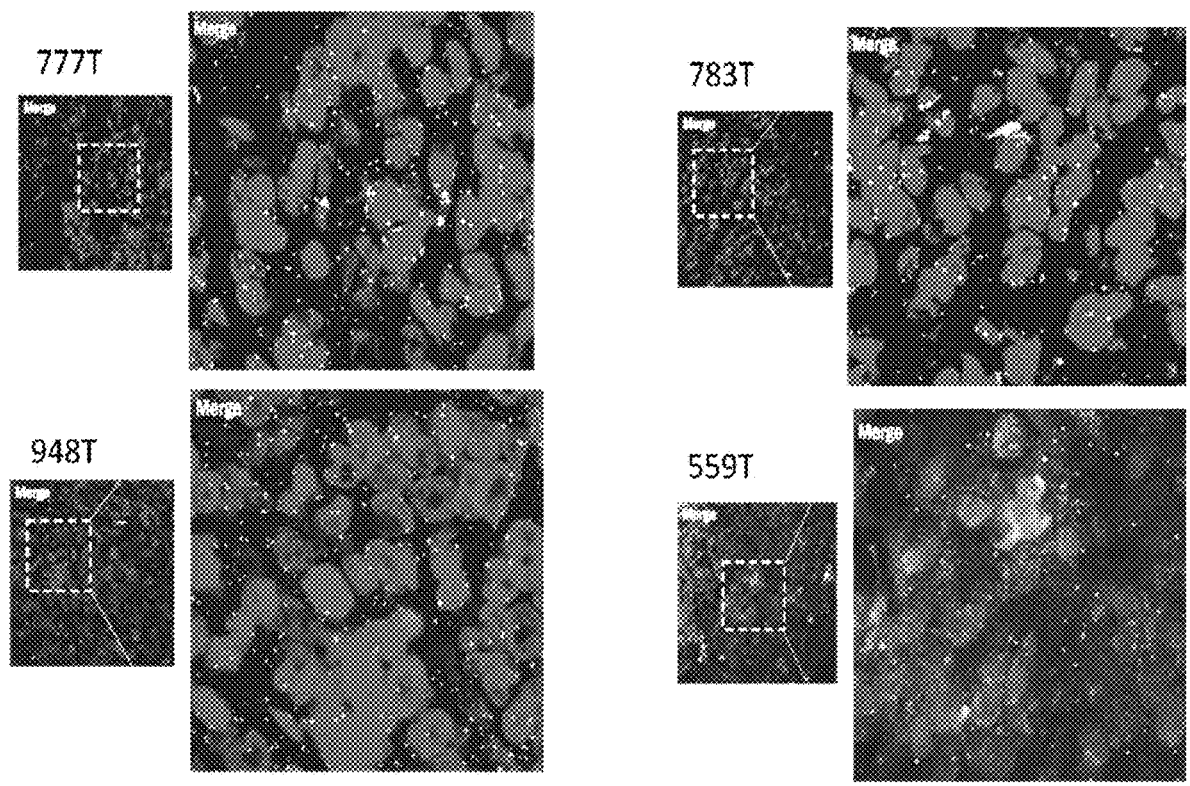
FIGS. 15A-15B: Shows results from CXCR4-GPCRx heteromer detection in PDX. GBM originated PDXs (sample IDs; 777T, 783T, 948T, 559T) were detected CXCR4-ADRB2 heteromer by PLA with CXCR4 and ADRB2 specific antibodies.
Figure 15B:
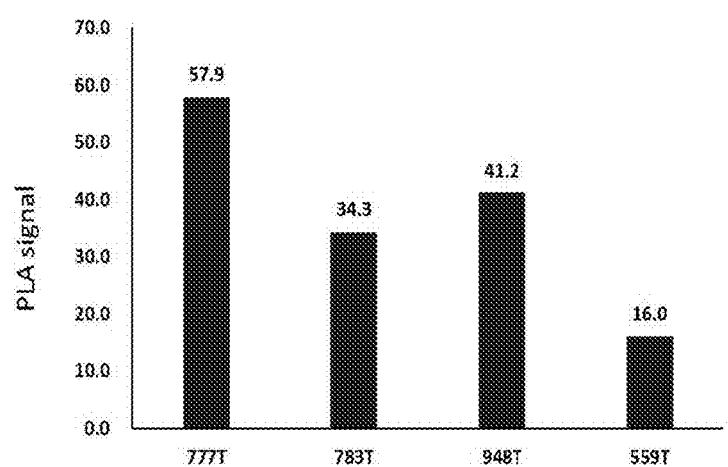

In the FIG. 15A, nuclei were visualized with DAPI staining, and CXCR4-ADRB4 heteromers were stained with PLA as small dots. As shown in FIG. 15B, PLA ratio is different according to the patient and based on this result, indicating that it is possible to perform personalized medicine by the companion diagnostics.

Figure 16A:
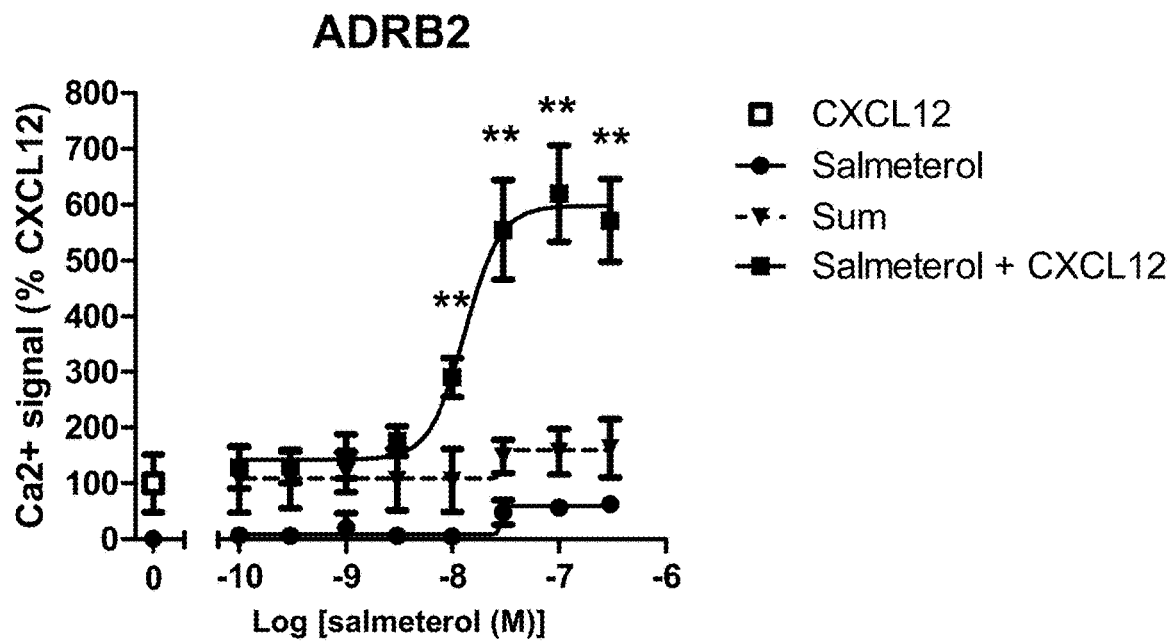
FIGS. 16A-16B: Shows the enhancement of the calcium response in cells co-expressing CXCR4 and GPCRx upon co-stimulation with their respective agonists. MBA-MB-231 cells were transduced with adenoviruses encoding CXCR4 and ADRB2 (FIG. 16A) or CXCR4 and HRH1 (FIG. 16B). Cells were cultured for 3 days, stained with Cal-520 AM, and were treated with either CXCL12 (30 nM) alone, increasing doses of histamine or salmeterol alone, or increasing doses of histamine or salmeterol in combination with 30 nM of CXCL12. Calcium mobilization was measured using FlexStation 3. Sum represents the calculated additive value of the responses evoked by 30 nM of CXCL12 alone (open square) and GPCRx ligand alone at indicated doses (filled circle). Sum graph was depicted as a broken line with inverted triangles. Statistically significant differences between the sum (inverted triangle) and co-treatment (filled square) at each point were determined by Student's t test. *P<0.05; P<0.01; *P<0.001; Data represent mean±SD (n=3).

Example 8. Evaluation by Ca2+ Mobilization Assay of Enhanced CXCR4 Downstream Signaling Upon CXCR4-GPCRx Heteromer Formation In cells overexpressing both CXCR4 and ADRB2, stimulation with salmeterol alone did not elicit calcium mobilization dose-dependently (FIG. 16A). But when the cells were co-stimulated with salmeterol in the presence of CXCL12, calcium signaling was greatly enhanced in a broad range of salmeterol concentrations, such as concentrations in the range of between 10 nM to 300 nM.

Figure 16B:
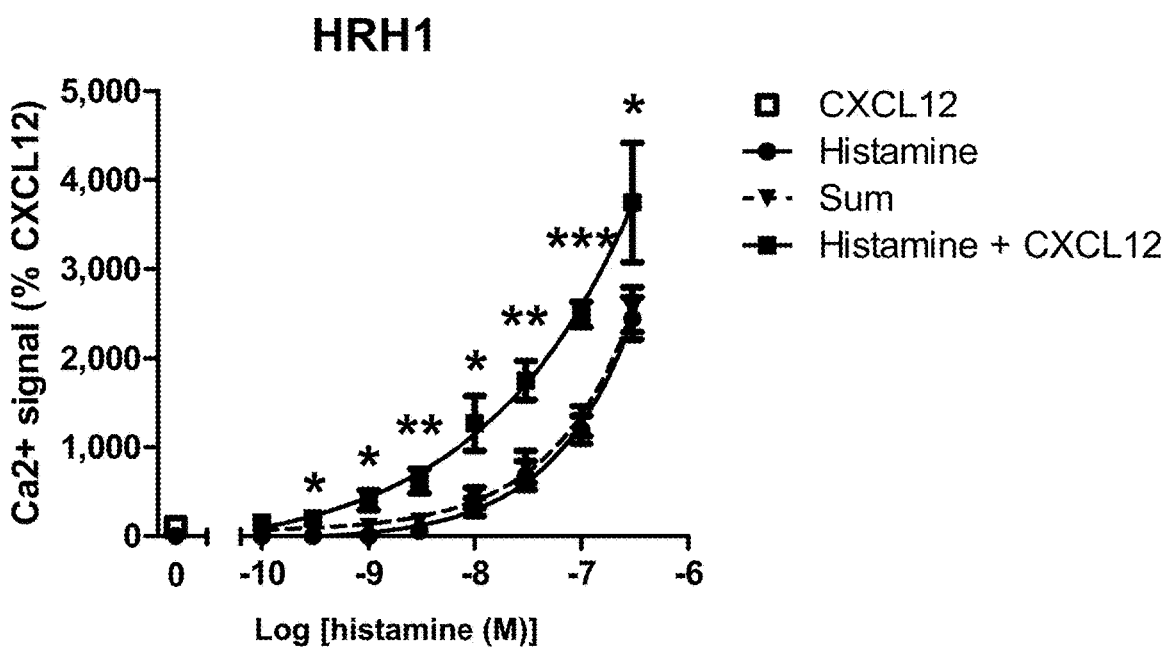

Similarly, co-treatment with histamine and CXCL12 also significantly enhanced calcium responses in cells overexpressing both CXCR4 and HRH1 over a broad range of histamine concentrations (0.3 nM to 300 nM), even at histamine concentrations that did not evoke any calcium responses when treated alone (0.3 nM and 1 nM) (FIG. 16B). Considering that the concentration of histamine in human plasma and glomeruli is below 10 nM and 2 μM, respectively (Sedor and Abboud, 1984), this result indicates that enhanced calcium signaling by CXCR4-HRH1 heteromer can occur at physiological levels of histamine concentration in vivo.

In cells expressing CXCR4-APLNR (FIG. 17A), CXCR4-PTGER3 (FIG. 17B), or CXCR4-SSTR2 (FIG. 17C), stimulation with GPCRx agonist (Apelin-13, PGE2, or octreotide, respectively) alone increased calcium signal dose-dependently. However, unlike in cells expressing CXCR4-ADRB2 or CXCR4-HRH1, calcium signal was not enhanced any further upon co-stimulation with both agonists (CXCL12 and GPCRx agonist) in any dose ranges tested in cells expressing CXCR4-APLNR, CXCR4-PTGER3, or CXCR4-SSTR2. These results are consistent with the results shown in FIGS. 7A, 7D, 7E, respectively, and show that the lack of signal enhancement in cells expressing CXCR4-APLNR or CXCR4-SSTR2 upon co-stimulation was not due to the use of a specific dose of GPCRx agonist, but due to the intrinsic nature of these heteromers. These results also clearly demonstrate that the enhanced calcium responses shown in FIG. 6A-6L and FIGS. 16A-16B are unique features of CXCR4-GPCRx heteromers such as CXCR4-ADRB2 or CXCR4-HRH1 described in FIGS. 5C-5D and FIG. 6H, respectively.

Example 9. Evaluation of Enhanced Ca2+ Mobilization Upon Co-Stimulation of Endogenous CXCR4-HRH1 Heteromer in MDA-MB-231 Cells Using RT-qPCR, the endogenous expression levels of CXCR4 and HRH1 in MDA-MB-231 cells were measured. The threshold cycles (Ct) of CXCR4 and HRH1 were 28.5 and 27.7, respectively, when 12.5 ng of total RNA was analyzed. Stimulation of MDA-MB-231 cells with either CXCL12 (100 nM), or histamine (10 nM) alone, elicit weak calcium responses (FIG. 18A). But when the cells were co-stimulated with CXCL12 and histamine together, greatly enhanced calcium response was observed similar to the enhancement observed in cells overexpressing CXCR4 and HRH1 together (FIGS. 18A and 18B, compared with FIG. 16B). The result clearly indicates that the enhanced calcium response upon co-stimulation with both agonists could occur in native cells expressing both CXCR4 and HRH1 together.

Example 10. Evaluation of Enhanced Migration of Cancer Cells by CXCR4-HRH1 Heteromer Upon Co-Stimulation with Both Ligands Since MDA-MB-231 cells express about twice more HRH1 mRNA compared with CXCR4 mRNA when measured by RT-qPCR, the MDA-MB-231 cells were transduced with small amount of lentivirus encoding CXCR4 (1 MOI) and chemotactic migration of the cells toward CXCL12 and HRH1 was measured (FIGS. 19A and 19B). Histamine (50 nM) alone, sufficient to produce calcium signaling as shown in FIG. 27A (see below), did not induce cell migration. On the other hand, when treated together with CXCL12, histamine significantly enhanced the migration of MDA-MB-231 cells towards CXCL12. However, in the presence of pyrilamine, a HRH1-selective inverse agonist, co-stimulation of the cells with CXCL12 and histamine failed to enhance the cell migration elicited by CXCL12. The results clearly demonstrate that the enhancement of observed cancer cell migration was specifically induced by HRH1, and not by other histamine receptor subtypes.

Example 11. Evaluation by Ca2+ Mobilization Assay of Enhanced CXCR4 Downstream Signaling Upon CXCR4-GPCRx Heteromer Formation and Inhibition of the Enhanced Signaling In cells overexpressing both CXCR4 and ADRB2, co-treatment of both agonists CXCL12, a CXCR4 agonist and salmeterol, an ADRB2-selective agonist significantly increased the calcium response compared to the ones evoked by individual agonists (FIG. 2O). These results clearly demonstrate that CXCR4-ADRB2 heteromer exhibit properties distinct from those of the individual GPCRs.

It was examined if enhanced calcium responses in cells co-expressing CXCR4 and ADRB2 upon co-stimulation with CXCL12 and ADRB2 ligands are inhibited by anti-CXCR4 antibody as a CXCR4 antagonist. In cells co-expressing CXCR4 and ADRB2, treatment of 2 μg of anti-CXCR4 antibody, 12G5, suppressed the enhanced calcium signaling as shown in FIG. 20. And co-treatment of both antagonists (Carvedilol, ADRB2 antagonist and 12G5, CXCR4 antagonist together) resulted in a more significant suppression. These results demonstrated that anti-CXCR4 antibody and ADRB2 antagonist could be used as an efficient therapeutics against CXCR4-ADRB2 heteromer.

Utilizing the Calcium mobilization assay, MDA-MB-231 human breast cancer cells were seeded at 20,000 cells per well in a black clear bottom 96-well plate (Corning Costar, #3340) in 100 μL of RPMI 1640 supplemented with 10% FBS. The next day, cells were co-transduced with 10 MOI of CXCR4 and 30 MOI of GPCRx. After 2 days, cells were treated with ADRB2 antagonist, Carvedilol(Tocris), anti-CXCR4 antibody, 12G5 (Thermo Scientific, 35-8800) with indicated amounts and incubated with Cal 6 (FLIPR® Calcium 6 Assay Kit by Molecular Devices, Cat. R8191) for 2 hr. And then, cells were stimulated with indicated amounts of CXCL12, ADRB2 agonist, or CXCL12 and ADRB2 agonist. Calcium mobilization was measured using FlexStation 3 Multi-Mode Microplate Reader. The results were normalized for base-line activity. Calcium mobilization was quantified by calculating the area-under-the-curve (AUC) of each graph. Data were normalized to CXCL12-stimulated calcium response in cells expressing CXCR4 alone. Data represent three independent experiments (mean±SEM). *P<0.05; Student's t test.

Example 12. Evaluation of CXCR4-GPCRx Heteromer Formation in CXCR4-GPCRx Expressing Cell Using PLA A process for screening a CXCR4-GPCRx heteromer is essential for the treatment of CXCR4-GPCRx targeted anti-cancer drug. First, for the quantitative detection of CXCR4 and GPCRx heteromer, PLA was performed in CXCR4-GPCRx expressing cells. CXCR4 overexpressing cell line, the U2OS-CXCR4 was infected with GPCRx expressing adenovirus, Ad-GPCRx at the dose of 0, 2.5, 10, 40 MOIs for 2 days. And then, the transduced cells were fixed with 4% paraformaldehyde and performed PLA was performed. The number of PLA signals means quantitatively demonstrating the formation of CXCR4-GPCRx heteromerization.

As shown in the FIGS. 21A-21B, the PLA signal increased proportionate to the expression level of CHRM1 (FIG. 21A) and HRH1 (FIG. 21B) in a dose dependent manner. These results demonstrate detection of different types of CXCR-GPCRx heteromer and quantitative analysis of CXCR4-GPCRx heteromer in cancer patient samples.

Utilizing the PLA in cells, CXCR4 overexpression cell lines, the U2OS-CXCR4 was infected with GPCRx expressing adenovirus, Ad-GPCRx at the dose of 0, 2.5, 10, 40 MOIs for 2 days. PLA was performed as described previously (Brueggemann et al., 2014; Tripathi et al., 2014). To perform PLA, infected cells were fixed with 4% PFA on sixteen-well tissue culture slides. Slides were blocked with blocking solution provided by Duolink and incubated with mouse anti-CXCR4 (Santacruz, Sc-53534), rabbit anti-CHRM1 (LS Bio, LS-C313301), or rabbit anti-HRH1 (Thermoscientific, PAS-27817) at 37° C. for 1 h in a humidifying chamber. Slides were then washed and incubated (1 h at 37° C.) with secondary anti-rabbit and anti-mouse antibodies conjugated with plus and minus Duolink II PLA probes. Slides were washed again and then incubated with ligation-ligase solution (30 min at 37° C.) followed by incubation with amplification-polymerase solution (2 h at 37° C.). Slides were then mounted with minimal volume of Duolink II mounting medium with 4',6-diamidino-2phenylindole (DAPI) for 15-30 min, and PLA signals [Duolink In Situ Detection Reagents Green (λ excitation/emission 495/527 nm) or Red (λ excitation/emission 575/623 nm)] were identified as fluorescent spots under a IN Cell analyzer 2500.

Example 13. Ca2+ Mobilization Inhibition of the Enhanced CXCR4 Downstream Signaling Upon CXCR4-GPCRx Heteromer Formation—Comparison of Single Inhibitor Treatment to Combination Inhibitor Treatment The data shown above (see Example 3, FIG. 8A) demonstrated that an increased Ca2+ signal due to CXCR4-ADRB2 heteromer formation was significantly decreased when treated simultaneously with a CXCR4 inhibitor and an ADRB2 inhibitor. The degree of inhibition (measured as IC50 values for $Ca^{2+}$ response) was compared for a series of CXCR4 inhibitors, evaluated as single treatment in cells expressing CXCR4 alone (individual protomer context), as single treatment in CXCR4-ADRB2 heteromer-expressing cells, and as co-treatment with an ADRB2 inhibitor (Carvedilol; 10 μM) in CXCR4-ADRB2 heteromer-expressing cells.

MDA-MB-231 cells were transduced with adenoviruses encoding CXCR4 only, or CXCR4 and ADRB. The cells were cultured for 2 days and were treated CXCR4 inhibitor alone or co-treated with a CXCR4 inhibitor and an ADRB2 inhibitor (Carvedilol; 10 uM). The cells were then stained with Cal-6 for 2 hours and stimulated with CXCR4 agonsit (CXCL12; 20 nM) and ADRB2 agonist (Salmeterol; 1 μM). Calcium mobilization was measured using FlexStation3, the results of which are shown in Table 6, showing IC50 of $Ca^{2+}$ response in: (1) MDA-MB-231 cells expressing CXCR4 alone (individual protomer context), treated with CXCR4 inhibitor only ($2^{nd}$ column); (2) MDA-MB-231 cells expressing CXCR4-ADRB2 heteromer, treated simultaneously with CXCR4 inhibitor and ADRB2 inhibitor Carvedilol ($3^{rd}$ column); and (3) MDA-MB-231 cells expressing CXCR4-ADRB2 heteromer, treated only with CXCR4 inhibitor ($4^{th}$ column).

TABLE 6

| CXCR4 inhibitor | CXCR4 IC$_{50}$ [nM] | CXCR4 + ADRB2 (+Carvedilol) IC$_{50}$ [nM] | CXCR4 + ADRB2 (−Carvedilol) IC$_{50}$ [nM] |
|---|---|---|---|
| AMD3100 | 57.80 ± 20.36 | 0.053 ± 0.07 | 28.65 ± 13.23 |
| AMD070 | 43.37 ± 0.57 | 1.40 ± 2.2 | 24.69 ± 8.88 |
| 12G5 | 80.19 ± 48.5 | 2.784 ± 0.86 | 13.95 ± 10.04 |
| Ulocuplumab | 0.42 ± 0.09 | 0.0008 ± 0.0002 | 1.12 ± 0.56 |
| BKT140 | 434 ± 4.38 | 0.81 ± 0.41 | 130.40 ± 49.78 |
| TZ14011 | 23.93 ± 3.58 | 0.02 ± 0.02 | 17.78 ± 7.84 |

As shown in Table 6, the IC50 value of $Ca^{2+}$ response was CXCR4 inhibitor dependent in the context of single treatment of MDA-MB-231 cells expressing CXCR4 alone, and in the single treatment context and the co-treatment context with an ADRB2 inhibitor of MDA-MB-231 cells expressing CXCR4-ADRB2 heteromer. Depending on the identity of the CXCR4 inhibitor, the IC50 value of $Ca^{2+}$ response in the CXCR4-ADRB2 heteromer context decreased by 1400 times or more when treated in combination with an ADRB2 inhibitor ($3^{rd}$ column), relative to single treatment with the CXCR4 inhibitor alone ($4^{th}$ column). For instance, the IC50 value of $Ca^{2+}$ response in the CXCR4-ADRB2 heteromer context decreased about 540 fold (from 28.65 nM to 0.053 nM), about 1400 fold (from 1.12 nM to 0.0008 nM), or about 890 fold (from 17.78 nM to 0.02 nM), upon co-treatment of Carvedilol with AMD3100, Ulocuplumab, or TZ14011, relative to single treatment with AMD3100, Ulocuplumab, or TZ14011, respectively. These results suggest that co-treating with a CXCR4 inhibitor and ADRB2 inhibitor more effectively inhibits increased $Ca^{2+}$ response than single treatment with a CXCR4 inhibitor alone in CXCR4-ADRB2 heteromer expressing cells.

To determine the possibility that CXCR4-ADRB2 heteromer formation induces conformation change and/or changes the binding affinity for the CXCR4 inhibitor, the IC50 values of $Ca^{2+}$ response were compared between single treatment with a CXCR4 inhibitor of cells expressing CXCR4 alone and cells expressing CXCR4-ADRB2 heteromer. The results showed that single treatment with a CXCR4 inhibitor altered the IC50 value only by about 0.4-5 fold in cells expressing CXCR4-ADRB2 heteromer ($4^{th}$ column), relative to cells expressing CXCR4 alone ($2^{nd}$ column). These results suggest that co-treatment with CXCR4 inhibitor and ADRB2 inhibitor can increase, to a dramatic extent for certain CXCR4 inhibitors, the therapeutic efficacy towards CXCR4-ADRB2 heteromer expressing patients and/or patient cells/tissues, compared with single treatment with CXCR4 inhibitor.

Example 14. Effect of CXCR4—ADRB2 Heteromer on Tumor Growth

To investigate the effect of CXCR4-ADRB2 heteromer on tumor growth, cell lines stably overexpressing CXCR4 alone or CXCR4-ADRB2 heteromer were prepared in A549 lung cancer cell, and the same amount of cells ($1\times10^7$ cell/head) were injected subcutaneously in nude mice to compare tumor growth rates. As shown in FIGS. 22A-22B, the tumor size at 28 days after transplantation was 351.4±214.7 mm³ for A549, 726.9±259.6 mm³ for A549-CXCR4, and 1012.2±556.1 mm³ for A549-CXCR4-ADRB2. The tumor growth rate of mice transplanted with the A549-CXCR4 overexpressing CXCR4 was faster than that of mice bearing only parental A549, and the fastest tumor growth was observed in mice transplanted with cells overexpressing the CXCR4-ADRB2 heteromer. These results suggest that the formation of CXCR4-ADRB2 heteromer synergistically increases the $Ca^{2+}$ response and thus promotes tumor growth.

Images of three mice which were transplanted with either parental cell A549, A549-CXCR4 stably overexpressing CXCR4, or A549-CXCR4-ADRB2 stably overexpressing CXCR4-ADRB2 heteromer, at 28 days after transplantation, are shown in FIG. 22A. These images show that the tumor size of the mouse bearing the cell expressing CXCR4-ADRB2 heteromer is the largest (accelerated the most) among them. The tumor growth rates of these three different mice over time are graphically illustrated in FIG. 22B. Tumor growth was monitored every third or fourth day by measuring the length (L) and width (W) of the tumor and calculating tumor volume on the basis of the following formula: Volume=0.5 $LW^2$. The mice bearing CXCR4-expressing cell show relatively fast tumor growth as compared to the mice bearing parental cell A549, and the tumor growth is the fastest in mice transplanted with cells overexpressing the CXCR4-ADRB2 heteromer.

Example 15. Evaluation by Ca2+ Mobilization Assay of Enhanced CXCR4 Downstream Signaling Upon Co-Stimulation of CXCR4-GPCRx Heteromer with Endogenous Ligands The enhancement of the calcium response in MDA-MB-231 cells co-expressing CXCR4 and GPCRx upon co-stimulation with CXCL12 and endogenous ligand for GPCRx, are shown in FIGS. 23A-23G. MDA-MB-231 cells were transduced with adenoviruses encoding CXCR4 and HA-VC, GPCRx and HA-VC, or CXCR4 and GPCRx where GPCRx represents ADCYAP1R1 (FIG. 23A), ADORA2B (FIG. 23B), ADORA3 (FIG. 23C), CHRM1 (FIG. 23D), EDNRB (FIG. 23E), MLNR (FIG. 23F), and TACR3 (FIG. 23G). Cells were treated with CXCL12 alone, GPCRx endogenous ligand alone, or CXCL12 and GPCRx ligand together. Calcium mobilization was calculated as described in FIG. 5D. Statistically significant difference between the sum (square with dots) and co-treatment (filled square) was determined by Student's t test. *P<0.05; P<0.01; *P<0.001; Mean±SEM (n=3).

Figure 6A:
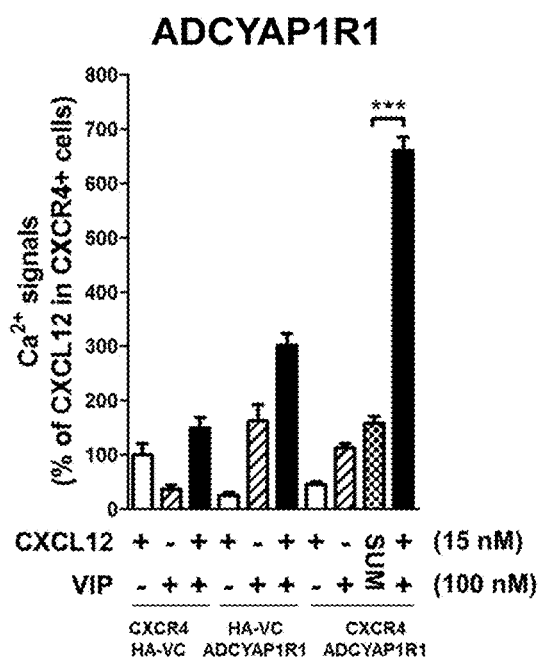
FIGS. 6A-6L: Shows enhancement of the calcium response in cells co-expressing CXCR4 and GPCRx upon co-stimulation with their respective selective agonists as shown in FIGS. 5A-C. MDA-MB-231 cells were transduced with adenoviruses encoding CXCR4 and HA-VC, GPCRx and HA-VC, or CXCR4 and GPCRx. GPCRx represents ADCYAP1R1 (FIG. 6A), ADORA2B (FIG. 6B), ADORA3 (FIG. 6C), C5AR1 (FIG. 6D), CALCR (FIG. 6E), CHRM1 (FIG. 6F), EDNRB (FIG. 6G), HRH1 (FIG. 6H), MLNR (FIG. 6I), NTSR1 (FIG. 6J), PTGER2 (FIG. 6K), and TACR3 (FIG. 6L). Cells were incubated with Cal-520 AM, and were treated with CXCL12, GPCRx agonist, or CXCL12 and GPCRx agonist together. Calcium responses were quantified as described in FIG. 5. Data represent three independent experiments (mean±SEM). *P<0.05, P<0.01, *P<0.001; Student's t test.
Figure 6B:
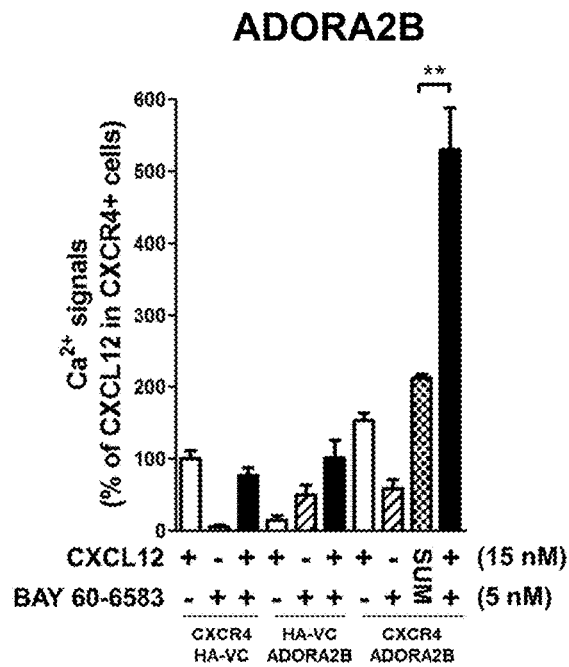
Figure 6C:
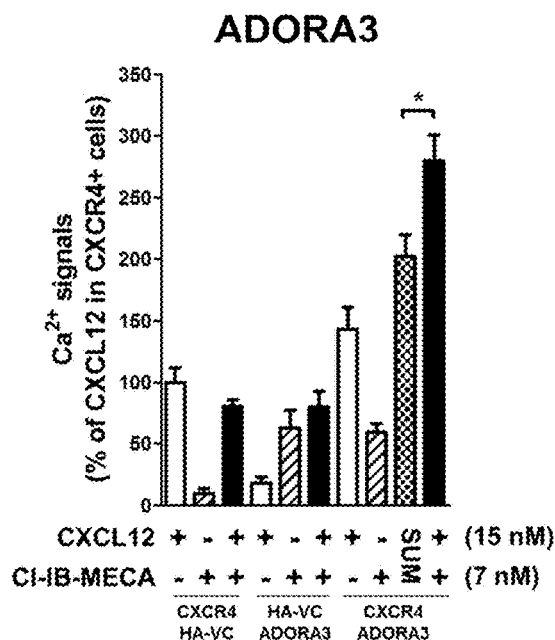
Figure 6D:
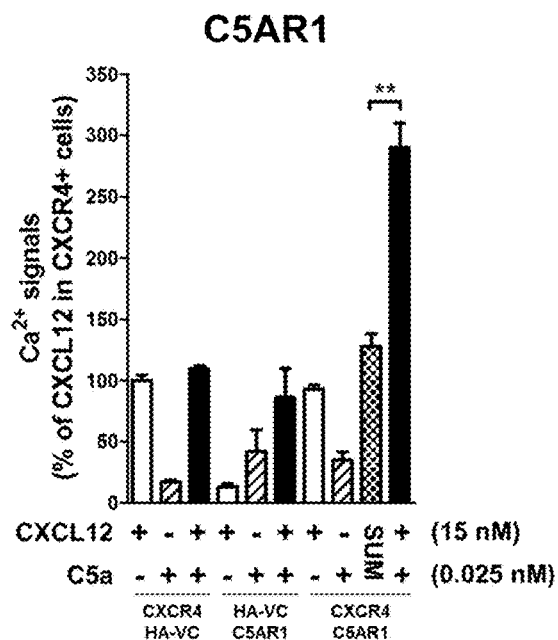
Figure 6E:
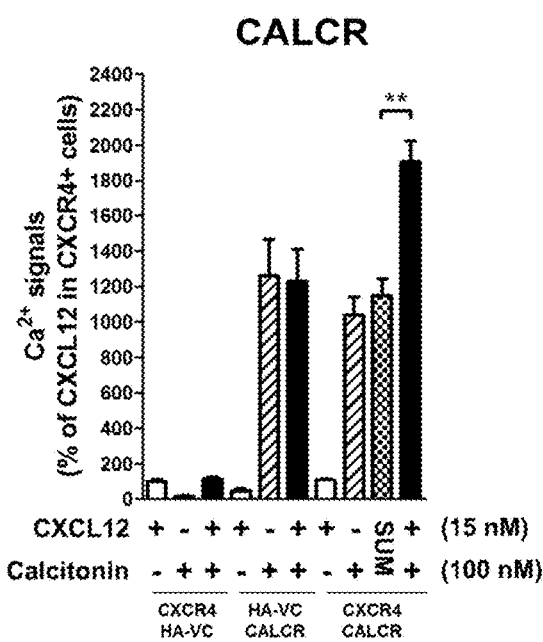
Figure 7A:
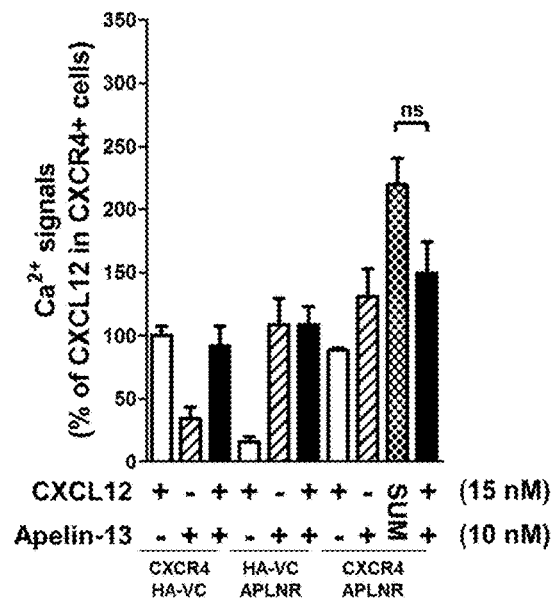
FIGS. 7A-7E: Shows examples of CXCR4-GPCRx heteromer that failed to show enhanced calcium signaling in cells co-expressing CXCR4 and GPCRx in the presence of agonists to both GPCRs. MDA-MB-231 cells were transduced with adenoviruses encoding CXCR4 and HA-VC, GPCRx and HA-VC, or CXCR4 and GPCRx. GPCRx represents APLNR (FIG. 7A), CCR5 (FIG. 7B), GALR1 (FIG. 7C), PTGER3 (FIG. 7D), and SSTR2 (FIG. 7E). Cells were incubated with Cal-520 AM, and were treated with CXCL12, GPCRx agonist, or CXCL12 and GPCRx agonist together. Calcium mobilization was quantified as described in FIG. 5. Data represent three independent experiments (mean±SEM). Student's t test. ns: not significant.
Figure 7B:
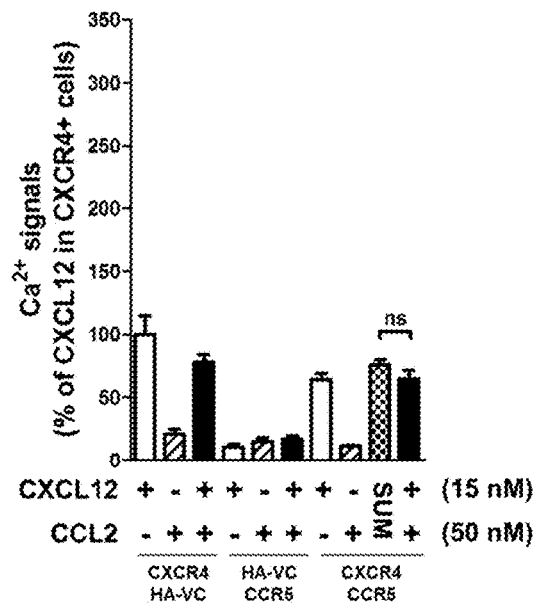
Figure 7C:
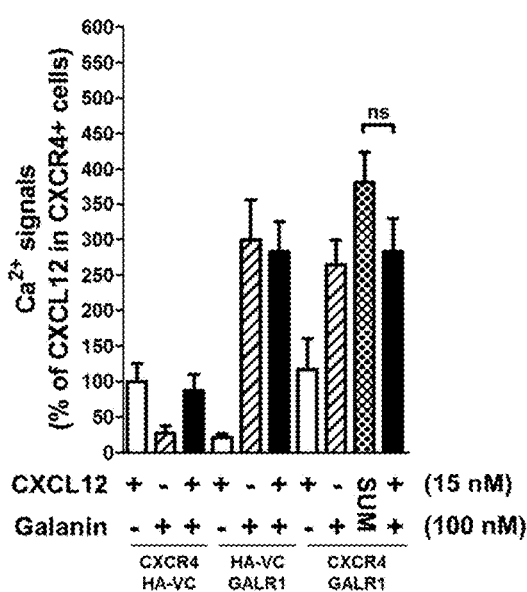
Figure 7D:
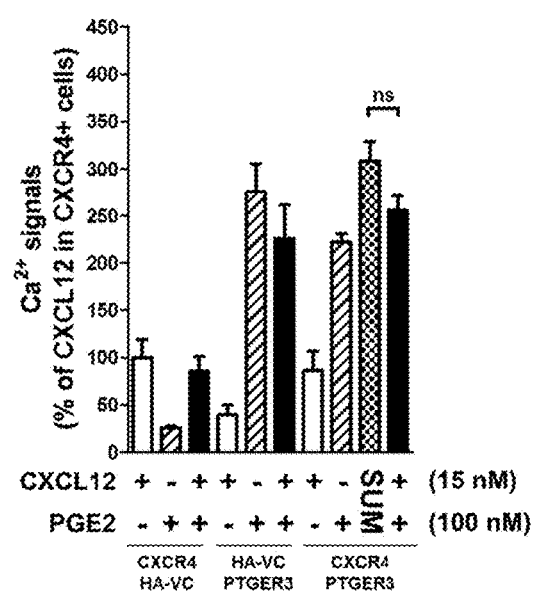
Figure 7E:
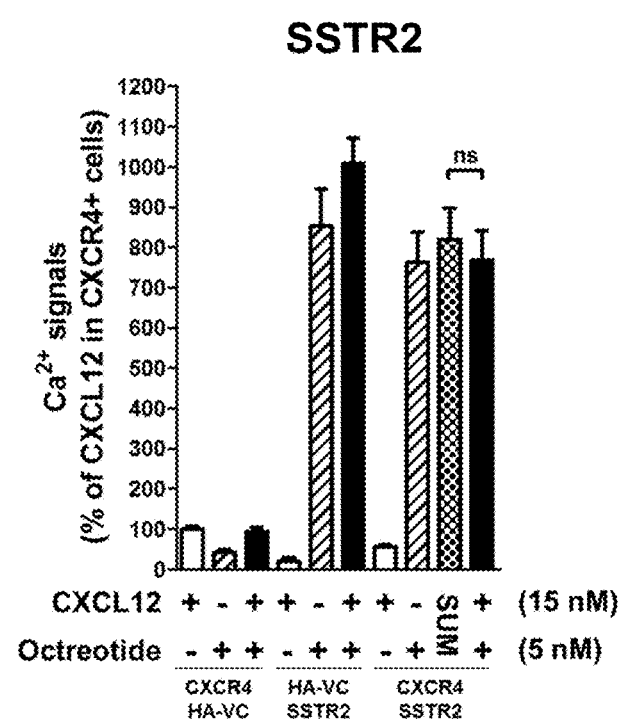

In FIG. 6A, enhanced $Ca^{2+}$ signaling was observed in cells expressing CXCR4 and ADCYAP1R1 together, but not in cells expressing individual GPCR alone, upon co-treatment with CXCL12 and VIP, a non-selective endogenous ADCYAP1R1 ligand. When the cells were co-treated with CXCL12 and PACAP-38, an ADCYAP1R1-selective endogenous ligand, enhanced $Ca^{2+}$ signaling was also observed (FIG. 23A). The result demonstrates that enhanced signaling of CXCR4-ADCYAP1R1 heteromer upon co-stimulation with CXCL12 is not only limited to VIP, but also selective ADCYAP1R1 natural ligand. It further suggests this enhancement could happen in vivo in cells expressing CXCR4 and ADCYAP1R1 together by their natural ligands.

Enhanced $Ca^{2+}$ signaling was observed in cells expressing CXCR4 and ADORA2B (FIG. 6B) or CXCR4 and ADORA3 together (FIG. 6C), but not in cells expressing individual GPCR alone, upon co-treatment with CXCL12 and BAY 60-6583 (ADORA2B-selective agonist), or CXCL12 and Cl-IB-MECA (ADORA3-selective agonist), respectively. When these cells were co-treated with CXCL12 and adenosine, endogenous ligand for all adenosine receptors, enhanced $Ca^{2+}$ signaling was also observed (FIGS. 23B and 23C). The result demonstrates that natural endogenous ligand, not only synthetic agonists, enhances downstream signaling of CXCR4-ADORA2B and CXCR4-ADORA3 heteromers upon co-stimulation with CXCL12. It further suggests that synergistic enhancement of downstream signaling could happen in vivo in cells expressing CXCR4 and ADORA2B or CXCR4 and ADORA3 together by their natural ligands.

Figure 6F:
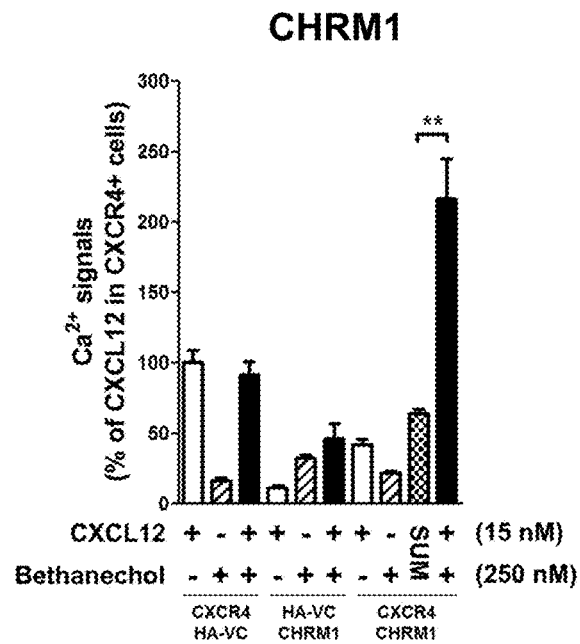

In FIG. 6F, enhanced $Ca^{2+}$ signaling was observed in cells expressing CXCR4 and CHRM1 together, but not in cells expressing individual GPCR alone, upon co-treatment with CXCL12 and bethanechol, a synthetic CHRM1 agonist. When the cells were co-treated with CXCL12 and acetylcholine, endogenous ligand for all acetylcholine receptors, enhanced $Ca^{2+}$ signaling was also observed (FIG. 23D). The result demonstrates that natural endogenous ligand, not only synthetic agonist, enhances signaling of CXCR4-CHRM1 heteromer upon co-stimulation with CXCL12. It further suggests that synergistic enhancement of downstream signaling could happen in vivo in cells expressing CXCR4 and CHRM1 together by their natural ligands.

Figure 6G:
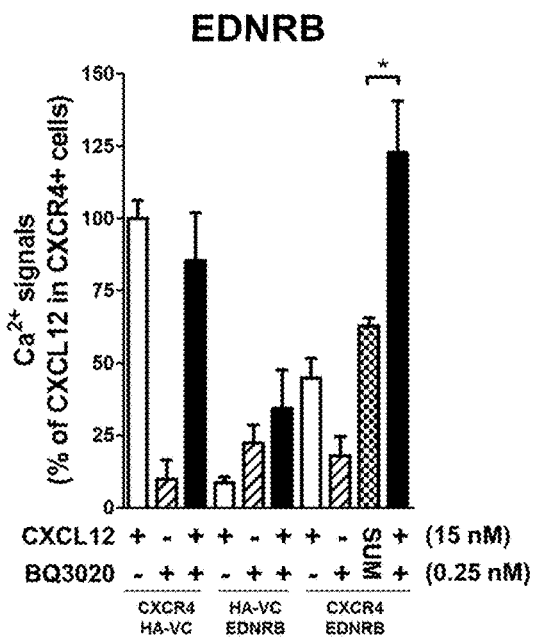
Figure 6H:
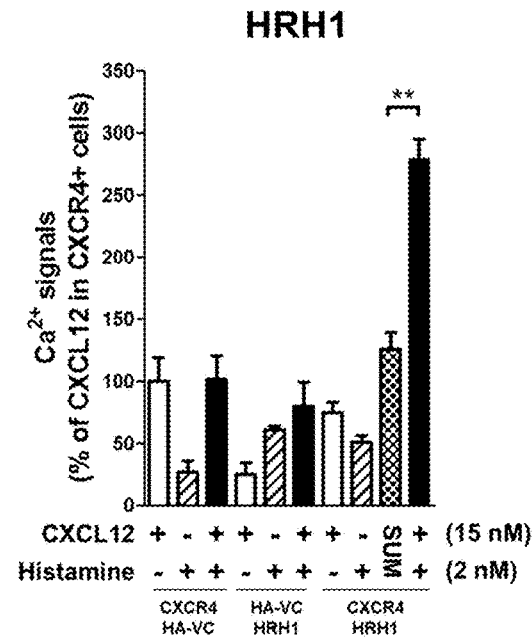

In FIG. 6G, enhanced $Ca^{2+}$ signaling was observed in cells expressing CXCR4 and EDNRB together, but not in cells expressing individual GPCR alone, upon co-treatment with CXCL12 and BQ3020, an EDNRB-selective agonist. When the cells were co-treated with CXCL12 and endothelin-1, endogenous ligand for endothelin receptors, enhanced $Ca^{2+}$ signaling was also observed (FIG. 23E). The result demonstrates that natural endogenous ligand, not only synthetic agonist, enhances signaling of CXCR4-EDNRB heteromer upon co-stimulation with CXCL12. It further suggests that synergistic enhancement of downstream signaling could happen in vivo in cells expressing CXCR4 and EDNRB together by their natural ligands.

Figures 6I, 6J:
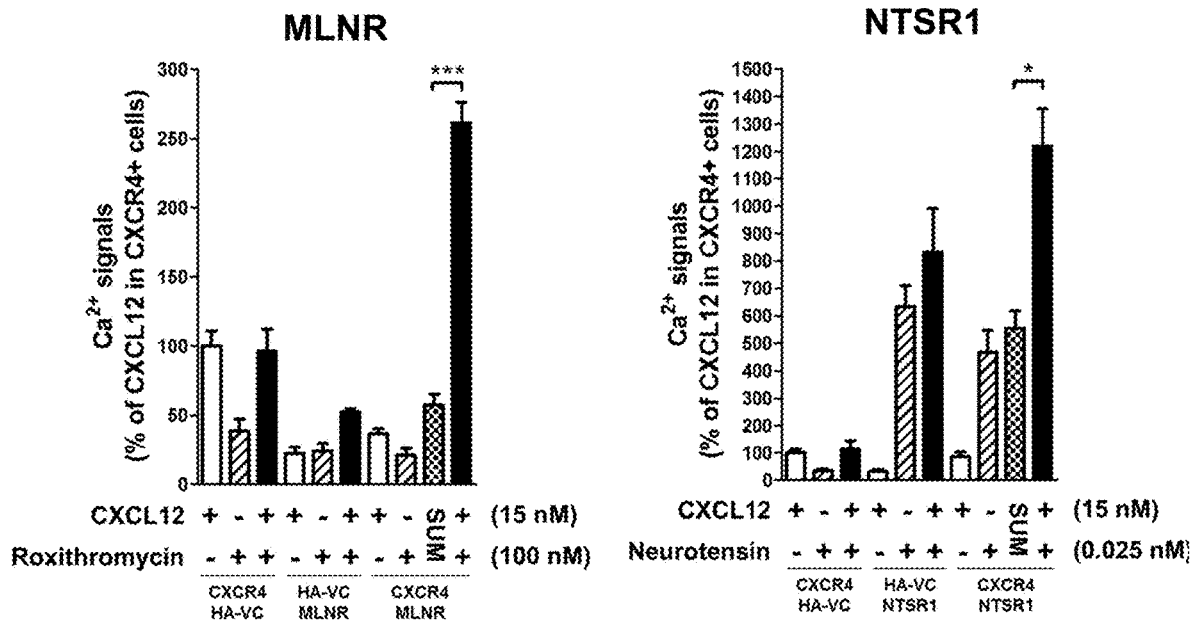

In FIG. 6I, enhanced $Ca^{2+}$ signaling was observed in cells expressing CXCR4 and MLNR together, but not in cells expressing individual GPCR alone, upon co-treatment with CXCL12 and roxithromycin, an antibiotic as well as full MLNR agonist. When the cells were co-treated with CXCL12 and motilin, a selective endogenous ligand for MLNR, enhanced $Ca^{2+}$ signaling was also observed (FIG. 23F). The result demonstrates that natural endogenous ligand, not only synthetic agonist, enhances signaling of CXCR4-MLNR heteromer upon co-stimulation with CXCL12. It further suggests that synergistic enhancement of downstream signaling could happen in vivo in cells expressing CXCR4 and MLNR together by their natural ligands.

Figures 6K, 6L:
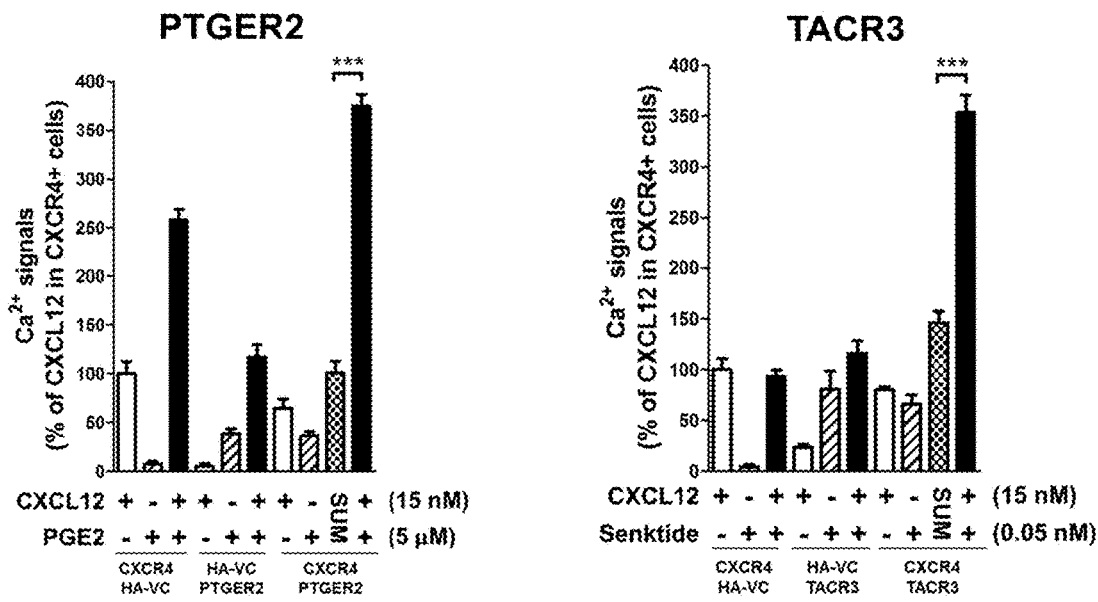

In FIG. 6L, enhanced $Ca^{2+}$ signaling was observed in cells expressing CXCR4 and TACR3 together, but not in cells expressing individual GPCR alone, upon co-treatment with CXCL12 and senktide, a TACR3-selective agonist. When the cells were co-treated with CXCL12 and neurokinin B, selective endogenous ligand for TACR3, enhanced $Ca^{2+}$ signaling was also observed (FIG. 23G). The result demonstrates that natural endogenous ligand, not only synthetic agonist, enhances signaling of CXCR4-TACR3 heteromer upon co-stimulation with CXCL12. It further suggests that synergistic enhancement of downstream signaling could happen in vivo in cells expressing CXCR4 and EDNRB together by their natural ligands.

Example 16. Evaluation by Ca2+ Mobilization Assay of Enhanced CXCR4 Downstream Signaling Upon Co-Stimulation of CXCR4-GPCRx Heteromer In MDA-MB-231 cells co-expressing CXCR4 and ADCYAP1R1, stimulation with selective endogenous ligands CXCL12 alone or PACAP38 alone, respectively, produced calcium signaling dose-dependently (FIGS. 24A-24B). MDA-MB-231 cells were transduced with adenoviruses encoding CXCR4 and ADCYAP1R1. As shown in FIG. 24A, addition of small amount of ADCYAP1R1 selective endogenous ligand (PACAP38; 1 nM) significantly enhanced calcium response in a broad range of CXCL12 concentrations compared with the sum values calculated by adding the responses obtained by PACAP38 alone and CXCL12 alone at indicated doses (FIG. 24A). Maximal $Ca^{2+}$ response evoked by CXCL12 alone was taken as 100%. Sum represents the calculated additive value of the responses evoked by 1 nM of PACAP38 and CXCL12 alone at indicated doses. Similarly, as shown in FIG. 24B, addition of CXCR4 selective endogenous ligand (CXCL12; 15 nM) significantly enhanced downstream response in a broad range of PACAP38 concentrations compared with the sum values calculated by adding the responses obtained by CXCL12 alone and PACAP38 alone at indicated doses, even at concentrations that did not evoke any response when treated alone (0.03~0.3 nM) (FIG. 24B). Maximal $Ca^{2+}$ response evoked by PACAP38 alone was taken as 100%. Sum represents the calculated additive value of the responses evoked by 15 nM of CXCL12 alone and PACAP38 alone at indicated doses. Statistically significant differences between the sum and co-treatment at each point were determined by Student's t test. *P<0.05; P<0.01; *P<0.001; Mean±SD (n=3). These results suggest an enhanced response in cells co-expressing CXCR4 and ADCYAP1R1 in vivo in the presence of small amounts of CXCL12 and ADCYAP1R1 ligands together.

The enhancement of calcium response in a broad range of ligand concentrations in cells co-expressing CXCR4 and TACR3 is shown in FIGS. 25A-25B. MDA-MB-231 cells were transduced with adenoviruses encoding CXCR4 and TACR3. Stimulation of the cells with CXCL12 alone or Neurokinin B alone, respectively, produced calcium signaling dose-dependently (FIGS. 25A-25B). As shown in FIG. 25A, addition of small amount of Neurokinin B (0.4 nM, TACR3-selective endogenous ligand) significantly enhanced calcium response in a broad range of CXCL12 concentrations compared with the sum values calculated by adding the responses obtained by Neurokinin B alone and CXCL12 alone at indicated doses. Maximal calcium response evoked by CXCL12 alone was taken as 100%. Sum represents the calculated additive value of the responses evoked by 0.4 nM of Neurokinin B alone and CXCL12 alone at indicated doses. Similarly, as shown in FIG. 25B, addition of CXCL12 significantly enhanced downstream response in a broad range of Neurokinin B concentrations compared with the sum values calculated by adding the responses obtained by CXCL12 alone and Neurokinin B alone at indicated doses. Maximal response evoked by Neurokinin B alone was taken as 100%. Sum represents the calculated additive value of the responses evoked by 30 nM of CXCL12 alone and Neurokinin B alone at indicated doses. Statistically significant differences between the sum and co-treatment at each point were determined by Student's t test. *P<0.05; **P<0.01; Mean±SD (n=3). These results suggest an enhanced response in cells co-expressing CXCR4 and TACR3 in vivo in the presence of small amounts of CXCL12 and Neurokinin B together.

Figure 8F:
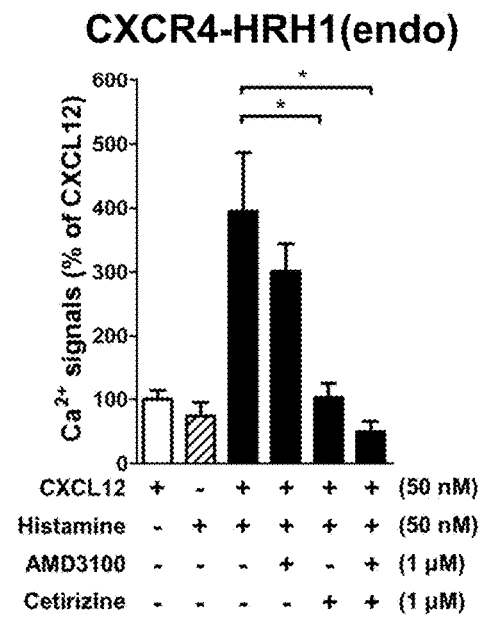
Figure 8G:
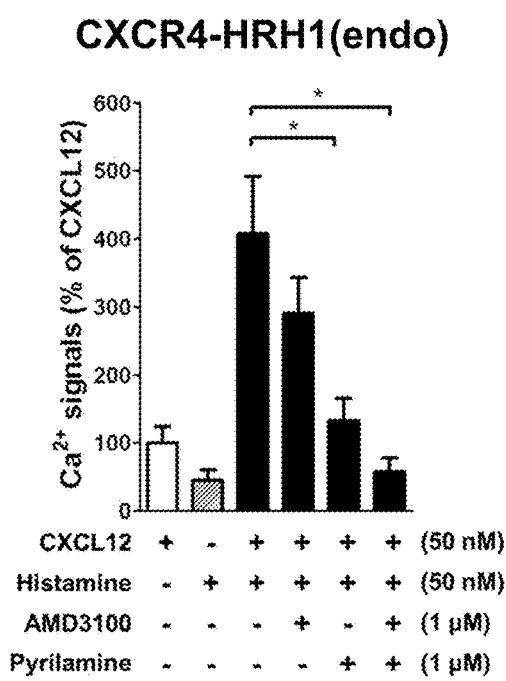
Figure 8H:
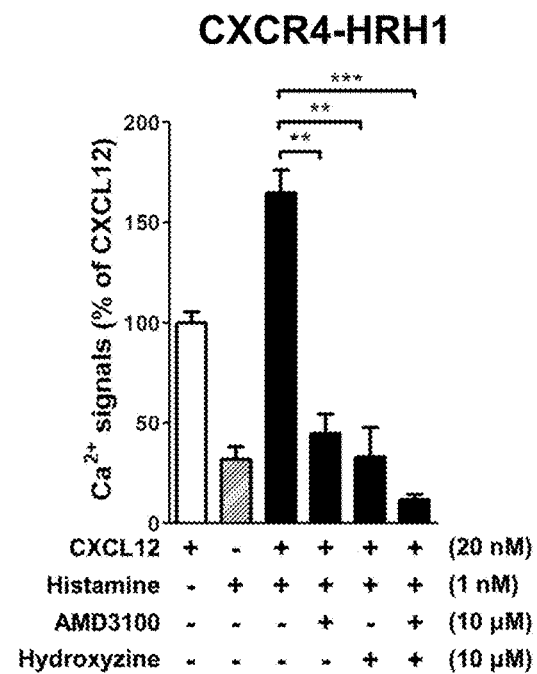
Figure 8I:
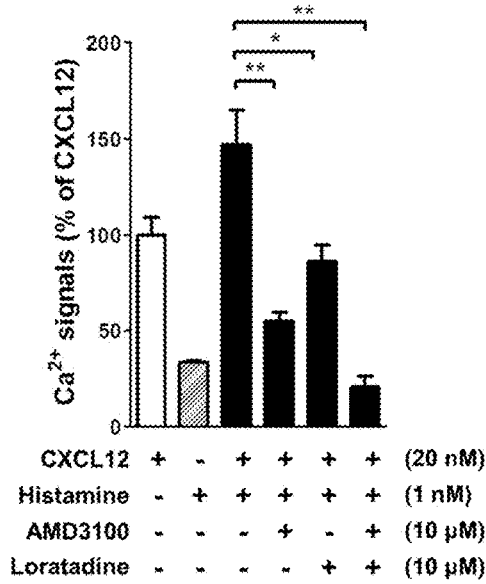
Figure 8J:
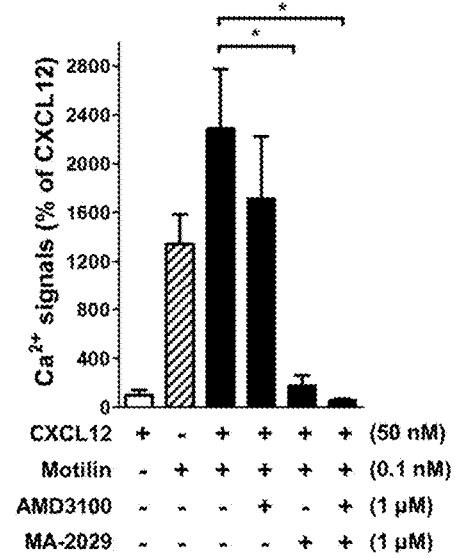
Figure 8K:
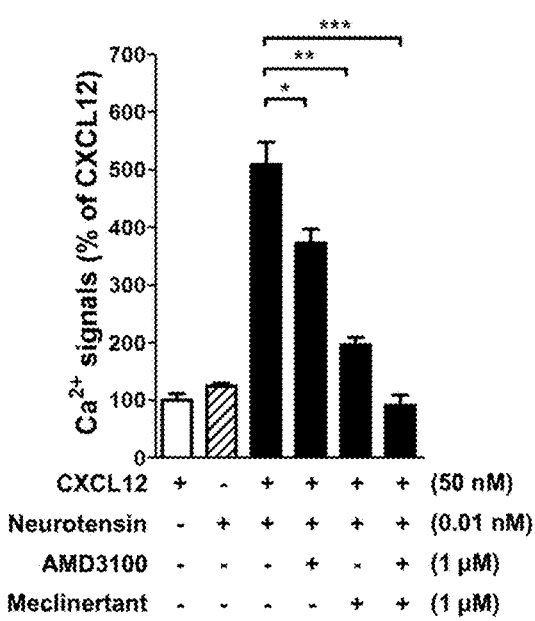
Figure 8L:
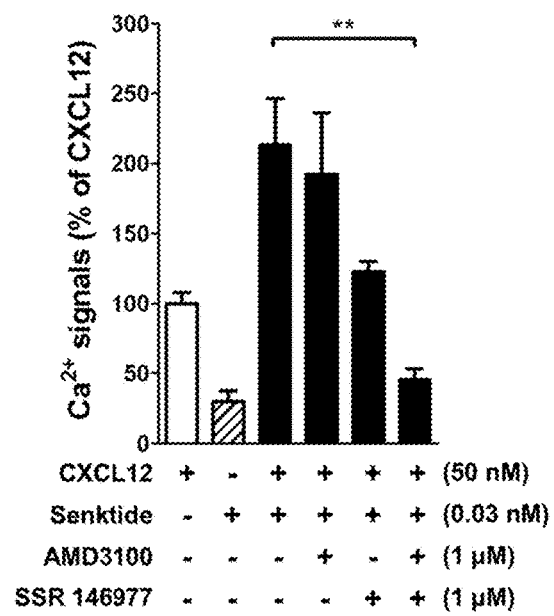

Example 17. Confirmation of a Loss of Heteromer-Specific Property Upon Deletion of One of the Protomers In FIGS. 8F & 8G, enhanced calcium signaling was observed in MDA-MB-231 cells overexpressing CXCR4 alone upon co-treatment with CXCL12 and histamine. Using RT-qPCR, MDA-MB-231 cells were previously shown to express HRH1 as well as low level of CXCR4 mRNAs, with about twice more HRH1 mRNA being expressed compared with CXCR4 mRNA (Example 9). To confirm if the enhanced calcium signaling shown in FIGS. 8F & 8G is due to the presence of endogenous HRH1 expression, and not to the presence of other histamine receptors, HRH1 gene in MDA$^{CXCR4+}$ cells was deleted using CRISPR/Cas9 system. MDA-MB-231 cells stably expressing CXCR4 (MDA$^{CXCR4+}$) were transduced with lentiviruses encoding Cas9 and guide RNA targeting HRH1. The presence of functional HRH1 was detected by measuring calcium responses upon exposure to histamine. While MDA$^{CXCR4+}$ cells showed dose-dependent increase in calcium signaling upon exposure to histamine, MDA$^{CXCR4+, HRH1-}$ cells did not show any calcium response even at 1 μM histamine (FIG. 26A). The result implies almost complete absence of functional HRH1 in MDA$^{CXCR4+, HRH1-}$ cells.

When MDA-MB-231 cells stably overexpressing CXCR4 (MDA$^{CXCR4+}$ cells) were treated with histamine, dose-dependent increase in calcium signaling was observed (FIG. 27A). When the cells were treated with histamine in the presence of CXCL12 (50 nM), significantly enhanced calcium response was obtained in a broad range of histamine concentrations, resulting in increased potency and efficacy as evidenced by the changes in $EC_{50}$ and $E_{max}$ values. However, in MDA$^{CXCR4+}$ cells depleted with HRH1 using CRISPR/Cas9 system (MDA$^{CXCR4+, HRH1-}$ cells), no histamine-mediated response was obtained in the absence or presence of CXCL12 (50 nM), reconfirming the absence of functional HRH1 in these cells. Maximal calcium response evoked by histamine alone in MDA$^{CXCR4+}$ cells was taken as 100%. Sum represents the calculated additive value of the responses evoked by 50 nM of CXCL12 alone and histamine alone at indicated doses.

In MDA$^{CXCR4+}$ cells, stimulation with CXCL12 produced calcium response dose-dependently (FIG. 27B). Addition of non-signaling concentration of histamine (15 nM) significantly enhanced calcium response in a broad range of CXCL12 concentrations, resulting in greatly increased potency and efficacy as evidenced by the changes in $EC_{50}$ and $E_{max}$ values. CXCL12-mediated calcium response in MDA$^{CXCR4+, HRH1-}$ cells was similar to the response observed in MDA$^{CXCR4+}$ cells. However, addition of histamine failed to increase CXCL12-mediated calcium response in MDA$^{CXCR4+, HRH1-}$ cells, demonstrating the loss of heteromer-specific property upon deletion of HRH1. Maximal response evoked by CXCL12 alone in MDA$^{CXCR4+}$ cells was taken as 100%. Sum represents the calculated additive value of the responses evoked by 15 nM of histamine alone and CXCL12 alone at indicated doses. Statistically significant differences between the sum and co-treatment at each point were determined by Student's t test. *P<0.05; P<0.01; *P<0.001; Mean±SD (n=3). $EC_{50}$ and $E_{max}$ values were calculated using GraphPad Prism software.

In FIGS. 18A-18B, significant enhancement in calcium signaling was also observed in wildtype MDA-MB-231 cells in the presence of CXCL12 and histamine together although individual ligand alone only produced faint signals. To confirm if the enhanced response is due to the endogenous expression of CXCR4, CXCR4 gene was targeted using CRISPR/Cas9 system, and expression of CXCR4 was detected using immunoblotting. Expression of CXCR4 was significantly decreased in MDA-MB-231 cells treated with guide RNA targeting CXCR4 compared to the expression in cells treated with control non-targeting guide RNA (FIG. 26B).

Enhanced calcium response in MDA-MB-231 cells upon co-treatment with CXCL12 and histamine is abrogated in the absence of CXCR4. As shown in FIG. 28A, in MDA-MB-231 cells (MDA-MB-231 cells (MDA$^{WT}$), but not in MDA$^{WT}$ cells depleted with CXCR4 using CRISPR/Cas9 system (MDA$^{CXCR4-}$)), enhanced signaling in the presence of small amount of histamine (15 nM) was evident in a broad range of CXCL12 concentrations although CXCL12-mediated dose-dependent increase in calcium response was not observed due to the low level expression of CXCR. Maximal calcium response evoked by CXCL12 alone in MDA$^{WT}$ cells was taken as 100%. Sum represents the calculated additive value of the responses evoked by 15 nM of histamine alone and CXCL12 alone at indicated doses. Deletion of CXCR4 completely abrogate the enhanced signaling in the presence of histamine, demonstrating loss of heteromer-specific property upon deletion of CXCR4.

Similarly, as shown in FIG. 28B, addition of CXCL12 enhanced histamine-mediated response in a broad range of histamine concentrations in MDA-MB-231 cells compared with the sum values calculated by adding the responses obtained by CXCL12 alone and histamine alone at indicated doses. The enhanced signaling shown in MDA-MB-231 cells was not observed in MDA$^{CXCR4-}$ cells, although MDA$^{CXCR4-}$ cells retained histamine responses. Maximal response evoked by histamine alone in MDA$^{WT}$ cells was taken as 100%. Sum represents the calculated additive value of the responses evoked by 100 nM of CXCL12 alone and histamine alone at indicated doses. Statistically significant differences between the sum and co-treatment at each point were determined by Student's t test. P<0.01; *P<0.001; Mean±SD (n=3). $EC_{50}$ and $E_{max}$ values were calculated using GraphPad Prism software. Taken together, these results demonstrate that CXCR4-HRH1 heteromer is responsible for the enhanced signaling upon co-treatment with CXCL12 and histamine in wildtype MDA-MB-231 cells.

Example 18. Ca2+ Mobilization Inhibition of the Enhanced CXCR4 Downstream Signaling Upon CXCR4-GPCRx Heteromer Formation—Comparison of Single Inhibitor Treatment to Combination Inhibitor Treatment Overview: As illustrated below (see Tables 7-14), co-treatment by various combinations of a CXCR4 inhibitor and a GPCRx inhibitor in a series of CXCR4-GPCRx heteromer-expressing cells results in a significantly reduced calcium response compared to single treatment by a CXCR4 inhibitor alone. The GPCRx protomers of the series of CXCR4-GPCRx heteromers evaluated in Tables 7-14 are: ADRB2, HRH1, ADCYAP1R1, C5AR1, CALCR, EDNRB, MLNR, and TACR3, respectively. MDA-MB-231 cells were transduced with adenoviruses encoding CXCR4 only, or CXCR4 and the specified GPCRx. The cells were cultured for 2 days and were treated CXCR4 antagonist alone or co-treatment of CXCR4 antagonist and the specified GPCRx antagonist. And then, cells were stained with Cal-6 for 2 hours and stimulated with CXCL12 (20 nM) and the specified GPCRx agonist. Calcium mobilization was measured using FlexStation3. A value in the column labeled "None" is the IC50 of Ca2+ response in the specified CXCR4-GPCRx heteromer-expressing MDA-MB-231 treated with CXCR4 inhibitor only (in the absence of a specified GPCRx antagonist). A value in the remaining columns is the IC50 of Ca2+ response in the specified CXCR4-GPCRx heteromer-expressing MDA-MB-231 from the simultaneous treatment with CXCR4 antagonist and the specified GPCRx antagonist.

The efficiency of CXCR4 inhibitors in suppressing the enhanced signaling of CXCR4-ADRB2 heteromer was measured in the absence or presence of the representative ADRB2 inhibitors Carazolol or Propranolol (Table 7). MDA-MB-231 cells were co-transduced with adenoviruses encoding CXCR4 and ADRB2, and Ca2+ signaling was measured upon co-stimulating the cells with CXCL12 (20 nM) and Salmeterol (1 μM). Inhibitors were treated 30 min before agonist stimulation. Ca2+ mobilization was measured as described in FIG. 5, and $IC_{50}$ values were calculated using GraphPad Prism software.

TABLE 7

| | ADRB2 inhibitors | | |
|---|---|---|---|
| CXCR4 inhibitors | None IC50 [nM] | Carazolol (10 µM) IC50 [nM] | Propranolol (10 µM) IC50 [nM] |
| AMD3100 | 22.10 ± 8.53 | 2.69 ± 3.41 | 6.23 ± 4.90 |
| Ulocuplumab | 0.226 ± 0.144 | 0.009 ± 0.004 | 0.041 ± 0.024 |
| BKT140 | 123.86 ± 76.91 | 26.66 ± 19.32 | 66.14 ± 53.77 |

CXCR4 inhibitors AMD-3100, Ulocuplumab and BKT140 suppressed the CXCR4-ADRB2 signaling more efficiently (greater potency) in the presence of 10 µM of Carazolol or Propranolol as shown with the reduced $IC_{50}$ values compared to the $IC_{50}$ values of CXCR4 inhibitors in the absence of ADRB2 inhibitors. Depending on the identity of the CXCR4 inhibitor, the IC50 value of Ca response in the CXCR4-ADRB2 heteromer context decreased by up to about 25 times or more when treated in combination with an ADRB2 inhibitor (Carazolol or Propranolol), relative to single treatment with the CXCR4 inhibitor alone ("None" column). These results suggest that co-treating with a CXCR4 inhibitor and ADRB2 inhibitor more effectively inhibits increased Ca response than single treatment with a CXCR4 inhibitor alone in CXCR4-ADRB2 heteromer expressing cells.

The efficiency of CXCR4 inhibitors in suppressing the enhanced signaling of CXCR4-HRH1 heteromer was measured in the absence or presence of the representative HRH1 inhibitors Hydroxyzine, Promethazine, or Cyproheptadine (Table 8). MDA-MB-231 cells were co-transduced with adenoviruses encoding CXCR4 and HRH1, and Ca2+ signaling was measured upon co-stimulating the cells with CXCL12 (20 nM) and Histamine (1 nM). Inhibitors were treated 30 min before agonist stimulation. Ca2+ mobilization was measured as described in FIG. 5, and $IC_{50}$ values were calculated using GraphPad Prism software.

TABLE 8

| | HRH1 inhibitors | | | |
|---|---|---|---|---|
| CXCR4 inhibitors | None IC50 [nM] | Hydroxyzine (10 µM) IC50 [nM] | Promethazine (10 µM) IC50 [nM] | Cyproheptadine (10 µM) IC50 [nM] |
| AMD3100 | 39.07 ± 14.5 | 1.58 ± 1.14 | 2.59 ± 2.06 | 0.75 ± 0.49 |
| Ulocuplumab | 0.5 ± 0.44 | 0.003 ± 0.003 | 0.000098 ± 0.0001 | 0.003 ± 0.001 |
| BKT140 | 232.3 ± 91.95 | 53.75 ± 21.24 | 1.66 ± 1.13 | 9.71 ± 7.17 |

CXCR4 inhibitors AMD-3100, Ulocuplumab and BKT140 suppressed the CXCR4-HRH1 signaling more efficiently (greater potency) in the presence of 10 µM of Hydroxyzine, Promethazine, or Cyproheptadine as shown with the reduced $IC_{50}$ values compared to the $IC_{50}$ values of CXCR4 inhibitors in the absence of HRH1 inhibitors. Depending on the identity of the CXCR4 inhibitor, the IC50 value of Ca response in the CXCR4-HRH1 heteromer context decreased by up to about 5,100 times or more when treated in combination with an HRH1 inhibitor (Hydroxyzine, Promethazine, or Cyproheptadine), relative to single treatment with the CXCR4 inhibitor alone ("None" column). These results suggest that co-treating with a CXCR4 inhibitor and HRH1 inhibitor more effectively inhibits increased Ca response than single treatment with a CXCR4 inhibitor alone in CXCR4-HRH1 heteromer expressing cells.

The efficiency of CXCR4 inhibitors in suppressing the enhanced signaling of CXCR4-ADCYAP1R1 heteromer was measured in the absence or presence of the representative ADCYAP1R1 inhibitors M65 or PACAP-(6-38) (Table 9). MDA-MB-231 cells were co-transduced with adenoviruses encoding CXCR4 and ADCYAP1R1, and Ca2+ signaling was measured upon co-stimulating the cells with CXCL12 (20 nM) and PACAP-38 (1 nM). Inhibitors were treated 30 min before agonist stimulation. Ca2+ mobilization was measured as described in FIG. 5, and $IC_{50}$ values were calculated using GraphPad Prism software.

TABLE 9

| | ADCYAP1R1 inhibitors | | |
|---|---|---|---|
| CXCR4 inhibitors | None IC50 [nM] | M65 (1 µM) IC50 [nM] | PACAP-(6-38) (1 µM) IC50 [nM] |
| AMD3100 | 546.8 ± 337.8 | 20.21 ± 12.83 | 2.42 ± 0.09 |
| BKT140 | 213.08 ± 142.72 | 7.46 ± 1.93 | 19.56 ± 3.1 |

CXCR4 inhibitors AMD-3100 and BKT140 suppressed the CXCR4-ADCYAP1R1 signaling more efficiently (greater potency) in the presence of 1 µM of M65 or 1 µM of PACAP-(6-38) as shown with the reduced $IC_{50}$ values compared to the $IC_{50}$ values of CXCR4 inhibitors in the absence of ADCYAP1R1 inhibitors. Depending on the identity of the CXCR4 inhibitor, the IC50 value of Ca response in the CXCR4-ADCYAP1R1 heteromer context decreased by up to about 225 times or more when treated in combination with an ADCYAP1R1 inhibitor (M65 or PACAP-(6-38)), relative to single treatment with the CXCR4 inhibitor alone ("None" column). These results suggest that co-treating with a CXCR4 inhibitor and ADCYAP1R1 inhibitor more effectively inhibits increased Ca response than single treatment with a CXCR4 inhibitor alone in CXCR4-ADCYAP1R1 heteromer expressing cells.

The efficiency of CXCR4 inhibitors in suppressing the enhanced signaling of CXCR4-C5AR1 heteromer was measured in the absence or presence of the representative C5AR1 inhibitor W54011 (Table 10). MDA-MB-231 cells were co-transduced with adenoviruses encoding CXCR4 and C5AR1, and Ca2+ signaling was measured upon co-stimulating the cells with CXCL12 (20 nM) and C5a (0.03 nM). Inhibitors were treated 30 min before agonist stimulation. Ca2+ mobilization was measured as described in FIG. 5, and $IC_{50}$ values were calculated using GraphPad Prism software.

TABLE 10

| CXCR4 inhibitors | C5AR1 inhibitors | |
|---|---|---|
| | None IC50 [nM] | W54011 (10 μM) IC50 [nM] |
| AMD3100 | 769.34 ± 240.77 | 434.00 ± 82.94 |
| Ulocuplumab | 3.80 ± 0.22 | 1.06 ± 0.25 |
| BKT140 | 118.01 ± 56.52 | 9.72 ± 6.87 |

CXCR4 inhibitors AMD-3100, BKT140, and Ulocuplumab suppressed the CXCR4-O5AR1 signaling more efficiently (greater potency) in the presence of 10 μM of W54011, as shown with the reduced $IC_{50}$ values compared to the $IC_{50}$ values of CXCR4 inhibitors in the absence of C5AR1 inhibitors. Depending on the identity of the CXCR4 inhibitor, the IC50 value of Ca response in the CXCR4-O5AR1 heteromer context decreased by up to about 12 times or more when treated in combination with an C5AR1 inhibitor (W54011), relative to single treatment with the CXCR4 inhibitor alone ("None" column). These results suggest that co-treating with a CXCR4 inhibitor and C5AR1 inhibitor more effectively inhibits increased Ca response than single treatment with a CXCR4 inhibitor alone in CXCR4-O5AR1 heteromer expressing cells.

The efficiency of CXCR4 inhibitors in suppressing the enhanced signaling of CXCR4-CALCR heteromer was measured in the absence or presence of the representative CALCR inhibitor CT-(8-32) (Table 11). MDA-MB-231 cells were co-transduced with adenoviruses encoding CXCR4 and CALCR, and Ca2+ signaling was measured upon co-stimulating the cells with CXCL12 (20 nM) and calcitonin (100 nM). Inhibitors were treated 30 min before agonist stimulation. Ca2+ mobilization was measured as described in FIG. 5, and $IC_{50}$ values were calculated using GraphPad Prism software.

TABLE 11

| CXCR4 inhibitor | CALCR inhibitors | |
|---|---|---|
| | None IC50 [nM] | CT-(8-32) (salmon) (10 μM) IC50 [nM] |
| AMD3100 | 2677.67 ± 953.23 | 12.54 ± 14.7 |
| BKT140 | 1041.6 ± 756.9 | 15.62 ± 3.71 |

CXCR4 inhibitors AMD-3100 and BKT140 suppressed the CXCR4-CALCR signaling more efficiently (greater potency) in the presence of 10 μM of CT-(8-32) as shown with the reduced $IC_{50}$ values compared to the $IC_{50}$ values of CXCR4 inhibitors in the absence of CALCR inhibitors. Depending on the identity of the CXCR4 inhibitor, the IC50 value of Ca response in the CXCR4-CALCR heteromer context decreased by up to about 210 times or more when treated in combination with an CALCR inhibitor (CT-(8-32)), relative to single treatment with the CXCR4 inhibitor alone ("None" column). These results suggest that co-treating with a CXCR4 inhibitor and CALCR inhibitor more effectively inhibits increased Ca response than single treatment with a CXCR4 inhibitor alone in CXCR4-CALCR heteromer expressing cells.

The efficiency of CXCR4 inhibitors in suppressing the enhanced signaling of CXCR4-EDNRB heteromer was measured in the absence or presence of the representative EDNRB inhibitors ambrisentan or bosentan (Table 12). MDA-MB-231 cells were co-transduced with adenoviruses encoding CXCR4 and EDNRB, and Ca2+ signaling was measured upon co-stimulating the cells with CXCL12 (20 nM) and BQ3020 (0.5 nM). Inhibitors were treated 30 min before agonist stimulation. Ca2+ mobilization was measured as described in FIG. 5, and $IC_{50}$ values were calculated using GraphPad Prism software.

TABLE 12

| CXCR4 inhibitor | EDNRB inhibitors | | |
|---|---|---|---|
| | None IC50 [nM] | Ambrisentan (10 μM) IC50 [nM] | Bosentan (10 μM) IC50 [nM] |
| AMD3100 | 926.10 ± 346.23 | 287.13 ± 88.75 | 169.12 ± 147.30 |
| Ulocuplumab | 14.11 ± 2.31 | 2.24 ± 0.18 | 4.68 ± 2.81 |
| BKT140 | 2680.5 ± 3927.44 | 529.37 ± 122.26 | 8.50 ± 7.37 |

CXCR4 inhibitors AMD-3100, BKT140, and Ulocuplumab suppressed the CXCR4-EDNRB signaling more efficiently (greater potency) in the presence of 10 μM of ambrisentan or 10 μM of bosentan, as shown with the reduced $IC_{50}$ values compared to the $IC_{50}$ values of CXCR4 inhibitors in the absence of EDNRB inhibitors. Depending on the identity of the CXCR4 inhibitor, the IC50 value of Ca response in the CXCR4-EDNRB heteromer context decreased by up to about 315 times or more when treated in combination with an EDNRB inhibitor (ambrisentan or bosentan), relative to single treatment with the CXCR4 inhibitor alone ("None" column). These results suggest that co-treating with a CXCR4 inhibitor and EDNRB inhibitor more effectively inhibits increased Ca response than single treatment with a CXCR4 inhibitor alone in CXCR4-EDNRB heteromer expressing cells.

The efficiency of CXCR4 inhibitors in suppressing the enhanced signaling of CXCR4-MLNR heteromer was measured in the absence or presence of the representative MLNR inhibitor MA-2029 (Table 13). MDA-MB-231 cells were co-transduced with adenoviruses encoding CXCR4 and MLNR, and Ca2+ signaling was measured upon co-stimulating the cells with CXCL12 (20 nM) and motilin (0.2 nM). Inhibitors were treated 30 min before agonist stimulation. Ca2+ mobilization was measured as described in FIG. 5, and $IC_{50}$ values were calculated using GraphPad Prism software.

TABLE 13

| CXCR4 inhibitor | MLNR inhibitors | |
|---|---|---|
| | None IC50 [nM] | MA-2029 (10 uM) IC50 [nM] |
| AMD3100 | 946.1 ± 171.4 | 199.23 ± 64.34 |
| Ulocuplumab | 25.51 ± 16.48 | 2.25 ± 1.30 |
| BKT140 | 643.6 ± 162.9 | 93.39 ± 155.20 |

CXCR4 inhibitors AMD-3100, BKT140, and Ulocuplumab suppressed the CXCR4-MLNR signaling more efficiently (greater potency) in the presence of 10 µM of MA-2029 as shown with the reduced $IC_{50}$ values compared to the $IC_{50}$ values of CXCR4 inhibitors in the absence of MLNR inhibitor. Depending on the identity of the CXCR4 inhibitor, the IC50 value of Ca response in the CXCR4-MLNR heteromer context decreased by up to about 11 times or more when treated in combination with an MLNR inhibitor (MA-2029), relative to single treatment with the CXCR4 inhibitor alone ("None" column). These results suggest that co-treating with a CXCR4 inhibitor and MLNR inhibitor more effectively inhibits increased Ca response than single treatment with a CXCR4 inhibitor alone in CXCR4-MLNR heteromer expressing cells.

The efficiency of CXCR4 inhibitors in suppressing the enhanced signaling of CXCR4-TACR3 heteromer was measured in the absence or presence of the representative TACR3 inhibitors SB 222200, osanetant, or talnetant (Table 14). MDA-MB-231 cells were co-transduced with adenoviruses encoding CXCR4 and TACR3, and Ca2+ signaling was measured upon co-stimulating the cells with CXCL12 (20 nM) and neurokinin B (0.3 nM). Inhibitors were treated 30 min before agonist stimulation. Ca2+ mobilization was measured as described in FIG. 5, and $IC_{50}$ values were calculated using GraphPad Prism software.

When tumor sizes were reached an average of 50-100 mm³, CXCR4 inhibitor, ADRB2 inhibitor alone or combination of CXCR4 and ADRB2 inhibitors were treated.

FIG. 29A is a graph comparing tumor growth rates for the in vivo antitumor effect of CXCR4 inhibitor LY2510924 (3 mg/kg), ADRB2 inhibitor Carvedilol (30 mg/kg), or combination of LY2510924 (3 mg/kg) and Carvedilol (30 mg/kg). FIG. 29B is a graph comparing tumor growth rates for the antitumor effect of CXCR4 inhibitor AMD070 (10 mg/kg), ADRB2 inhibitor Carvedilol (30 mg/kg), or combination of AMD070 (10 mg/kg) and Carvedilol (30 mg/kg). The tumor growth was monitored every third or fourth day by measuring the length (L) and width (W) of the tumor and calculating tumor volume based on the following formula: Volume=0.5 $LW^2$.

As shown in FIG. 29A, CXCR4-ADRB2 overexpressing mice were more inhibited tumor growth by the CXCR4 inhibitor, LY2510924 or the ADRB2 inhibitor, Carvedilol than the control mice. In addition, the combination of LY2510924 and Carvedilol demonstrated that the tumor growth inhibitory effect was superior to the single administration group. More specifically CXCR4-ADRB2 overexpressing A549 bearing mice treated with vehicle as a control reached an average tumor volume of 554.2±152.7 mm³ at day 21 post-treatment, as compared to LY2510924, Carvedilol or LY2510924 and Carvedilol, which reached an

TABLE 14

| | TACR3 inhibitors | | | |
|---|---|---|---|---|
| CXCR4 inhibitor | None IC50 [nM] | SB-222200 (10 µM) IC50 [nM] | Osanetant (10 µM) IC50 [nM] | Talnetant (10 µM) IC50 [nM] |
| AMD3100 | 2680.33 ± 210.49 | 343.13 ± 199.54 | 567.53 ± 322.61 | 179.63 ± 52.11 |
| Ulocuplumab | 50.65 ± 23.57 | 3.07 ± 1.18 | 4.61 ± 4.36 | 3.30 ± 0.89 |
| BKT140 | 1497.67 ± 419.98 | 217.90 ± 92.86 | 194.33 ± 91.07 | 230.30 ± 33.86 |

CXCR4 inhibitors AMD-3100, BKT140, and ulocuplumab suppressed the CXCR4-TACR3 signaling more efficiently (greater potency) in the presence of 10 µM of SB-222200, 10 µM of osanetant, or 10 µM of talnetant as shown with the reduced $IC_{50}$ values compared to the $IC_{50}$ values of CXCR4 inhibitors in the absence of TACR3 inhibitors. Depending on the identity of the CXCR4 inhibitor, the IC50 value of Ca response in the CXCR4-TACR3 heteromer context decreased by up to about 16 times or more when treated in combination with an TACR3 inhibitor (SB-222200, osanetant, or talnetant), relative to single treatment with the CXCR4 inhibitor alone ("None" column). These results suggest that co-treating with a CXCR4 inhibitor and TACR3 inhibitor more effectively inhibits increased Ca response than single treatment with a CXCR4 inhibitor alone in CXCR4-TACR3 heteromer expressing cells.

Example 19. Anti-Tumor Effect of CXCR4-ADRB2 Heteromer Inhibitors on Tumor Growth In FIG. 22, we observed that the CXCR4 and ADRB2 overexpressing cells bearing mice showed a dramatic increase in tumor proliferation compared to the A549 parent cell bearing mice. This suggests that CXCR4 ADRB2 heteromer promotes tumor proliferation.

To investigate the anti-tumor effect of CXCR4-ADRB2 heteromer inhibitors on tumor growth, the A549-CXCR4-ADRB2, stably overexpressing CXCR4-ADRB2 heteromer ($1\times10^7$ cell/head) was injected subcutaneously in nude mice.

average tumor volume of 488.9±135.2 mm³, and 432.0±206.4 mm³, 356.3±125.4 mm³ respectively, in the same time period.

A similar pattern was observed in the group treated with AMD070, another inhibitor of CXCR4.

FIG. 29B shows CXCR4-ADRB2 heteromer-overexpressing cell lines were transplanted at nude mouse and when tumor size reached 50-100 mm³, CXCR4 inhibitor, AMD070 or ADRB2 inhibitor, Carvedilol was administered orally alone or in combination for 23 days. As shown in FIG. 29B, the size of the tumor on the 23 days after administration of the drug was 618.5±190.9 mm³ in the control group, 543.2+260.4 mm³ or 510.4±139.9 mm³ in the group treated with AMD070 or Carvedilol, respectively. The tumor size of drug treated group is shown to be smaller than that of control group. In addition, in the combination of AMD070 and Carvedilol, the size of the tumor was 418.0±238.4 mm³, which indicates that the antitumor effect is superior to that of the single administration group.

These results suggest that co-treatment of CXCR4 and ADRB2 inhibitors may provide a better therapeutic effect for CXCR4 and ADRB2 heteromer expressing patients.

All publications and patent applications mentioned in this specification are herein incorporated by reference to the same extent as if each individual publication or patent application was specifically and individually indicated to be incorporated by reference.

While preferred embodiments have been shown and described herein, it will be obvious to those skilled in the art that such embodiments are provided by way of example only. It is intended that the following claims define the scope of the invention and that methods and structures within the scope of these claims and their equivalents be covered thereby.

Exemplary Embodiments

In an embodiment, a method for treating cancer in a subject having a cell containing a CXCR4-GPCRx heteromer, the method comprising: administering to the subject a therapeutically effective amount of an inhibitor or a combination of inhibitors selected from the group consisting of: an inhibitor of CXCR4, an inhibitor of GPCRx, and an inhibitor of the CXCR4-GPCRx heteromer.

In an embodiment, a method for treating cancer in a subject having CXCR4-GPCRx heteromer, the method comprising: administering to the subject a therapeutically effective amount of an inhibitor or a combination of inhibitors selected from the group consisting of: an inhibitor of CXCR4, an inhibitor of GPCRx, and an inhibitor of the CXCR4-GPCRx heteromer; wherein the cell containing the CXCR4-GPCRx heteromer has enhanced downstream signaling.

In an embodiment, a method for treatment, amelioration, or prevention of a cancer in a subject having CXCR4-GPCRx heteromer, the method comprising: administering to the subject a therapeutically effective amount of an inhibitor of a CXCR4-GPCRx heteromer, wherein: GPCRx heteromerizes with CXCR4 in the subject, the heteromerization of GPCRx with CXCR4 is accompanied by enhancement of signaling downstream of CXCR4; and the enhancement of signaling downstream of CXCR4 is suppressed by the inhibitor of the CXCR4-GPCRx heteromer.

In an embodiment, a method for assessing response, or potential response, of a subject having CXCR4-GPCRx heteromer to treatment, amelioration, or prevention of a cancer, the method comprising: obtaining a sample from the subject; detecting heteromerization of CXCR4 and GPCRx in the sample; and based at least in part on detection of the heteromerization of CXCR4 and GPCRx, assessing the subject's response, or potential response, to the treatment, amelioration, or prevention of a cancer.

In an embodiment, a method for treating cancer in a patient having a cell containing a CXCR4-GPCRx heteromer, the method comprising: administering to the patient an inhibitor or a combination of inhibitors selected from the group consisting of: an inhibitor of CXCR4, an inhibitor of GPCRx, and an inhibitor of the CXCR4-GPCRx heteromer; wherein:
  i) the CXCR4-GPCRx heteromer has enhanced downstream signaling; and
  ii) the administered inhibitor or combination of inhibitors suppresses the enhanced downstream signaling from said CXCR4-GPCRx heteromer in the cancer patient.

In an embodiment, a method of suppressing enhanced downstream signaling from a CXCR4-GPCRx heteromer in a cell of a patient suffering from cancer, the method comprising: administering to the patient an inhibitor or a combination of inhibitors selected from the group consisting of: an inhibitor of CXCR4, an inhibitor of GPCRx, and an inhibitor of the CXCR4-GPCRx heteromer; wherein:
  i) the CXCR4-GPCRx heteromer has enhanced downstream signaling; and
  ii) the administered inhibitor or combination of inhibitors suppresses the enhanced downstream signaling from said CXCR4-GPCRx heteromer in the cancer patient.

In an embodiment, a pharmaceutical kit for use in treating cancer in a patient having a cell containing a CXCR4-GPCRx heteromer, the pharmaceutical kit comprising: an inhibitor or a combination of inhibitors selected from the group consisting of: an inhibitor of CXCR4, an inhibitor of GPCRx, and an inhibitor of the CXCR4-GPCRx heteromer; wherein the CXCR4-GPCRx heteromer has enhanced downstream signaling.

In an embodiment, a pharmaceutical composition for use in treating cancer in a patient having a cell containing a CXCR4-GPCRx heteromer, the pharmaceutical composition comprising:
  i) an inhibitor or a combination of inhibitors selected from the group consisting of: an inhibitor of CXCR4, an inhibitor of GPCRx, and an inhibitor of the CXCR4-GPCRx heteromer; and
  ii) a pharmaceutically acceptable carrier;
wherein the CXCR4-GPCRx heteromer has enhanced downstream signaling.

In an embodiment, a method for treating cancer in a patient having a cancer cell containing a CXCR4-GPCRx heteromer, wherein the CXCR4-GPCRx heteromer has enhanced downstream signaling, the method comprising:
  1) determining whether the patient has the cancer cell containing the CXCR4-GPCRx heteromer having enhanced downstream signaling by: obtaining or having obtained a biological sample from the patient; and performing or having performed an assay on the biological sample to determine if:
    i) the patient's cancer cell contains said CXCR4-GPCRx heteromer; or
    ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing the CXCR4-GPCRx heteromer; or decreases cell proliferation of a patient derived cell(s) containing the CXCR4-GPCRx heteromer; and
  2) if the patient has a cancer cell containing said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the cancer patient.

In an embodiment, a method for treating cancer in a patient having a cancer cell containing a CXCR4-GPCRx heteromer, the method comprising:
  1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein:
    a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; and
    b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, or a fluorescent animal assay; and 2) if the patient's cancer cell contains said CXCR4-GPCRx heteromer, then internally administering an inhibitor or a combination of inhibitors selected from the group consisting of: an inhibitor of CXCR4, an inhibitor of GPCRx, and an inhibitor of the CXCR4-GPCRx heteromer to the patient.

In an embodiment, a method for treating cancer in a patient having a cancer cell containing a CXCR4-GPCRx heteromer having enhanced downstream signaling, the method comprising:
1) determining whether the patient has the cancer cell containing the CXCR4-GPCRx heteromer having enhanced downstream signaling by: obtaining or having obtained a biological sample from the patient; and performing or having performed an assay on the biological sample to determine if:
   i) the patient's cancer cell contains said CXCR4-GPCRx heteromer; or
   ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing said CXCR4-GPCRx heteromer; or decreases cell proliferation of a patient derived cell(s) containing said CXCR4-GPCRx heteromer; and
2) if the patient has a cancer cell containing said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
3) if the patient does not have a cancer cell containing said CXCR4-GPCRx heteromer, then internally administering to the cancer patient either the CXCR4 inhibitor or the GPCRx inhibitor as a single inhibitor.

In an embodiment, a method for treating cancer in a patient having a cancer cell containing a CXCR4-GPCRx heteromer having enhanced downstream signaling, the method comprising:
1) determining whether the patient has the cancer cell containing the CXCR4-GPCRx heteromer having enhanced downstream signaling by: obtaining or having obtained a biological sample from the patient; and performing or having performed an assay on the biological sample to determine if:
   i) the patient's cancer cell contains said CXCR4-GPCRx heteromer; or
   ii) a CXCR4-GPCRx heteromer-selective reagent: alters heteromer-specific properties or function of said CXCR4-GPCRx heteromer in a patient derived cell(s); alters heteromer-specific properties of a patient derived cell(s) containing said CXCR4-GPCRx heteromer; or decreases cell proliferation of a patient derived cell(s) containing said CXCR4-GPCRx heteromer; and
2) if the patient has a cancer cell containing said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
3) if the patient does not have a cancer cell containing said CXCR4-GPCRx heteromer, then internally administering to the cancer patient either the CXCR4 inhibitor or the GPCRx inhibitor as a single inhibitor;

wherein:
a) progression of the cancer in the patient having said cancer cell containing the CXCR4-GPCRx heteromer is decreased in the range of 5-100% more upon administration of the combination of inhibitors, relative to administering the CXCR4 inhibitor or GPCRx inhibitor as the single inhibitor to said patient;
b) efficacy of a CXCR4 inhibitor is increased in the range of 5-2000% when administered in combination with the GPCRx inhibitor to the patient having said cancer cell containing the CXCR4-GPCRx heteromer, relative to efficacy of the CXCR4 inhibitor when administered as a single inhibitor; and/or
c) efficacy of a GPCRx inhibitor is increased in the range of 5-2000% when administered in combination with the CXCR4 inhibitor to the patient having said cancer cell containing the CXCR4-GPCRx heteromer, relative to efficacy of the GPCRx inhibitor when administered as a single inhibitor.

In an embodiment, a method for treating cancer in a patient having a cancer cell containing a CXCR4-GPCRx heteromer, the method comprising:
1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein:
   a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; and
   b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay; and
2) if the patient's cancer cell contains said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
3) if the patient's cancer cell does not contain said CXCR4-GPCRx heteromer, then internally administering to the cancer patient either the CXCR4 inhibitor or the GPCRx inhibitor as a single inhibitor.

In an embodiment, a method for treating cancer in a patient having a cancer cell containing a CXCR4-GPCRx heteromer, the method comprising:
1) determining whether the patient's cancer cell contains the CXCR4-GPCRx heteromer by: obtaining or having obtained a biological sample from the patient and performing or having performed an assay on the biological sample to determine if said CXCR4-GPCRx heteromer is present in the patient's cancer cell; wherein:
   a) the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; and
  b) the assay performed on the biological sample is or comprises one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay; and
  2) if the patient's cancer cell contains said CXCR4-GPCRx heteromer, then internally administering to the cancer patient a combination of inhibitors selected from the group consisting of: an inhibitor of CXCR4, an inhibitor of GPCRx, and an inhibitor of the CXCR4-GPCRx heteromer; and
  3) if the patient's cancer cell does not contain said CXCR4-GPCRx heteromer, then internally administering to the cancer patient either the CXCR4 inhibitor or the GPCRx inhibitor as a single inhibitor;
wherein:
  a) progression of the cancer in the patient having said cancer cell containing the CXCR4-GPCRx heteromer is decreased in the range of 5-100% more upon administration of the combination of inhibitors, relative to administering the CXCR4 inhibitor or GPCRx inhibitor as the single inhibitor to said patient;
  b) efficacy of a CXCR4 inhibitor is increased in the range of 5-2000% when administered in combination with the GPCRx inhibitor to the patient having said cancer cell containing the CXCR4-GPCRx heteromer, relative to efficacy of the CXCR4 inhibitor when administered as a single inhibitor; and/or
  c) efficacy of a GPCRx inhibitor is increased in the range of 5-2000% when administered in combination with the CXCR4 inhibitor to the patient having said cancer cell containing the CXCR4-GPCRx heteromer, relative to efficacy of the GPCRx inhibitor when administered as a single inhibitor.

In certain embodiments, one or more than one (including for instance all) of the following further embodiments may comprise each of the other embodiments or parts thereof.

In a further embodiment, the method of treating, method of suppressing, pharmaceutical composition, or pharmaceutical kit, of any one of the above embodiments and any one or more of the further embodiments herein, wherein the CXCR4-GPCRx heteromer has, causes, or produces, the enhanced downstream signaling.

In a further embodiment, the method of treating, method of suppressing, pharmaceutical composition, or pharmaceutical kit, of any one of the above embodiments and any one or more of the further embodiments herein, wherein the enhanced downstream signaling results from the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling results from agonism of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling results from CXCR4 agonism of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling results from GPCRx agonism of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling results from CXCR4 agonism and GPCRx agonism of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling is downstream of the CXCR4, the respective GPCRx, or the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling is downstream of the CXCR4.

In a further embodiment, the method of treating, method of suppressing, pharmaceutical composition, or pharmaceutical kit, of any one of the above embodiments and any one or more of the further embodiments herein, wherein the enhanced downstream signaling is downstream of the respective GPCRx.

In a further embodiment, the method of treating, method of suppressing, pharmaceutical composition, or pharmaceutical kit, of any one of the above embodiments and any one or more of the further embodiments herein, wherein the enhanced downstream signaling is downstream of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the enhanced downstream signaling from the CXCR4-GPCRx heteromer is relative to downstream signaling from a CXCR4 protomer or a respective GPCRx protomer in their respective individual protomer context.

In a further embodiment, the method of treating, method of suppressing, pharmaceutical composition, or pharmaceutical kit, of any one of the above embodiments and any one or more of the further embodiments herein, wherein the enhanced downstream signaling from the CXCR4-GPCRx heteromer is relative to downstream signaling from a CXCR4 protomer in an individual protomer context.

In a further embodiment, the method of treating, method of suppressing, pharmaceutical composition, or pharmaceutical kit, of any one of the above embodiments and any one or more of the further embodiments herein, wherein the enhanced downstream signaling from the CXCR4-GPCRx heteromer is relative to downstream signaling from a respective GPCRx protomer in an individual protomer context.

In a further embodiment, the method of treating, method of suppressing, pharmaceutical composition, or pharmaceutical kit, of any one of the above embodiments and any one or more of the further embodiments herein, wherein the enhanced downstream signaling from the CXCR4-GPCRx heteromer is relative to downstream signaling from a CXCR4 protomer and a respective GPCRx protomer in their respective individual protomer context.

In a further embodiment, the method of treating, method of suppressing, pharmaceutical composition, or pharmaceutical kit, of any one of the above embodiments and any one or more of the further embodiments herein, wherein the inhibitor or combination of inhibitors suppresses the enhanced downstream signaling from said CXCR4-GPCRx heteromer in the cancer patient.

In a further embodiment, the method of treating, method of suppressing, pharmaceutical composition, or pharmaceutical kit, of any one of the above embodiments and any one or more of the further embodiments herein, wherein the administered inhibitor or combination of inhibitors suppresses the enhanced downstream signaling from said CXCR4-GPCRx heteromer in the patient's cancer cells.

In a further embodiment, the method of treating, method of suppressing, pharmaceutical composition, or pharmaceutical kit, of any one of the above embodiments and any one or more of the further embodiments herein, wherein the method further comprises determining or diagnosing the presence of a CXCR4-GPCRx heteromer.

In a further embodiment, the method of treating, method of suppressing, pharmaceutical composition, or pharmaceutical kit, of any one of the above embodiments and any one or more of the further embodiments herein, wherein the method further comprises determining or diagnosing the presence of a CXCR4-GPCRx heteromer in a cancer patient.

In a further embodiment, the method of treating, method of suppressing, pharmaceutical composition, or pharmaceutical kit, of any one of the above embodiments and any one or more of the further embodiments herein, wherein the method further comprises determining or diagnosing the presence of a CXCR4-GPCRx heteromer in a cancer cell or cancer tissue.

In a further embodiment, the method of treating, method of suppressing, pharmaceutical composition, or pharmaceutical kit, of any one of the above embodiments and any one or more of the further embodiments herein, wherein the method further comprises determining or diagnosing the presence of a CXCR4-GPCRx heteromer in a cancer cell or cancer tissue obtained from a cancer patient.

In a further embodiment, the method of treating, method of suppressing, pharmaceutical composition, or pharmaceutical kit, of any one of the above embodiments and any one or more of the further embodiments herein, wherein the method further comprises determining or diagnosing the presence of a CXCR4-GPCRx heteromer; and wherein the determining or diagnosing comprises:
1) obtaining or having obtained a biological sample (e.g., cells or tissue, such as cells or tissue from a cancer patient); and
2) performing or having performed an assay on the biological sample, wherein the assay is or comprises one or more of the following: a co-internalization assay, a colocalization assay, in situ hybridization, immunohistochemistry, immunoelectron microscopy, a proximity-based assay, a co-immunoprecipitation assay, or a fluorescent animal assay.

In a further embodiment, the method of treating, method of suppressing, pharmaceutical composition, or pharmaceutical kit, of any one of the above embodiments and any one or more of the further embodiments herein, wherein the enhanced downstream signaling from the CXCR4-GPCRx heteromer is determined by an intracellular Ca2+ assay.

In a further embodiment, the method of treating, method of suppressing, pharmaceutical composition, or pharmaceutical kit, of any one of the above embodiments and any one or more of the further embodiments herein, wherein the enhanced downstream signaling is an enhanced amount of calcium mobilization.

In a further embodiment, the method of treating, method of suppressing, pharmaceutical composition, or pharmaceutical kit, of any one of the above embodiments and any one or more of the further embodiments herein, wherein the enhanced amount of calcium mobilization from the CXCR4-GPCRx heteromer is a calcium mobilization amount that, upon co-stimulation with the CXCL12 and the respective selective GPCRx agonist, is at least 10% greater, at least 20% greater, at least 30% greater, at least 40% greater, at least 50% greater, at least 75% greater, or at least 90% greater, than the sum of calcium mobilization amounts resulting from single agonist stimulation of said cells with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization from the CXCR4-GPCRx heteromer is a calcium mobilization amount that, upon co-stimulation with the CXCL12 and the respective selective GPCRx agonist, is between 10-100% greater than the sum of calcium mobilization amounts resulting from single agonist stimulation of said cells with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization from the CXCR4-GPCRx heteromer is a calcium mobilization amount that, upon co-stimulation with the CXCL12 and the respective selective GPCRx agonist, is between 25-100% greater than the sum of calcium mobilization amounts resulting from single agonist stimulation of said cells with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization is determined by an intracellular Ca2+ assay.

In a further embodiment, the method of treating, method of suppressing, pharmaceutical composition, or pharmaceutical kit, of any one of the above embodiments and any one or more of the further embodiments herein, wherein the intracellular Ca2+ assay is a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization is a synergistic amount of calcium mobilization.

In a further embodiment, the method of treating, method of suppressing, pharmaceutical composition, or pharmaceutical kit, of any one of the above embodiments and any one or more of the further embodiments herein, wherein the synergistic amount of calcium mobilization from the cells containing the CXCR4-GPCRx heteromer is a calcium mobilization amount that, upon co-stimulation with the CXCL12 and the respective selective GPCRx agonist, is at least 10% greater, at least 20% greater, at least 30% greater, at least 40% greater, at least 50% greater, at least 75% greater, or at least 90% greater, than the sum of calcium mobilization amounts resulting from single agonist stimulation of said cells with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the CXCR4-GPCRx heteromer has two or more of the following characteristics:

1) the CXCR4-GPCRx heteromer components in a cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, or a fluorescent animal assay;
2) an enhanced amount of calcium mobilization, such that:
   a) either CXCR4 or the respective GPCRx in an individual protomer context in a cell, upon co-stimulation with CXCL12 and a respective selective GPCRx agonist, results in a calcium mobilization amount that is equal to or less than the sum of calcium mobilization amounts resulting from single agonist stimulation with either the CXCL12 or the respective selective GPCRx agonist; and
   b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist; as determined via a calcium mobilization assay; or
3) a CXCR4-GPCRx heteromer-selective reagent:
   i) alters heteromer-specific properties of the CXCR4-GPCRx heteromer in a patient derived cell;
   ii) alters heteromer-specific function of the CXCR4-GPCRx heteromer in a patient derived cell;
   iii) alters heteromer-specific properties of a patient derived cell containing the CXCR4-GPCRx heteromer; or
   iv) decreases cell proliferation of a patient derived cell(s) containing the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific properties of the CXCR4-GPCRx heteromer in a patient derived cell, as determined by at least one of the following methods: PLA, radioligand binding assays, [35S] GTP-rS Binding assays, Calcium assay, cAMP assay, GTPase assay, PKA activation, ERK1/2 and/or Akt/PKB Phosphorylation assays, Src and STAT3 phosphorylation assays, CRE-reporter assay, NFAT-RE-reporter assay, SRE-reporter assay, SRF-RE reporter assay, NF-kB-RE reporter assay, Secreted alkaline phosphatase Assay, Inositol 1-Phosphate Production assay, Adenylyl Cyclase Activity assay, analysis of target gene expression by RT-PCR, RT-qPCR, RNAseq, or microarray.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific function of the CXCR4-GPCRx heteromer in a patient derived cell, as determined by at least one of the following methods: PLA, radioligand binding assays, [35S] GTP-rS Binding assays, Calcium assay, cAMP assay, GTPase assay, PKA activation, ERK1/2 and/or Akt/PKB Phosphorylation assays, Src and STAT3 phosphorylation assays, CRE-reporter assay, NFAT-RE-reporter assay, SRE-reporter assay, SRF-RE reporter assay, NF-kB-RE reporter assay, Secreted alkaline phosphatase Assay, Inositol 1-Phosphate Production assay, Adenylyl Cyclase Activity assay, analysis of target gene expression by RT-PCR, RT-qPCR, RNAseq, next generation sequencing (NGS), or microarray.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific properties of a patient derived cell containing the CXCR4-GPCRx heteromer, as determined by at least one of the following methods: assays on proliferation, migration, invasion, and drug resistance (survival) of cancer cells, modulation of immune cell function, angiogenesis, vasculogenesis, metastasis, drug resistance, tissue microarray (TMA), and cancer cell-tumor microenvironment (TME) interaction.

In a further embodiment, the method of treating, method of suppressing, pharmaceutical composition, or pharmaceutical kit, of any one of the above embodiments and any one or more of the further embodiments herein, wherein the CXCR4-GPCRx heteromer components comprise individual protomers CXCR4 and GPCRx.

In a further embodiment, the method of treating, method of suppressing, pharmaceutical composition, or pharmaceutical kit, of any one of the above embodiments and any one or more of the further embodiments herein, wherein the cell containing either the CXCR4 or the respective GPCRx in an individual protomer context comprises, independently:
   i) the individual protomer CXCR4 in the absence of the respective individual protomer GPCRx; or
   ii) the respective individual protomer GPCRx in the absence of the individual protomer CXCR4;
respectively.

In a further embodiment, the method of treating, method of suppressing, pharmaceutical composition, or pharmaceutical kit, of any one of the above embodiments and any one or more of the further embodiments herein, wherein the cell containing the CXCR4 in an individual protomer context comprises said individual protomer CXCR4 in the absence of the respective individual protomer GPCRx.

In a further embodiment, the method of treating, method of suppressing, pharmaceutical composition, or pharmaceutical kit, of any one of the above embodiments and any one or more of the further embodiments herein, wherein the cell containing the respective GPCRx in an individual protomer context comprises said respective individual protomer GPCRx in the absence of the individual protomer CXCR4.

In a further embodiment, the method of treating, method of suppressing, pharmaceutical composition, or pharmaceutical kit, of any one of the above embodiments and any one or more of the further embodiments herein, wherein the CXCR4-GPCRx heteromer components in the cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, or a fluorescent animal assay.

In a further embodiment, the method of treating, method of suppressing, pharmaceutical composition, or pharmaceutical kit, of any one of the above embodiments and any one or more of the further embodiments herein, wherein the proximity-based assay is, or comprises, resonance energy transfer (RET), bioluminescence RET (BRET), fluorescence RET (FRET), time-resolved fluorescence RET (TR-FRET), antibody-aided FRET, ligand-aided FRET, bimolecular fluorescence complementation (BiFC), or a proximity ligation assay (PLA).

In a further embodiment, the method of treating, method of suppressing, pharmaceutical composition, or pharmaceutical kit, of any one of the above embodiments and any one or more of the further embodiments herein, wherein the CXCR4-GPCRx heteromer components in the cell colocalize and physically interact, either directly or via intermediate proteins acting as conduits for allosterism, as determined via one or more of the following: a co-internalization assay, bimolecular fluorescence complementation (BiFC), or a proximity ligation assay (PLA).

In a further embodiment, the method of treating, method of suppressing, pharmaceutical composition, or pharmaceutical kit, of any one of the above embodiments and any one or more of the further embodiments herein, wherein the patient's cancer cell contains the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4-GPCRx heteromer exhibits the enhanced amount of calcium mobilization, such that:
  a) either the CXCR4 or the respective GPCRx in an individual protomer context in the cell upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist; and
  b) the CXCR4-GPCRx heteromer exhibits an enhanced calcium mobilization upon co-stimulation with the CXCL12 and the respective selective GPCRx agonist relative to the sum of calcium mobilization amounts resulting from single agonist stimulation with either the CXCL12 or the respective selective GPCRx agonist;
as determined via a calcium mobilization assay.

In a further embodiment, the method of treating, method of suppressing, pharmaceutical composition, or pharmaceutical kit, of any one of the above embodiments and any one or more of the further embodiments herein, wherein:
  i) the calcium mobilization from the protomer CXCR4 or GPCRx, in the individual protomer context in the cell, is non-synergistic, as determined via calcium mobilization assay; and
  ii) the calcium mobilization from the CXCR4-GPCRx heteromer in the cell is synergistic, as determined via a calcium mobilization assay.

In a further embodiment, the method of treating, method of suppressing, pharmaceutical composition, or pharmaceutical kit, of any one of the above embodiments and any one or more of the further embodiments herein, wherein in the individual protomer context:
  a) the individual protomer CXCR4 in the cell, in the absence of the respective individual protomer GPCRx; or
  b) the respective individual protomer GPCRx in the cell, in the absence of the individual protomer CXCR4;
upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein in the individual protomer context, independently:
  a) the individual protomer CXCR4 in the cell, in the absence of the respective individual protomer GPCRx; and
  b) the respective individual protomer GPCRx in the cell, in the absence of the individual protomer CXCR4;
upon co-stimulation with CXCL12 and a respective selective GPCRx agonist results in a calcium mobilization amount that is equal to or less than the sum of calcium mobilization amounts resulting from single agonist stimulation with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the CXCR4-GPCRx heteromer upon co-stimulation with the CXCL12 and the respective selective GPCRx agonist results in a calcium mobilization amount that is greater than the sum of calcium mobilization amounts resulting from single agonist stimulation of said cells with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the calcium mobilization amount resulting from the co-stimulation of the CXCR4-GPCRx heteromer is an enhanced amount of calcium mobilization, relative to the sum of calcium mobilizations resulting from single agonist stimulation of said CXCR4-GPCRx heteromer, as determined via a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization is at least 10% greater, at least 20% greater, at least 30% greater, at least 40% greater, at least 50% greater, at least 75% greater, or at least 90% greater, than the sum of calcium mobilizations resulting from single agonist stimulation with either the CXCL12 or the respective selective GPCRx agonist, as determined via a calcium mobilization assay.

In a further embodiment, the method of treating, method of suppressing, pharmaceutical composition, or pharmaceutical kit, of any one of the above embodiments and any one or more of the further embodiments herein, wherein the enhanced amount of calcium mobilization is a synergistic amount of calcium mobilization.

In a further embodiment, the method of treating, method of suppressing, pharmaceutical composition, or pharmaceutical kit, of any one of the above embodiments and any one or more of the further embodiments herein, wherein the method administers a CXCR4-GPCRx heteromer-selective reagent.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent:
  i) alters heteromer-specific properties of the CXCR4-GPCRx heteromer in the patient derived cell;
  ii) alters heteromer-specific function of the CXCR4-GPCRx heteromer in the patient derived cell;
  iii) alters heteromer-specific properties of the patient derived cell containing the CXCR4-GPCRx heteromer; or
  iv) decreases cell proliferation of the patient derived cell containing the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific properties of the CXCR4-GPCRx heteromer in the patient derived cell.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific function of the CXCR4-GPCRx heteromer in the patient derived cell.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent alters heteromer-specific properties of the patient derived cell containing the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent decreases cell proliferation of the patient derived cell containing the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent is a CXCR4 inhibitor, a GPCRx inhibitor, or a CXCR4-GPCRx heteromer inhibitor.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent is a CXCR4 antagonist, a GPCRx antagonist, or a CXCR4-GPCRx heteromer antagonist.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent is administered as a pharmaceutical composition.

In a further embodiment, the method of treating, method of suppressing, pharmaceutical composition, or pharmaceutical kit, of any one of the above embodiments and any one or more of the further embodiments herein, wherein the method administers an inhibitor selected from the group consisting of: the CXCR4 inhibitor, the GPCRx inhibitor, or the CXCR4-GPCRx heteromer inhibitor.

In a further embodiment, the method of treating, method of suppressing, pharmaceutical composition, or pharmaceutical kit, of any one of the above embodiments and any one or more of the further embodiments herein, wherein the inhibitor is administered as a pharmaceutical composition.

In a further embodiment, the method of treating, method of suppressing, pharmaceutical composition, or pharmaceutical kit, of any one of the above embodiments and any one or more of the further embodiments herein, wherein the administered inhibitor is the CXCR4 inhibitor.

In a further embodiment, the method of treating, method of suppressing, pharmaceutical composition, or pharmaceutical kit, of any one of the above embodiments and any one or more of the further embodiments herein, wherein the administered inhibitor is the GPCRx inhibitor.

In a further embodiment, the method of treating, method of suppressing, pharmaceutical composition, or pharmaceutical kit, of any one of the above embodiments and any one or more of the further embodiments herein, wherein the administered inhibitor is the inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the method administers the combination of inhibitors selected from the group consisting of: the CXCR4 inhibitor, the GPCRx inhibitor, and the inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the combination of inhibitors is administered as a pharmaceutical composition.

In a further embodiment, the method of treating, method of suppressing, pharmaceutical composition, or pharmaceutical kit, of any one of the above embodiments and any one or more of the further embodiments herein, wherein the combination of inhibitors comprises the CXCR4 inhibitor and the GPCRx inhibitor.

In a further embodiment, the method of treating, method of suppressing, pharmaceutical composition, or pharmaceutical kit, of any one of the above embodiments and any one or more of the further embodiments herein, wherein the combination of inhibitors comprises the CXCR4 inhibitor and the inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the combination of inhibitors comprises the GPCRx inhibitor and the inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the combination of inhibitors are administered sequentially, concurrently, or simultaneously.

In a further embodiment, the method of treating, method of suppressing, pharmaceutical composition, or pharmaceutical kit, of any one of the above embodiments and any one or more of the further embodiments herein, wherein the combination of inhibitors are administered as a pharmaceutical composition further comprising a pharmaceutically acceptable carrier.

In a further embodiment, the method of treating, method of suppressing, pharmaceutical composition, or pharmaceutical kit, of any one of the above embodiments and any one or more of the further embodiments herein, wherein the combination of inhibitors are administered as separate pharmaceutical compositions, wherein the separate pharmaceutical compositions independently further comprise a pharmaceutically acceptable carrier.

In a further embodiment, the method of treating, method of suppressing, pharmaceutical composition, or pharmaceutical kit, of any one of the above embodiments and any one or more of the further embodiments herein, wherein the CXCR4 inhibitor is an antagonist of CXCR4, an inverse agonist of CXCR4, a partial antagonist of CXCR4, an allosteric modulator of CXCR4, an antibody of CXCR4, an antibody fragment of CXCR4, or a ligand of CXCR4.

In a further embodiment, the method of treating, method of suppressing, pharmaceutical composition, or pharmaceutical kit, of any one of the above embodiments and any one or more of the further embodiments herein, wherein the GPCRx inhibitor is an antagonist of GPCRx, an inverse agonist of GPCRx, a partial antagonist of GPCRx, an allosteric modulator of GPCRx, an antibody of GPCRx, an antibody fragment of GPCRx, or a ligand of GPCRx.

In a further embodiment, the method of treating, method of suppressing, pharmaceutical composition, or pharmaceutical kit, of any one of the above embodiments and any one or more of the further embodiments herein, wherein the inhibitor of the CXCR4-GPCRx heteromer is an antagonist of the CXCR4-GPCRx heteromer, an inverse agonist of the CXCR4-GPCRx heteromer, a partial antagonist of the CXCR4-GPCRx heteromer, an allosteric modulator of the CXCR4-GPCRx heteromer, an antibody of the CXCR4-GPCRx heteromer, an antibody fragment of the CXCR4-GPCRx heteromer, a ligand of the CXCR4-GPCRx heteromer, or a protein-protein interaction (PPI) inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the CXCR4 inhibitor, the GPCRx inhibitor, or the inhibitor of the CXCR4-GPCRx heteromer, is an antibody-drug conjugate.

In a further embodiment, the method of treating, method of suppressing, pharmaceutical composition, or pharmaceutical kit, of any one of the above embodiments and any one or more of the further embodiments herein, wherein a therapeutically effective amount of the inhibitor of the CXCR4-GPCRx heteromer is administered to the patient.

In a further embodiment, the method of treating, method of suppressing, pharmaceutical composition, or pharmaceutical kit, of any one of the above embodiments and any one or more of the further embodiments herein, wherein a sub-therapeutically effective amount of the inhibitor of the CXCR4-GPCRx heteromer is administered to the patient.

In a further embodiment, the method of treating, method of suppressing, pharmaceutical composition, or pharmaceutical kit, of any one of the above embodiments and any one or more of the further embodiments herein, wherein a therapeutically effective amount of the CXCR4 inhibitor is administered to the patient.

In a further embodiment, the method of treating, method of suppressing, pharmaceutical composition, or pharmaceutical kit, of any one of the above embodiments and any one or more of the further embodiments herein, wherein a sub-therapeutically effective amount of the CXCR4 inhibitor is administered to the patient.

In a further embodiment, the method of treating, method of suppressing, pharmaceutical composition, or pharmaceutical kit, of any one of the above embodiments and any one or more of the further embodiments herein, wherein the CXCR4 inhibitor is selected from the group consisting of:

AD-114, AD-114-6H, AD-114-Im7-FH, AD-114-PA600-6H, ALX-0651, ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMT-1359, GSK812397, GST-NT21MP, isothiourea-1a, isothiourea-1t (IT1t), KRH-1636, KRH-3955, LY2510924, LY2624587, MSX-122, N-[$^{11}$C]Methyl-AMD3465, PF-06747143, POL6326, SDF-1 1-9[P2G] dimer, SDF1 P2G, T134, T140, T22, TC 14012, TG-0054 (Burixafor), USL311, ulocuplumab (MDX1338/BMS-936564), viral macrophage inflammatory protein-II (vMIP-II), WZ811, 12G5, 238D2, 238D4, [$^{64}$Cu]-AMD3100, [$^{64}$Cu]-AMD3465, [$^{68}$Ga]pentixafor, [$^{90}$Y]pentixather, [$^{99m}$Tc]O$_2$-AMD3100, [$^{177}$Lu]pentixather, and 508MCl (Compound 26).

In a further embodiment, the method of treating, method of suppressing, pharmaceutical composition, or pharmaceutical kit, of any one of the above embodiments and any one or more of the further embodiments herein, wherein a therapeutically effective amount of the GPCRx inhibitor is administered to the patient.

In a further embodiment, the method of treating, method of suppressing, pharmaceutical composition, or pharmaceutical kit, of any one of the above embodiments and any one or more of the further embodiments herein, wherein a sub-therapeutically effective amount of the GPCRx inhibitor is administered to the patient.

In a further embodiment, the method of treating, method of suppressing, pharmaceutical composition, or pharmaceutical kit, of any one of the above embodiments and any one or more of the further embodiments herein, wherein the GPCRx is selected from the group consisting of:

ADCYAP1R1, ADORA2B, ADORA3, ADRB2, C5AR1, CALCR, CHRM1, EDNRB, HRH1, MLNR, NTSR1, and TACR3.

In a further embodiment, the method of treating, method of suppressing, pharmaceutical composition, or pharmaceutical kit, of any one of the above embodiments and any one or more of the further embodiments herein, wherein the GPCRx is ADRB2 or HRH1.

In a further embodiment, the method of treating, method of suppressing, pharmaceutical composition, or pharmaceutical kit, of any one of the above embodiments and any one or more of the further embodiments herein, wherein the GPCRx is ADCYAP1R1.

In a further embodiment, the method of treating, method of suppressing, pharmaceutical composition, or pharmaceutical kit, of any one of the above embodiments and any one or more of the further embodiments herein, wherein the ADCYAP1R1 inhibitor is selected from the group consisting of:

M65, Max.d.4, MK-0893, N-stearyl-[Nle$^{17}$] neurotensin-(6-11)/VIP-(7-28), PACAP-(6-38), and PG 97-269.

In a further embodiment, the method of treating, method of suppressing, pharmaceutical composition, or pharmaceutical kit, of any one of the above embodiments and any one or more of the further embodiments herein, wherein the GPCRx is ADORA2B.

In a further embodiment, the method of treating, method of suppressing, pharmaceutical composition, or pharmaceutical kit, of any one of the above embodiments and any one or more of the further embodiments herein, wherein the ADORA2B inhibitor is selected from the group consisting of:

3-isobutyl-8-pyrrolidinoxanthine, alloxazine, AS16, AS70, AS74, AS94, AS95, AS96, AS99, AS100, AS101, ATL802, BW-A1433, caffeine, CGS 15943, CPX, CSC, CVT-6883, DAX, DEPX, derenofylline, DPCPX, FK-453, I-ABOPX, istradefylline, KF26777, LAS38096, LUF5981, MRE 2029F20, MRE 3008F20, MRS1191, MRS1220, MRS1523, MRS1706, MRS1754, MSX-2, OSIP339391, pentoxifylline, preladenant, PSB-10, PSB-11, PSB36, PSB603, PSB-0788, PSB1115, rolofylline, SCH 58261, SCH442416, ST-1535, theophylline, tonapofylline, vipadenant, xanthine amine congener, XCC, and ZM-241385.

In a further embodiment, the method of treating, method of suppressing, pharmaceutical composition, or pharmaceutical kit, of any one of the above embodiments and any one or more of the further embodiments herein, wherein the GPCRx is ADORA3.

In a further embodiment, the method of treating, method of suppressing, pharmaceutical composition, or pharmaceutical kit, of any one of the above embodiments and any one or more of the further embodiments herein, wherein the ADORA3 inhibitor is selected from the group consisting of:

ATL802, BW-A1433, caffeine, CGS 15943, CSC, CVT-6883, derenofylline, dexniguldipine, DPCPX, FK-453, flavanone, flavone, galangin, I-ABOPX, istradefylline, KF26777, LAS38096, LUF5981, MRE 2029F20, MRE 3008F20, MRE 3010F20, MRS1041, MRS1042, MRS1067, MRS1088, MRS1093, MRS1097, MRS1177, MRS1186, MRS1191, MRS1191, MRS1220, MRS1476, MRS1486, MRS1505, MRS1523, MRS1754, MRS928, MSX-2, nicardipine, preladenant, PSB-10, PSB-11, PSB36, PSB603, PSB1115, rolofylline, sakuranetin, SCH 58261, SCH442416, ST-1535, theophylline, tonapofylline, vipadenant, visnagin, VUF5574, VUF8504, VUF8507, xanthine amine congener, and ZM-241385.

In a further embodiment, the method of treating, method of suppressing, pharmaceutical composition, or pharmaceutical kit, of any one of the above embodiments and any one or more of the further embodiments herein, wherein the GPCRx is ADRB2.

In a further embodiment, the method of treating, method of suppressing, pharmaceutical composition, or pharmaceutical kit, of any one of the above embodiments and any one or more of the further embodiments herein, wherein the ADRB2 inhibitor is selected from the group consisting of:

Alprenolol, atenolol, betaxolol, bupranolol, butoxamine, carazolol, carvedilol, CGP 12177, cicloprolol, ICI 118551, ICYP, labetalol, levobetaxolol, levobunolol, LK 204-545, metoprolol, nadolol, NIHP, NIP, propafenone, propranolol, sotalol, SR59230A, and timolol.

In a further embodiment, the method of treating, method of suppressing, pharmaceutical composition, or pharmaceutical kit, of any one of the above embodiments and any one or more of the further embodiments herein, wherein the GPCRx is C5AR1.

In a further embodiment, the method of treating, method of suppressing, pharmaceutical composition, or pharmaceutical kit, of any one of the above embodiments and any one or more of the further embodiments herein, wherein the C5AR1 inhibitor is selected from the group consisting of:

A8$^{\Delta 71-73}$, AcPhe-Orn-Pro-D-Cha-Trp-Arg, avacopan, C089, CHIPS, DF2593A, JPE1375, L-156,602, NDT9520492, N-methyl-Phe-Lys-Pro-D-Cha-Trp-D-Arg-CO$_2$H, PMX205, PMX53, RPR121154, and W54011.

In a further embodiment, the method of treating, method of suppressing, pharmaceutical composition, or pharmaceutical kit, of any one of the above embodiments and any one or more of the further embodiments herein, wherein the GPCRx is CALCR.

In a further embodiment, the method of treating, method of suppressing, pharmaceutical composition, or pharmaceutical kit, of any one of the above embodiments and any one or more of the further embodiments herein, wherein the CALCR inhibitor is selected from the group consisting of:

α-CGRP-(8-37) (human), AC187, CT-(8-32) (salmon), and olcegepant.

In a further embodiment, the method of treating, method of suppressing, pharmaceutical composition, or pharmaceutical kit, of any one of the above embodiments and any one or more of the further embodiments herein, wherein the GPCRx is CHRM1.

In a further embodiment, the method of treating, method of suppressing, pharmaceutical composition, or pharmaceutical kit, of any one of the above embodiments and any one or more of the further embodiments herein, wherein the CHRM1 inhibitor is selected from the group consisting of:

3-Quinuclidinyl benzilate (QNB), 4-DAMP, aclidinium, AE9C9OCB, AFDX384, amitriptyline, AQ-RA 741, atropine, benzatropine, biperiden, darifenacin, dicyclomine, dosulepin, ethopropazine, glycopyrrolate, guanylpirenzepine, hexahydrodifenidol, hexahydrosiladifenidol, hexocyclium, himbacine, ipratropium, lithocholylcholine, methoctramine, ML381, muscarinic toxin 1, muscarinic toxin 2, muscarinic toxin 3, N-methyl scopolamine, otenzepad, oxybutynin, p-F-HHSiD, pirenzepine, propantheline, (R,R)-quinuclidinyl-4-fluoromethyl-benzilate, scopolamine, silahexocyclium, solifenacin, telenzepine, tiotropium, tolterodine, trihexyphenidyl, tripitramine, UH-AH 37, umeclidinium, and VU0255035.

In a further embodiment, the method of treating, method of suppressing, pharmaceutical composition, or pharmaceutical kit, of any one of the above embodiments and any one or more of the further embodiments herein, wherein the GPCRx is EDNRB.

In a further embodiment, the method of treating, method of suppressing, pharmaceutical composition, or pharmaceutical kit, of any one of the above embodiments and any one or more of the further embodiments herein, wherein the EDNRB inhibitor is selected from the group consisting of:

A192621, ambrisentan, atrasentan, bosentan (RO 470203, Tracleer), BQ788, IRL 2500, K-8794, macitentan, RES7011, Ro 46-8443, SB209670, SB217242 (enrasentan), TAK 044, and tezosentan (RO610612).

In a further embodiment, the method of treating, method of suppressing, pharmaceutical composition, or pharmaceutical kit, of any one of the above embodiments and any one or more of the further embodiments herein, wherein the GPCRx is HRH1.

In a further embodiment, the method of treating, method of suppressing, pharmaceutical composition, or pharmaceutical kit, of any one of the above embodiments and any one or more of the further embodiments herein, wherein the HRH1 inhibitor is selected from the group consisting of:

(−)-chlorpheniramine, (+)-chlorpheniramine, (−)-trans-H₂-PAT, (+)-cis-H₂-PAT, (+)-trans-H₂-PAT, (±)-cis-H₂-PAT, (±)-trans-H₂-PAT, (R)-cetirizine, (S)-cetirizine, 9-OH-risperidone, A-317920, A-349821, ABT-239, alimemazine, amitriptyline, aripiprazole, arpromidine, asenapine, astemizole, AZD3778, azelastine, BU-E 47, cetirizine, chlorpheniramine, chlorpromazine, ciproxifan, clemastine, clobenpropit, clozapine, conessine, cyclizine, cyproheptadine, desloratadine, diphenhydramine, dosulepin, doxepin, epinastine, fexofenadine, fluphenazine, fluspirilene, haloperidol, hydroxyzine, impromidine, INCB-38579, JNJ-39758979, ketotifen, loratadine, loxapine, MK-0249, molindone, olanzapine, perphenazine, pimozide, pipamperone, pitolisant, promethazine, pyrilamine, quetiapine, risperidone, sertindole, terfenadine, thioridazine, thiothixene, trifluoperazine, tripelennamine, triprolidine, ziprasidone, and zotepine.

In a further embodiment, the method of treating, method of suppressing, pharmaceutical composition, or pharmaceutical kit, of any one of the above embodiments and any one or more of the further embodiments herein, wherein the GPCRx is MLNR.

In a further embodiment, the method of treating, method of suppressing, pharmaceutical composition, or pharmaceutical kit, of any one of the above embodiments and any one or more of the further embodiments herein, wherein the MLNR inhibitor is selected from the group consisting of: GM-109, MA-2029, and OHM-11526.

In a further embodiment, the method of treating, method of suppressing, pharmaceutical composition, or pharmaceutical kit, of any one of the above embodiments and any one or more of the further embodiments herein, wherein the GPCRx is NTSR1.

In a further embodiment, the method of treating, method of suppressing, pharmaceutical composition, or pharmaceutical kit, of any one of the above embodiments and any one or more of the further embodiments herein, wherein the NTSR1 inhibitor is selected from the group consisting of: Meclinertant, SR48527, SR48692, and SR142948A.

In a further embodiment, the method of treating, method of suppressing, pharmaceutical composition, or pharmaceutical kit, of any one of the above embodiments and any one or more of the further embodiments herein, wherein the GPCRx is TACR3.

In a further embodiment, the method of treating, method of suppressing, pharmaceutical composition, or pharmaceutical kit, of any one of the above embodiments and any one or more of the further embodiments herein, wherein the TACR3 inhibitor is selected from the group consisting of:

[Trp$^7$, β-Ala$^8$] neurokinin A-(4-10), AZD2624, FK 224, GR138676, GSK 172981, GSK 256471, N',2-diphenylquinoline-4-carbohydrazide 8m, N',2-diphenylquinoline-4-carbohydrazide, osanetant, PD 154740, PD 161182, PD157672, saredutant, SB 218795, SB 222200, SB 235375, SCH 206272, SSR 146977, and talnetant.

In a further embodiment, the method of treating, method of suppressing, pharmaceutical composition, or pharmaceutical kit, of any one of the above embodiments and any one or more of the further embodiments herein, wherein the respective selective GPCRx agonist is natural ligand of the respective GPCRx, respectively.

In a further embodiment, the method of treating, method of suppressing, pharmaceutical composition, or pharmaceutical kit, of any one of the above embodiments and any one or more of the further embodiments herein, wherein the method further comprises detecting the CXCR4-GPCRx heteromer in the cancer patient.

In a further embodiment, the method of treating, method of suppressing, pharmaceutical composition, or pharmaceutical kit, of any one of the above embodiments and any one or more of the further embodiments herein, wherein the method further comprises identifying the CXCR4-GPCRx heteromer in the cancer patient.

In a further embodiment, the method of treating, method of suppressing, pharmaceutical composition, or pharmaceutical kit, of any one of the above embodiments and any one or more of the further embodiments herein, wherein the method further comprises:

i) obtaining or having obtained a biological sample from the cancer patient;
ii) conducting or having conducted a diagnostic assay to determine presence, identity, or presence and identity, of a CXCR4-GPCRx heteromer in the obtained biological sample from the cancer patient; and
iii) selecting the inhibitor or combination of inhibitors to suppress enhanced downstream signaling from the CXCR4-GPCRx heteromer.

In a further embodiment, the method of treating, method of suppressing, pharmaceutical composition, or pharmaceutical kit, of any one of the above embodiments and any one or more of the further embodiments herein, wherein the cancer is selected from the group consisting of: breast cancer, lung cancer, brain cancer, kidney cancer, pancreatic cancer, ovarian cancer, prostate cancer, melanoma, multiple myeloma, gastrointestinal cancers, renal cell carcinoma, soft tissue sarcomas, hepatocellular carcinoma, stomach cancer, colorectal cancer, esophageal cancer, and leukemia.

In a further embodiment, the method of treating, method of suppressing, pharmaceutical composition, or pharmaceutical kit, of any one of the above embodiments and any one or more of the further embodiments herein, wherein the patient's biological sample is a biological fluid sample.

In a further embodiment, the method of treating, method of suppressing, pharmaceutical composition, or pharmaceutical kit, of any one of the above embodiments and any one or more of the further embodiments herein, wherein a liquid biopsy is performed on the biological fluid sample. In some embodiments, the biological fluid sample includes circulating tumor cells (CTCs), tumor-derived cell-free DNA (cfDNA), circulating small RNAs, and extracellular vesicles including exosomes, from bodily fluids as disclosed, for example, in Campos C D M et al., "Molecular Profiling of Liquid Biopsy Samples for Precision Medicine," Cancer J. 2018 March/April; 24(2):93-103, which is incorporated hereby in its entirety.

In a further embodiment, the method of treating, method of suppressing, pharmaceutical composition, or pharmaceutical kit, of any one of the above embodiments and any one or more of the further embodiments herein, wherein the biological fluid sample is a blood sample, a plasma sample, a saliva sample, a cerebral fluid sample, an eye fluid sample, or a urine sample.

In a further embodiment, the method of treating, method of suppressing, pharmaceutical composition, or pharmaceutical kit, of any one of the above embodiments and any one or more of the further embodiments herein, wherein the patient's biological sample is a biological tissue sample.

In a further embodiment, the method of treating, method of suppressing, pharmaceutical composition, or pharmaceutical kit, of any one of the above embodiments and any one or more of the further embodiments herein, wherein a liquid biopsy is performed on the biological tissue sample.

In a further embodiment, the method of treating, method of suppressing, pharmaceutical composition, or pharmaceutical kit, of any one of the above embodiments and any one or more of the further embodiments herein, wherein the biological tissue sample is an organ tissue sample, a bone tissue sample, or a tumor tissue sample.

In a further embodiment, the method of treating, method of suppressing, pharmaceutical composition, or pharmaceutical kit, of any one of the above embodiments and any one or more of the further embodiments herein, wherein the cancer cell contains the CXCR4-GPCRx heteromer.

In a further embodiment, the method of treating, method of suppressing, pharmaceutical composition, or pharmaceutical kit, of any one of the above embodiments and any one or more of the further embodiments herein, wherein a normal, non-cancerous cell, does not contain the CXCR4-GPCRx heteromer.

In a further embodiment, the method of treating, method of suppressing, pharmaceutical composition, or pharmaceutical kit, of any one of the above embodiments and any one or more of the further embodiments herein, wherein the cancer cell of the patient contains the CXCR4-GPCRx heteromer in a greater concentration than a normal, non-cancerous cell from said patient, for example, 10% greater concentration than a normal, non-cancerous cell from said patient, such as 25% greater, 50% greater, 100% greater, 200% greater, or 300% greater, than a normal, non-cancerous cell from said patient.

In a further embodiment, the method of treating, method of suppressing, pharmaceutical composition, or pharmaceutical kit, of any one of the above embodiments and any one or more of the further embodiments herein, wherein the CXCR4-GPCRx heteromer contained in the cancer cell of the patient is in a greater concentration than a normal, non-cancerous cell from said patient, for example, 10% greater concentration than a normal, non-cancerous cell from said patient, such as 25% greater, 50% greater, 100% greater, 200% greater, or 300% greater, than a normal, non-cancerous cell from said patient; and wherein the GPCRx of the CXCR4-GPCRx heteromer contained in the cancer cell of the patient is selected from the group consisting of: ADCYAP1R1, ADORA2B, ADORA3, ADRB2, C5AR1, CALCR, CHRM1, EDNRB, HRH1, MLNR, NTSR1, and TACR3.

In a further embodiment, the method of treating, method of suppressing, pharmaceutical composition, or pharmaceutical kit, of any one of the above embodiments and any one or more of the further embodiments herein, wherein the presence of the CXCR4-GPCRx heteromer in the cancer cell of the patient identifies a sub-population of CXCR4-mediated cancer patients.

In a further embodiment, the method of treating, method of suppressing, pharmaceutical composition, or pharmaceutical kit, of any one of the above embodiments and any one or more of the further embodiments herein, wherein the presence of the CXCR4-GPCRx heteromer in the cancer cell of the patient is a biomarker of a sub-population of CXCR4-mediated cancer patients.

In a further embodiment, the method of treating, method of suppressing, pharmaceutical composition, or pharmaceutical kit, of any one of the above embodiments and any one or more of the further embodiments herein, wherein the biomarker of the sub-population of CXCR4-mediated cancer patients allows for precision medicine, patient stratification, or patient classification.

In a further embodiment, the method of treating, method of suppressing, pharmaceutical composition, or pharmaceutical kit, of any one of the above embodiments and any one or more of the further embodiments herein, wherein the biomarker of the sub-population of CXCR4-mediated cancer patients allows for GPCR-based precision cancer therapeutics.

In a further embodiment, the method of treating, method of suppressing, pharmaceutical composition, or pharmaceutical kit, of any one of the above embodiments and any one or more of the further embodiments herein, wherein the presence of the CXCR4-GPCRx heteromer in the cancer cell of the patient identifies a sub-population of CXCR4-mediated cancer patients; and wherein the GPCRx of the CXCR4-GPCRx heteromer present in the cancer cell of the patient is selected from the group consisting of: ADCYAP1R1, ADORA2B, ADORA3, ADRB2, C5AR1, CALCR, CHRM1, EDNRB, HRH1, MLNR, NTSR1, and TACR3.

In a further embodiment, the method of treating, method of suppressing, pharmaceutical composition, or pharmaceutical kit, of any one of the above embodiments and any one or more of the further embodiments herein, wherein the presence of the CXCR4-GPCRx heteromer in the cancer cell of the patient is a biomarker of a sub-population of CXCR4-mediated cancer patients; and wherein the GPCRx of the CXCR4-GPCRx heteromer present in the cancer cell of the patient is selected from the group consisting of: ADCYAP1R1, ADORA2B, ADORA3, ADRB2, C5AR1, CALCR, CHRM1, EDNRB, HRH1, MLNR, NTSR1, and TACR3.

In a further embodiment, the method of treating, method of suppressing, pharmaceutical composition, or pharmaceutical kit, of any one of the above embodiments and any one or more of the further embodiments herein, wherein the inhibitor is an antibody.

In a further embodiment, the method of treating, method of suppressing, pharmaceutical composition, or pharmaceutical kit, of any one of the above embodiments and any one or more of the further embodiments herein, wherein the CXCR4-GPCRx heteromer-selective reagent is an antibody.

In a further embodiment, the method of treating, method of suppressing, pharmaceutical composition, or pharmaceutical kit, of any one of the above embodiments and any one or more of the further embodiments herein, wherein the antibody is a bi-specific antibody of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the antibody is a heteromer-specific antibody of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the inhibitor is a bi-specific ligand(s) of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the antibody is an antibody-drug conjugate (ADC), as disclosed in, for example, Beck a et al., "Strategies and challenges for the next generation of antibody-drug conjugates", Nature Reviews Drug Discovery, 16:315-337, (2017) and Lambert, et al., "Antibody-Drug Conjugates for Cancer Treatment", Annual Review of Medicine, 69:191-207 (2018), each of which are incorporated hereby in its entirety.

In a further embodiment, the method of treating, method of suppressing, pharmaceutical composition, or pharmaceutical kit, of any one of the above embodiments and any one or more of the further embodiments herein, wherein the method comprises: administering to the patient an inhibitor or a combination of inhibitors selected from the group consisting of: an inhibitor of CXCR4, an inhibitor of GPCRx, and an inhibitor of the CXCR4-GPCRx heteromer; wherein: i) the CXCR4-GPCRx heteromer has enhanced downstream signaling; and ii) the administered inhibitor or combination of inhibitors suppresses the enhanced downstream signaling from said CXCR4-GPCRx heteromer in the cancer patient.

In a further embodiment, the method of treating, method of suppressing, pharmaceutical composition, or pharmaceutical kit, of any one of the above embodiments and any one or more of the further embodiments herein, wherein the pharmaceutical kit or pharmaceutical composition, such as for use in treating cancer in a patient having a cell containing a CXCR4-GPCRx heteromer, comprises: an inhibitor or a combination of inhibitors selected from the group consisting of: an inhibitor of CXCR4, an inhibitor of GPCRx, and an inhibitor of the CXCR4-GPCRx heteromer; wherein the CXCR4-GPCRx heteromer has enhanced downstream signaling.

In a further embodiment, the method of treating, method of suppressing, pharmaceutical composition, or pharmaceutical kit, of any one of the above embodiments and any one or more of the further embodiments herein, wherein progression of the cancer in the patient having said cancer cell containing the CXCR4-GPCRx heteromer is decreased in the range of 5-100% more, 10-100% more, 20-100% more, 30-100% more, 40-100% more, 50-100% more, 60-100% more, 75-100% more, 5-75% more, 5-50% more, or 5-25% more, upon administration of the combination of inhibitors, relative to administering the CXCR4 inhibitor or GPCRx inhibitor as the single inhibitor to said patient.

In a further embodiment, the method of treating, method of suppressing, pharmaceutical composition, or pharmaceutical kit, of any one of the above embodiments and any one or more of the further embodiments herein, wherein the efficacy of a CXCR4 inhibitor is increased in the range of 5-2000%, 5-1750%, 5-1500%, 5-1250%, 5-1000%, 5-900%, 5-800%, 5-700%, 5-500%, 5-400%, 5-250%, 5-200%, 5-100%, 5-75%, 5-50%, 5-40%, 5-30%, 5-25%, 100-2000%, 200-2000%, 300-2000%, 500-2000%, 750-2000%, 1000-2000%, 1250-2000%, 1500-2000%, 5-1500%, 25-1500%, 50-1500%, 75-1500%, 100-1500%, 200-1500%, 300-1500%, 500-1500%, 750-1500%, 1000-1500%, or 1250-1500%, when administered in combination with the GPCRx inhibitor to the patient having said cancer cell containing the CXCR4-GPCRx heteromer, relative to efficacy of the CXCR4 inhibitor when administered as a single inhibitor.

In a further embodiment, the method of treating, method of suppressing, pharmaceutical composition, or pharmaceutical kit, of any one of the above embodiments and any one or more of the further embodiments herein, wherein the efficacy of a GPCRx inhibitor is increased in the range of 5-2000%, 5-1750%, 5-1500%, 5-1250%, 5-1000%, 5-900%, 5-800%, 5-700%, 5-500%, 5-400%, 5-250%, 5-200%, 5-100%, 5-75%, 5-50%, 5-40%, 5-30%, 5-25%, 100-2000%, 200-2000%, 300-2000%, 500-2000%, 750-2000%, 1000-2000%, 1250-2000%, 1500-2000%, 5-1500%, 25-1500%, 50-1500%, 75-1500%, 100-1500%, 200-1500%, 300-1500%, 500-1500%, 750-1500%, 1000-1500%, or 1250-1500%, when administered in combination with the CXCR4 inhibitor to the patient having said cancer cell containing the CXCR4-GPCRx heteromer, relative to efficacy of the GPCRx inhibitor when administered as a single inhibitor.

In a further embodiment, the method of treating, method of suppressing, pharmaceutical composition, or pharmaceutical kit, of any one of the above embodiments and any one or more of the further embodiments herein, wherein the method administers a combination of inhibitors selected from the group consisting of: an inhibitor of CXCR4, an inhibitor of GPCRx, and an inhibitor of the CXCR4-GPCRx heteromer; or the pharmaceutical kit or pharmaceutical composition comprises a combination of inhibitors selected from the group consisting of: an inhibitor of CXCR4, an inhibitor of GPCRx, and an inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the combination of inhibitors is a combination of two inhibitors selected from the group consisting of: an inhibitor of CXCR4, an inhibitor of GPCRx, and an inhibitor of the CXCR4-GPCRx heteromer.

In a further embodiment, the method of treating, method of suppressing, pharmaceutical composition, or pharmaceutical kit, of any one of the above embodiments and any one or more of the further embodiments herein, wherein the method administers a combination of a CXCR4 inhibitor and a GPCRx inhibitor; or the pharmaceutical kit or pharmaceutical composition comprises a combination of a CXCR4 inhibitor and a GPCRx inhibitor.

In a further embodiment, the method of treating, method of suppressing, pharmaceutical composition, or pharmaceutical kit, of any one of the above embodiments and any one or more of the further embodiments herein, wherein the method administers a CXCR4-GPCRx heteromer inhibitor; or the pharmaceutical kit or pharmaceutical composition comprises a CXCR4-GPCRx heteromer inhibitor.

In a further embodiment, the method of treating, method of suppressing, pharmaceutical composition, or pharmaceutical kit, of any one of the above embodiments and any one or more of the further embodiments herein, wherein the administering of the combination of inhibitors suppresses the enhanced downstream signaling from said CXCR4-GPCRx heteromer in the cancer patient in the range of between 5-2000 fold, 5-1750 fold, 5-1500 fold, 5-1250 fold, 5-1000 fold, 5-900 fold, 5-800 fold, 5-700 fold, 5-500 fold, 5-400 fold, 5-250 fold, 5-200 fold, 5-100 fold, 5-75 fold, 5-50 fold, 5-40 fold, 5-30 fold, 5-25 fold, 100-2000 fold, 200-2000 fold, 300-2000 fold, 500-2000 fold, 750-2000 fold, 1000-2000 fold, 1250-2000 fold, 1500-2000 fold, 5-1500 fold, 25-1500 fold, 50-1500 fold, 75-1500 fold, 100-1500 fold, 200-1500 fold, 300-1500 fold, 500-1500 fold, 750-1500 fold, 1000-1500 fold, or 1250-1500 fold, relative to single inhibitor administration.

In a further embodiment, the method of treating, method of suppressing, pharmaceutical composition, or pharmaceutical kit, of any one of the above embodiments and any one or more of the further embodiments herein, wherein the administering of the inhibitor or combination of inhibitors suppresses the enhanced downstream signaling from said CXCR4-GPCRx heteromer in the cancer patient in the range of between 5-2000 fold, 5-1750 fold, 5-1500 fold, 5-1250 fold, 5-1000 fold, 5-900 fold, 5-800 fold, 5-700 fold, 5-500 fold, 5-400 fold, 5-250 fold, 5-200 fold, 5-100 fold, 5-75 fold, 5-50 fold, 5-40 fold, 5-30 fold, 5-25 fold, 100-2000 fold, 200-2000 fold, 300-2000 fold, 500-2000 fold, 750-2000 fold, 1000-2000 fold, 1250-2000 fold, 1500-2000 fold, 5-1500 fold, 25-1500 fold, 50-1500 fold, 75-1500 fold, 100-1500 fold, 200-1500 fold, 300-1500 fold, 500-1500 fold, 750-1500 fold, 1000-1500 fold, or 1250-1500 fold, relative to suppression of downstream signaling from either a CXCR4 protomer or a GPCRx protomer in their respective individual protomer context.

In a further embodiment, the method of treating, method of suppressing, pharmaceutical composition, or pharmaceutical kit, of any one of the above embodiments and any one or more of the further embodiments herein, wherein the GPCRx of the CXCR4-GPCRx heteromer is selected from the group consisting of: ADCYAP1R1, ADORA2B, ADORA3, ADRB2, C5AR1, CALCR, CHRM1, EDNRB, HRH1, MLNR, NTSR1, and TACR3; for example, selected from the group consisting of: ADCYAP1R1, ADORA2B, ADORA3, ADRB2, C5AR1, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, MLNR, NTSR1, and TACR3; selected from the group consisting of: ADCYAP1R1, ADORA2B, ADORA3, ADRB2, CHRM1, EDNRB, HRH1, NTSR1, and TACR3; selected from the group consisting of: ADCYAP1R1, ADORA2B, ADORA3, ADRB2, CHRM1, HRH1, NTSR1, and TACR3; selected from the group consisting of: ADORA2B, ADORA3, ADRB2, CHRM1, EDNRB, HRH1, NTSR1, and TACR3; selected from the group consisting of: ADRB2, CHRM1, EDNRB, HRH1, NTSR1, and TACR3; selected from the group consisting of: ADRB2, CHRM1, EDNRB, HRH1, and TACR3; selected from the group consisting of: ADRB2, CHRM1, HRH1, and TACR3; selected from the group consisting of: ADRB2, EDNRB, HRH1, and TACR3; selected from the group consisting of: ADRB2, EDNRB, and HRH1; selected from the group consisting of: ADRB2, CHRM1, and HRH1; or selected from the group consisting of: ADRB2, HRH1, and TACR3.

In a further embodiment, the method of treating, method of suppressing, pharmaceutical composition, or pharmaceutical kit, of any one of the above embodiments and any one or more of the further embodiments herein, wherein the GPCRx inhibitor is selected from the group consisting of: ADCYAP1R1 inhibitor, ADORA2B inhibitor, ADORA3 inhibitor, ADRB2 inhibitor, C5AR1 inhibitor, CALCR inhibitor, CHRM1 inhibitor, EDNRB inhibitor, HRH1 inhibitor, MLNR inhibitor, NTSR1 inhibitor, and TACR3 inhibitor; for example, selected from the group consisting of: ADCYAP1R1 inhibitor, ADORA2B inhibitor, ADORA3 inhibitor, ADRB2 inhibitor, C5AR1 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, MLNR inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADCYAP1R1 inhibitor, ADORA2B inhibitor, ADORA3 inhibitor, ADRB2 inhibitor, CHRM1 inhibitor, HRH1 inhibitor, NTSR1 inhibitor, and TACR3 inhibitor; selected from the group consisting of: ADORA2B inhibitor, ADORA3 inhibitor, ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, NTSR1 inhibitor, and TACR3 inhibitor; selected from the group consisting of: ADRB2 inhibitor, CHRM1 inhibitor, EDNRB inhibitor, HRH1 inhibitor, and TACR3 inhibitor; selected from the group consisting of: ADRB2 inhibitor, CHRM1 inhibitor, HRH1 inhibitor, and TACR3 inhibitor; selected from the group consisting of: ADRB2 inhibitor, EDNRB inhibitor, HRH1 inhibitor, and TACR3 inhibitor; selected from the group consisting of: ADRB2 inhibitor, EDNRB inhibitor, and HRH1 inhibitor; selected from the group consisting of: ADRB2 inhibitor, CHRM1 inhibitor, and HRH1 inhibitor; or selected from the group consisting of: ADRB2 inhibitor, HRH1, inhibitor and TACR3 inhibitor.

In a further embodiment, the method of treating, method of suppressing, pharmaceutical composition, or pharmaceutical kit, of any one of the above embodiments and any one or more of the further embodiments herein, wherein the initial concentration of the inhibitor is in the range of between 1-10 uM (or each of the inhibitors of the combination at concentrations in the range of between 1-10 uM), such as at a concentration of 1, 2, 3, 4, 5, 6, 7, 8, 9, or 10 uM, in testing and/or evaluating said inhibitor, or combination of inhibitors, regarding whether effective, or therapeutically effective, in suppressing an enhanced downstream signaling from a CXCR4-GPCRx heteromer.

Materials and Methods

Reagents

BAY 60-6583, CGS 21680, C5a, acetylcholine, motilin, neurotensin, senktide, salmeterol, Cl-IB-MECA, salmon calcitonin, BQ-3020, octreotide, VU0255035, cetirizine, pyrilamine, MA-2029, meclinertant, and SSR 146977 were purchased from Tocris Bioscience (Ellisville, Mo., USA). Galanin, endothelin-1, histamine, Prostaglandin E2 (PGE2), SRIF-14 (somatostatin), and bethanechol were purchased from Sigma-Aldrich (St Louis, Mo., USA). CXCL12, vasoactive intestinal peptide (VIP), and CCL2 were purchased from R&D systems (Minneapolis, Minn., USA). Formoterol, carvedilol, oxybutynin, bosentan, hydroxyzine, and loratadine were from Prestwick Chemical (Illkirch, France). Apelin-13, roxithromycin, AMD3100, umeclidinium were obtained from Cayman Chemical Company (Ann Arbor, Mich., USA), Selleckchem (Houston, Tex., USA), Medchem express (Princeton, N.J., USA), and Santa Cruz Biotechnology (Santa Cruz, Calif., USA), respectively.

Construction of Adenoviral Vectors Containing GPCR cDNAs

Vectors containing BiFC fragments, pCS2+ VNm10 and pBiFC-VC155, were obtained from Chang-Deng Hu (Hu et al., 2002) and James Smith (Saka et al., 2007), respectively. The VNm10 is a Venus VN154 variant containing L46F and L64F mutations. To construct pAdBiFC-VN and pAdBiFC-VC vectors, DNAs containing VNm10 and VC155 were amplified by PCR and cloned into pShuttle-CMV. pAdBiFC-VN and pAdBiFC-VC vectors were obtained through homologous recombination between pAdEasy-1 and either pShuttle-CMV-VNm10 or pShuttle-CMV-VC155 using AdEasy vector system according to the manufacturer's instructions (Qbiogene, Carlsbad, Calif.). Human GPCR cDNA clones were obtained from the Missouri S&T cDNA Resource Center (Rolla, Mo., USA). GPCR cDNAs were amplified by PCR and cloned into pDONR201 vector. Adenoviruses encoding GPCR, GPCR-VN, GPCR-VC, and GPCR-EGFP were obtained through in vitro LR recombination between entry clones containing GPCR and either pAdHTS, pAdBiFC-VN, pAdBiFC-VC, or pAdHTS-GFPC vectors, and subsequent transfection into 293A cells using AdHTS system as described previously (Choi et al., 2012; Song et al., 2014).

Cell Culture

U-2 OS cells and MDA-MB-231 cells were purchased from the American Type Culture Collection (Manassas, Va., USA), and 293A cells were from Invitrogen (Carlsbad, Calif., USA). U-2 OS cells, MDA-MB-231 cells, and 293A cells were grown in McCoy's 5A medium, RPMI 1640, and Modified Eagle's medium, respectively, in the presence of 10% fetal bovine serum (FBS), 100 units/ml of penicillin, and 100 µg/ml of streptomycin. Cells were cultured with 5% $CO_2$ at 37° C.

BiFC Assay

U-2 OS cells were seeded at a density of 3000 cells per well in a black 96-well clear-bottom plate in 100 µl of McCoy's 5A medium supplemented with 10% FBS. On the following day, the cells were transduced with 30 MOI each of adenoviruses encoding GPCR-VN and GPCR-VC. Three days post-transduction, cells were fixed with 2% formaldehyde and nuclei were stained with Hoechst 33342 (Invitrogen, Carlsbad, Calif.). Images were acquired using IN cell Analyzer 1000 and analyzed with IN Cell Developer Tool-Box (GE Healthcare, Waukesha, Wis.). BiFC and nuclear images were visualized using a ×20 objective and 360-nm (Hoechst) and 480-nm excitation filters, and monitored through 460- and 535-nm emission filters, respectively, with a 61002 trichroic mirror.

Co-Internalization Assay

U-2 OS cells were seeded at a density of 3000 cells per well in a black 96-well clear-bottom plate in 100 µl of McCoy's 5A medium supplemented with 10% FBS. On the following day, the cells were co-transduced with adenoviruses encoding CXCR4-EGFP (10 MOI) and GPCR-VC or GPCR-VN (30 MOI). Two days post-transduction, cells were stimulated with GPCRx agonists for 30 min and fixed with 2% formaldehyde. Images were obtained using IN cell analyzer 2000 using an excitation wavelength of 480 nm and an emission wavelength of 535 nm.

Calcium Mobilization Assay

MDA-MB-231 human breast cancer cells were seeded at 20,000 cells per well in a black clear bottom 96-well plate (Corning Costar, #3340) in 100 µl of RPMI 1640 supplemented with 10% FBS. The next day, cells were co-transduced with 10 MOI of CXCR4 and 30 MOI of HA-VC, 10 MOI of HA-VC and 30 MOI of GPCRx, or 10 MOI of CXCR4 and 30 MOI of GPCRx. Adenoviruses encoding HA-VC were used to adjust the total amount of adenoviruses transduced. After 2 days, cells were washed twice with assay buffer (Hank's balanced salt solution without phenol red, supplemented with 0.1% BSA and 20 mM HEPES, pH7.4), and stained with 5 µg/ml of Cal-520 AM (AAT Bioquest, Sunnyvale, Calif., USA) diluted in assay buffer for 2 hr. Cells were washed with assay buffer three times, and incubated at 37° C. for another 30 min. Plate was loaded on a FlexStation 3 Multi-Mode Microplate Reader (Molecular Devices, Sunnyvale, Calif., USA) and GPCRx agonists were added. Intracellular Ca2+ mobilization was measured at 37° C. using an excitation wavelength of 490 nm and an emission wavelength of 525 nm. Antagonists or vehicles were added 30 min before agonist treatment.

Internalization Inhibition Assay

CXCR4-GFP expressed U-2 OS cells were seeded at a density of 5000 cells per well in a black 96-well clear-bottom plate in 100 µl of McCoy's 5A medium supplemented with 10% FBS. On the following day, the cells were transduced with adenoviruses encoding GPCRx (30 MOI). Two days post-transduction, cells were stimulated with SDF-1 and/or GPCRx agonists for 20 min and fixed with 4% paraformaldehyde. Images were obtained using IN cell analyzer 2500 using an excitation wavelength of 480 nm and an emission wavelength of 535 nm.

Proliferation Assay

PDCs were seeded in 384-well plate at 500 ea/well in 40 ul culture media. After overnight growth, the cells were cultured for 7 days in the presence of several dose of GPCRx antagonist or DMSO alone. After the 7-day incubation, 15 ul ATPlite (PerkinElmer, Cat. No. 6016739) was added into the each well and the plates were shaken for 5 minutes in an orbital shaker at 700 rpm. The luminescent signal was detected within 30 minutes at PerkinElmer TopCount detection instrument. The cell viability was calculated using the equation: Cell viability (%)=(OD of antagonist treatment/OD of DMSO only treatment)×100%.

Proximity Ligation Assay in Cell

CXCR4 overexpression cell lines, the U2OS-CXCR4 was infected with ADRB2 expressing adenovirus, Ad-ADRB2 at the dose of 0, 2.5, 10, 40 MOIs for 2 days. Proximity ligation assays (PLA) were performed as described previously (Brueggemann et al., 2014; Tripathi et al., 2014). To perform PLA, infected cells were fixed with 4% paraformaldehyde (PFA) on sixteen-well tissue culture slides. Slides were blocked with blocking solution provided by Duolink and incubated with mouse anti-CXCR4 (1:200, Santacruz, Sc-53534), Rabbit anti-ADRB2 (1:200, Thermoscientific, PAS-33333) at 37° C. for 1 h in a humidifying chamber. Slides were then washed and incubated (1 h at 37° C.) with secondary anti-rabbit and anti-mouse antibodies conjugated with plus and minus Duolink II PLA probes. Slides were washed again and then incubated with ligation-ligase solution (30 min at 37° C.) followed by incubation with amplification-polymerase solution (2 h at 37° C.). Slides were then mounted with minimal volume of Duolink II mounting medium with 4',6-diamidino-2phenylindole (DAPI) for 15-30 min, and PLA signals [Duolink In Situ Detection Reagents Green (λ excitation/emission 495/527 nm) or Red (λ excitation/emission 575/623 nm)] were identified as fluorescent spots under a IN Cell analyzer 2500.

Proximity Ligation Assay in PDC

PDCs were seeded in 96-chamber slide at 100000 ea/well in 100 ul culture media. To perform PLA, PDCs were fixed with 4% paraformaldehyde (PFA) and were blocked with blocking solution provided by Duolink and incubated with mouse anti-CXCR4 (1:200, Santacruz, Sc-53534), Rabbit anti-ADRB2 (1:200, Thermoscientific, PAS-33333), Rabbit anti-CHRM1 (1:200, Ls bio, Ls-C313301) at 37° C. for 1 h in a humidifying chamber. Slides were then washed and incubated (1 h at 37° C.) with secondary anti-rabbit and anti-mouse antibodies conjugated with plus and minus Duolink II PLA probes. Slides were washed again and then incubated with ligation-ligase solution (30 min at 37° C.) followed by incubation with amplification-polymerase solution (2 h at 37° C.). Slides were then mounted with minimal volume of Duolink II mounting medium with 4',6-diamidino-2phenylindole (DAPI) for 15-30 min, and PLA signals [Duolink In Situ Detection Reagents Green (λ excitation/ emission 495/527 nm) or Red (λ excitation/emission 575/623 nm)] were identified as fluorescent spots under a IN Cell analyzer 2500.

Proximity Ligation Assay in PDX

To perform PLA with PDX samples, the glioblastoma patient derived FFPE samples were used (provided by Samsung Seoul hospital in Seoul, Korea). After FFPE sample were de-paraffinized and performed heat induced antigen retrieval for 15 minutes at 100° C. Slides were blocked with blocking solution provided by Duolink and incubated with rabbit anti-CXCR4 (1:200, Thermoscientific, PA3305), mouse anti-ADRB2 (1:200, Santacruz, Sc-271322), at 37° C. for 1 h in a humidifying chamber. The other process was same as described above (PLA with PDC).

Chemotactic Migration Assay

Transwell plates (8 μm pore size polycarbonate membrane, 6.5-mm diameter) were coated with 50 μg/mL collagen for 2 h at 37° C. (Corning Inc.). MDA-MB-231 cells were serum-starved 24 h and then plated in serum-free medium containing 0.5% BSA in the top chamber (20,000 cells/100 μL). Antagonists or inverse agonists were added to the cells 30 min before plating the cells in the transwell plates. Attractants were added in the bottom chamber. Antagonists or inverse agonists were also included in the bottom chamber. After 3 h at 37° C., cells on the top transwell membrane were removed using a cotton swab, fixed, and stained with 0.1% Crystal violet. Chemotaxis was quantified by counting the migrated cells on the lower surface of the membrane of 10 fields per chamber at 10× objective.

Reverse Transcription-Quantitative Polymerase Chain Reaction (RT-qPCR)

Total RNA was extracted using TRIzol (Invitrogen) and cDNA was synthesized from 1 μg of total RNA after treatment with DNase I (Sigma). RT-qPCR was conducted using SensiFAST SYBR kit (Bioline). Primer sequences are as follows:

```
ADRB2-F:
                                         (SEQ ID NO: 1)
5'-CTCTTCCATCGTGTCCTTCTAC-3',

ADRB2-R:
                                         (SEQ ID NO: 2)
5'-AATCTTCTGGAGCTGCCTTT-3';

HRH1-F:
                                         (SEQ ID NO: 3)
5'-CCTCTGCTGGATCCCTTATTTC-3',

HRH1-R:
                                         (SEQ ID NO: 4)
5'-GGTTCAGTGTGGAGTTGATGTA-3';

CXCR4-F:
                                         (SEQ ID NO: 5)
5'-CCACCATCTACTCCATCATCTTC-3',

CXCR4-R:
                                         (SEQ ID NO: 6)
5'-ACTTGTCCGTCATGCTTCTC-3';

β-actin-F:
                                         (SEQ ID NO: 7)
5'-GGAAATCGTGCGTGACATTAAG-3', β-actin-R:
                                         (SEQ ID NO: 8)
5'-AGCTCGTAGCTCTTCTCCA-3';

GAPDH-F:
                                         (SEQ ID NO: 9)
5'-ATGACATCAAGAAGGTGGTGAA-3',

GAPDH-R:
                                         (SEQ ID NO: 10)
5'-GCTGTTGAAGTCAGAGGAGAC-3'.
```

Threshold cycles (Ct) were calculated by QuantStudio 3 Real-Time PCR system (Thermo Fisher Scientific).

Lentivirus Production pLenti CMV Hygro DEST (w117-1) was a gift from Eric Campeau & Paul Kaufman (Addgene plasmid #17454) (Campeau et al., 2009). CXCR4 cDNA was inserted into the lentiviral vector using LR recombination. Lentiviruses encoding CXCR4 were produced using ViraPower Lentiviral Expression Systems (Invitrogen).

Construction of Stable Cell Lines Expressing CXCR4 Alone or CXCR4 and ADRB2 Heteromer To establish stable CXCR4 expressing cell lines, lentiviral stock (containing the packaged pLenti6-CXCR4 expression construct which inserted with CXCR4 gene in pLenti-CMV Hygro DEST (Addgene, #17454)), were produced by co-transfecting the ViraPower Lentiviral Packaging Mix (Invitrogen, K497500) and pLenti6-CXCR4 expression construct into 293FT producer cell line. Transduction of this lentiviral stock into A549 cell line was performed and followed by selection with hygromycin (100 μg/mL) and blasticidine (5 μg/mL). To establish stable CXCR4-ADRB2 heteromer expressing cell lines, lentiviral stock (containing the packaged pLenti6/V5-ADRB2 expression construct which inserted with ADRB2 gene in pLenti6/V5-DEST Gateway™ Vector (Invitrogen, V49610)), were produced by co-transfecting the ViraPower Packaging Mix and pLenti6/V5-ADRB2 expression construct into 293FT producer cell line. Transduction of this lentiviral stock into A549-CXCR4 cell line was performed and followed by selection with hygromycin (100 μg/mL) and blasticidine (5 μg/mL). Then clones resistant to antibiotics were selected and performed RT-qPCR and immunofluorescence to confirm the expression of the inserted gene, CXCR4 and ADRB2.

Mouse Xenograft Model

Five week-old, female Balb/c-nu/nu mice were obtained from Envigo (France) and maintained in specific pathogen-free animal facility. All protocols for animal use and euthanasia were approved by the Qubest Bio (South Korea) Animal Experimental Ethics Committee based on the Animal Protection Act. The $1 \times 10^7$ cells of A549, A549-CXCR4 or A549-CXCR4-ADRB2 were suspended in 100 μL of phosphate-buffered saline (PBS) and were implanted by subcutaneously in axillary region between the clavicular and chest wall on the right side of the mouse. The tumor growth was monitored every third or fourth day by measuring the length (L) and width (W) of the tumor with an electronic caliper and calculating tumor volume in the basis of the following formula: Volume=$0.5 \, LW^2$.

Generation of CXCR4 or HRH1 Knockout Cells Using CRISPR/Cas9 System

CRISPR guide RNAs targeting CXCR4 and HRH1, and non-targeting guide RNA cloned in lentiCRISPR v2 vector were purchased from GenScript (Piscataway, N.J.) (Sanjana et al., 2014). The guide RNA sequences are as follows:

```
                             (CXCR4 gRNA #1; (SEQ ID NO: 11))
TGTTGGCTGCCTTACTACAT,
```

```
                    (HRH gRNA #3; (SEQ ID NO: 12))
CGATCAAGTCCGCCACCGAG,
and (non-targeting gRNA; (SEQ ID NO: 13))
ACGGAGGCTAAGCGTCGCAA.
```

Lentiviruses were produced using ViraPower Lentiviral Expression Systems (Invitrogen). MDA-MB-231 cells and MDA-MB-231 cells overexpressing CXCR4 (MDA$^{CXCR4+}$) were transduced with lentiviruses encoding non-targeting gRNA, CXCR4 gRNA, or HRH1 gRNAs. Cells were selected with puromycin (3 µM) for 2 weeks and loss of CXCR4 and HRH1 was estimated with immunoblotting and calcium responses, respectively. For detecting CXCR4, anti-CXCR4 rabbit monoclonal antibody (Abcam, # ab124824) was used.

Source of GPCRx Inhibitors

Ulocuplumab was purchased from Creative Biolabs (Shirley, N.Y., USA). BKT140 was purchased from Chem Scene (Monmouth Junction, N.J., USA). Carazolol was purchased from Santacruz Biotech (Dallas, Tex., USA). Osanetant was purchased from Axon Medchem, (Groningen, Netherland). M65 and CT-(8-32) (salmon) were from Bachem (San Diego, Calif., USA). PACAP-(6-38), W54011, PMX205, PMX53, AC187, SB 222200, and Talnetant were from Tocris Bioscience (Ellisville, Mo., USA). Propranolol, Promethazine, Cyproheptadine, Hydroxyzine, Ambrisentan and macitentan were from Prestwick Chemical (Illkirch, France), and Selleckchem (Houston, Tex., USA), respectively.

In Vivo Studies

For the antitumor efficacy test using CXCR4 and ADRB2 inhibitor, A549-CXCR4-ADRB2 cell line overexpressing CXCR4 and ADRB2 in A549, lung cancer cell line was subcutaneously administered (1×10$^7$ cell in 100 µL PBS/head) to BALB/c-nu. When Tumor size reached 50-100 mm$^3$, groups of ten mice were administrated with vehicle (1% dimethylcellulose in PBS), CXCR4 inhibitor (3 mg/kg of LY2510924 formulated in PBS, 10 mg/kg of AMD070 formulated in DMSO), ADRB2 inhibitor (30 mg/kg of Carvedilol formulated in 1% dimethylcellulose in PBS) or combination of CXCR4 and ADRB2 inhibitor, AMD070 and Carvedilol, or LY2510924 and Carvedilol once a day for 21-23 days. LY2510924 was subcutaneously injected and AMD070 or Carvedilol was administrated orally. The tumor growth was monitored every third or fourth day by measuring the length(L) and width(W) of the tumor: Volume=0.5 LW$^2$.

REFERENCES

Each of the following references, in their entirety, are incorporated herein by reference:

Abd Alla, J., Reeck, K., Langer, A., Streichert, T., and Quitterer, U. (2009). Calreticulin enhances B2 bradykinin receptor maturation and heterodimerization. Biochem Biophys Res Commun 387, 186-190;

Agrawal, L., Lu, X., Qingwen, J., VanHorn-Ali, Z., Nicolescu, I. V., McDermott, D. H., Murphy, P. M., and Alkhatib, G. (2004). Role for CCR5Delta32 protein in resistance to R5, R5X4, and X4 human immunodeficiency virus type 1 in primary CD4+ cells. J Virol 78, 2277-2287;

Albrandt, K., Brady, E. M., Moore, C. X., Mull, E., Sierzega, M. E., and Beaumont, K. (1995). Molecular cloning and functional expression of a third isoform of the human calcitonin receptor and partial characterization of the calcitonin receptor gene. Endocrinology 136, 5377-5384;

Allen, C. D., Ansel, K. M., Low, C., Lesley, R., Tamamura, H., Fujii, N., and Cyster, J. G. (2004). Germinal center dark and light zone organization is mediated by CXCR4 and CXCR5. Nat Immunol 5, 943-952;

Ara, T., Itoi, M., Kawabata, K., Egawa, T., Tokoyoda, K., Sugiyama, T., Fujii, N., Amagai, T., and Nagasawa, T. (2003). A role of CXC chemokine ligand 12/stromal cell-derived factor-1/pre-B cell growth stimulating factor and its receptor CXCR4 in fetal and adult T cell development in vivo. J Immunol 170, 4649-4655;

Armando, S., Quoyer, J., Lukashova, V., Maiga, A., Percherancier, Y., Heveker, N., Pin, J. P., Prezeau, L., and Bouvier, M. (2014). The chemokine CXC4 and CC2 receptors form homo- and heterooligomers that can engage their signaling G-protein effectors and betaarrestin. FASEB J 28, 4509-4523;

Barmania, F., and Pepper, M. S. (2013). C-C chemokine receptor type five (CCR5): An emerging target for the control of HIV infection. Appl Transl Genom 2, 3-16;

Bartolome, R. A., Ferreiro, S., Miquilena-Colina, M. E., Martinez-Prats, L., Soto-Montenegro, M. L., Garcia-Bernal, D., Vaquero, J. J., Agami, R., Delgado, R., Desco, M., et al. (2009). The chemokine receptor CXCR4 and the metalloproteinase MT1-MMP are mutually required during melanoma metastasis to lungs. Am J Pathol 174, 602-612;

Batlle, E., and Clevers, H. (2017). Cancer stem cells revisited. Nat Med 23, 1124-1134;

Bazin, H., Trinquet, E., and Mathis, G. (2002). Time resolved amplification of cryptate emission: a versatile technology to trace biomolecular interactions. J Biotechnol 82, 233-250;

Beck a et al., "Strategies and challenges for the next generation of antibody-drug conjugates", Nature Reviews Drug Discovery, 16:315-337, (2017);

Bjarnadottir, T. K., Gloriam, D. E., Hellstrand, S. H., Kristiansson, H., Fredriksson, R., and Schioth, H. B. (2006). Comprehensive repertoire and phylogenetic analysis of the G protein-coupled receptors in human and mouse. Genomics 88, 263-273;

Bodart, V., Anastassov, V., Darkes, M. C., Idzan, S. R., Labrecque, J., Lau, G., Mosi, R. M., Neff, K. S., Nelson, K. L., Ruzek, M. C., et al. (2009). Pharmacology of AMD3465: a small molecule antagonist of the chemokine receptor CXCR4. Biochem Pharmacol 78, 993-1000;

Braadland, P. R., Ramberg, H., Grytli, H. H., and Tasken, K. A. (2014). beta-Adrenergic Receptor Signaling in Prostate Cancer. Front Oncol 4, 375;

Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human hematopoietic stem and progenitor cells with AMD3100, a CXCR4 antagonist. J Exp Med 201, 1307-1318;

Brueggemann, L. I., Mackie, A. R., Cribbs, L. L., Freda, J., Tripathi, A., Majetschak, M., and Byron, K. L. (2014). Differential protein kinase C-dependent modulation of Kv7.4 and Kv7.5 subunits of vascular Kv7 channels. J Biol Chem 289, 2099-2111;

Buckley, C. D., Amft, N., Bradfield, P. F., Pilling, D., Ross, E., Arenzana-Seisdedos, F., Amara, A., Curnow, S. J., Lord, J. M., Scheel-Toellner, D., et al. (2000). Persistent induction of the chemokine receptor CXCR4 by TGF-beta 1 on synovial T cells contributes to their accumulation within the rheumatoid synovium. J Immunol 165, 3423-3429;

Burbassi, S., Sengupta, R., and Meucci, 0. (2010). Alterations of CXCR4 function in mu-opioid receptor-deficient glia. Eur J Neurosci 32, 1278-1288;

Burger, J. A., Burger, M., and Kipps, T. J. (1999). Chronic lymphocytic leukemia B cells express functional CXCR4 chemokine receptors that mediate spontaneous migration beneath bone marrow stromal cells. Blood 94, 3658-3667;

Burger, J. A., and Kipps, T. J. (2006). CXCR4: a key receptor in the crosstalk between tumor cells and their microenvironment. Blood 107, 1761-1767;

Burger, J. A., and Peled, A. (2009). CXCR4 antagonists: targeting the microenvironment in leukemia and other cancers. Leukemia 23, 43-52;

Burger, J. A., Stewart, D. J., Wald, O., and Peled, A. (2011). Potential of CXCR4 antagonists for the treatment of metastatic lung cancer. Expert Rev Anticancer Ther 11, 621-630;

Bushlin, I., Gupta, A., Stockton, S. D., Jr., Miller, L. K., and Devi, L. A. (2012). Dimerization with cannabinoid receptors allosterically modulates delta opioid receptor activity during neuropathic pain. PLoS One 7, e49789;

Callen, L., Moreno, E., Barroso-Chinea, P., Moreno-Delgado, D., Cortes, A., Mallol, J., Casado, V., Lanciego, J. L., Franco, R., Lluis, C., et al. (2012). Cannabinoid receptors CB1 and CB2 form functional heteromers in brain. J Biol Chem 287, 20851-20865;

Campeau, E., Ruhl, V. E., Rodier, F., Smith, C. L., Rahmberg, B. L., Fuss, J. O., Campisi, J., Yaswen, P., Cooper, P. K., and Kaufman, P. D. (2009). A versatile viral system for expression and depletion of proteins in mammalian cells. PLoS One 4, e6529;

Canonica, G. W., and Blaiss, M. (2011). Antihistaminic, anti-inflammatory, and antiallergic properties of the nonsedating second-generation antihistamine desloratadine: a review of the evidence. World Allergy Organ J 4, 47-53;

Cao, H. L., Liu, Z. J., and Chang, Z. (2017). Cordycepin induces apoptosis in human bladder cancer cells via activation of A3 adenosine receptors. Tumour Biol 39, 1010428317706915;

Cashen, A. F., Nervi, B., and DiPersio, J. (2007). AMD3100: CXCR4 antagonist and rapid stem cell-mobilizing agent. Future Oncol 3, 19-27;

Chatterjee, S., Behnam Azad, B., and Nimmagadda, S. (2014). The intricate role of CXCR4 in cancer. Adv Cancer Res 124, 31-82;

Chen, J. F., Eltzschig, H. K., and Fredholm, B. B. (2013). Adenosine receptors as drug targets—what are the challenges? Nat Rev Drug Discov 12, 265-286;

Chen, Y., Ramjiawan, R. R., Reiberger, T., Ng, M. R., Hato, T., Huang, Y., Ochiai, H., Kitahara, S., Unan, E. C., Reddy, T. P., et al. (2015). CXCR4 inhibition in tumor microenvironment facilitates anti-programmed death receptor-1 immunotherapy in sorafenib-treated hepatocellular carcinoma in mice. Hepatology 61, 1591-1602;

Cheng, X., Wang, H., Zhang, X., Zhao, S., Zhou, Z., Mu, X., Zhao, C., and Teng, W. (2017). The Role of SDF-1/CXCR4/CXCR7 in Neuronal Regeneration after Cerebral Ischemia. Front Neurosci 11, 590;

Cho, K. S., Yoon, S. J., Lee, J. Y., Cho, N. H., Choi, Y. D., Song, Y. S., and Hong, S. J. (2013). Inhibition of tumor growth and histopathological changes following treatment with a chemokine receptor CXCR4 antagonist in a prostate cancer xenograft model. Oncol Lett 6, 933-938;

Choi, E. W., Seen, D. S., Song, Y. B., Son, H. S., Jung, N. C., Huh, W. K., Hahn, J. S., Kim, K., Jeong, J. Y., and Lee, T. G. (2012). AdHTS: a high-throughput system for generating recombinant adenoviruses. J Biotechnol 162, 246-252;

Chong, B. F., and Mohan, C. (2009). Targeting the CXCR4/CXCL12 axis in systemic lupus erythematosus. Expert Opin Ther Targets 13, 1147-1153;

Choy, C., Raytis, J. L., Smith, D. D., Duenas, M., Neman, J., Jandial, R., and Lew, M. W. (2016). Inhibition of beta2-adrenergic receptor reduces triple-negative breast cancer brain metastases: The potential benefit of perioperative beta-blockade. Oncol Rep 35, 3135-3142;

Chu, T., Shields, L. B. E., Zhang, Y. P., Feng, S. Q., Shields, C. B., and Cai, J. (2017). CXCL12/CXCR4/CXCR7 Chemokine Axis in the Central Nervous System: Therapeutic Targets for Remyelination in Demyelinating Diseases. Neuroscientist 23, 627-648;

Chung, S. H., Seki, K., Choi, B. I., Kimura, K. B., Ito, A., Fujikado, N., Saijo, S., and Iwakura, Y. (2010). CXC chemokine receptor 4 expressed in T cells plays an important role in the development of collagen-induced arthritis. Arthritis Res Ther 12, R188;

Comps-Agrar, L., Maurel, D., Rondard, P., Pin, J. P., Trinquet, E., and Prezeau, L. (2011). Cell-surface protein-protein interaction analysis with time-resolved FRET and snap-tag technologies: application to G protein-coupled receptor oligomerization. Methods Mol Biol 756, 201-214;

Cooper, A. J., Narasimhan, S., Rickels, K., and Lohoff, F. W. (2013). Genetic polymorphisms in the PACAP and PAC1 receptor genes and treatment response to venlafaxine XR in generalized anxiety disorder. Psychiatry Res 210, 1299-1300;

Covic, L., Gresser, A. L., Talavera, J., Swift, S., and Kuliopulos, A. (2002). Activation and inhibition of G protein-coupled receptors by cell-penetrating membrane-tethered peptides. Proc Natl Acad Sci USA, 99, 643-648;

Crawford, J. B., Chen, G., Gauthier, D., Wilson, T., Carpenter, B., Baird, I. R., McEachern, E., and Alan Kaller, C. H., Bem Atsma, Renato T. Skerlj, and Gary J. Bridger (2008). AMD070, a CXCR4 Chemokine Receptor Antagonist: Practical Large-Scale Laboratory Synthesis. Organic Process Research & Development 12, 823-830;

D'Alterio, C., Barbieri, A., Portella, L., Palma, G., Polimeno, M., Riccio, A., Ierano, C., Franco, R., Scognamiglio, G., Bryce, J., et al. (2012). Inhibition of stromal CXCR4 impairs development of lung metastases. Cancer Immunol Immunother 61, 1713-1720;

Dacquin, R., Davey, R. A., Laplace, C., Levasseur, R., Morris, H. A., Goldring, S. R., Gebre-Medhin, S., Galson, D. L., Zajac, J. D., and Karsenty, G. (2004). Amylin inhibits bone resorption while the calcitonin receptor controls bone formation in vivo. J Cell Biol 164, 509-514;

Davey, R. A., Turner, A. G., McManus, J. F., Chiu, W. S., Tjahyono, F., Moore, A. J., Atkins, G. J., Anderson, P. H., Ma, C., Glatt, V., et al. (2008). Calcitonin receptor plays a physiological role to protect against hypercalcemia in mice. J Bone Miner Res 23, 1182-1193;

De Clercq, E. (2003). The bicyclam AMD3100 story. Nat Rev Drug Discov 2, 581-587;

De Falco, V., Guarino, V., Avilla, E., Castellone, M. D., Salerno, P., Salvatore, G., Faviana, P., Basolo, F., Santoro, M., and Melillo, R. M. (2007). Biological role and potential therapeutic targeting of the chemokine receptor CXCR4 in undifferentiated thyroid cancer. Cancer Res 67, 11821-11829;

de Graaf, C., Kooistra, A. J., Vischer, H. F., Katritch, V., Kuijer, M., Shiroishi, M., Iwata, S., Shimamura, T., Stevens, R. C., de Esch, I. J., et al. (2011). Crystal structure-based virtual screening for fragment-like ligands of the human histamine H(1) receptor. J Med Chem 54, 8195-8206;

De Klerck, B., Geboes, L., Hatse, S., Kelchtermans, H., Meyvis, Y., Vermeire, K., Bridger, G., Billiau, A., Schols, D., and Matthys, P. (2005). Pro-inflammatory properties of stromal cell-derived factor-1 (CXCL12) in collagen-induced arthritis. Arthritis Res Ther 7, R1208-1220;

de Nigris, F., Schiano, C., Infante, T., and Napoli, C. (2012). CXCR4 inhibitors: tumor vasculature and therapeutic challenges. Recent Pat Anticancer Drug Discov 7, 251-264;

de Poorter, C., Baertsoen, K., Lannoy, V., Parmentier, M., and Springael, J. Y. (2013). Consequences of ChemR23 heteromerization with the chemokine receptors CXCR4 and CCR7. PLoS One 8, e58075;

Debnath, B., Xu, S., Grande, F., Garofalo, A., and Neamati, N. (2013). Small molecule inhibitors of CXCR4. Theranostics 3, 47-75;

Decaillot, F. M., Kazmi, M. A., Lin, Y., Ray-Saha, S., Sakmar, T. P., and Sachdev, P. (2011). CXCR7/CXCR4 heterodimer constitutively recruits beta-arrestin to enhance cell migration. J Biol Chem 286, 32188-32197;

Decaillot, F. M., Rozenfeld, R., Gupta, A., and Devi, L. A. (2008). Cell surface targeting of mu-delta opioid receptor heterodimers by RTP4. Proc Natl Acad Sci USA 105, 16045-16050;

Demmer, O., Gourni, E., Schumacher, U., Kessler, H., and Wester, H. J. (2011). PET imaging of CXCR4 receptors in cancer by a new optimized ligand. ChemMedChem 6, 1789-1791;

Depoortere, I. (2001). Motilin and motilin receptors: characterization and functional significance. Verh K Acad Geneeskd Belg 63, 511-529;

Desmet, C. J., Gallenne, T., Prieur, A., Reyal, F., Visser, N. L., Wittner, B. S., Smit, M. A., Geiger, T. R., Laoukili, J., Iskit, S., et al. (2013). Identification of a pharmacologically tractable Fra-1/ADORA2B axis promoting breast cancer metastasis. Proc Natl Acad Sci USA 110, 5139-5144;

DiPersio, J. F., Micallef, I. N., Stiff, P. J., Bolwell, B. J., Maziarz, R. T., Jacobsen, E., Nademanee, A., McCarty, J., Bridger, G., Calandra, G., et al. (2009a). Phase III prospective randomized double-blind placebo-controlled trial of plerixafor plus granulocyte colony-stimulating factor compared with placebo plus granulocyte colony-stimulating factor for autologous stem-cell mobilization and transplantation for patients with non-Hodgkin's lymphoma. J Clin Oncol 27, 4767-4773;

DiPersio, J. F., Stadtmauer, E. A., Nademanee, A., Micallef, I. N., Stiff, P. J., Kaufman, J. L., Maziarz, R. T., Hosing, C., Fruehauf, S., Horwitz, M., et al. (2009b). Plerixafor and G-CSF versus placebo and G-CSF to mobilize hematopoietic stem cells for autologous stem cell transplantation in patients with multiple myeloma. Blood 113, 5720-5726;

Domanska, U. M., Kruizinga, R. C., Nagengast, W. B., Timmer-Bosscha, H., Huls, G., de Vries, E. G., and Walenkamp, A. M. (2013). A review on CXCR4/CXCL12 axis in oncology: no place to hide. Eur J Cancer 49, 219-230;

Donzella, G. A., Schols, D., Lin, S. W., Este, J. A., Nagashima, K. A., Maddon, P. J., Allaway, G. P., Sakmar, T. P., Henson, G., De Clercq, E., et al. (1998). AMD3100, a small molecule inhibitor of HIV-1 entry via the CXCR4 co-receptor. Nat Med 4, 72-77;

Doranz, B. J., Filion, L. G., Diaz-Mitoma, F., Sitar, D. S., Sahai, J., Baribaud, F., Orsini, M. J., Benovic, J. L., Cameron, W., and Doms, R. W. (2001). Safe use of the CXCR4 inhibitor ALX40-4C in humans. AIDS Res Hum Retroviruses 17, 475-486;

Doring, Y., Pawig, L., Weber, C., and Noels, H. (2014). The CXCL12/CXCR4 chemokine ligand/receptor axis in cardiovascular disease. Front Physiol 5, 212;

Doucette, L. P., and Walter, M. A. (2017). Prostaglandins in the eye: Function, expression, and roles in glaucoma. Ophthalmic Genet 38, 108-116;

Du, Y., Long, Q., Guan, B., and Mu, L. (2015). Prognostic Value of High CXCR4 Expression in Renal Cell Carcinoma: A System Review and Meta-Analysis. Dis Markers 2015, 568980;

Eidne, K. A., Kroeger, K. M., and Hanyaloglu, A. C. (2002). Applications of novel resonance energy transfer techniques to study dynamic hormone receptor interactions in living cells. Trends Endocrinol Metab 13, 415-421;

Endres, M. J., Clapham, P. R., Marsh, M., Ahuj a, M., Turner, J. D., McKnight, A., Thomas, J. F., Stoebenau-Haggarty, B., Choe, S., Vance, P. J., et al. (1996). CD4-independent infection by HIV-2 is mediated by fusin/CXCR4. Cell 87, 745-756;

Fagerberg, L., Hallstrom, B. M., Oksvold, P., Kampf, C., Djureinovic, D., Odeberg, J., Habuka, M., Tahmasebpoor, S., Danielsson, A., Edlund, K., et al. (2014). Analysis of the human tissue-specific expression by genome-wide integration of transcriptomics and antibody-based proteomics. Mol Cell Proteomics 13, 397-406;

Fahham, D., Weiss, I. D., Abraham, M., Beider, K., Hanna, W., Shlomai, Z., Eizenberg, O., Zamir, G., Izhar, U., Shapira, O. M., et al. (2012). In vitro and in vivo therapeutic efficacy of CXCR4 antagonist BKT140 against human non-small cell lung cancer. J Thorac Cardiovasc Surg 144, 1167-1175 e1161;

Farran, B. (2017). An update on the physiological and therapeutic relevance of GPCR oligomers. Pharmacol Res 117, 303-327;

Feig, C., Jones, J. O., Kraman, M., Wells, R. J., Deonarine, A., Chan, D. S., Connell, C. M., Roberts, E. W., Zhao, Q., Caballero, O. L., et al. (2013). Targeting CXCL12 from FAP-expressing carcinoma-associated fibroblasts synergizes with anti-PD-L1 immunotherapy in pancreatic cancer. Proc Natl Acad Sci USA 110, 20212-20217;

Fernandez-Duenas, V., Taura, J. J., Cottet, M., Gomez-Soler, M., Lopez-Cano, M., Ledent, C., Watanabe, M., Trinquet, E., Pin, J. P., Luj an, R., et al. (2015). Untangling dopamine-adenosine receptor-receptor assembly in experimental parkinsonism in rats. Dis Model Mech 8, 57-63;

Ferre, S., Baler, R., Bouvier, M., Caron, M. G., Devi, L. A., Durroux, T., Fuxe, K., George, S. R., Javitch, J. A., Lohse, M. J., et al. (2009). Building a new conceptual framework for receptor heteromers. Nat Chem Biol 5, 131-134;

Ferre, S., Navarro, G., Casado, V., Cortes, A., Mallol, J., Canela, E. I., Lluis, C., and Franco, R. (2010). G protein-coupled receptor heteromers as new targets for drug development. Prog Mol Biol Transl Sci 91, 41-52;

Filmore, D. (2004). It's a GPCR world. Modern Drug Discovery American Chemical Society 2004 (November), 24-28;

Fitzpatrick, D., Purves, D., Augustine, G. (2004). "Table 20:2" (Mass: Sunderland);

Fotiadis, D., Jastrzebska, B., Philippsen, A., Muller, D. J., Palczewski, K., and Engel, A. (2006). Structure of the rhodopsin dimer: a working model for G-protein-coupled receptors. Curr Opin Struct Biol 16, 252-259;

Frederick, A. L., Yano, H., Trifilieff, P., Vishwasrao, H. D., Biezonski, D., Meszaros, J., Urizar, E., Sibley, D. R., Kellendonk, C., Sonntag, K. C., et al. (2015). Evidence against dopamine D1/D2 receptor heteromers. Mol Psychiatry 20, 1373-1385;

Furusato, B., Mohamed, A., Uhlen, M., and Rhim, J. S. (2010). CXCR4 and cancer. Pathol Int 60, 497-505;

Gao, Z. G., Ye, K., Goblyos, A., Ijzerman, A. P., and Jacobson, K. A. (2008). Flexible modulation of agonist efficacy at the human A3 adenosine receptor by the imidazoquinoline allosteric enhancer LUF6000. BMC Pharmacol 8, 20;

George, S. R., Fan, T., Xie, Z., Tse, R., Tam, V., Varghese, G., and O'Dowd, B. F. (2000). Oligomerization of mu- and delta-opioid receptors. Generation of novel functional properties. J Biol Chem 275, 26128-26135;

Gerard, C., and Gerard, N. P. (1994). C5A anaphylatoxin and its seven transmembrane-segment receptor. Annu Rev Immunol 12, 775-808;

Gianetti, E., and Seminara, S. (2008). Kisspeptin and KISS1R: a critical pathway in the reproductive system. Reproduction 136, 295-301;

Gomes, I., Ayoub, M. A., Fujita, W., Jaeger, W. C., Pfleger, K. D., and Devi, L. A. (2016). G Protein-Coupled Receptor Heteromers. Annu Rev Pharmacol Toxicol 56, 403-425;

Gomes, I., Gupta, A., Filipovska, J., Szeto, H. H., Pintar, J. E., and Devi, L. A. (2004). A role for heterodimerization of mu and delta opiate receptors in enhancing morphine analgesia. Proc Natl Acad Sci USA 101, 5135-5139;

Goodman, R. L., Lehman, M. N., Smith, J. T., Coolen, L. M., de Oliveira, C. V, Jafarzadehshirazi, M. R., Pereira, A., Iqbal, J., Caraty, A., Ciofi, P., et al. (2007). Kisspeptin neurons in the arcuate nucleus of the ewe express both dynorphin A and neurokinin B. Endocrinology 148, 5752-5760;

Gourni, E., Demmer, O., Schottelius, M., D'Alessandria, C., Schulz, S., Dijkgraaf, I., Schumacher, U., Schwaiger, M., Kessler, H., and Wester, H. J. (2011). PET of CXCR4 expression by a (68)Ga-labeled highly specific targeted contrast agent. J Nucl Med 52, 1803-1810;

Gregorio, G. G., Masureel, M., Hilger, D., Terry, D. S., Juette, M., Zhao, H., Zhou, Z., Perez-Aguilar, J. M., Hauge, M., Mathiasen, S., et al. (2017). Single-molecule analysis of ligand efficacy in beta2AR-G-protein activation. Nature 547, 68-73;

Griffith, J. W., Sokol, C. L., and Luster, A. D. (2014). Chemokines and chemokine receptors: positioning cells for host defense and immunity. Annu Rev Immunol 32, 659-702;

Griffiths, K., Dolezal, O., Cao, B., Nilsson, S. K., See, H. B., Pfleger, K. D., Roche, M., Gorry, P. R., Pow, A., Viduka, K., et al. (2016). i-bodies, Human Single Domain Antibodies That Antagonize Chemokine Receptor CXCR4. J Biol Chem 291, 12641-12657;

Griffiths, K., Habiel, D. M., Jaffar, J., Binder, U., Darby, W. G., Hosking, C. G., Skerra, A., Westall, G. P., Hogaboam, C. M., and Foley, M. (2018). Anti-fibrotic Effects of CXCR4-Targeting i-body AD-114 in Preclinical Models of Pulmonary Fibrosis. Sci Rep 8, 3212;

Guidotti, G., Brambilla, L., and Rossi, D. (2017). Cell-Penetrating Peptides: From Basic Research to Clinics. Trends Pharmacol Sci 38, 406-424;

Gullberg, M., Gustafsdottir, S. M., Schallmeiner, E., Jarvius, J., Bjarnegard, M., Betsholtz, C., Landegren, U., and Fredriksson, S. (2004). Cytokine detection by antibody-based proximity ligation. Proc Natl Acad Sci USA 101, 8420-8424;

Guo, F., Wang, Y., Liu, J., Mok, S. C., Xue, F., and Zhang, W. (2016). CXCL12/CXCR4: a symbiotic bridge linking cancer cells and their stromal neighbors in oncogenic communication networks. Oncogene 35, 816-826;

Gustafsdottir, S. M., Schallmeiner, E., Fredriksson, S., Gullberg, M., Soderberg, O., Jarvius, M., Jarvius, J., Howell, M., and Landegren, U. (2005). Proximity ligation assays for sensitive and specific protein analyses. Anal Biochem 345, 2-9;

Habert-Ortoli, E., Amiranoff, B., Loquet, I., Laburthe, M., and Mayaux, J. F. (1994). Molecular cloning of a functional human galanin receptor. Proc Natl Acad Sci USA 91, 9780-9783;

Hansen, J. L., Hansen, J. T., Speerschneider, T., Lyngso, C., Erikstrup, N., Burstein, E. S., Weiner, D. M., Walther, T., Makita, N., Iiri, T., et al. (2009). Lack of evidence for AT1R/B2R heterodimerization in COS-7, HEK293, and NIH3T3 cells: how common is the AT1R/B2R heterodimer? J Biol Chem 284, 1831-1839;

Hartimath, S. V., Domanska, U. M., Walenkamp, A. M., Rudi, A. J. O. D., and de Vries, E. F. (2013). [(9)(9)mTc]O(2)-AMD3100 as a SPECT tracer for CXCR4 receptor imaging. Nucl Med Biol 40, 507-517;

Hassan, S., Buchanan, M., Jahan, K., Aguilar-Mahecha, A., Gaboury, L., Muller, W. J., Alsawafi, Y., Mourskaia, A. A., Siegel, P. M., Salvucci, O., et al. (2011). CXCR4 peptide antagonist inhibits primary breast tumor growth, metastasis and enhances the efficacy of anti-VEGF treatment or docetaxel in a transgenic mouse model. Int J Cancer 129, 225-232;

Hatse, S., Princen, K., Bridger, G., De Clercq, E., and Schols, D. (2002). Chemokine receptor inhibition by AMD3100 is strictly confined to CXCR4. FEBS Lett 527, 255-262;

He, S. Q., Zhang, Z. N., Guan, J. S., Liu, H. R., Zhao, B., Wang, H. B., Li, Q., Yang, H., Luo, J., Li, Z. Y., et al. (2011). Facilitation of mu-opioid receptor activity by preventing delta-opioid receptor-mediated codegradation. Neuron 69, 120-131;

Heakal, Y., Woll, M. P., Fox, T., Seaton, K., Levenson, R., and Kester, M. (2011). Neurotensin receptor-1 inducible palmitoylation is required for efficient receptor-mediated mitogenic-signaling within structured membrane microdomains. Cancer Biol Ther 12, 427-435;

Hendrix, C. W., Collier, A. C., Lederman, M. M., Schols, D., Pollard, R. B., Brown, S., Jackson, J. B., Coombs, R. W., Glesby, M. J., Flexner, C. W., et al. (2004). Safety, pharmacokinetics, and antiviral activity of AMD3100, a selective CXCR4 receptor inhibitor, in HIV-1 infection. J Acquir Immune Defic Syndr 37, 1253-1262;

Hendrix, C. W., Flexner, C., MacFarland, R. T., Giandomenico, C., Fuchs, E. J., Redpath, E., Bridger, G., and Henson, G. W. (2000). Pharmacokinetics and safety of AMD-3100, a novel antagonist of the CXCR-4 chemokine receptor, in human volunteers. Antimicrob Agents Chemother 44, 1667-1673;

Henson, B. S., Neubig, R. R., Jang, I., Ogawa, T., Zhang, Z., Carey, T. E., and D'Silva, N. J. (2005). Galanin receptor 1 has anti-proliferative effects in oral squamous cell carcinoma. J Biol Chem 280, 22564-22571;

Hernandez, P. A., Gorlin, R. J., Lukens, J. N., Taniuchi, S., Bohinjec, J., Francois, F., Klotman, M. E., and Diaz, G. A.

(2003). Mutations in the chemokine receptor gene CXCR4 are associated with WHIM syndrome, a combined immunodeficiency disease. Nat Genet 34, 70-74;

Herrmann, K., Schottelius, M., Lapa, C., Osl, T., Poschenrieder, A., Hanscheid, H., Luckerath, K., Schreder, M., Bluemel, C., Knott, M., et al. (2016). First-in-Human Experience of CXCR4-Directed Endoradiotherapy with 177Lu- and 90Y-Labeled Pentixather in Advanced-Stage Multiple Myeloma with Extensive Intra- and Extramedullary Disease. J Nucl Med 57, 248-251;

Hillion, J., Canals, M., Torvinen, M., Casado, V., Scott, R., Terasmaa, A., Hansson, A., Watson, S., Olah, M. E., Mallol, J., et al. (2002). Coaggregation, cointernalization, and codesensitization of adenosine A2A receptors and dopamine D2 receptors. J Biol Chem 277, 18091-18097;

Hsu, W. T., Jui, H. Y., Huang, Y. H., Su, M. Y., Wu, Y. W., Tseng, W. Y., Hsu, M. C., Chiang, B. L., Wu, K. K., and Lee, C. M. (2015). CXCR4 Antagonist TG-0054 Mobilizes Mesenchymal Stem Cells, Attenuates Inflammation, and Preserves Cardiac Systolic Function in a Porcine Model of Myocardial Infarction. Cell Transplant 24, 1313-1328;

Hu, C. D., Chinenov, Y., and Kerppola, T. K. (2002). Visualization of interactions among bZIP and Rel family proteins in living cells using bimolecular fluorescence complementation. Mol Cell 9, 789-798;

Hu, F., Miao, L., Zhao, Y., Xiao, Y. Y., and Xu, Q. (2015). A meta-analysis for C-X-C chemokine receptor type 4 as a prognostic marker and potential drug target in hepatocellular carcinoma. Drug Des Devel Ther 9, 3625-3633;

Huang, E. H., Singh, B., Cristofanilli, M., Gelovani, J., Wei, C., Vincent, L., Cook, K. R., and Lucci, A. (2009). A CXCR4 antagonist CTCE-9908 inhibits primary tumor growth and metastasis of breast cancer. J Surg Res 155, 231-236;

Hutter, G., Nowak, D., Mossner, M., Ganepola, S., Mussig, A., Allers, K., Schneider, T., Hofmann, J., Kucherer, C., Blau, O., et al. (2009). Long-term control of HIV by CCR5 Delta32/Delta32 stem-cell transplantation. N Engl J Med 360, 692-698;

Ichiyama, K., Yokoyama-Kumakura, S., Tanaka, Y., Tanaka, R., Hirose, K., Bannai, K., Edamatsu, T., Yanaka, M., Niitani, Y., Miyano-Kurosaki, N., et al. (2003). A duodenally absorbable CXC chemokine receptor 4 antagonist, KRH-1636, exhibits a potent and selective anti-HIV-1 activity. Proc Natl Acad Sci USA 100, 4185-4190;

Inokuchi, E., Oishi, S., Kubo, T., Ohno, H., Shimura, K., Matsuoka, M., and Fujii, N. (2011). Potent CXCR4 antagonists containing amidine type Peptide bond isosteres. ACS Med Chem Lett 2, 477-480;

Jafari, S. M., Panjehpour, M., Aghaei, M., Joshaghani, H. R., and Enderami, S. E. (2017). A3 Adenosine Receptor Agonist Inhibited Survival of Breast Cancer Stem Cells via GLI-1 and ERK1/2 Pathway. J Cell Biochem 118, 2909-2920;

Jahnichen, S., Blanchetot, C., Maussang, D., Gonzalez-Pajuelo, M., Chow, K. Y., Bosch, L., De Vrieze, S., Serruys, B., Ulrichts, H., Vandevelde, W., et al. (2010). CXCR4 nanobodies (VHH-based single variable domains) potently inhibit chemotaxis and HIV-1 replication and mobilize stem cells. Proc Natl Acad Sci USA 107, 20565-20570;

Jenkinson, S., Thomson, M., McCoy, D., Edelstein, M., Danehower, S., Lawrence, W., Wheelan, P., Spaltenstein, A., and Gudmundsson, K. (2010). Blockade of X4-tropic HIV-1 cellular entry by GSK812397, a potent noncompetitive CXCR4 receptor antagonist. Antimicrob Agents Chemother 54, 817-824;

Jiang, X. R., Song, A., Bergelson, S., Arroll, T., Parekh, B., May, K., Chung, S., Strouse, R., Mire-Sluis, A., and Schenerman, M. (2011). Advances in the assessment and control of the effector functions of therapeutic antibodies. Nat Rev Drug Discov 10, 101-111;

Johnson, G. (2002). PDQ Pharmacology (2nd ed.) (Hamilton, Ontario: BC Decker Inc.);

Kalatskaya, I., Berchiche, Y. A., Gravel, S., Limberg, B. J., Rosenbaum, J. S., and Heveker, N. (2009). AMD3100 is a CXCR7 ligand with allosteric agonist properties. Mol Pharmacol 75, 1240-1247;

Kasama, H., Sakamoto, Y., Kasamatsu, A., Okamoto, A., Koyama, T., Minakawa, Y, Ogawara, K., Yokoe, H., Shiiba, M., Tanzawa, H., et al. (2015). Adenosine A2b receptor promotes progression of human oral cancer. BMC Cancer 15, 563;

Kawai, T., and Malech, H. L. (2009). WHIM syndrome: congenital immune deficiency disease. Curr Opin Hematol 16, 20-26;

Keating, G. M. (2011). Plerixafor: a review of its use in stem-cell mobilization in patients with lymphoma or multiple myeloma. Drugs 71, 1623-1647;

Kerppola, T. K. (2006). Design and implementation of bimolecular fluorescence complementation (BiFC) assays for the visualization of protein interactions in living cells. Nat Protoc 1, 1278-1286;

Kim, H. Y., Hwang, J. Y., Kim, S. W., Lee, H. J., Yun, H. J., Kim, S., and Jo, D. Y. (2010). The CXCR4 Antagonist AMD3100 Has Dual Effects on Survival and Proliferation of Myeloma Cells In vitro. Cancer Res Treat 42, 225-234;

Kim, S .Y., Lee, C. H., Midura, B. V., Yeung, C., Mendoza, A., Hong, S. H., Ren, L., Wong, D., Korz, W., Merzouk, A., et al. (2008). Inhibition of the CXCR4/CXCL12 chemokine pathway reduces the development of murine pulmonary metastases. Clin Exp Metastasis 25, 201-211;

Kitazawa, T., Taneike, T., and Ohga, A. (1995). Excitatory action of [Leu13]motilin on the gastrointestinal smooth muscle isolated from the chicken. Peptides 16, 1243-1252;

Kitazawa, T., Taneike, T., and Ohga, A. (1997). Functional characterization of neural and smooth muscle motilin receptors in the chicken proventriculus and ileum. Regul Pept 71, 87-95;

Klein, R. S., and Rubin, J. B. (2004). Immune and nervous system CXCL12 and CXCR4: parallel roles in patterning and plasticity. Trends Immunol 25, 306-314;

Klos, A., Wende, E., Wareham, K. J., and Monk, P. N. (2013). International Union of Basic and Clinical Pharmacology. [corrected]. LXXXVII. Complement peptide C5a, C4a, and C3a receptors. Pharmacol Rev 65, 500-543;

Knutsson, M., and Edvinsson, L. (2002). Distribution of mRNA for VIP and PACAP receptors in human cerebral arteries and cranial ganglia. Neuroreport 13, 507-509;

Kristensen, M., Birch, D., and Morck Nielsen, H. (2016). Applications and Challenges for Use of Cell-Penetrating Peptides as Delivery Vectors for Peptide and Protein Cargos. Int J Mol Sci 17;

Kroeze, W. K., Sassano, M. F., Huang, X. P., Lansu, K., McCorvy, J. D., Giguere, P. M., Sciaky, N., and Roth, B. L. (2015). PRESTO-Tango as an open-source resource for interrogation of the druggable human GPCRome. Nat Struct Mol Biol 22, 362-369;

Kuhne, M. R., Mulvey, T., Belanger, B., Chen, S., Pan, C., Chong, C., Cao, F., Niekro, W., Kempe, T., Henning, K. A., et al. (2013). BMS-936564/MDX-1338: a fully human anti-CXCR4 antibody induces apoptosis in vitro and shows antitumor activity in vivo in hematologic malignancies. Clin Cancer Res 19, 357-366;

Lambert, et al., "Antibody-Drug Conjugates for Cancer Treatment", Annual Review of Medicine, 69:191-207 (2018);

LaRocca, T. J., Schwarzkopf, M., Altman, P., Zhang, S., Gupta, A., Gomes, I., Alvin, Z., Champion, H. C., Haddad, G., Hajjar, R. J., et al. (2010). beta2-Adrenergic receptor signaling in the cardiac myocyte is modulated by interactions with CXCR4. J Cardiovasc Pharmacol 56, 548-559;

Law, P. Y., Erickson-Herbrandson, L. J., Zha, Q. Q., Solberg, J., Chu, J., Sarre, A., and Loh, H. H. (2005). Heterodimerization of mu- and delta-opioid receptors occurs at the cell surface only and requires receptor-G protein interactions. J Biol Chem 280, 11152-11164;

Lee, C. H., Kakinuma, T., Wang, J., Zhang, H., Palmer, D. C., Restifo, N. P., and Hwang, S. T. (2006). Sensitization of B16 tumor cells with a CXCR4 antagonist increases the efficacy of immunotherapy for established lung metastases. Mol Cancer Ther 5, 2592-2599;

Lee, H., Whitfeld, P. L., and Mackay, C. R. (2008). Receptors for complement C5a. The importance of C5aR and the enigmatic role of C5L2. Immunol Cell Biol 86, 153-160;

Levoye, A., Balabanian, K., Baleux, F., Bachelerie, F., and Lagane, B. (2009). CXCR7 heterodimerizes with CXCR4 and regulates CXCL12-mediated G protein signaling. Blood 113, 6085-6093;

Li, M., Thompson, D. D., and Paralkar, V. M. (2007). Prostaglandin E(2) receptors in bone formation. Int Orthop 31, 767-772;

Li, Y. P., Pang, J., Gao, S., Bai, P. Y., Wang, W. D., Kong, P., and Cui, Y (2017). Role of CXCR4 and SDF1 as prognostic factors for survival and the association with clinicopathology in colorectal cancer: A systematic meta-analysis. Tumour Biol 39, 1010428317706206;

Liang, J. X., Gao, W., Liang, Y., and Zhou, X. M. (2015). Chemokine receptor CXCR4 expression and lung cancer prognosis: a meta-analysis. Int J Clin Exp Med 8, 5163-5174;

Liang, Z., Zhan, W., Zhu, A., Yoon, Y., Lin, S., Sasaki, M., Klapproth, J. M., Yang, H., Grossniklaus, H. E., Xu, J., et al. (2012). Development of a unique small molecule modulator of CXCR4. PLoS One 7, e34038;

Liao, Y. X., Fu, Z. Z., Zhou, C. H., Shan, L. C., Wang, Z. Y., Yin, F., Zheng, L. P., Hua, Y. Q., and Cai, Z. D. (2015). AMD3100 reduces CXCR4-mediated survival and metastasis of osteosarcoma by inhibiting JNK and Akt, but not p38 or Erk1/2, pathways in in vitro and mouse experiments. Oncol Rep 34, 33-42;

Liles, W. C., Broxmeyer, H. E., Rodger, E., Wood, B., Hubel, K., Cooper, S., Hangoc, G., Bridger, G. J., Henson, G. W., Calandra, G., et al. (2003). Mobilization of hematopoietic progenitor cells in healthy volunteers by AMD3100, a CXCR4 antagonist. Blood 102, 2728-2730;

Ling, X., Spaeth, E., Chen, Y., Shi, Y., Zhang, W., Schober, W., Hail, N., Jr., Konopleva, M., and Andreeff, M. (2013). The CXCR4 antagonist AMD3465 regulates oncogenic signaling and invasiveness in vitro and prevents breast cancer growth and metastasis in vivo. PLoS One 8, e58426;

Liu, S. H., Gu, Y., Pascual, B., Yan, Z., Hallin, M., Zhang, C., Fan, C., Wang, W., Lam, J., Spilker, M. E., et al. (2017). A novel CXCR4 antagonist IgG1 antibody (PF-06747143) for the treatment of hematologic malignancies. Blood Adv 1, 1088-1100;

Liu, X. Y., Liu, Z. C., Sun, Y. G., Ross, M., Kim, S., Tsai, F. F., Li, Q. F., Jeffry, J., Kim, J. Y., Loh, H. H., et al. (2011). Unidirectional cross-activation of GRPR by MOR1D uncouples itch and analgesia induced by opioids. Cell 147, 447-458;

Lohse, M. J., Nuber, S., and Hoffmann, C. (2012). Fluorescence/bioluminescence resonance energy transfer techniques to study G-protein-coupled receptor activation and signaling. Pharmacol Rev 64, 299-336;

Lowe, S. R., Pothen, J., Quinn, J. W., Rundle, A., Bradley, B., Galea, S., Ressler, K. J., and Koenen, K. C. (2015). Gene-by-social-environment interaction (GxSE) between ADCYAP1R1 genotype and neighborhood crime predicts major depression symptoms in trauma-exposed women. J Affect Disord 187, 147-150;

Machado-Carvalho, L., Roca-Ferrer, J., and Picado, C. (2014). Prostaglandin E2 receptors in asthma and in chronic rhinosinusitis/nasal polyps with and without aspirin hypersensitivity. Respir Res 15, 100;

Markovic, T., Jakopin, Z., Dolenc, M. S., and Mlinaric-Rascan, I. (2017). Structural features of subtype-selective EP receptor modulators. Drug Discov Today 22, 57-71;

Marlo, J. E., Niswender, C. M., Days, E. L., Bridges, T. M., Xiang, Y., Rodriguez, A. L., Shirey, J. K., Brady, A. E., Nalywajko, T., Luo, Q., et al. (2009). Discovery and characterization of novel allosteric potentiators of M1 muscarinic receptors reveals multiple modes of activity. Mol Pharmacol 75, 577-588;

Martinez-Munoz, L., Barroso, R., Dyrhaug, S. Y., Navarro, G., Lucas, P., Soriano, S. F., Vega, B., Costas, C., Munoz-Fernandez, M. A., Santiago, C., et al. (2014). CCR5/CD4/CXCR4 oligomerization prevents HIV-1 gp120IIM binding to the cell surface. Proc Natl Acad Sci USA 111, E1960-1969;

Masuda, M., Nakashima, H., Ueda, T., Naba, H., Ikoma, R., Otaka, A., Terakawa, Y, Tamamura, H., Ibuka, T., Murakami, T., et al. (1992). A novel anti-HIV synthetic peptide, T-22 ([Tyr5,12,Lys7]-polyphemusin II). Biochem Biophys Res Commun 189, 845-850;

Medhurst, A. D., Jennings, C. A., Robbins, M. J., Davis, R. P., Ellis, C., Winborn, K. Y., Lawrie, K. W., Hervieu, G., Riley, G., Bolaky, J. E., et al. (2003). Pharmacological and immunohistochemical characterization of the APJ receptor and its endogenous ligand apelin. J Neurochem 84, 1162-1172;

Miller, G. M., Alexander, J. M., Bikkal, H. A., Katznelson, L., Zervas, N. T., and Klibanski, A. (1995). Somatostatin receptor subtype gene expression in pituitary adenomas. J Clin Endocrinol Metab 80, 1386-1392;

Milligan, G. (2008). A day in the life of a G protein-coupled receptor: the contribution to function of G protein-coupled receptor dimerization. Br J Pharmacol 153 *Suppl* 1, S216-229;

Miwatashi, S., Arikawa, Y., Matsumoto, T., Uga, K., Kanzaki, N., Imai, Y. N., and Ohkawa, S. (2008). Synthesis and biological activities of 4-phenyl-5-pyridyl-1,3-thiazole derivatives as selective adenosine A3 antagonists. Chem Pharm Bull (Tokyo) 56, 1126-1137;

Moreno, J. J. (2017). Eicosanoid receptors: Targets for the treatment of disrupted intestinal epithelial homeostasis. Eur J Pharmacol 796, 7-19;

Morimoto, M., Matsuo, Y., Koide, S., Tsuboi, K., Shamoto, T., Sato, T., Saito, K., Takahashi, H., and Takeyama, H. (2016). Enhancement of the CXCL12/CXCR4 axis due to acquisition of gemcitabine resistance in pancreatic cancer: effect of CXCR4 antagonists. BMC Cancer 16, 305;

Muller, A., Homey, B., Soto, H., Ge, N., Catron, D., Buchanan, M. E., McClanahan, T., Murphy, E., Yuan, W., Wagner, S. N., et al. (2001). Involvement of chemokine receptors in breast cancer metastasis. Nature 410, 50-56;

Murakami, T., Kumakura, S., Yamazaki, T., Tanaka, R., Hamatake, M., Okuma, K., Huang, W., Toma, J., Komano, J., Yanaka, M., et al. (2009). The novel CXCR4 antagonist KRH-3955 is an orally bioavailable and extremely potent inhibitor of human immunodeficiency virus type 1 infection: comparative studies with AMD3100. Antimicrob Agents Chemother 53, 2940-2948;

Mustafa, S., Ayoub, M. A., Pfleger, K. D. G. (2010). Uncovering GPCR heteromer-biased ligands. Drug Discov Today Technol 7, e1-e94;

Mustafa, S., and Pfleger, K. D. (2011). G protein-coupled receptor heteromer identification technology: identification and profiling of GPCR heteromers. J Lab Autom 16, 285-291;

Mustafa, S., See, H. B., Seeber, R. M., Armstrong, S. P., White, C. W., Ventura, S., Ayoub, M. A., and Pfleger, K. D. (2012). Identification and profiling of novel alpha1A-adrenoceptor-CXC chemokine receptor 2 heteromer. J Biol Chem 287, 12952-12965;

Nakai, A., Hayano, Y., Furuta, F., Noda, M., and Suzuki, K. (2014). Control of lymphocyte egress from lymph nodes through beta2-adrenergic receptors. J Exp Med 211, 2583-2598;

Nakasone, T., Kumakura, S., Yamamoto, M., Murakami, T., and Yamamoto, N. (2013). Single oral administration of the novel CXCR4 antagonist, KRH-3955, induces an efficient and long-lasting increase of white blood cell count in normal macaques, and prevents CD4 depletion in SHIV-infected macaques: a preliminary study. Med Microbiol Immunol 202, 175-182;

Norel, X., Jones, R. L., Giembycz, M., Narumiya, S., Woodward, D. F., Coleman, R. A., Abramovitz, M., Breyer, R. M., Hills, R. (2016). Prostanoid receptors: EP3 receptor. IUPHAR/BPS Guide to Pharmacology;

O'Boyle, G., Swidenbank, I., Marshall, H., Barker, C. E., Armstrong, J., White, S. A., Fricker, S. P., Plummer, R., Wright, M., and Lovat, P. E. (2013). Inhibition of CXCR4-CXCL12 chemotaxis in melanoma by AMD11070. Br J Cancer 108, 1634-1640;

O'Callaghan, K., Kuliopulos, A., and Covic, L. (2012). Turning receptors on and off with intracellular pepducins: new insights into G-protein-coupled receptor drug development. J Biol Chem 287, 12787-12796;

O'Callaghan, G., and Houston, A. (2015). Prostaglandin E2 and the EP receptors in malignancy: possible therapeutic targets? Br J Pharmacol 172, 5239-5250;

Ogi, K., Miyamoto, Y., Masuda, Y., Habata, Y., Hosoya, M., Ohtaki, T., Masuo, Y., Onda, H., and Fujino, M. (1993). Molecular cloning and functional expression of a cDNA encoding a human pituitary adenylate cyclase activating polypeptide receptor. Biochem Biophys Res Commun 196, 1511-1521;

Okada, T., Ernst, O. P., Palczewski, K., and Hofmann, K. P. (2001). Activation of rhodopsin: new insights from structural and biochemical studies. Trends Biochem Sci 26, 318-324;

Otani, Y., Kijima, T., Kohmo, S., Oishi, S., Minami, T., Nagatomo, I., Takahashi, R., Hirata, H., Suzuki, M., Inoue, K., et al. (2012). Suppression of metastases of small cell lung cancer cells in mice by a peptidic CXCR4 inhibitor TF14016. FEBS Lett 586, 3639-3644;

Overington, J. P., Al-Lazikani, B., and Hopkins, A. L. (2006). How many drug targets are there? Nat Rev Drug Discov 5, 993-996;

Owen, J. L., and Mohamadzadeh, M. (2013). Macrophages and chemokines as mediators of angiogenesis. Front Physiol 4, 159;

Page, N. M., Bell, N. J., Gardiner, S. M., Manyonda, I. T., Brayley, K. J., Strange, P. G., and Lowry, P. J. (2003). Characterization of the endokinins: human tachykinins with cardiovascular activity. Proc Natl Acad Sci USA 100, 6245-6250;

Pal, J., Patil, V., Kumar, A., Kaur, K., Sarkar, C., and Somasundaram, K. (2018). Loss-of-Function Mutations in Calcitonin Receptor (CALCR) Identify Highly Aggressive Glioblastoma with Poor Outcome. Clin Cancer Res 24, 1448-1458;

Parameswaran, R., Yu, M., Lim, M., Groffen, J., and Heisterkamp, N. (2011). Combination of drug therapy in acute lymphoblastic leukemia with a CXCR4 antagonist. Leukemia 25, 1314-1323;

Park, P. S., and Palczewski, K. (2005). Diversifying the repertoire of G protein-coupled receptors through oligomerization. Proc Natl Acad Sci USA 102, 8793-8794;

Patel, K., Dixit, V. D., Lee, J. H., Kim, J. W., Schaffer, E. M., Nguyen, D., and Taub, D. D. (2012). Identification of ghrelin receptor blocker, D-[Lys3] GHRP-6 as a CXCR4 receptor antagonist. Int J Biol Sci 8, 108-117;

Patel, R. C., Kumar, U., Lamb, D. C., Eid, J. S., Rocheville, M., Grant, M., Rani, A., Hazlett, T., Patel, S. C., Gratton, E., et al. (2002). Ligand binding to somatostatin receptors induces receptor-specific oligomer formation in live cells. Proc Natl Acad Sci USA 99, 3294-3299;

Peled, A., Wald, O., and Burger, J. (2012). Development of novel CXCR4-based therapeutics. Expert Opin Investig Drugs 21, 341-353;

Pello, O. M., Martinez-Munoz, L., Parrillas, V., Serrano, A., Rodriguez-Frade, J. M., Toro, M. J., Lucas, P., Monterrubio, M., Martinez, A. C., and Mellado, M. (2008). Ligand stabilization of CXCR4/delta-opioid receptor heterodimers reveals a mechanism for immune response regulation. Eur J Immunol 38, 537-549;

Peng, S. B., Zhang, X., Paul, D., Kays, L. M., Gough, W., Stewart, J., Uhlik, M. T., Chen, Q., Hui, Y. H., Zamek-Gliszczynski, M. J., et al. (2015). Identification of LY2510924, a novel cyclic peptide CXCR4 antagonist that exhibits antitumor activities in solid tumor and breast cancer metastatic models. Mol Cancer Ther 14, 480-490;

Pfeiffer, M., Koch, T., Schroder, H., Laugsch, M., Hollt, V., and Schulz, S. (2002). Heterodimerization of somatostatin and opioid receptors cross-modulates phosphorylation, internalization, and desensitization. J Biol Chem 277, 19762-19772;

Pfleger, K. D., and Eidne, K. A. (2006). Illuminating insights into protein-protein interactions using bioluminescence resonance energy transfer (BRET). Nat Methods 3, 165-174;

Pin, J. P., Neubig, R., Bouvier, M., Devi, L., Filizola, M., Javitch, J. A., Lohse, M. J., Milligan, G., Palczewski, K., Parmentier, M., et al. (2007). International Union of Basic and Clinical Pharmacology. LXVII. Recommendations for the recognition and nomenclature of G protein-coupled receptor heteromultimers. Pharmacol Rev 59, 5-13;

Planesas, J. M., Perez-Nueno, V. I., Borrell, J. I., and Teixido, J. (2015). Studying the binding interactions of allosteric agonists and antagonists of the CXCR4 receptor. J Mol Graph Model 60, 1-14;

Pondel, M. (2000). Calcitonin and calcitonin receptors: bone and beyond. Int J Exp Pathol 81, 405-422;

Qin, K., Dong, C., Wu, G., and Lambert, N. A. (2011). Inactive-state preassembly of G(q)-coupled receptors and G(q) heterotrimers. Nat Chem Biol 7, 740-747;

Rang, H. P., Dale, M. M., Ritter, J. M., Moore, P. K. (2003). "Ch. 10", Pharmacology (5th ed.). (Elsevier Churchill Livingstone);

Redondo-Munoz, J., Escobar-Diaz, E., Samaniego, R., Terol, M. J., Garcia-Marco, J. A., and Garcia-Pardo, A. (2006). MMP-9 in B-cell chronic lymphocytic leukemia is up-regulated by alpha4beta1 integrin or CXCR4 engagement via distinct signaling pathways, localizes to podosomes, and is involved in cell invasion and migration. Blood 108, 3143-3151;

Reubi, J. C. (2000). In vitro evaluation of VIP/PACAP receptors in healthy and diseased human tissues. Clinical implications. Ann NY Acad Sci 921, 1-25;

Reubi, J. C., Laderach, U., Waser, B., Gebbers, J. O., Robberecht, P., and Laissue, J. A. (2000). Vasoactive intestinal peptide/pituitary adenylate cyclase-activating peptide receptor subtypes in human tumors and their tissues of origin. Cancer Res 60, 3105-3112;

Reya, T., Morrison, S. J., Clarke, M. F., and Weissman, I. L. (2001). Stem cells, cancer, and cancer stem cells. Nature 414, 105-111;

Rios, C., Gomes, I., and Devi, L. A. (2006). mu opioid and CB1 cannabinoid receptor interactions: reciprocal inhibition of receptor signaling and neuritogenesis. Br J Pharmacol 148, 387-395;

Roccaro, A. M., Sacco, A., Purschke, W. G., Moschetta, M., Buchner, K., Maasch, C., Zboralski, D., Zollner, S., Vonhoff, S., Mishima, Y., et al. (2014). SDF-1 inhibition targets the bone marrow niche for cancer therapy. Cell Rep 9, 118-128;

Rodriguez-Frade, J. M., del Real, G., Serrano, A., Hernanz-Falcon, P., Soriano, S. F., Vila-Coro, A. J., de Ana, A. M., Lucas, P., Prieto, I., Martinez, A. C., et al. (2004). Blocking HIV-1 infection via CCR5 and CXCR4 receptors by acting in trans on the CCR2 chemokine receptor. EMBO J 23, 66-76;

Roess, D. A., Horvat, R. D., Munnelly, H., and Barisas, B. G. (2000). Luteinizing hormone receptors are self-associated in the plasma membrane. Endocrinology 141, 4518-4523;

Rozenfeld, R., Bushlin, I., Gomes, I., Tzavaras, N., Gupta, A., Neves, S., Battini, L., Gusella, G. L., Lachmann, A., Ma'ayan, A., et al. (2012). Receptor heteromerization expands the repertoire of cannabinoid signaling in rodent neurons. PLoS One 7, e29239;

Rozenfeld, R., and Devi, L. A. (2010). Receptor heteromerization and drug discovery. Trends Pharmacol Sci 31, 124-130;

Rubin, J. B., Kung, A. L., Klein, R. S., Chan, J. A., Sun, Y., Schmidt, K., Kieran, M. W., Luster, A. D., and Segal, R. A. (2003). A small-molecule antagonist of CXCR4 inhibits intracranial growth of primary brain tumors. Proc Natl Acad Sci USA 100, 13513-13518;

Saka, Y., Hagemann, A. I., Piepenburg, O., and Smith, J. C. (2007). Nuclear accumulation of Smad complexes occurs only after the midblastula transition in Xenopus. Development 134, 4209-4218;

Sanjana, N. E., Shalem, O., and Zhang, F. (2014). Improved vectors and genome-wide libraries for CRISPR screening. Nat Methods 11, 783-784;

Sato-Jin, K., Nishimura, E. K., Akasaka, E., Huber, W., Nakano, H., Miller, A., Du, J., Wu, M., Hanada, K., Sawamura, D., et al. (2008). Epistatic connections between microphthalmia-associated transcription factor and endothelin signaling in Waardenburg syndrome and other pigmentary disorders. FASEB J 22, 1155-1168;

Scala, S. (2015). Molecular Pathways: Targeting the CXCR4-CXCL12 Axis—Untapped Potential in the Tumor Microenvironment. Clin Cancer Res 21, 4278-4285;

Schimanski, C. C., Bahre, R., Gockel, I., Muller, A., Freirichs, K., Homer, V., Teufel, A., Simiantonaki, N., Biesterfeld, S., Wehler, T., et al. (2006). Dissemination of hepatocellular carcinoma is mediated via chemokine receptor CXCR4. Br J Cancer 95, 210-217;

Sedor, J. R., and Abboud, H. E. (1984). Actions and metabolism of histamine in glomeruli and tubules of the human kidney. Kidney Int 26, 144-152;

Shen, Z., Chen, X., Li, Q., Zhou, C., Li, J., Ye, H., and Duan, S. (2016). SSTR2 promoter hypermethylation is associated with the risk and progression of laryngeal squamous cell carcinoma in males. Diagn Pathol 11, 10;

Sicoli, D., Jiao, X., Ju, X., Velasco-Velazquez, M., Ertel, A., Addya, S., Li, Z., Ando, S., Fatatis, A., Paudyal, B., et al. (2014). CCR5 receptor antagonists block metastasis to bone of v-Src oncogene-transformed metastatic prostate cancer cell lines. Cancer Res 74, 7103-7114;

Sierro, F., Biben, C., Martinez-Munoz, L., Mellado, M., Ransohoff, R. M., Li, M., Woehl, B., Leung, H., Groom, J., Batten, M., et al. (2007). Disrupted cardiac development but normal hematopoiesis in mice deficient in the second CXCL12/SDF-1 receptor, CXCR7. Proc Natl Acad Sci USA 104, 14759-14764;

Smith, M. C., Luker, K. E., Garbow, J. R., Prior, J. L., Jackson, E., Piwnica-Worms, D., and Luker, G. D. (2004). CXCR4 regulates growth of both primary and metastatic breast cancer. Cancer Res 64, 8604-8612;

Sohy, D., Parmentier, M., and Springael, J. Y. (2007). Allosteric transinhibition by specific antagonists in CCR2/CXCR4 heterodimers. J Biol Chem 282, 30062-30069;

Sohy, D., Yano, H., de Nadai, P., Urizar, E., Guillabert, A., Javitch, J. A., Parmentier, M., and Springael, J. Y. (2009). Hetero-oligomerization of CCR2, CCR5, and CXCR4 and the protean effects of "selective" antagonists. J Biol Chem 284, 31270-31279;

Song, J. S., Kang, C. M., Kang, H. H., Yoon, H. K., Kim, Y. K., Kim, K. H., Moon, H. S., and Park, S. H. (2010). Inhibitory effect of CXC chemokine receptor 4 antagonist AMD3100 on bleomycin induced murine pulmonary fibrosis. Exp Mol Med 42, 465-472;

Song, Y. B., Park, C. O., Jeong, J. Y., and Huh, W. K. (2014). Monitoring G protein-coupled receptor activation using an adenovirus-based beta-arrestin bimolecular fluorescence complementation assay. Anal Biochem 449, 32-41;

Stefan, E., Aquin, S., Berger, N., Landry, C. R., Nyfeler, B., Bouvier, M., and Michnick, S. W. (2007). Quantification of dynamic protein complexes using Renilla luciferase fragment complementation applied to protein kinase A activities in vivo. Proc Natl Acad Sci USA 104, 16916-16921;

Stevenson, L., Allen, W. L., Turkington, R., Jithesh, P. V., Proutski, I., Stewart, G., Lenz, H. J., Van Schaeybroeck, S., Longley, D. B., and Johnston, P. G. (2012). Identification of galanin and its receptor GalR1 as novel determinants of resistance to chemotherapy and potential biomarkers in colorectal cancer. Clin Cancer Res 18, 5412-5426;

Stone, N. D., Dunaway, S. B., Flexner, C., Tierney, C., Calandra, G. B., Becker, S., Cao, Y. J., Wiggins, I. P., Conley, J., MacFarland, R. T., et al. (2007). Multiple-dose escalation study of the safety, pharmacokinetics, and biologic activity of oral AMD070, a selective CXCR4 receptor inhibitor, in human subjects. Antimicrob Agents Chemother 51, 2351-2358;

Struyf, S., Menten, P., Lenaerts, J. P., Put, W., D'Haese, A., De Clercq, E., Schols, D., Proost, P., and Van Damme, J. (2001). Diverging binding capacities of natural LD78beta isoforms of macrophage inflammatory protein-1alpha to the CC chemokine receptors 1, 3 and 5 affect their anti-HIV-1 activity and chemotactic potencies for neutrophils and eosinophils. Eur J Immunol 31, 2170-2178;

Sugimoto, Y., Inazumi, T., and Tsuchiya, S. (2015). Roles of prostaglandin receptors in female reproduction. J Biochem 157, 73-80;

Swift, S. L., Burns, J. E., and Maitland, N. J. (2010). Altered expression of neurotensin receptors is associated with the differentiation state of prostate cancer. Cancer Res 70, 347-356;

Taichman, R. S., Cooper, C., Keller, E. T., Pienta, K. J., Taichman, N. S., and McCauley, L. K. (2002). Use of the stromal cell-derived factor-1/CXCR4 pathway in prostate cancer metastasis to bone. Cancer Res 62, 1832-1837;

Tamamura, H., Xu, Y., Hattori, T., Zhang, X., Arakaki, R., Kanbara, K., Omagari, A., Otaka, A., Ibuka, T., Yamamoto, N., et al. (1998). A low-molecular-weight inhibitor against the chemokine receptor CXCR4: a strong anti-HIV peptide T140. Biochem Biophys Res Commun 253, 877-882;

Tanaka, H., Moroi, K., Iwai, J., Takahashi, H., Ohnuma, N., Hori, S., Takimoto, M., Nishiyama, M., Masaki, T., Yanagisawa, M., et al. (1998). Novel mutations of the endothelin B receptor gene in patients with Hirschsprung's disease and their characterization. J Biol Chem 273, 11378-11383;

Tanaka, T., Nomura, W., Narumi, T., Esaka, A., Oishi, S., Ohashi, N., Itotani, K., Evans, B. J., Wang, Z. X., Peiper, S. C., et al. (2009). Structure-activity relationship study on artificial CXCR4 ligands possessing the cyclic pentapeptide scaffold: the exploration of amino acid residues of pentapeptides by substitutions of several aromatic amino acids. Org Biomol Chem 7, 3805-3809;

Tanaka, T., Tsutsumi, H., Nomura, W., Tanabe, Y., Ohashi, N., Esaka, A., Ochiai, C., Sato, J., Itotani, K., Murakami, T., et al. (2008). Structure-activity relationship study of CXCR4 antagonists bearing the cyclic pentapeptide scaffold: identification of the new pharmacophore. Org Biomol Chem 6, 4374-4377;

Terrillon, S., and Bouvier, M. (2004). Roles of G-protein-coupled receptor dimerization. EMBO Rep 5, 30-34;

Topaloglu, A. K., Reimann, F., Guclu, M., Yalin, A. S., Kotan, L. D., Porter, K. M., Serin, A., Mungan, N. O., Cook, J. R., Imamoglu, S., et al. (2009). TAC3 and TACR3 mutations in familial hypogonadotropic hypogonadism reveal a key role for Neurokinin B in the central control of reproduction. Nat Genet 41, 354-358;

Torvinen, M., Toni, C., Tombesi, A., Marcellino, D., Watson, S., Lluis, C., Franco, R., Fuxe, K., and Agnati, L. F. (2005). Trafficking of adenosine A2A and dopamine D2 receptors. J Mol Neurosci 25, 191-200;

Tripathi, A., Davis, J. D., Staren, D. M., Volkman, B. F., and Majetschak, M. (2014). CXC chemokine receptor 4 signaling upon co-activation with stromal cell-derived factor-1alpha and ubiquitin. Cytokine 65, 121-125;

Tripathi, A., Vana, P. G., Chavan, T. S., Brueggemann, L. I., Byron, K. L., Tarasova, N. I., Volkman, B. F., Gaponenko, V., and Majetschak, M. (2015). Heteromerization of chemokine (C-X-C motif) receptor 4 with alpha1 A/B-adrenergic receptors controls alpha1-adrenergic receptor function. Proc Natl Acad Sci USA 112, E1659-1668;

Vaudry, D., Gonzalez, B. J., Basille, M., Yon, L., Fournier, A., and Vaudry, H. (2000). Pituitary adenylate cyclase-activating polypeptide and its receptors: from structure to functions. Pharmacol Rev 52, 269-324;

Velasco-Velazquez, M., Jiao, X., De La Fuente, M., Pestell, T. G., Ertel, A., Lisanti, M. P., and Pestell, R. G. (2012). CCR5 antagonist blocks metastasis of basal breast cancer cells. Cancer Res 72, 3839-3850;

Vincent, J. P. (1995). Neurotensin receptors: binding properties, transduction pathways, and structure. Cell Mol Neurobiol 15, 501-512;

Walenkamp, A. M. E., Lapa, C., Herrmann, K., and Wester, H. J. (2017). CXCR4 Ligands: The Next Big Hit? J Nucl Med 58, 77S-82S;

Wang, A., Fairhurst, A. M., Tus, K., Subramanian, S., Liu, Y., Lin, F., Igarashi, P., Zhou, X. J., Batteux, F., Wong, D., et al. (2009). CXCR4/CXCL12 hyperexpression plays a pivotal role in the pathogenesis of lupus. J Immunol 182, 4448-4458;

Wang, A., Guilpain, P., Chong, B. F., Chouzenoux, S., Guillevin, L., Du, Y., Zhou, X. J., Lin, F., Fairhurst, A. M., Boudreaux, C., et al. (2010). Dysregulated expression of CXCR4/CXCL12 in subsets of patients with systemic lupus erythematosus. Arthritis Rheum 62, 3436-3446;

Wang, F., Li, S., Zhao, Y., Yang, K., Chen, M., Niu, H., Yang, J., Luo, Y., Tang, W., and Sheng, M. (2016). Predictive role of the overexpression for CXCR4, C-Met, and VEGF-C among breast cancer patients: A meta-analysis. Breast 28, 45-53;

Wang, L. P., Jin, J., Lv, F. F., Cao, J., Zhang, J., Wang, B. Y., Shao, Z. M., Hu, X. C., and Wang, Z. H. (2015a). Norepinephrine attenuates CXCR4 expression and the corresponding invasion of MDA-MB-231 breast cancer cells via beta2-adrenergic receptors. Eur Rev Med Pharmacol Sci 19, 1170-1181;

Wang, W., Erbe, A. K., Hank, J. A., Morris, Z. S., and Sondel, P. M. (2015b). NK Cell-Mediated Antibody-Dependent Cellular Cytotoxicity in Cancer Immunotherapy. Front Immunol 6, 368;

Wang, Z., Ma, Q., Liu, Q., Yu, H., Zhao, L., Shen, S., and Yao, J. (2008). Blockade of SDF-1/CXCR4 signalling inhibits pancreatic cancer progression in vitro via inactivation of canonical Wnt pathway. Br J Cancer 99, 1695-1703;

Wang, Z., Yu, D., Wang, M., Wang, Q., Kouznetsova, J., Yang, R., Qian, K., Wu, W., Shuldiner, A., Sztalryd, C., et al. (2015c). Elabela-apelin receptor signaling pathway is functional in mammalian systems. Sci Rep 5, 8170;

Watts, A. O., van Lipzig, M. M., Jaeger, W. C., Seeber, R. M., van Zwam, M., Vinet, J., van der Lee, M. M., Siderius, M., Zaman, G. J., Boddeke, H. W., et al. (2013).

Identification and profiling of CXCR3-CXCR4 chemokine receptor heteromer complexes. Br J Pharmacol 168, 1662-1674;

Watts, S. W. (2010). Endothelin receptors: what's new and what do we need to know? Am J Physiol Regul Integr Comp Physiol 298, R254-260;

White, J. H., Wise, A., Main, M. J., Green, A., Fraser, N. J., Disney, G. H., Barnes, A. A., Emson, P., Foord, S. M., Marshall, F. H. (1998). Heterodimerization is required for the formation of a functional GABA(B) receptor. Nature 396, 679-682;

Wong, D., Kandagatla, P., Korz, W., and Chinni, S. R. (2014). Targeting CXCR4 with CTCE-9908 inhibits prostate tumor metastasis. BMC Urol 14, 12;

Woodward, D. F., Jones, R. L., and Narumiya, S. (2011). International Union of Basic and Clinical Pharmacology. LXXXIII: classification of prostanoid receptors, updating 15 years of progress. Pharmacol Rev 63, 471-538;

Wreggett, K. A., and Wells, J. W. (1995). Cooperativity manifest in the binding properties of purified cardiac muscarinic receptors. J Biol Chem 270, 22488-22499;

Wu, L., Chen, L., and Li, L. (2017). Apelin/APJ system: A novel promising therapy target for pathological angiogenesis. Clin Chim Acta 466, 78-84;

Wurth, R., Florio, T. (2016). Subventricular zone microenvironment protects glioblastoma cells from radiotherapy cytotoxicity: role of the chemokine CXCL12. Translational Cancer Research 5(Suppl 6): S1098-S1101;

Xie, H., and He, S. H. (2005). Roles of histamine and its receptors in allergic and inflammatory bowel diseases. World J Gastroenterol 11, 2851-2857;

Xu, H., Fu, S., Chen, Q., Gu, M., Zhou, J., Liu, C., Chen, Y., and Wang, Z. (2017). The function of oxytocin: a potential biomarker for prostate cancer diagnosis and promoter of prostate cancer. Oncotarget 8, 31215-31226;

Xu, L., Duda, D. G., di Tomaso, E., Ancukiewicz, M., Chung, D. C., Lauwers, G. Y., Samuel, R., Shellito, P., Czito, B. G., Lin, P. C., et al. (2009). Direct evidence that bevacizumab, an anti-VEGF antibody, up-regulates SDF lalpha, CXCR4, CXCL6, and neuropilin 1 in tumors from patients with rectal cancer. Cancer Res 69, 7905-7910;

Yagami, T., Koma, H., and Yamamoto, Y. (2016). Pathophysiological Roles of Cyclooxygenases and Prostaglandins in the Central Nervous System. Mol Neurobiol 53, 4754-4771;

Yang, D., Koupenova, M., McCrann, D. J., Kopeikina, K. J., Kagan, H. M., Schreiber, B. M., and Ravid, K. (2008). The A2b adenosine receptor protects against vascular injury. Proc Natl Acad Sci USA 105, 792-796;

Yang, Q., Zhang, F., Ding, Y., Huang, J., Chen, S., Wu, Q., Wang, Z., Wang, Z., and Chen, C. (2014). Antitumour activity of the recombination polypeptide GST-NT21MP is mediated by inhibition of CXCR4 pathway in breast cancer. Br J Cancer 110, 1288-1297;

Yang, T., and Du, Y (2012). Distinct roles of central and peripheral prostaglandin E2 and EP subtypes in blood pressure regulation. Am J Hypertens 25, 1042-1049;

Zabel, B. A., Lewen, S., Berahovich, R. D., Jaen, J. C., and Schall, T. J. (2011). The novel chemokine receptor CXCR7 regulates trans-endothelial migration of cancer cells. Mol Cancer 10, 73;

Zatelli, M. C., Ambrosio, M. R., Bondanelli, M., and Uberti, E. C. (2007). Control of pituitary adenoma cell proliferation by somatostatin analogs, dopamine agonists and novel chimeric compounds. Eur J Endocrinol 156 Suppl 1, S29-35;

Zeelenberg, I. S., Ruuls-Van Stalle, L., and Roos, E. (2003). The chemokine receptor CXCR4 is required for outgrowth of colon carcinoma micrometastases. Cancer Res 63, 3833-3839;

Zhan, W., Liang, Z., Zhu, A., Kurtkaya, S., Shim, H., Snyder, J. P., and Liotta, D. C. (2007). Discovery of small molecule CXCR4 antagonists. J Med Chem 50, 5655-5664;

Zhang, W. B., Navenot, J. M., Haribabu, B., Tamamura, H., Hiramatu, K., Omagari, A., Pei, G., Manfredi, J. P., Fujii, N., Broach, J. R., et al. (2002). A point mutation that confers constitutive activity to CXCR4 reveals that T140 is an inverse agonist and that AMD3100 and ALX40-4C are weak partial agonists. J Biol Chem 277, 24515-24521;

Zhao, H., Guo, L., Zhao, H., Zhao, J., Weng, H., and Zhao, B. (2015). CXCR4 over-expression and survival in cancer: a system review and meta-analysis. Oncotarget 6, 5022-5040;

Zhou, N., Fan, X., Mukhtar, M., Fang, J., Patel, C. A., DuBois, G. C., and Pomerantz, R. J. (2003). Cell-cell fusion and internalization of the CNS-based, HIV-1 co-receptor, APJ. Virology 307, 22-36;

Zhu, A., Zhan, W., Liang, Z., Yoon, Y., Yang, H., Grossniklaus, H. E., Xu, J., Rojas, M., Lockwood, M., Snyder, J. P., et al. (2010). Dipyrimidine amines: a novel class of chemokine receptor type 4 antagonists with high specificity. J Med Chem 53, 8556-8568; and Zitzer, H., Honck, H. H., Bachner, D., Richter, D., and Kreienkamp, H. J. (1999). Somatostatin receptor interacting protein defines a novel family of multidomain proteins present in human and rodent brain. J Biol Chem 274, 32997-33001.

What is claimed is:

1. A method of inhibiting cancer progression in a cancer patient having a CXCR4-ADRB2 heteromer in a cancer cell, the method comprising:

determining whether the cancer patient's cancer cell contains the CXCR4-ADRB2 heteromer;

if the CXCR4-ADRB2 heteromer is present in the cancer patient's cancer cell, then administering to said cancer patient having said CXCR4-ADRB2 in said cancer cell an inhibitor of CXCR4 and an inhibitor of ADRB2;

wherein:

i) the CXCR4-ADRB2 heteromer has an enhanced amount of downstream calcium mobilization relative to downstream calcium mobilization from a CXCR4 protomer or ADRB2 protomer;

ii) the administered combination of inhibitors suppresses the enhanced downstream calcium mobilization from said CXCR4-ADRB2 heteromer in the cell;

iii) the CXCR4 inhibitor is selected from the group consisting of: AD-114, AD-114-6H, AD-114-Im7-FH, AD-114-PA600-6H, ALX-0651, ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMI-1359, GSK812397, GST-NT21MP, isothiourea-1a, isothiourea-1t (IT1t), KRH-1636, KRH-3955, LY2510924, LY2624587, MSX-122, N-[$^{11}$C]Methyl-AMD3465, PF-06747143, POL6326, SDF-1 1-9[P2G] dimer, SDF1 P2G, T134, T140, T22, TC 14012, TG-0054 (Burixafor), USL311, ulocuplumab (MDX1338/BMS-936564), viral macrophage inflammatory protein-II (vMIP-II), WZ811, 12G5, 238D2, 238D4, [$^{64}$Cu]-AMD3100, [$^{64}$Cu]-AMD3465, [$^{68}$Ga]pentixafor, [$^{90}$Y]pentixather, [$^{99m}$Tc]O$_2$-AMD3100, [$^{177}$Lu]pentixather, and 508MCl (Compound 26); and iv) the ADRB2 inhibitor is selected from the group consisting of: Alprenolol, atenolol, betaxolol, bupranolol, butoxamine, carazolol, carvedilol, CGP 12177, cicloprolol, ICI 118551, ICYP, labetalol, levobetaxolol, levobunolol, LK 204-545, metoprolol, nadolol, NIHP, NIP, propafenone, propranolol, sotalol, SR59230A, and timolol.

2. The method of claim 1, wherein the enhanced amount of calcium mobilization from the CXCR4-ADRB2 heteromer is a calcium mobilization amount that, upon co-stimulation with CXCL12 and a selective ADRB2 agonist, is at least 10% greater than the sum of calcium mobilization amounts resulting from single agonist stimulation of said cells with either the CXCL12 or the selective ADRB2 agonist, as determined via a calcium mobilization assay.

3. The method of claim 2, wherein the CXCR4-ADRB2 heteromer has two or more of the following characteristics:
   1) the CXCR4-ADRB2 heteromer components in a cancer cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay;
   2) an enhanced amount of calcium mobilization, such that:
      a) either CXCR4 or ADRB2 in an individual protomer context in a cancer cell, upon co-stimulation with CXCL12 and a selective ADRB2 agonist, results in a calcium mobilization amount that is equal to or less than the sum of calcium mobilization amounts resulting from single agonist stimulation with either the CXCL12 or the ADRB2 agonist; and
      b) the CXCR4-ADRB2 heteromer exhibits an enhanced calcium mobilization upon co-stimulation with the CXCL12 and the selective ADRB2 agonist relative to the sum of calcium mobilization amounts resulting from single agonist stimulation with either the CXCL12 or the selective GPCRx agonist;
      as determined via a calcium mobilization assay; or
   3) a CXCR4-ADRB2 heteromer-selective reagent:
      i) alters heteromer-specific properties of the CXCR4-ADRB2 heteromer in the cell;
      ii) alters heteromer-specific function of the CXCR4-ADRB2 heteromer in the cell;
      iii) alters heteromer-specific properties of the cell containing the CXCR4-ADRB2 heteromer; or
      iv) decreases cancer progression of the cell containing the CXCR4-ADRB2 heteromer.

4. The method of claim 3, wherein the CXCR4-ADRB2 heteromer components in the cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay.

5. The method of claim 4, wherein the CXCR4-ADRB2 heteromer has enhanced amount of calcium mobilization, such that:
   a) either the CXCR4 or the ADRB2 in an individual protomer context in a cancer cell, upon co-stimulation with CXCL12 and a selective ADRB2 agonist, results in a calcium mobilization amount that is equal to or less than the sum of calcium mobilization amounts resulting from single agonist stimulation with either the CXCL12 or the ADRB2 agonist; and
   b) the CXCR4-ADRB2 heteromer exhibits an enhanced calcium mobilization upon co-stimulation with the CXCL12 and the selective ADRB2 agonist relative to the sum of calcium mobilization amounts resulting from single agonist stimulation with either the CXCL12 or the selective GPCRx agonist;
as determined via a calcium mobilization assay.

6. The method of claim 1, wherein the CXCR4 inhibitor is selected from the group consisting of AMD3100 (plerixafor), ulocuplumab (MDX1338/BMS-936564), and BKT140 (BL-8040; TF14016; 4F-Benzoyl-TN14003).

7. The method of claim 6, wherein the ADRB2 inhibitor is selected from the group consisting of carazolol, carvedilol, and propranolol.

8. A method of treating cancer in a patient having a CXCR4-ADRB2 heteromer in a cancer cell, the method comprising:
   determining whether the cancer patient's cancer cell contains the CXCR4-ADRB2 heteromer;
   if the CXCR4-ADRB2 heteromer is present in the cancer patient's cancer cell, then administering to said cancer patient having said CXCR4-ADRB2 heteromer in said cancer cell an inhibitor of CXCR4 and an inhibitor of ADRB2;
   wherein:
   i) the CXCR4-ADRB2 heteromer has an enhanced amount of downstream calcium mobilization relative to downstream calcium mobilization from a CXCR4 protomer or ADRB2 protomer;
   ii) the administered combination of inhibitors suppresses the enhanced downstream calcium mobilization from said CXCR4-ADRB2 heteromer in the cell;
   iii) the CXCR4 inhibitor is selected from the group consisting of: AD-114, AD-114-6H, AD-114-Im7-FH, AD-114-PA600-6H, ALX-0651, ALX40-4C, AMD070 (AMD11070, X4P-001), AMD3100 (plerixafor), AMD3465, ATI 2341, BKT140 (BL-8040; TF14016; 4F-Benzoyl-TN14003), CTCE-9908, CX549, D-[Lys3] GHRP-6, FC122, FC131, GMI-1359, GSK812397, GST-NT21MP, isothiourea-1a, isothiourea-1t (IT1t), KRH-1636, KRH-3955, LY2510924, LY2624587, MSX-122, N-[$^{11}$C]Methyl-AMD3465, PF-06747143, POL6326, SDF-1 1-9[P2G] dimer, SDF1 P2G, T134, T140, T22, TC 14012, TG-0054 (Burixafor), USL311, ulocuplumab (MDX1338/BMS-936564), viral macrophage inflammatory protein-II (vMIP-II), WZ811, 12G5, 238D2, 238D4, [$^{64}$Cu]-AMD3100, [$^{64}$Cu]-AMD3465, [$^{68}$Ga]pentixafor, [$^{90}$Y]pentixather, [$^{99m}$Tc]O$_2$-AMD3100, [$^{177}$Lu]pentixather, and 508MCl (Compound 26); and
   iv) the ADRB2 inhibitor is selected from the group consisting of: Alprenolol, atenolol, betaxolol, bupranolol, butoxamine, carazolol, carvedilol, CGP 12177, cicloprolol, ICI 118551, ICYP, labetalol, levobetaxolol, levobunolol, LK 204-545, metoprolol, nadolol, NIHP, NIP, propafenone, propranolol, sotalol, SR59230A, and timolol.

9. The method of treating of claim 8, wherein the enhanced amount of calcium mobilization from the CXCR4-ADRB2 heteromer is a calcium mobilization amount that, upon co-stimulation with CXCL12 and a selective ADRB2 agonist, is at least 10% greater than the sum of calcium mobilization amounts resulting from single agonist stimulation of said cells with either the CXCL12 or the selective ADRB2 agonist, as determined via a calcium mobilization assay.

10. The method of treating of claim 9, wherein the CXCR4-ADRB2 heteromer has two or more of the following characteristics:
   1) the CXCR4-ADRB2 heteromer components in a cancer cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay;
   2) an enhanced amount of calcium mobilization, such that:
      a) either CXCR4 or ADRB2 in an individual protomer context in a cancer cell, upon co-stimulation with CXCL12 and a selective ADRB2 agonist, results in a calcium mobilization amount that is equal to or less than the sum of calcium mobilization amounts resulting from single agonist stimulation with either the CXCL12 or the ADRB2 agonist; and
      b) the CXCR4-ADRB2 heteromer exhibits an enhanced calcium mobilization upon co-stimulation with the CXCL12 and the selective ADRB2 agonist relative to the sum of calcium mobilization amounts resulting from single agonist stimulation with either the CXCL12 or the selective GPCRx agonist;
   as determined via a calcium mobilization assay; or
   3) a CXCR4-ADRB2 heteromer-selective reagent:
      i) alters heteromer-specific properties of the CXCR4-ADRB2 heteromer in the cell;
      ii) alters heteromer-specific function of the CXCR4-ADRB2 heteromer in the cell;
      iii) alters heteromer-specific properties of the cell containing the CXCR4-ADRB2 heteromer; or
      iv) decreases cancer progression of the cell containing the CXCR4-ADRB2 heteromer.

11. The method of treating of claim 10, wherein the CXCR4-ADRB2 heteromer components in the cell colocalize and physically interact, either directly or via intermediate proteins acting as conduits for allosterism, as determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay.

12. The method of treating of claim 11, wherein the CXCR4-ADRB2 heteromer has enhanced amount of calcium mobilization, such that:
   a) either the CXCR4 or the ADRB2 in an individual protomer context in a cancer cell, upon co-stimulation with CXCL12 and a selective ADRB2 agonist, results in a calcium mobilization amount that is equal to or less than the sum of calcium mobilization amounts resulting from single agonist stimulation with either the CXCL12 or the ADRB2 agonist; and
   b) the CXCR4-ADRB2 heteromer exhibits an enhanced calcium mobilization upon co-stimulation with the CXCL12 and the selective ADRB2 agonist relative to the sum of calcium mobilization amounts resulting from single agonist stimulation with either the CXCL12 or the selective GPCRx agonist;
as determined via a calcium mobilization assay.

13. The method of treating of claim 8, wherein the CXCR4 inhibitor is selected from the group consisting of AMD3100 (plerixafor), ulocuplumab (MDX1338/BMS-936564), and BKT140 (BL-8040; TF14016; 4F-Benzoyl-TN14003).

14. The method of treating of claim 13, wherein the ADRB2 inhibitor is selected from the group consisting of carazolol, carvedilol, and propranolol.

15. The method of claim 1, wherein the presence of the CXCR4-ADRB2 heteromer in the cancer patient's cancer cell is determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay.

16. The method of claim 1, wherein the cancer is selected from the group consisting of: tumors of the gastrointestinal tract, breast cancer, lung cancer, small cell carcinoma of the lung, hepatocellular carcinoma, brain cancer, kidney cancer, pancreatic cancer or pancreatic adenocarcinoma, ovarian cancer, prostate cancer, melanoma, lymphoma, leukemia, multiple myeloma, renal cell carcinoma, soft tissue sarcoma, gastrointestinal cancer, stomach cancer, colon cancer, colorectal cancer, colorectal adenocarcinoma, bladder adenocarcinoma, esophageal cancer, and adenocarcinoma of the stomach, esophagus, throat, and urogenital tract.

17. The method of claim 8, wherein the presence of the CXCR4-ADRB2 heteromer in the cancer patient's cancer cell is determined via one or more of the following: a co-internalization assay, a colocalization assay, in situ hybridization, immunohistochemistry, immunoelectron microscopy, a proximity-based assay, a co-immunoprecipitation assay, enzyme-linked immunosorbent assay (ELISA), flow cytometry, RNAseq, qRT-PCR, microarray, or a fluorescent animal assay.

18. The method of claim 8, wherein the cancer is selected from the group consisting of: tumors of the gastrointestinal tract, breast cancer, lung cancer, small cell carcinoma of the lung, hepatocellular carcinoma, brain cancer, kidney cancer, pancreatic cancer or pancreatic adenocarcinoma, ovarian cancer, prostate cancer, melanoma, lymphoma, leukemia, multiple myeloma, renal cell carcinoma, soft tissue sarcoma, gastrointestinal cancer, stomach cancer, colon cancer, colorectal cancer, colorectal adenocarcinoma, bladder adenocarcinoma, esophageal cancer, and adenocarcinoma of the stomach, esophagus, throat, and urogenital tract.

* * * * *